(12) United States Patent
Sabatino et al.

(10) Patent No.: US 7,811,560 B2
(45) Date of Patent: Oct. 12, 2010

(54) COMPOSITIONS AND METHODS FOR TREATING COLLAGEN-MEDIATED DISEASES

(75) Inventors: Gregory L. Sabatino, Chester Springs, PA (US); Benjamin J. Del Tito, Jr., Doylestown, PA (US); Phillip J. Bassett, Newcastle-under-Lyme (GB); Hazel A. Tharia, Nr Crewe (GB); Antony G. Hitchcock, Crewe (GB)

(73) Assignee: Auxilium US Holdings, LLC, Wilmington, DE (US)

( * ) Notice: Subject to any disclaimer, the term of this patent is extended or adjusted under 35 U.S.C. 154(b) by 530 days.

(21) Appl. No.: 11/699,302

(22) Filed: Jan. 29, 2007

(65) Prior Publication Data

US 2007/0224183 A1  Sep. 27, 2007

Related U.S. Application Data

(60) Provisional application No. 60/763,470, filed on Jan. 30, 2006, provisional application No. 60/784,135, filed on Mar. 20, 2006.

(51) Int. Cl.
*A61K 38/46* (2006.01)

(52) U.S. Cl. .................................................. 424/94.67

(58) Field of Classification Search ....................... None
See application file for complete search history.

(56) References Cited

U.S. PATENT DOCUMENTS

| | | | | |
|---|---|---|---|---|
| 5,252,481 | A | * | 10/1993 | Holjevac et al. .......... 435/252.7 |
| 5,332,503 | A | * | 7/1994 | Lee et al. .................... 210/635 |
| 5,462,739 | A | * | 10/1995 | Dan et al. .................... 424/427 |
| 5,514,370 | A | | 5/1996 | Stern et al. |
| 5,753,485 | A | * | 5/1998 | Dwulet et al. ............... 435/220 |
| 5,830,741 | A | | 11/1998 | Dwulet et al. |
| 5,952,215 | A | | 9/1999 | Dwulet et al. |
| 5,989,888 | A | | 11/1999 | Dwulet et al. |
| 6,475,764 | B1 | | 11/2002 | Burtscher et al. |
| 2004/0137596 | A1 | * | 7/2004 | Kurfurst et al. ............. 435/212 |
| 2006/0204488 | A1 | * | 9/2006 | Badalamente ............ 424/94.63 |

OTHER PUBLICATIONS

Akers "Excipient-Drug Interactions in Parenteral Formulations," J. Pharm. Sci., 2002, 91, 2283-2300.*
Brandhorst et al. "Adjustment of the Ratio Between Collagenase Class II and I Improves Islet Isolation Outcome," Transplantation Proceedings, 2005, 37, 3450-3451.*
Bond et al. "Purification and Separation of Individual Collagenases of *Clostridium histolyticum* Using Red Dye Ligand Chromatography," Biochemistry, 1984, 23, 3077-3085.*
Takahashi et al. "New Culture Conditions for *Clostridium histolyticum* leading to Production of Collagenase of High Specific Activity," J. Appl. Bact., 1972, 35, 641-657.*
Matsushita, Osamu et al., "Gene Duplication and Multiplicity of Collagenases in *Clostridium histolyticum*," J. of Bacteriology, 181(3):923-933 (1999).
Ducka, Paulina et al., "A universal strategy for high-yield production of soluble and functional clostridial collagenases in *E. coli*," Appl. Microbiol Biotechnol 83:1055-1065 (2009).
Jung, Chang-Min et al., "Expression of the colH Gene Encoding *Clostridium histolyticum* Collagenase in *Bacillus subtilis* and Its Application to Enzyme Purification," Microbiol. Immunol., 40(12):923-929 (1996).
Hesse, F. et al., "Recombinant Enzymes for Islet Isolation: Purification of a Collagenase From *Clostridium histolyticum* and Cloning/Expression of the Gene," Transplantation Proceedings, 27(6):3287-3289 (1995).
U.S. Appl. No. 12/759,065 (Continuation of U.S. Appl. No. 11/699,302), filed Apr. 13, 2010 in the names of Sabatino, Del Tito, Bassett, Tharia, Hitchcock, Wegman and Yu, entitled "Compositions and Methods of Treating Collagen-Mediated Diseases" and all papers filed in connection therewith.

* cited by examiner

*Primary Examiner*—Christina Bradley
(74) *Attorney, Agent, or Firm*—Elmore Patent Law Group; Carolyn S. Elmore; Mahreen Chaudhry Hoda

(57) ABSTRACT

A drug product comprising a combination of highly purified collagenase I and collagenase II from *Colostridium histolyticum* is disclosed. The drug product includes collagenase I and collagenase II in a ratio of about 1 to 1, with a purity of greater than at least 95%. The invention further disclosed improved fermentation and purification processes for preparing the said drug product.

29 Claims, 94 Drawing Sheets

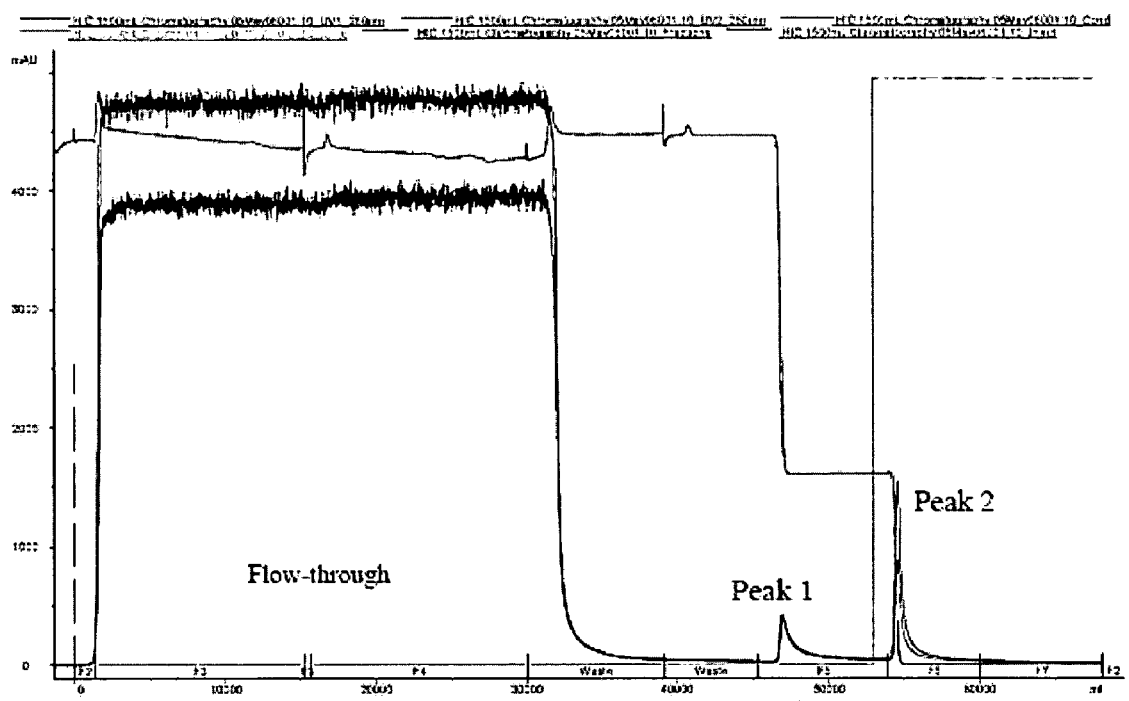
(a)
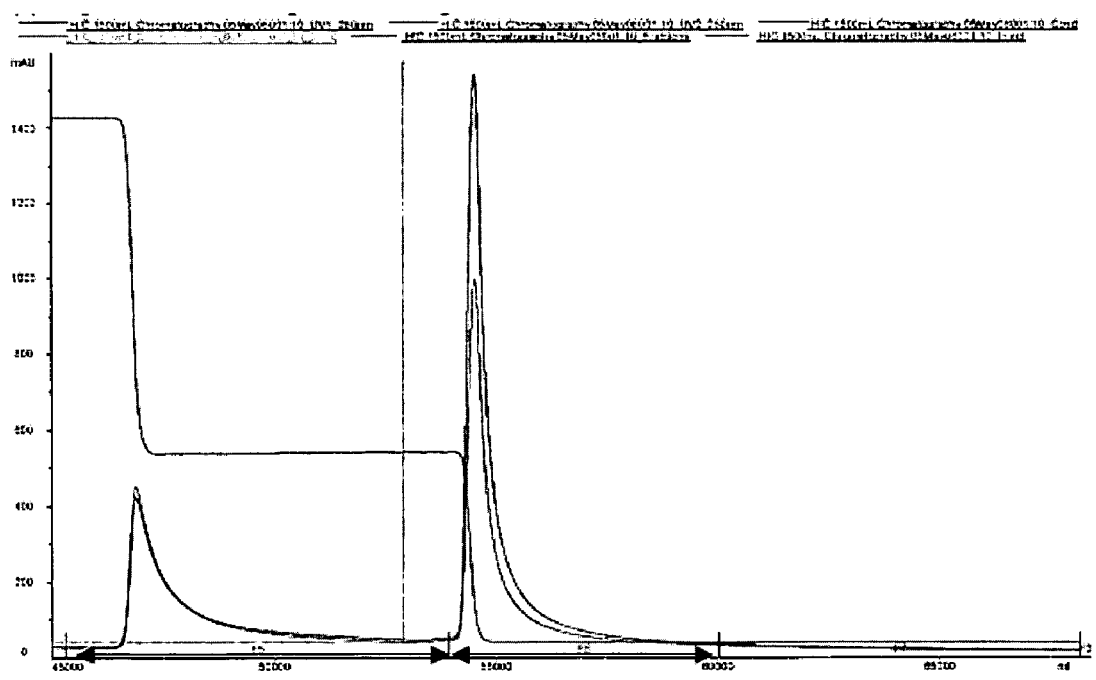
(b)
FIG. 70

Analytical chromatography

| Sample | RP-HPLC | | | | SEC-HPLC (AREA%) | | | |
|---|---|---|---|---|---|---|---|---|
| | AUX-I | AUX-II | Clostripain | Others | AUX-I | AUX-II | Aggregates | Others |
| Fermentation Filtrate Day 4 | 57.52 | 42.48 | 0.00 | 0.00 | 0.47 | 0.65 | 0.70 | 98.17 |
| Fermentation Filtrate Day 5 | 52.97 | 47.03 | 0.00 | 0.00 | 0.48 | 0.64 | 0.73 | 98.14 |
| Post Mustang Q Day 4 | 41.23 | 52.16 | 0.00 | 6.61 | 0.56 | 0.75 | 0.78 | 97.91 |
| Post HIC Day 3 | 44.00 | 55.00 | 0.00 | 1.00 | 49.46 | 48.72 | 0.00 | 1.83 |
| Post HIC Day 6 | 44.42 | 54.52 | 0.00 | 1.05 | 49.29 | 48.92 | 0.00 | 1.79 |
| Post TFF Day 2 | 49.69 | 48.09 | 0.14 | 2.07 | 50.77 | 47.37 | 0.00 | 1.86 |
| Post TFF Day 4 | 49.60 | 47.88 | 0.21 | 2.31 | 50.29 | 47.73 | 0.00 | 1.98 |
| Post IEX AUX-I Day 5 | 99.17 | 0.65 | 0.00 | 0.18 | 100.00 | 0.00 | 0.00 | 0.00 |
| Post IEX AUX-I Day 12 | 98.42 | 1.58 | 0.00 | 0.00 | 100.00 | 0.00 | 0.00 | 0.00 |
| Post IEX AUX-II Day 5 | 0.56 | 98.72 | 0.17 | 0.55 | 0.00 | 100.00 | 0.00 | 0.00 |
| Post IEX AUX-II Day 12 | 0.32 | 99.04 | 0.17 | 0.48 | 0.00 | 99.38 | 0.62 | 0.00 |
| AUX-I Intermediate Day 6 | 98.60 | 1.10 | 0.05 | 0.25 | 100.00 | 0.00 | 0.00 | 0.00 |
| AUX-I Intermediate Day 12 | 99.01 | 0.68 | 0.04 | 0.27 | 100.00 | 0.00 | 0.00 | 0.00 |
| AUX-II Intermediate Day 6 | 0.47 | 98.95 | 0.11 | 0.47 | 0.00 | 100.00 | 0.00 | 0.00 |
| AUX-II Intermediate Day 12 | 0.28 | 99.12 | 0.13 | 0.47 | 0.00 | 100.00 | 0.00 | 0.00 |

FIG. 82

Protein concentration determination by UV

| Sample description | Conc. by UV (mg/mL) |
|---|---|
| Fermentation Filtrate Day 4 | 22.1 |
| Fermentation Filtrate Day 5 | 22.0 |
| Post Mustang Q Day 4 | 47.2 |
| Post HIC Day 3 | 0.54 |
| Post HIC Day 6 | 0.55 |
| Post TFF Day 2 | 2.18 |
| Post TFF Day 4 | 2.13 |
| Post IEX AUX-I Day 5 | 1.09 |
| Post IEX AUX-I Day 12 | 1.09 |
| Post IEX AUX-II Day 5 | 1.16 |
| Post IEX AUX-II Day 12 | 1.18 |
| AUX-I Intermediate Day 6 | 1.09 |
| AUX-I Intermediate Day 12 | 1.13 |
| AUX-II Intermediate Day 6 | 0.94 |
| AUX-II Intermediate Day 12 | 0.97 |

COMPOSITIONS AND METHODS FOR TREATING COLLAGEN-MEDIATED DISEASES

RELATED APPLICATIONS

This application claims the benefit of U.S. Provisional Application No. 60/763,470 filed on Jan. 30, 2006 and U.S. Provisional Application No. 60/784,135, filed Mar. 20, 2006. The entire teachings of the above applications are incorporated herein by reference.

PARTIES TO A JOINT RESEARCH AGREEMENT

Auxilium Pharmaceuticals Inc. and BioSpecifics Technologies Corp. are parties to a "joint research agreement" as defined in 35 USC 103(c)(3).

BACKGROUND OF THE INVENTION

Collagen is the major structural constituent of mammalian organisms and makes up a large portion of the total protein content of skin and other parts of the animal body. In humans, it is particularly important in the wound healing process and in the process of natural aging. Various skin traumas such as burns, surgery, infection and accident are often characterized by the erratic accumulation of fibrous tissue rich in collagen and having increased proteoglycan content. In addition to the replacement of the normal tissue which has been damaged or destroyed, excessive and disfiguring deposits of new tissue sometimes form during the healing process. The excess collagen deposition has been attributed to a disturbance in the balance between collagen synthesis and collagen degradation.

Numerous diseases and conditions are associated with excess collagen deposition and the erratic accumulation of fibrous tissue rich in collagen. Such diseases and conditions are collectively referred to herein as "collagen-mediated diseases". Collagenase has been used to treat a variety of collagen-mediated diseases. Collagenase is an enzyme that has the specific ability to digest collagen.

Collagenase for use in therapy may be obtained from a variety of sources including mammalian (e.g. human), crustacean (e.g. crab, shrimp), fungal, and bacterial (e.g. from the fermentation of Clostridium, Streptomyces, Pseudomonas, or Vibrio). Collagenase has also been genetically engineered. One common source of crude collagenase is from a bacterial fermentation process, specifically the fermentation of C. histolyticum (C. his). The crude collagenase obtained from C. his may be purified using any of a number of chromatographic techniques.

One drawback of the fermentation process from C. his is that it yields uncertain ratios of the various collagenases such as collagenase I and collagenase II, often used in therapeutic compositions to treat collagen mediated conditions. Further, the culture has historically required the use of meat products. This meat culture was originally derived from the H4 strain of Clostridium histolyticum, Dr. I. Mandl's laboratory in Columbia University in 1956 and deposited with the ATCC. Lyophilized vials were made out of the cooked meat culture and named as ABC Clostridium histolyticum master cell bank.

Various ratios of collagenase I to collagenase II in a therapeutic collagenase preparation have different biological effects. Therefore, a therapeutic collagenase preparation in which the ratio of collagenase I to collagenase II in the preparation can be easily and efficiently determined and controlled to obtain superior, and consistent enzyme activity and therapeutic effect, would be desirable.

SUMMARY OF THE INVENTION

The present invention provides a collagenase composition comprising a combination of highly purified collagenase I and collagenase II. Preferably, the collagenase I and collagenase II are present in a mass ratio of about 1 to 1. When used as a pharmaceutical composition for treating collagen-mediated diseases, the composition of the invention provides improved and consistent therapeutic effect while lowering the potential for side effects.

The invention further provides methods for preparing a collagenase composition of the invention, pharmaceutical formulations comprising a composition of the invention and methods for treating patients suffering from a collagen-mediated disease using a collagenase composition of the invention.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Figure 6:
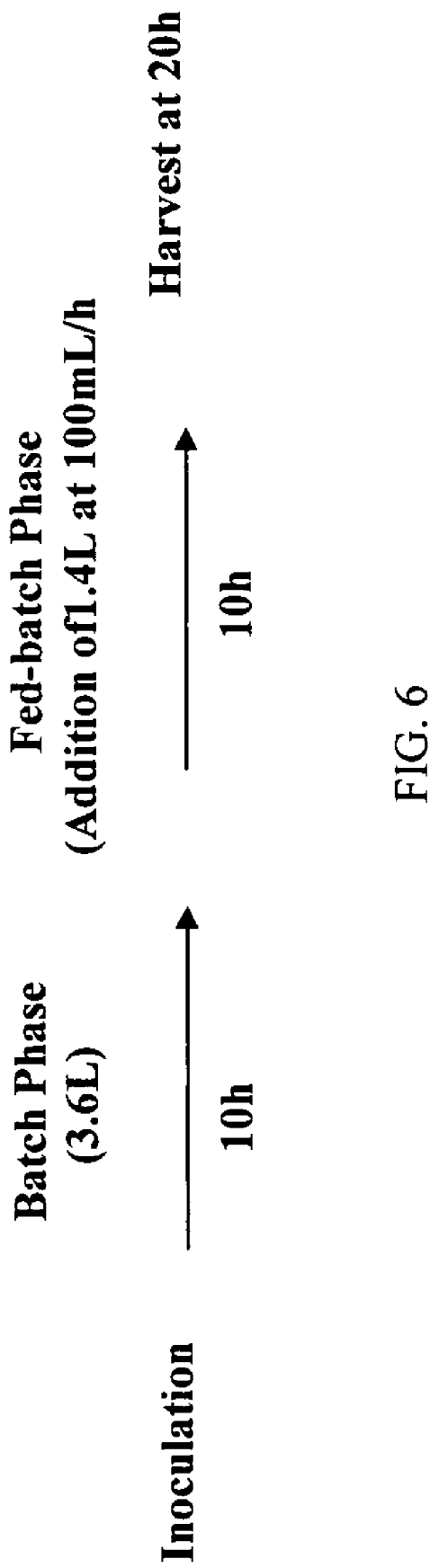
Figure 7:
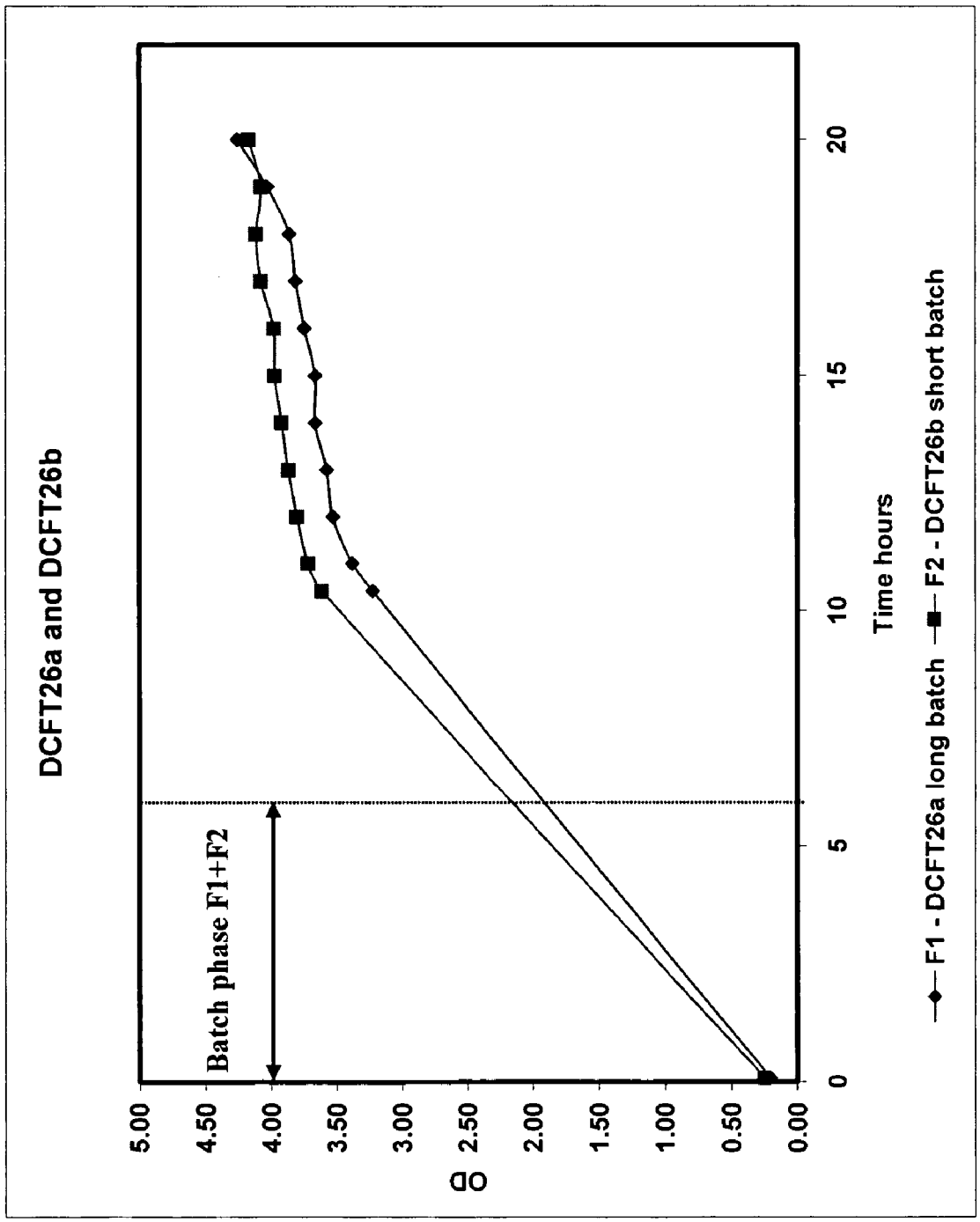
Figure 8:
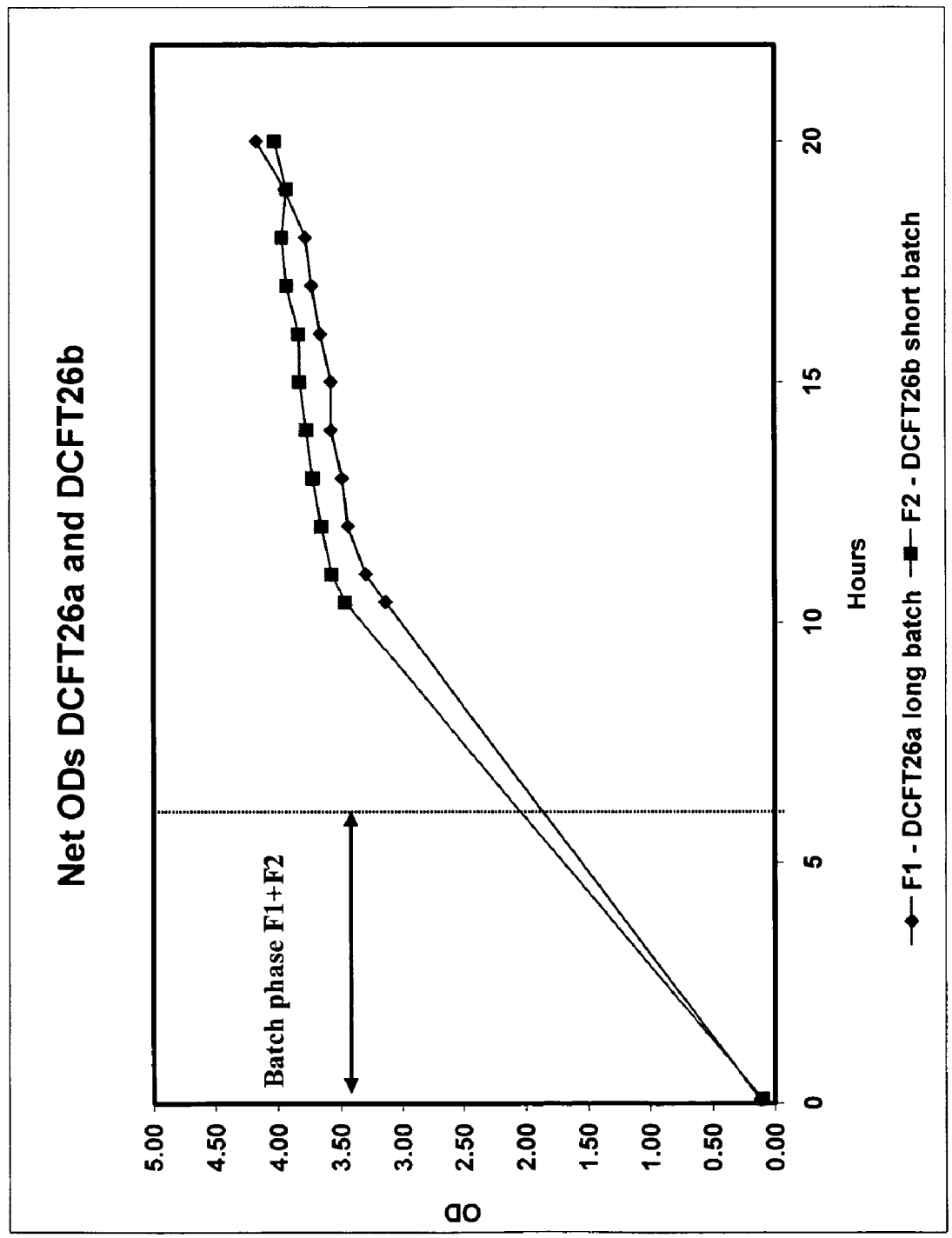
Figure 9:
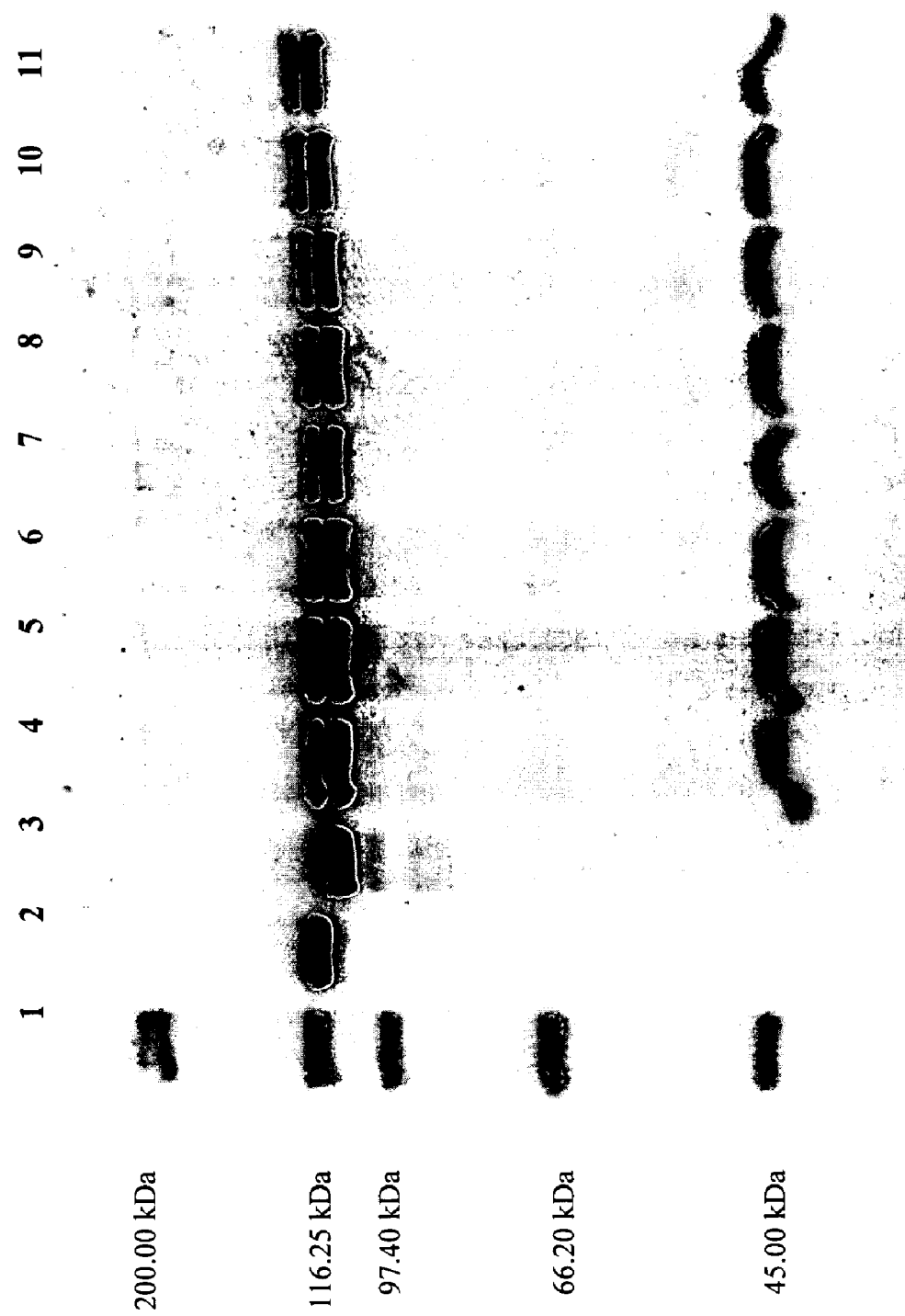
Figure 10:
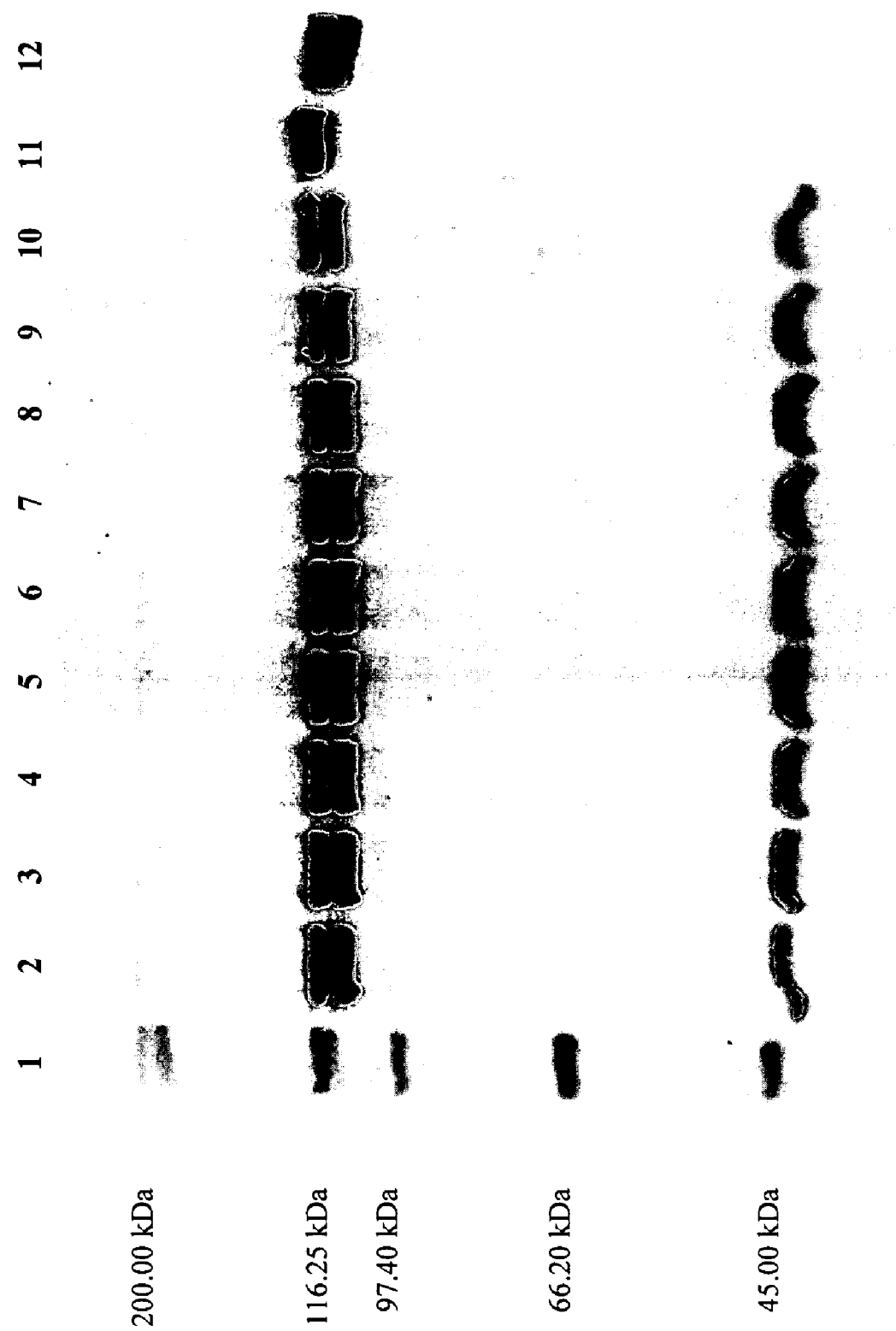
Figure 11:
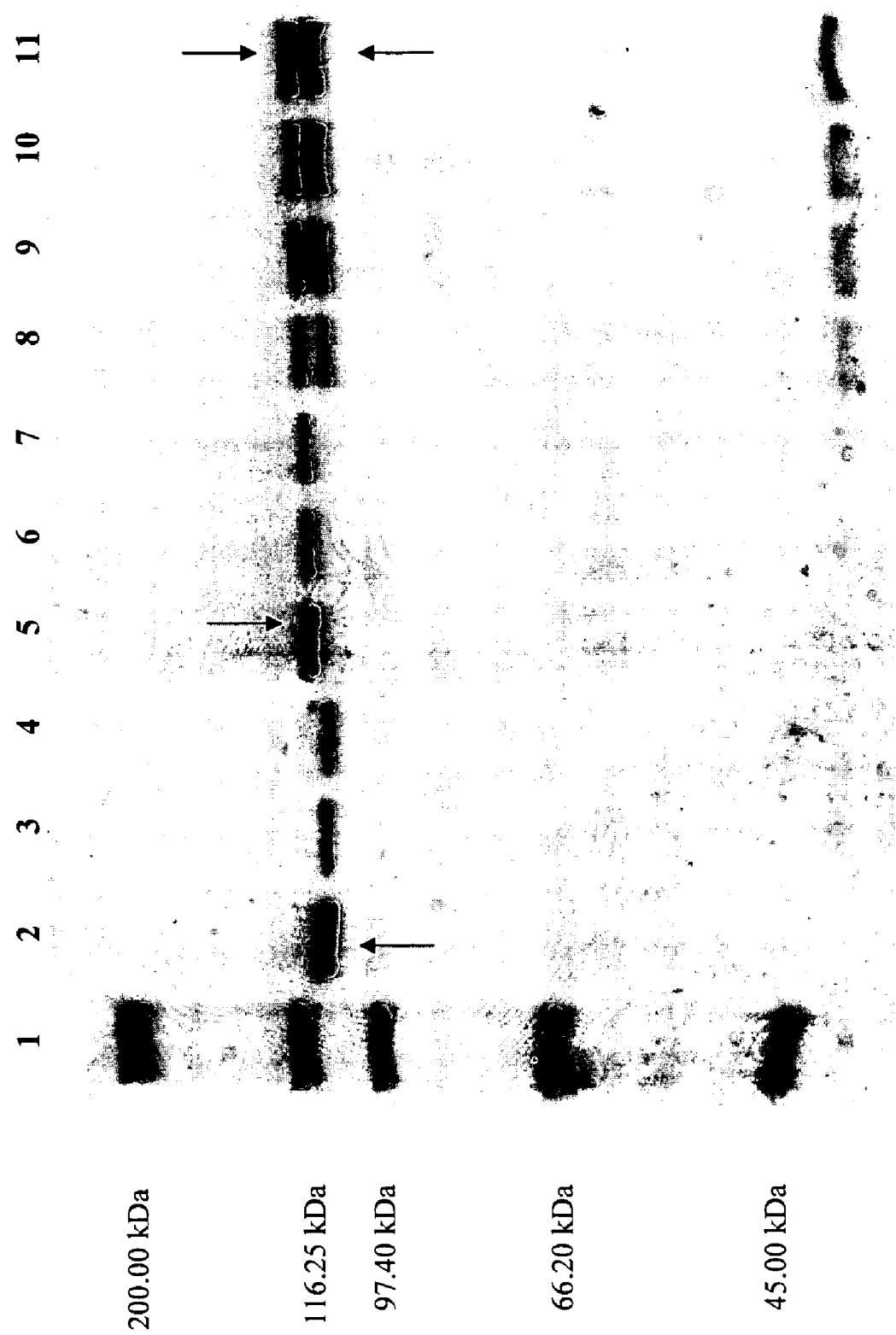
Figure 12:
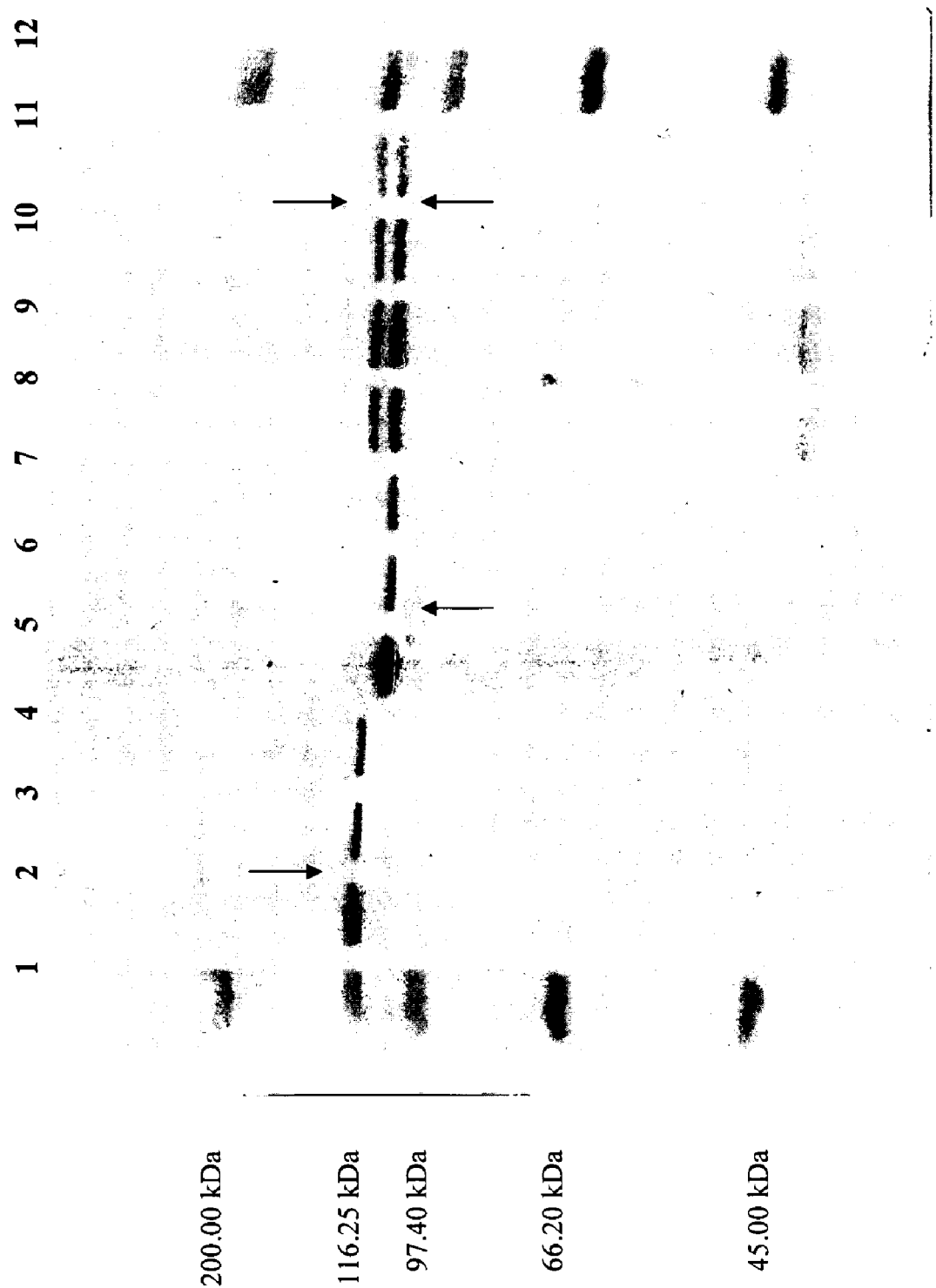
Figure 13:
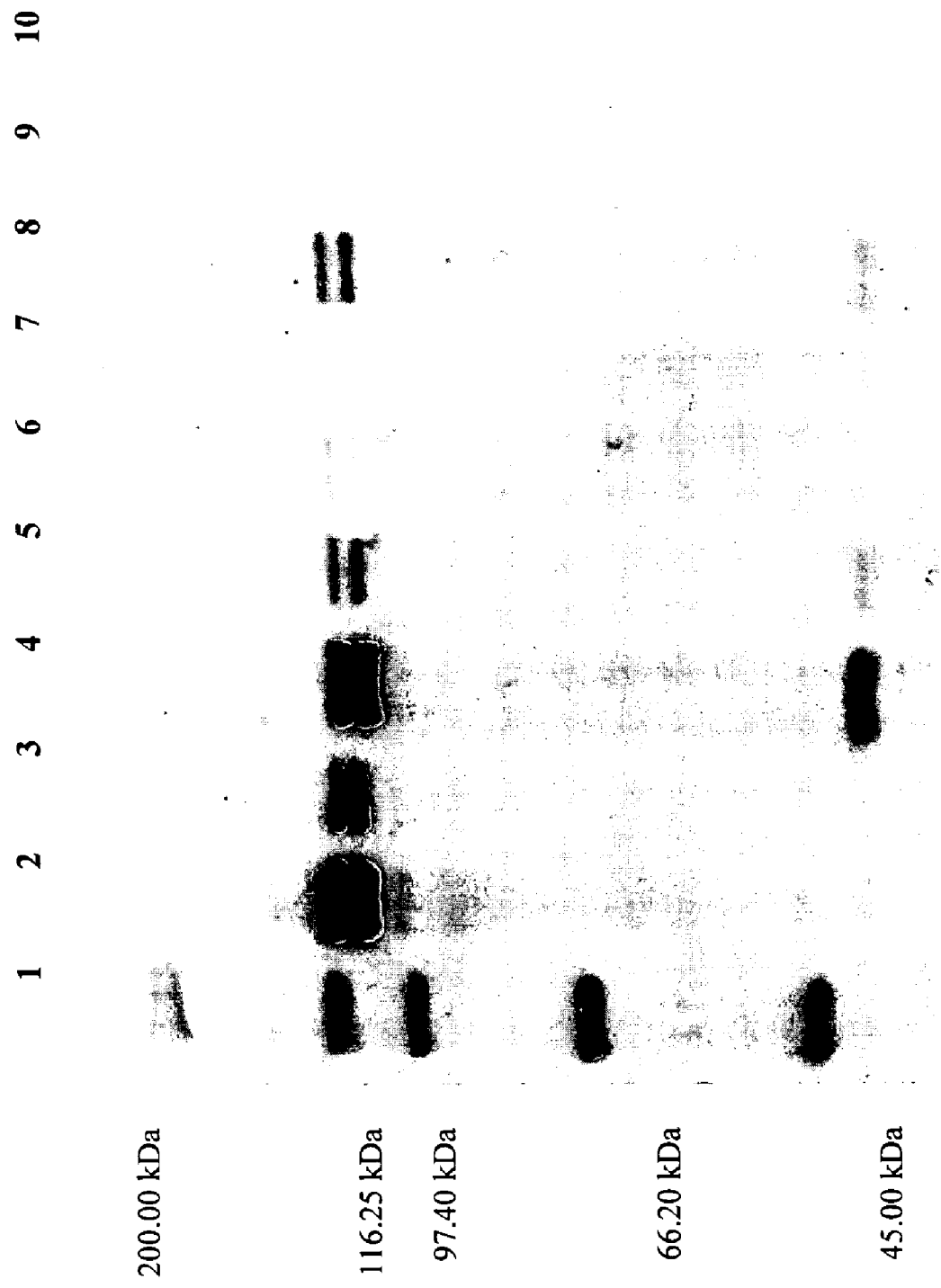
Figure 14:
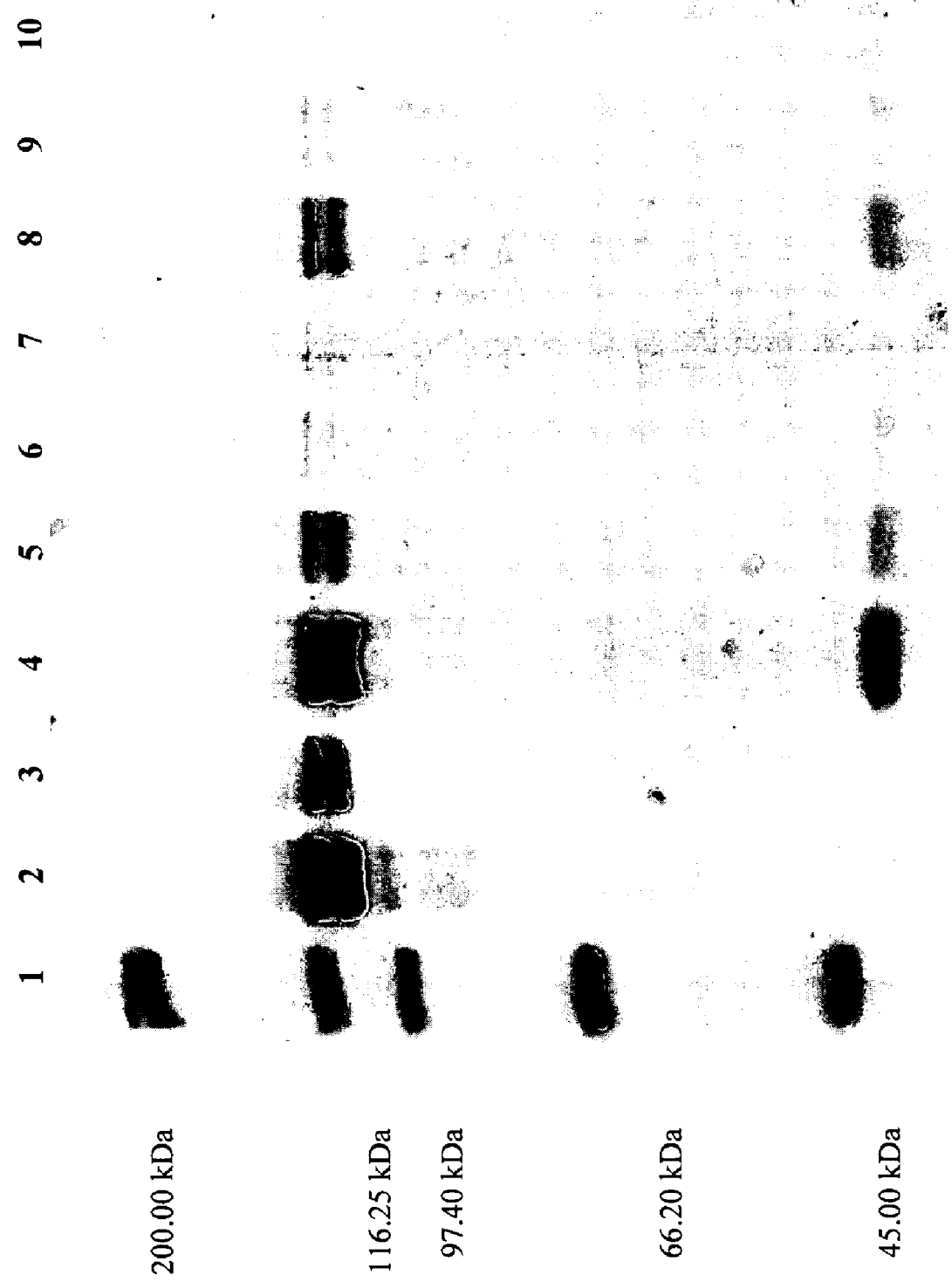
Figure 15:
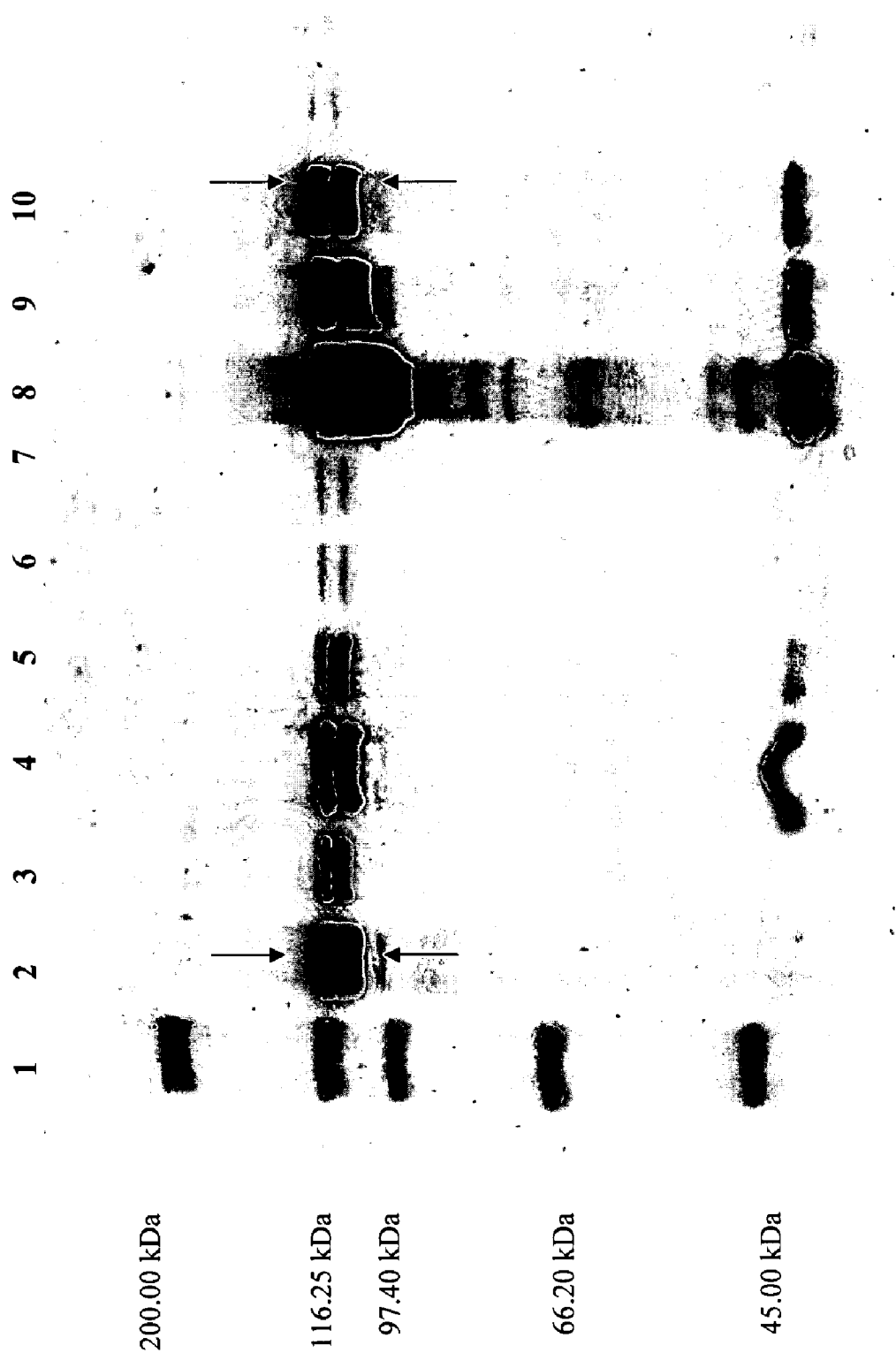
Figure 16:
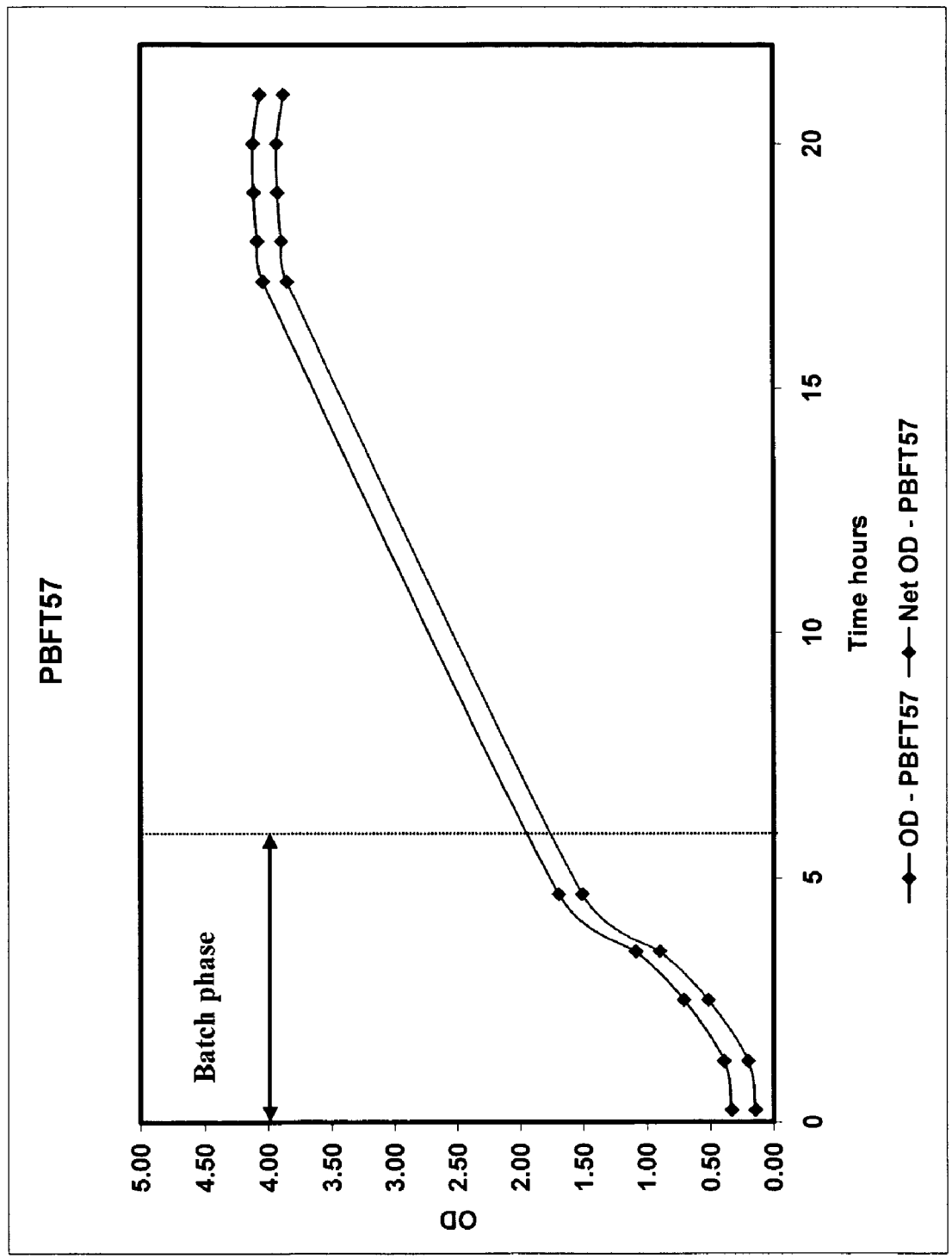
Figure 17:
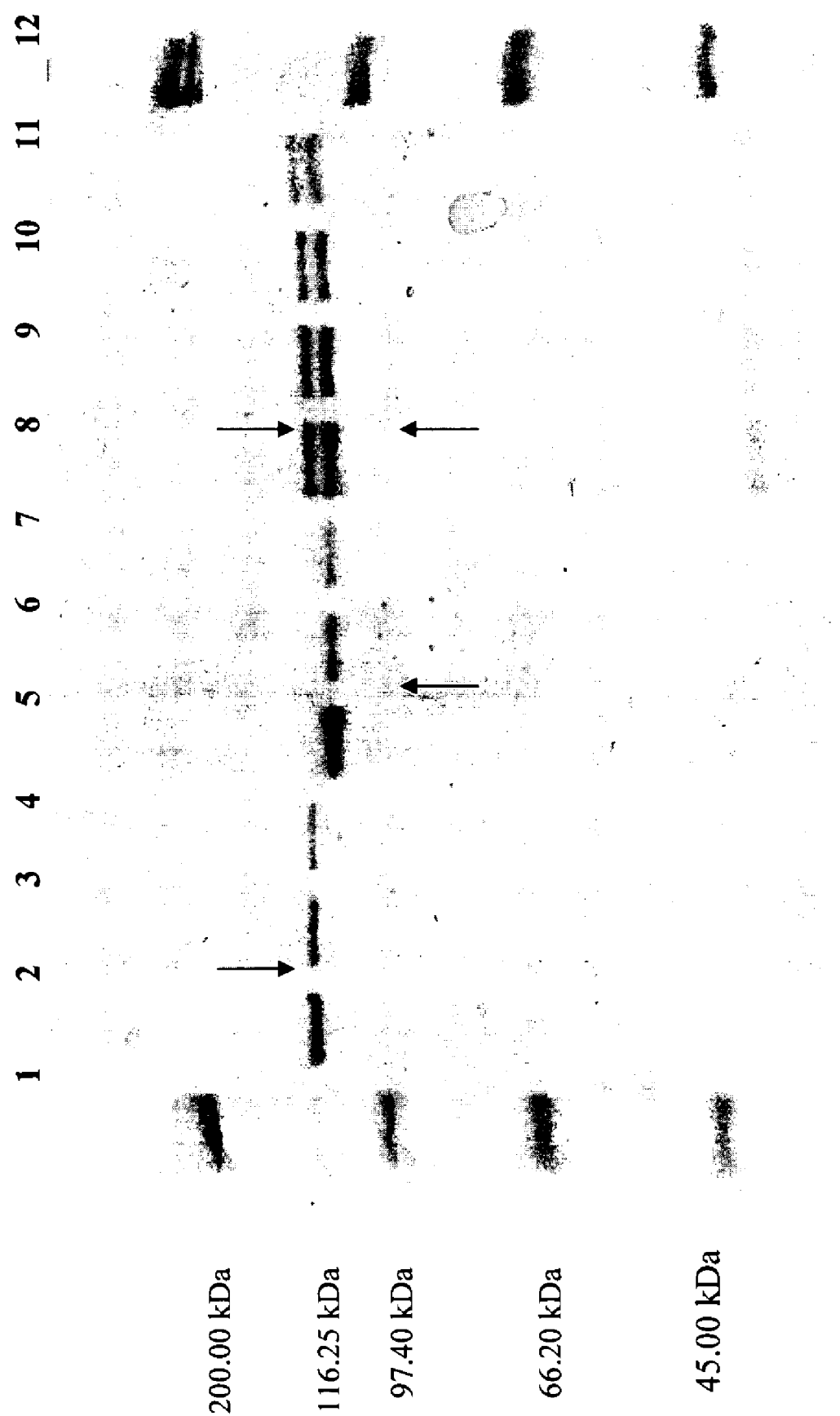

Lane 3: 1.22 µL of sample (1/5 dilution of fermentation sample)
Lane 4: 1.53 µL of sample (1/4 dilution of fermentation sample)
Lane 5: 2.04 µL of sample (1/3 dilution of fermentation sample)
Lane 6: 0.27 µg collagenase I
Lane 7: 0.18 µg collagenase I
Lane 8: 0.135 µg collagenase I
Lane 9: 0.29 µg collagenase II
Lane 10: 0.193 µg collagenase II
Lane 11: 0.145 µg collagenase II;

FIG. 6 represents fermentation strategy used for DCFT26a and DCFT26b;

FIG. 7 depicts growth curves (OD vs time) of *C. histolyticum* in 5 L DCFT26a,b fermentations;

FIG. 8 depicts net growth curves (Net OD vs time) of *C. histolyticum* in 5 L DCFT26a,b fermentations;

FIG. 9 is a SDS PAGE gel for DCFT26a:
Lane 1: High Molecular Weight Marker
Lane 2: Collagenase I-0.67 kg
Lane 3: Collagenase II-0.72 kg
Lane 4: 20 h (6.12 µL of sample)—Harvest Point
Lane 5: 19 h (6.12 µL of sample)
Lane 6: 18 h (6.12 µL of sample)
Lane 7: 17 h (6.12 µL of sample)
Lane 8: 16 h (6.12 µL of sample)
Lane 9: 14 h (6.12 µL of sample)
Lane 10: 13 h (6.12 µL of sample)
Lane 11: 11 h (6.12 µL of sample);

FIG. 10 is a SDS PAGE gel for DCFT26b:
Lane 1: High Molecular Weight Marker
Lane 2: 20 h (6.12 µL of sample)—Harvest point
Lane 3: 19 h (6.12 µL of sample)
Lane 4: 18 h (6.12 µL of sample)
Lane 5: 17 h (6.12 µL of sample)
Lane 6: 16 h (6.12 µL of sample)
Lane 7: 15 h (6.12 µL of sample)
Lane 8: 14 h (6.12 µL of sample)
Lane 9: 13 h (6.12 µL of sample)
Lane 10: 11 h (6.12 µL of sample)
Lane 11: Collagenase I-0.67 kg
Lane 12: Collagenase II-0.72 kg;

FIG. 11 is a semi-quantitative SDS PAGE gel for DCFT26a, harvest point sample:
Lane 1: High Molecular Weight Marker
Lane 2: 0.27 µg collagenase I
Lane 3: 0.18 µg collagenase I
Lane 4: 0.135 µg collagenase I
Lane 5: 0.29 µg collagenase II
Lane 6: 0.193 µg collagenase II
Lane 7: 0.145 µg collagenase II
Lane 8: 0.87 µL of sample (1/7 dilution of fermentation sample)
Lane 9: 1.22 µL of sample (1/5 dilution of fermentation sample)
Lane 10: 1.53 µL of sample (1/4 dilution of fermentation sample)
Lane 11: 2.04 µL of sample (1/3 dilution of fermentation sample);

FIG. 12 is a Semi-quantitative SDS PAGE gel for DCFT26b, harvest point sample:
Lane 1: High Molecular Weight Marker
Lane 2: 0.27 µg collagenase I
Lane 3: 0.18 µg collagenase I
Lane 4: 0.135 µg collagenase I
Lane 5: 0.29 µg collagenase II
Lane 6: 0.193 µg collagenase II
Lane 7: 0.145 µg collagenase II
Lane 8: 2.04 µL of sample (1/3 dilution of fermentation sample)
Lane 9: 1.53 µL of sample (1/4 dilution of fermentation sample)
Lane 10: 1.22 µL of sample (1/5 dilution of fermentation sample)
Lane 11: 0.87 µL of sample (1/7 dilution of fermentation sample);

FIG. 13 is a SDS PAGE gel for post-dialysed ammonium sulphate precipitated (100 g/L and 150 g/L) samples, DCFT26a, harvest point sample:
Lane 1: High Molecular Weight Marker
Lane 2: 0.67 µg collagenase I and 0.72 µg collagenase II
Lane 3: 0.27 µg collagenase I and 0.29 µg collagenase II
Lane 4: 6.12 µL of supernatant sample from SC11
Lane 5: post dialysed sample—100 g/L AS (Neat)
Lane 6: post dialysed sample—100 g/L AS (1/5)
Lane 7: post dialysed sample—100 g/L AS (1/10)
Lane 8: post dialysed sample—150 g/L AS (Neat)
Lane 9: post dialysed sample—150 g/L AS (1/5)
Lane 10: post dialysed sample—150 g/L AS (1/10);

FIG. 14 is a SDS PAGE gel for post-dialysed ammonium sulphate precipitated (200 g/L and 250 g/L) samples, DCFT26a, harvest point:
Lane 1: High Molecular Weight Marker
Lane 2: 0.67 µg collagenase I and 0.72 µg collagenase II
Lane 3: 0.27 µg collagenase I and 0.29 µg collagenase II
Lane 4: 6.12 µL of supernatant sample from SC 11
Lane 5: post dialysed sample—200 g/L AS (Neat)
Lane 6: post dialysed sample—200 g/L AS (1/5)
Lane 7: post dialysed sample—200 g/L AS (1/10)
Lane 8: post dialysed sample—250 g/L AS (Neat)
Lane 9: post dialysed sample—250 g/L AS (1/5)
Lane 10: post dialysed sample—250 g/L AS (1/10);

FIG. 15 is a SDS PAGE gel for post-dialysed ammonium sulphate precipitated (300 g/L and 400 g/L) samples, DCFT26a, harvest point:
Lane 1: High Molecular Weight Marker
Lane 2: 0.67 µg collagenase I and 0.72 µg collagenase II
Lane 3: 0.27 µg collagenase I and 0.29 µg collagenase II
Lane 4: 6.12 µL of supernatant sample from SC 1
Lane 5: post dialysed sample—300 g/L AS (Neat sample)
Lane 6: post dialysed sample—300 g/L AS (1/5 dilution)
Lane 7: post dialysed sample—300 g/L AS (1/10 dilution)
Lane 8: post dialysed sample—400 g/L AS (Neat)
Lane 9: post dialysed sample—4000 g/L AS (1/5 dilution)
Lane 10: post dialysed sample—400 g/L AS (1/10 dilution);

FIG. 16 depicts a Growth curves (OD vs time and net OD vs time) of *C. histolyticum* in PBFT57 fermentation;

FIG. 17 is a Semi-quantitative SDS PAGE gel, harvest point sample:
Lane 1: High Molecular Weight Marker
Lane 2: 0.27 µg collagenase I
Lane 3: 0.18 µg collagenase I
Lane 4: 0.135 µg collagenase I
Lane 5: 0.29 µg collagenase II
Lane 6: 0.193 µg collagenase II
Lane 7: 0.145 µg collagenase II
Lane 8: 2.04 µL of sample (1/3 dilution of fermentation harvest sample)
Lane 9: 1.53 µL of sample (1/4 dilution of fermentation harvest sample)
Lane 10: 1.22 µL of sample (1/5 dilution of fermentation harvest sample)

Figure 18A:
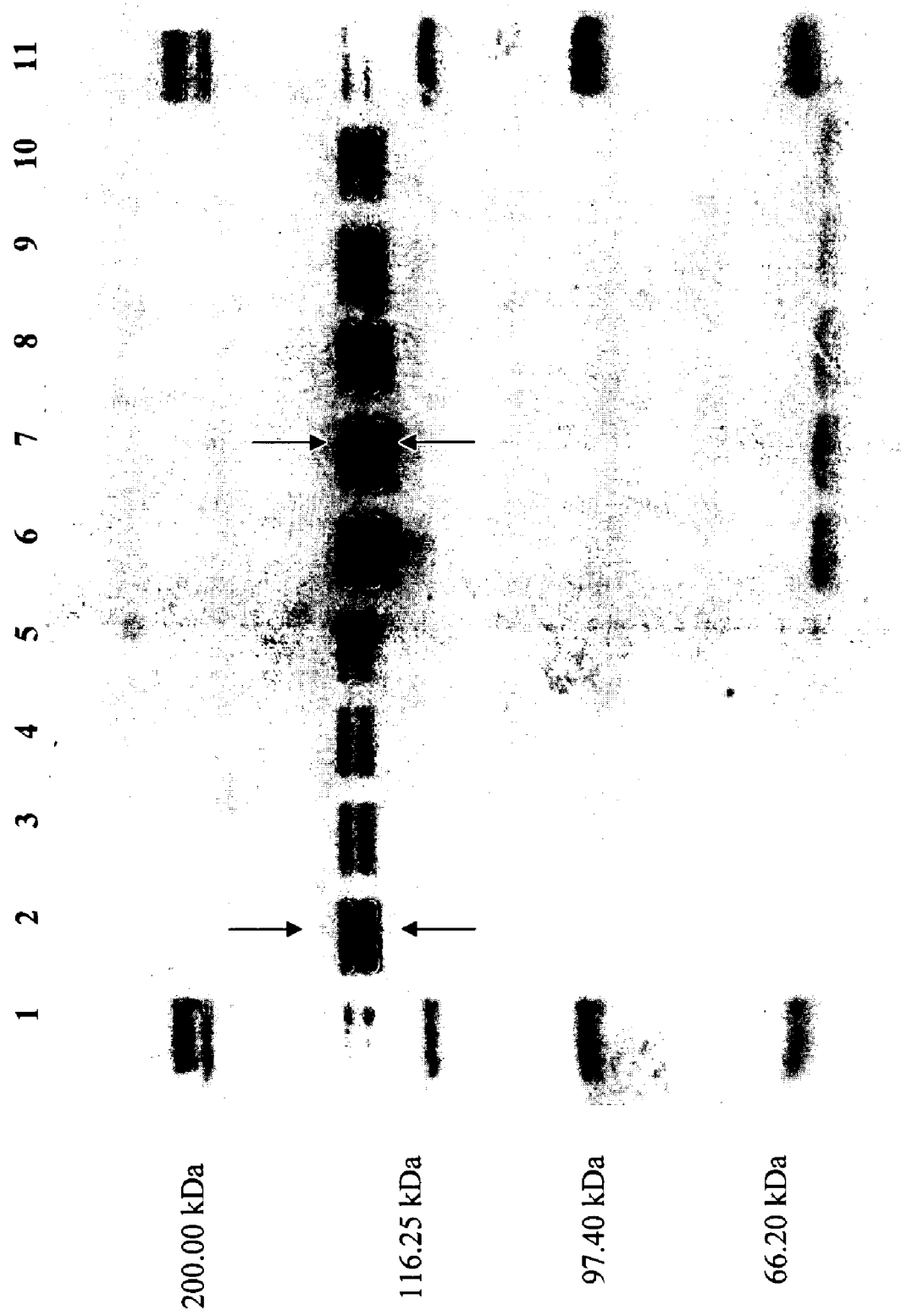
Figure 18B:
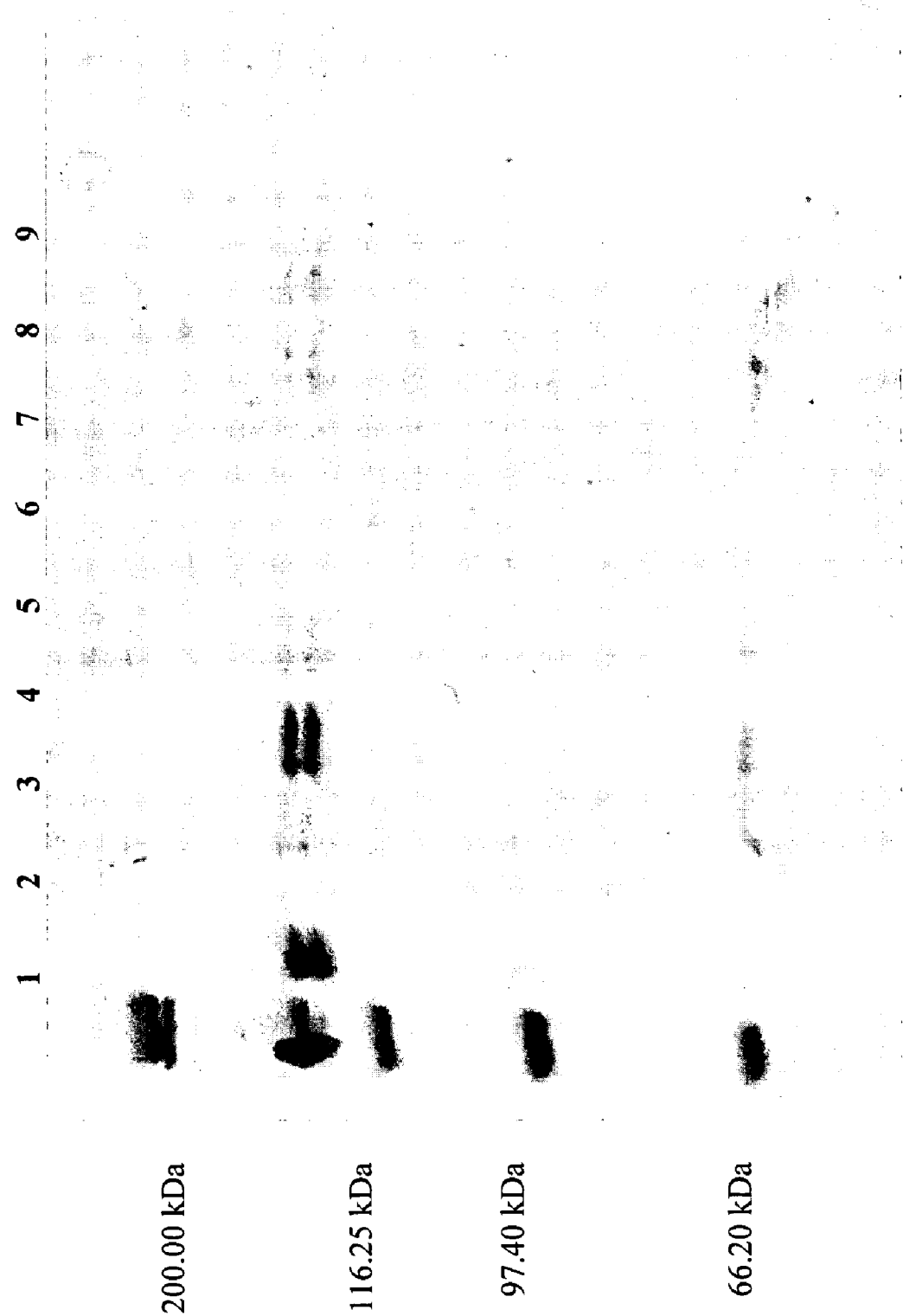
Figure 19:
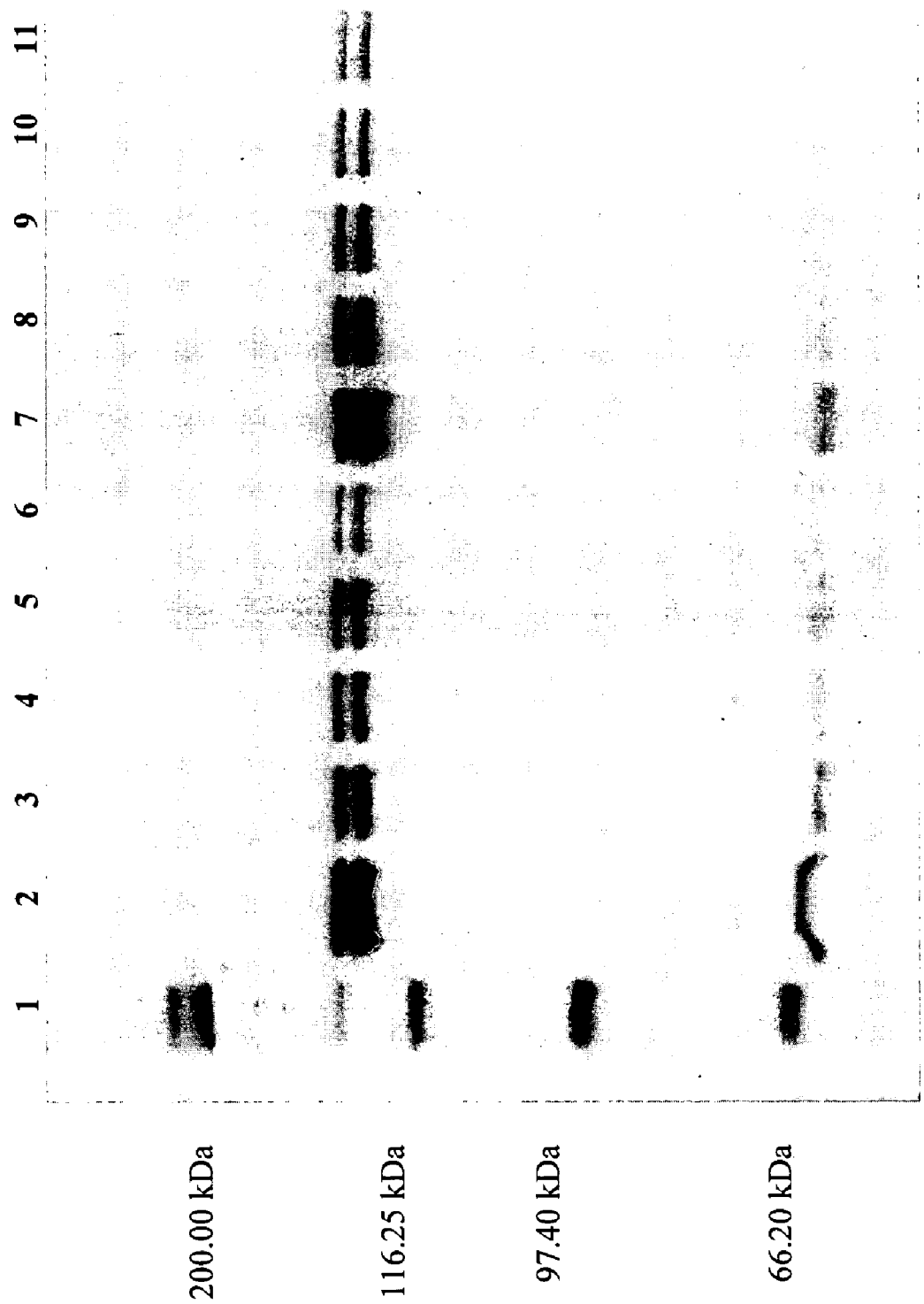
Figure 20:
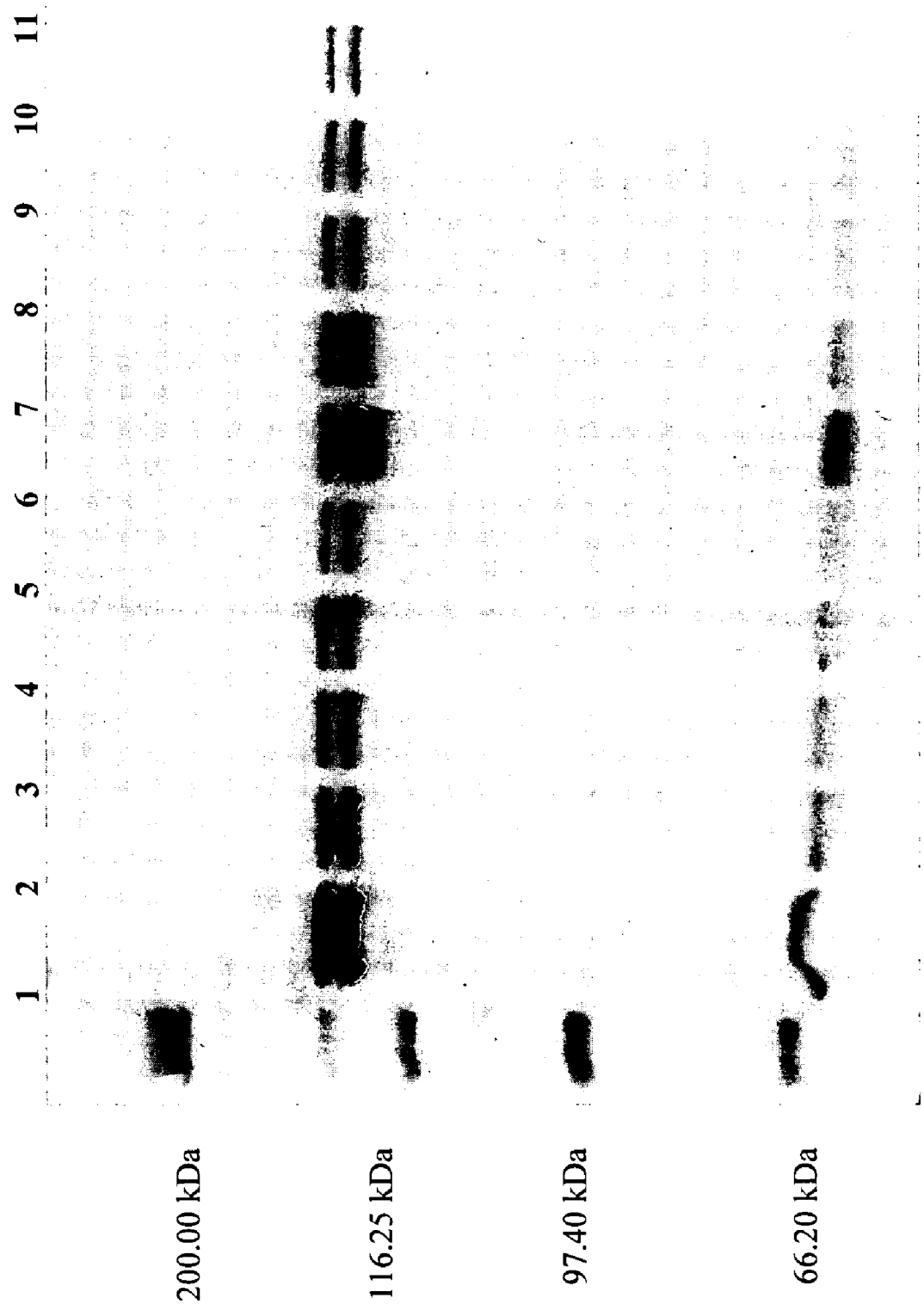
Figure 21:
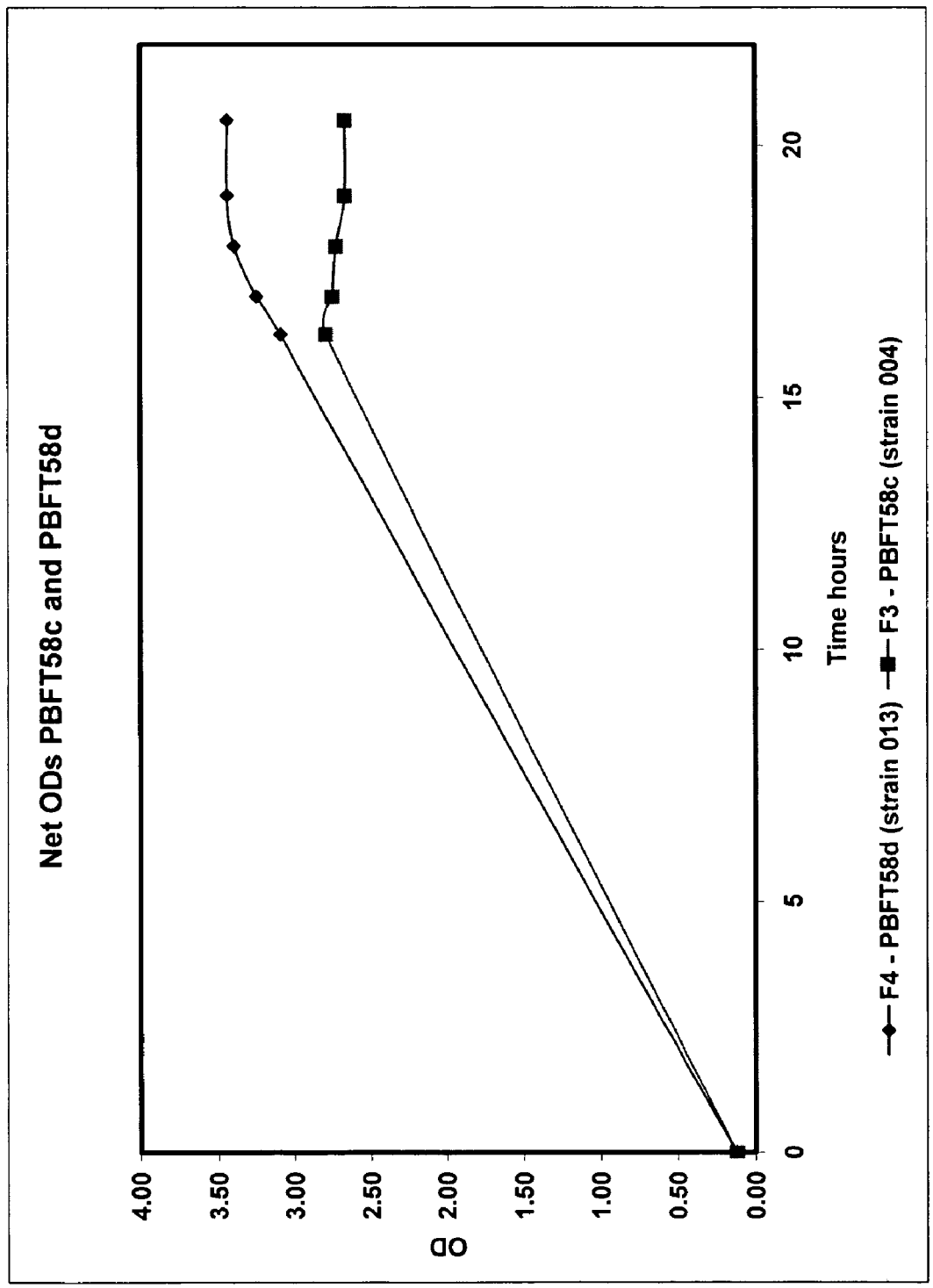
Figure 22:
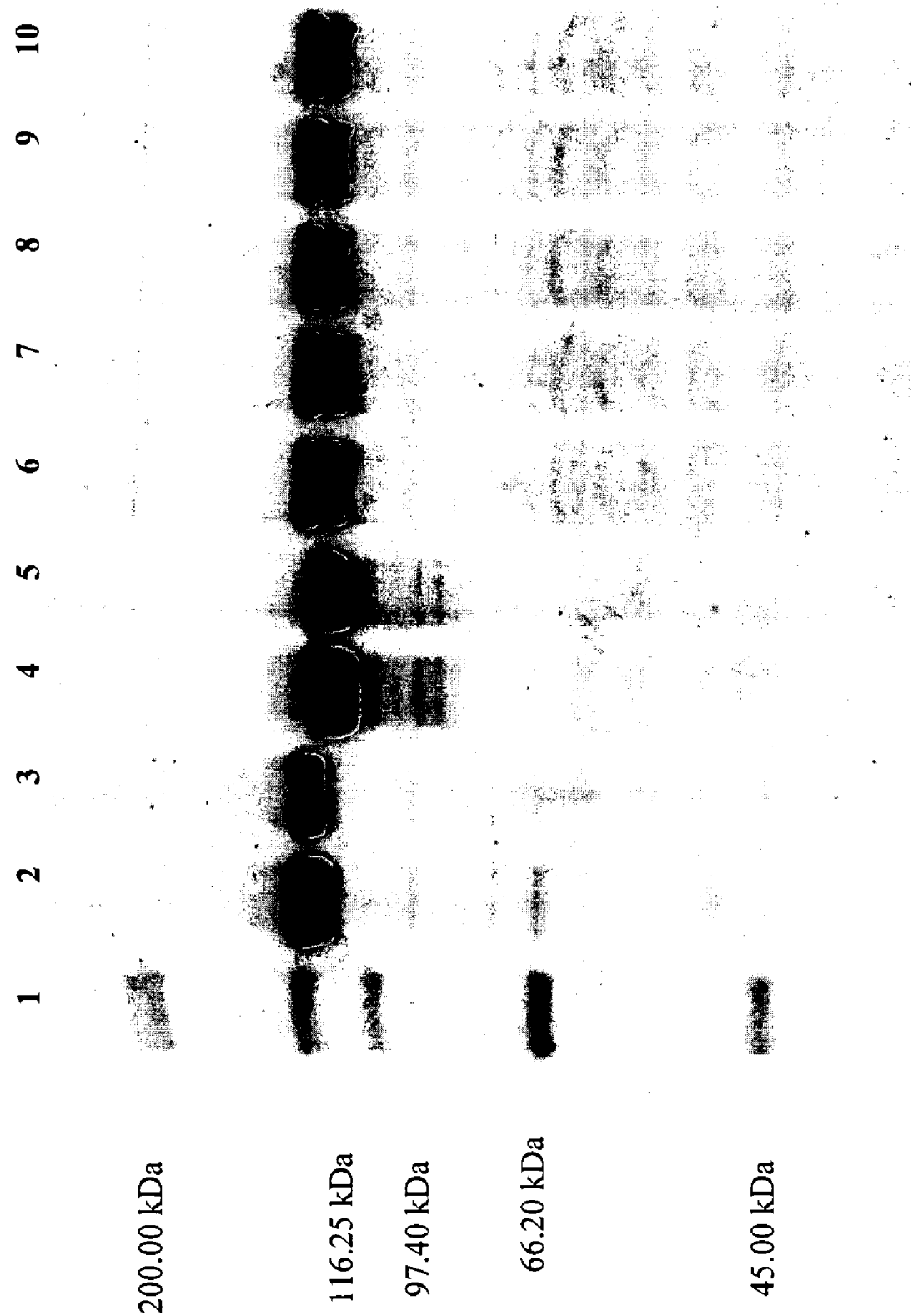
Figure 23:
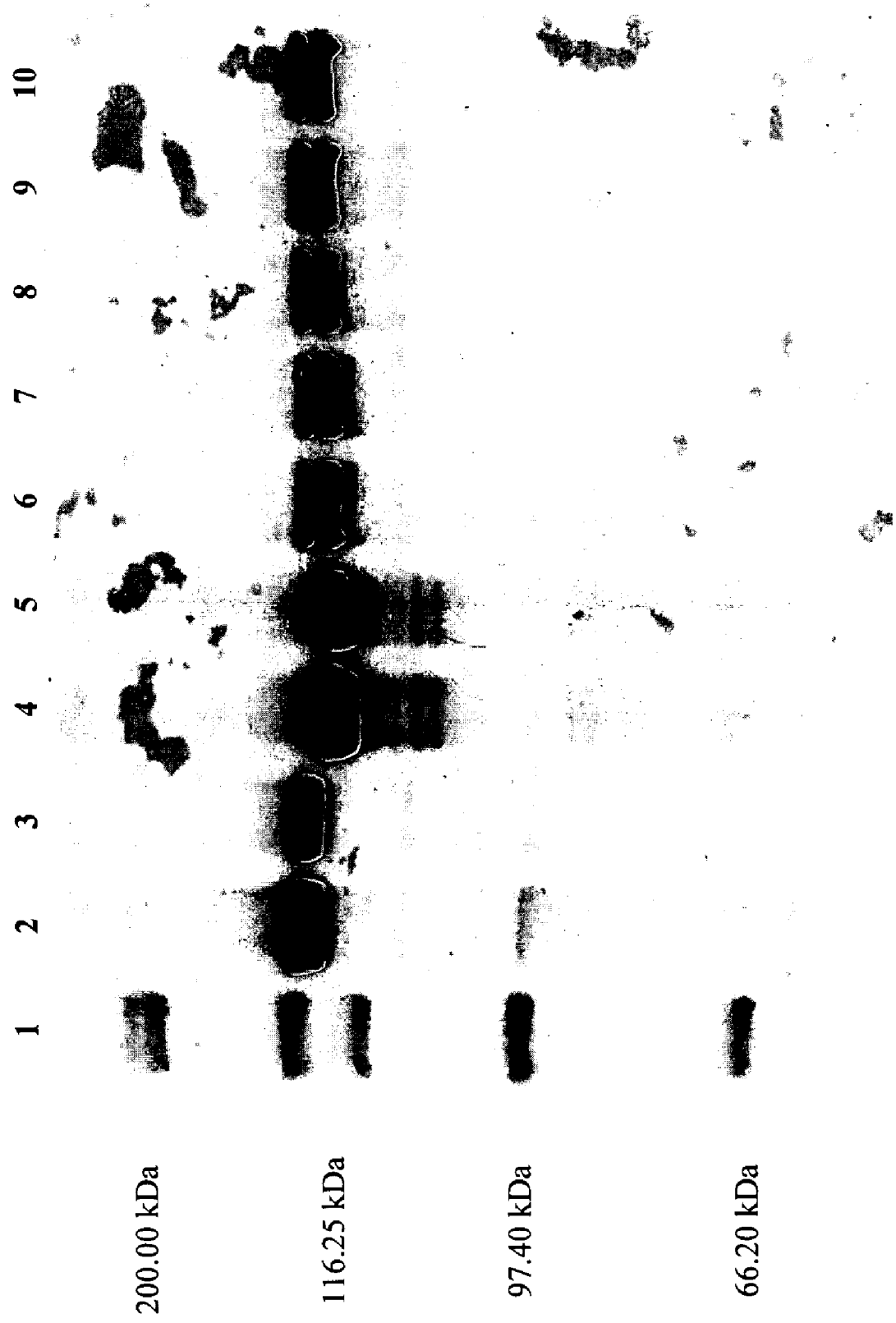
Figure 24:
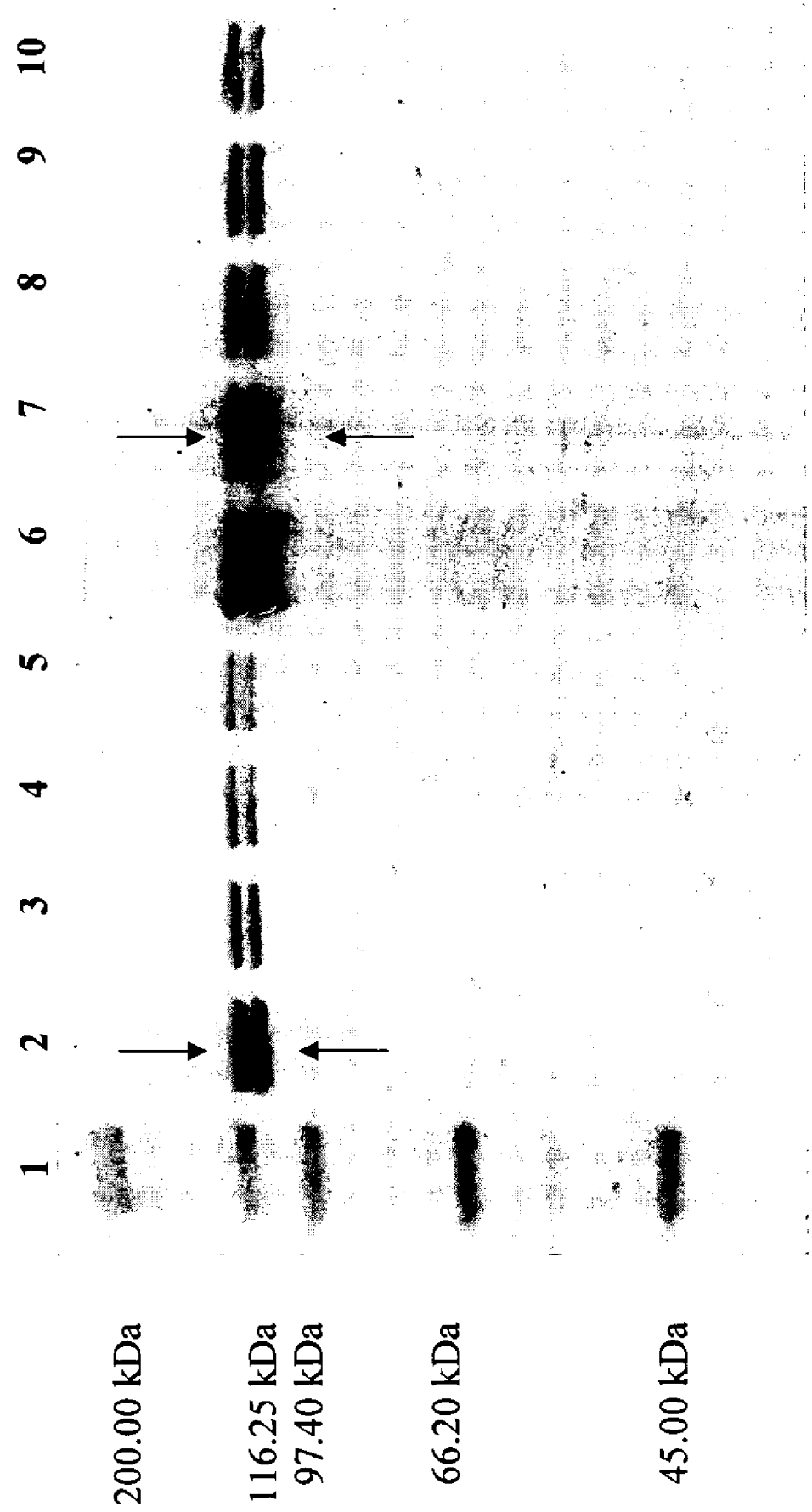
Figure 25:
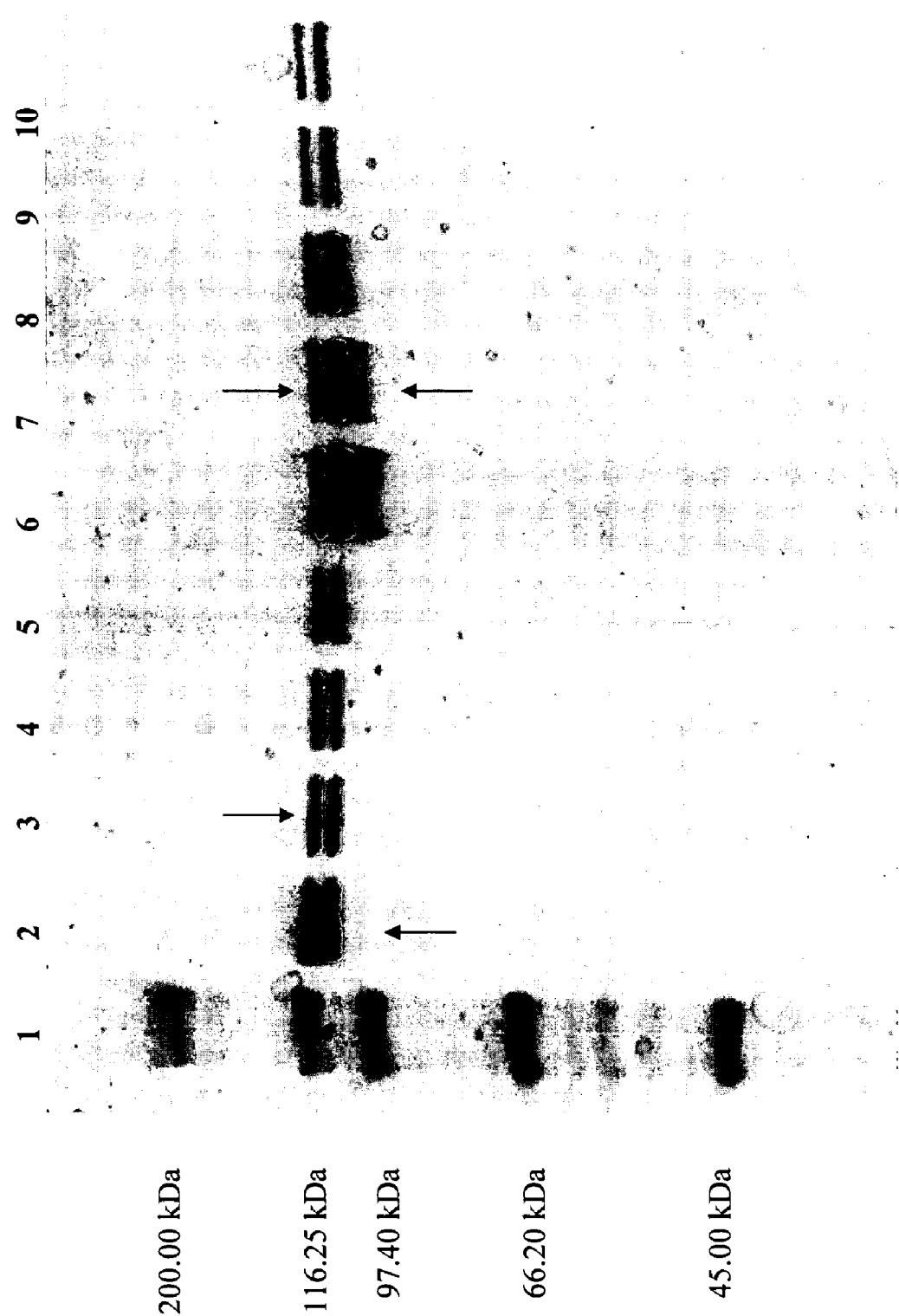
Figure 26:
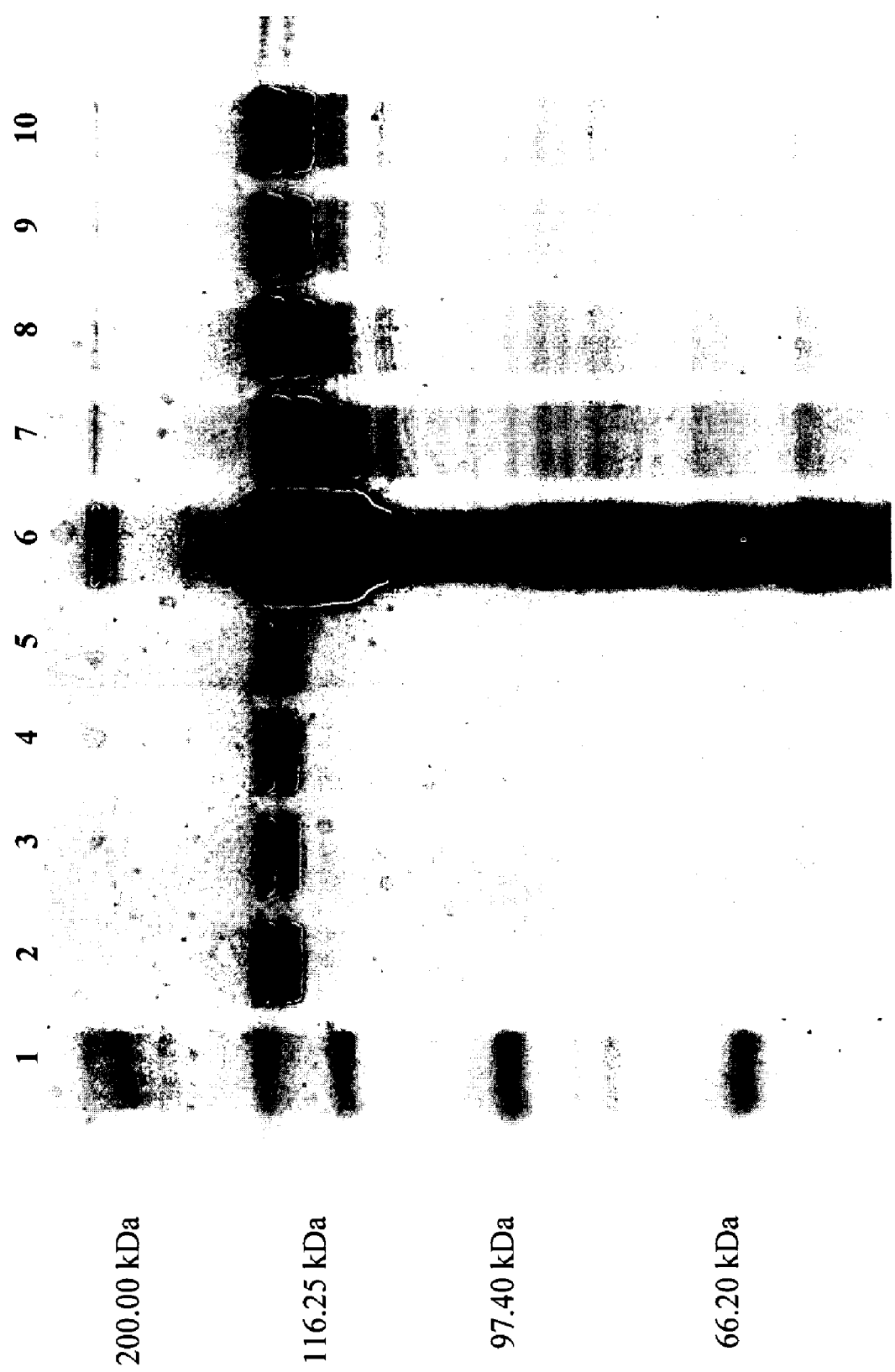

Lane 11: 0.87 µL of sample (1/7 dilution of fermentation harvest sample);

FIG. 18a is a quantitative SDS PAGE gel for post-dialysed 500 mL sample from fermentation PBFT57, harvest point sample. 400 g/L of ammonium sulphate added:
Lane 1: High Molecular Weight Marker
Lane 2: 0.272 µg collagenase I and 0.286 µg collagenase II
Lane 3: 0.181 µg collagenase I and 0.190 µg collagenase II
Lane 4: 0.136 µg collagenase I and 0.142 µg collagenase II
Lane 5: 0.109 µg collagenase I and 0.114 µg collagenase II
Lane 6: post dialysed sample—400 g/L AS (1/15 dilution)
Lane 7: post dialysed sample—400 g/L AS (1/20 dilution)
Lane 8: post dialysed sample—400 g/L AS (1/25 dilution)
Lane 9: post dialysed sample—400 g/L AS (1/30 dilution)
Lane 10: post dialysed sample—400 g/L AS (1/35 dilution)
Lane 11: High Molecular Weight Marker;

FIG. 18b is a SDS PAGE of the supernatants after centrifugation of the ammonium sulphate precipitated samples:
Lane 1: High Molecular Weight Marker
Lane 2: 0.27 µg Col 1 and 0.29 µg Col II
Lane 3: Supernatant (neat) of post ammonium sulphate precipitated sample (400 g/L slow addition)
Lane 4: Supernatant (neat) of post ammonium sulphate precipitated sample (400 g/L fast addition)
Lane 5: Supernatant (neat) of post ammonium sulphate precipitated sample (440 g/L slow addition)
Lane 6: Supernatant (neat) of post ammonium sulphate precipitated sample (480 g/L slow addition)
Lane 7: Supernatant (neat) of post ammonium sulphate precipitated sample (520 g/L slow addition)
Lane 8: Supernatant (neat) of post ammonium sulphate precipitated sample (400 g/L, pH 6)
Lane 9: Supernatant (neat) of post ammonium sulphate precipitated sample (400 g/L, oxygenated);

FIG. 19 is a Semi-quantitative SDS PAGE gel showing diluted samples from the harvest point supernatant and the post dialysed ammonium sulphate (with 400 g/L—fast addition) precipitated sample:
Lane 1: High Molecular Weight Marker
Lane 2: Fermentation sample—harvest (neat)
Lane 3: Fermentation sample—harvest (1/1 dilution)
Lane 4: Fermentation sample—harvest (1/2 dilution)
Lane 5: Fermentation sample—harvest (1/3 dilution)
Lane 6: Fermentation sample—harvest (1/4 dilution)
Lane 7: Post dialysed sample—harvest (1/17.54 dilution) corresponds to lane 1
Lane 8: Post dialysed sample—harvest (1/35.08 dilution) corresponds to lane 2
Lane 9: Post dialysed sample—harvest (1/52.62 dilution) corresponds to lane 3
Lane 10: Post dialysed sample—harvest (1/70.16 dilution) corresponds to lane 4
Lane 11: Post dialysed sample—harvest (1/87.70 dilution) corresponds to lane 5;

FIG. 20 is a semi-quantitative SDS PAGE gel for PBFT57 showing diluted samples from the harvest point supernatant and the post dialysed ammonium sulphate (with 520 g/L) precipitated sample:
Lane 1: High Molecular Weight Marker
Lane 2: Fermentation sample—harvest (neat)
Lane 3: Fermentation sample—harvest (1/1 dilution)
Lane 4: Fermentation sample—harvest (1/2 dilution)
Lane 5: Fermentation sample—harvest (1/3 dilution)
Lane 6: Fermentation sample—harvest (1/4 dilution)
Lane 7: Post dialysed sample—harvest (1/15.63) corresponds to lane 1
Lane 8: Post dialysed sample—harvest (1/31.26) corresponds to lane 2
Lane 9: Post dialysed sample—harvest (1/46.89) corresponds to lane 3
Lane 10: Post dialysed sample—harvest (1/62.52) corresponds to lane 4
Lane 11: Post dialysed sample—harvest (1/78.15) corresponds to lane 5;

FIG. 21 depicts growth curves (Net OD vs time) of *C. histolyticum* strains 004 and 013 in PBFT58c,d fermentations;

FIG. 22 is a SDS PAGE gel for PBFT58c (Strain 004):
Lane 1: High Molecular Weight Marker
Lane 2: Collagenase I-1.00 kg
Lane 3: Collagenase I-0.67 kg
Lane 4: Collagenase II —1.08 kg
Lane 5: Collagenase II —0.72 µg
Lane 6: 16.25 h (6.12 µL of sample)
Lane 7: 17 h (6.12 µL of sample)
Lane 8: 18 h (6.12 µL of sample)
Lane 9: 19 h (6.12 µL of sample)
Lane 10: 20.5 h (6.12 µL of sample);

FIG. 23 is a SDS PAGE gel for PBFT58d (Strain 013):
Lane 1: High Molecular Weight Marker
Lane 2: Collagenase I-1.00 µg
Lane 3: Collagenase I-0.67 kg
Lane 4: Collagenase II —1.08 kg
Lane 5: Collagenase II —0.72 µg
Lane 6: 16.25 h (6.12 µL of sample)
Lane 7: 17 h (6.12 µL of sample)
Lane 8: 18 h (6.12 µL of sample)
Lane 9: 19 h (6.12 µL of sample)
Lane 10: 20.5 h (6.12 µL of sample);

FIG. 24 is a semi-quantitative SDS PAGE gel for PBFT58c (strain 004), harvest point sample:
Lane 1: High Molecular Weight Marker
Lane 2: 0.27 µg collagenase I and 0.29 µg collagenase II
Lane 3: 0.18 µg collagenase I and 0.19 µg collagenase II
Lane 4: 0.135 µg collagenase I and 0.145 µg collagenase II
Lane 5: 0.108 µg collagenase I and 0.116 µg collagenase II
Lane 6: 6.12 µL of sample
Lane 7: 3.06 µL of sample
Lane 8: 2.04 µL of sample
Lane 9: 1.53 µL of sample
Lane 10: 1.22 µL of sample;

FIG. 25 is a semi-quantitative SDS PAGE gel for PBFT58d (strain 013), harvest point sample:
Lane 1: High Molecular Weight Marker
Lane 2: 0.27 µg collagenase I and 0.29 µg collagenase II
Lane 3: 0.18 µg collagenase I and 0.19 µg collagenase II
Lane 4: 0.135 µg collagenase I and 0.145 µg collagenase II
Lane 5: 0.108 µg collagenase I and 0.116 µg collagenase II
Lane 6: 6.12 µL of sample
Lane 7: 3.06 µL of sample
Lane 8: 2.04 µL of sample
Lane 9: 1.53 µL of sample
Lane 10: 1.22 µL of sample;

FIG. 26 is SDS PAGE gel for post-dialysed harvest point sample (520 g/L ammonium sulphate) of PBFT58c fermentation (strain 004):
Lane 1: High Molecular Weight Marker
Lane 2: 0.27 µg collagenase I and 0.29 µg collagenase II
Lane 3: 0.18 µg collagenase I and 0.19 µg collagenase II
Lane 4: 0.135 µg collagenase I and 0.145 µg collagenase II
Lane 5: 0.108 µg collagenase I and 0.116 µg collagenase II
Lane 6: post dialysed harvest point sample—Neat
Lane 7: post dialysed harvest point sample—(1/5 dilution)

Figure 27:
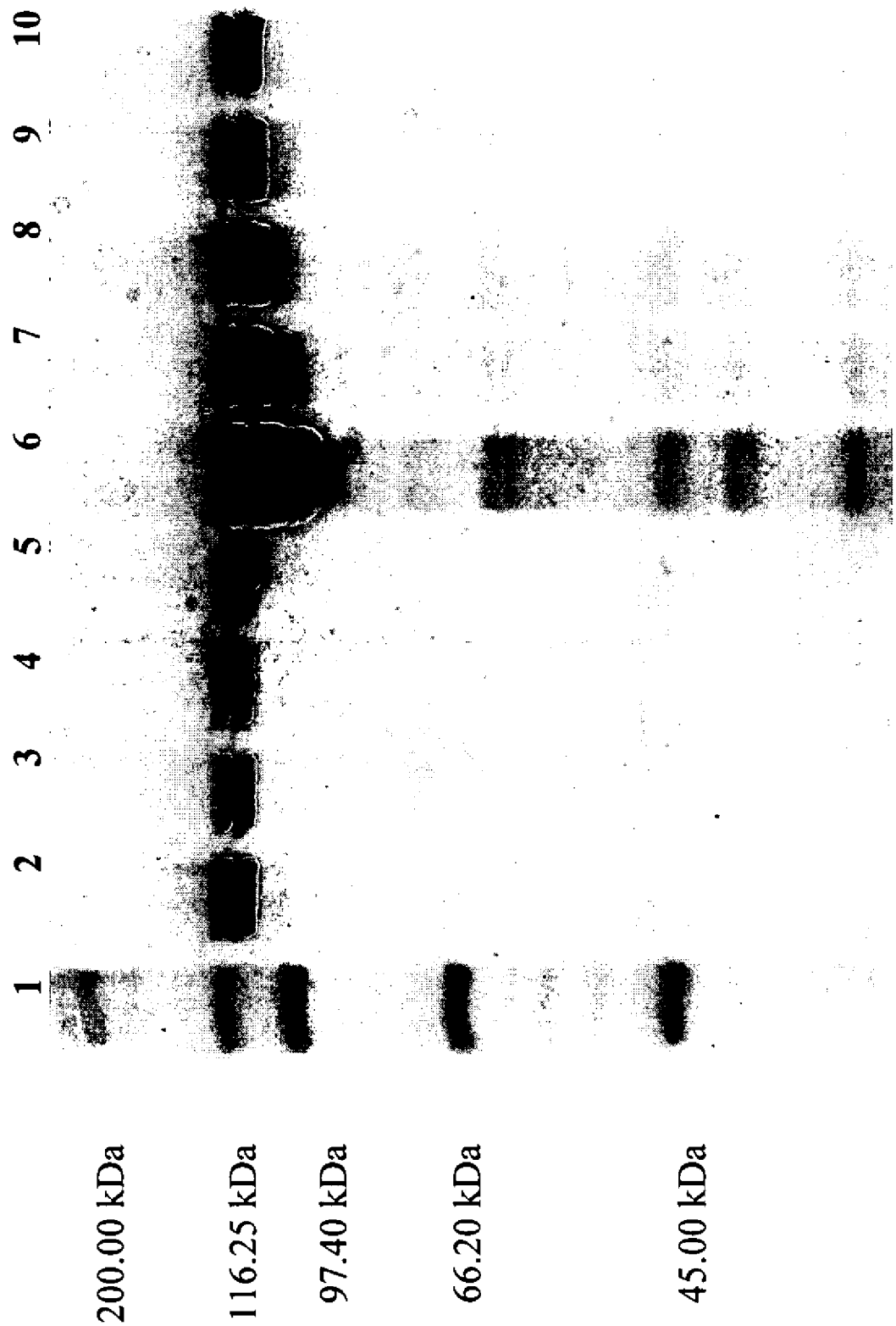
Figure 28:
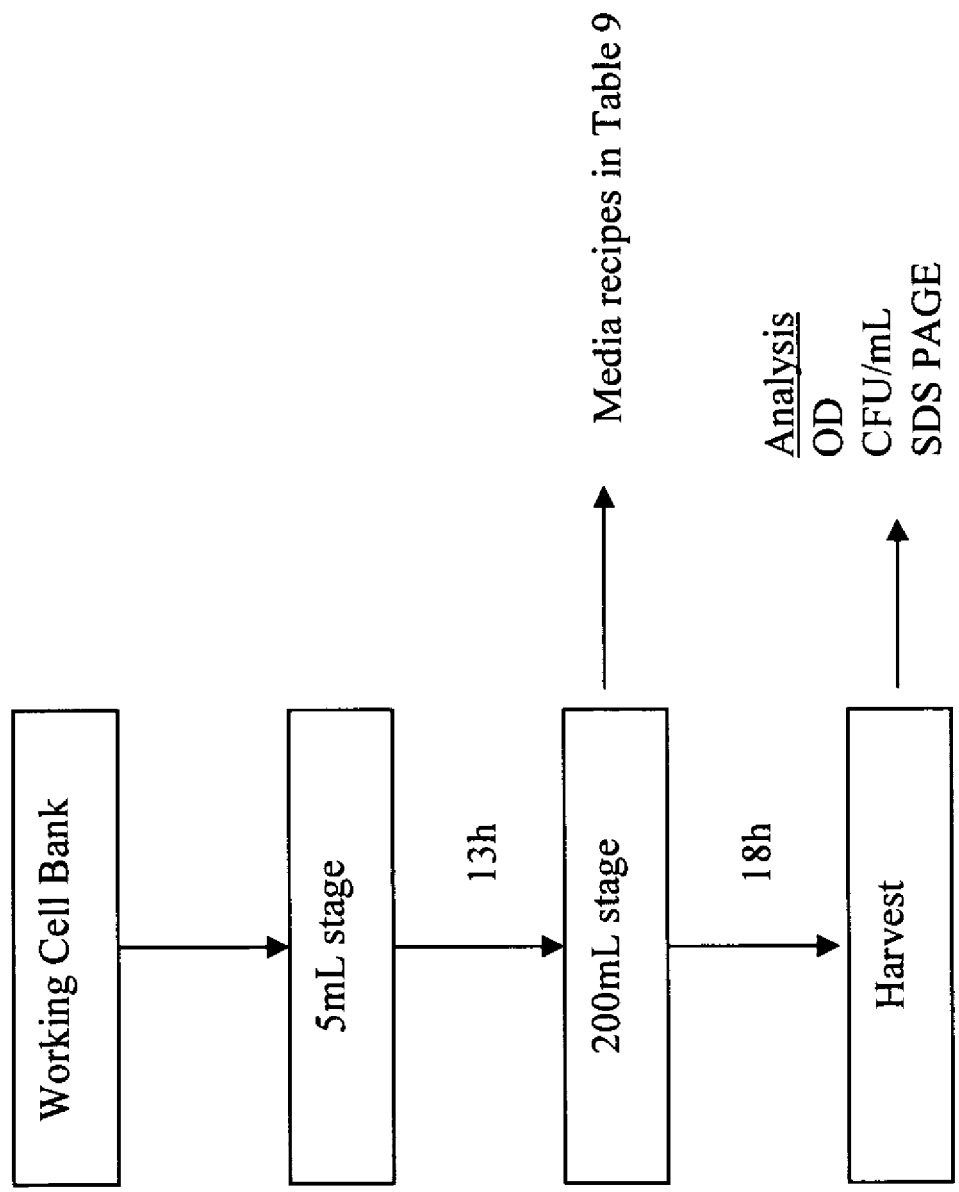
Figure 29:
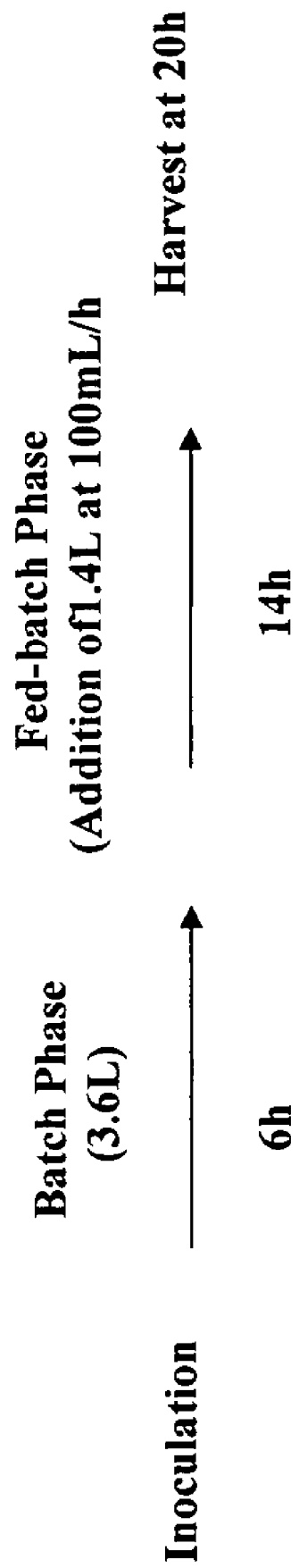
Figure 30:
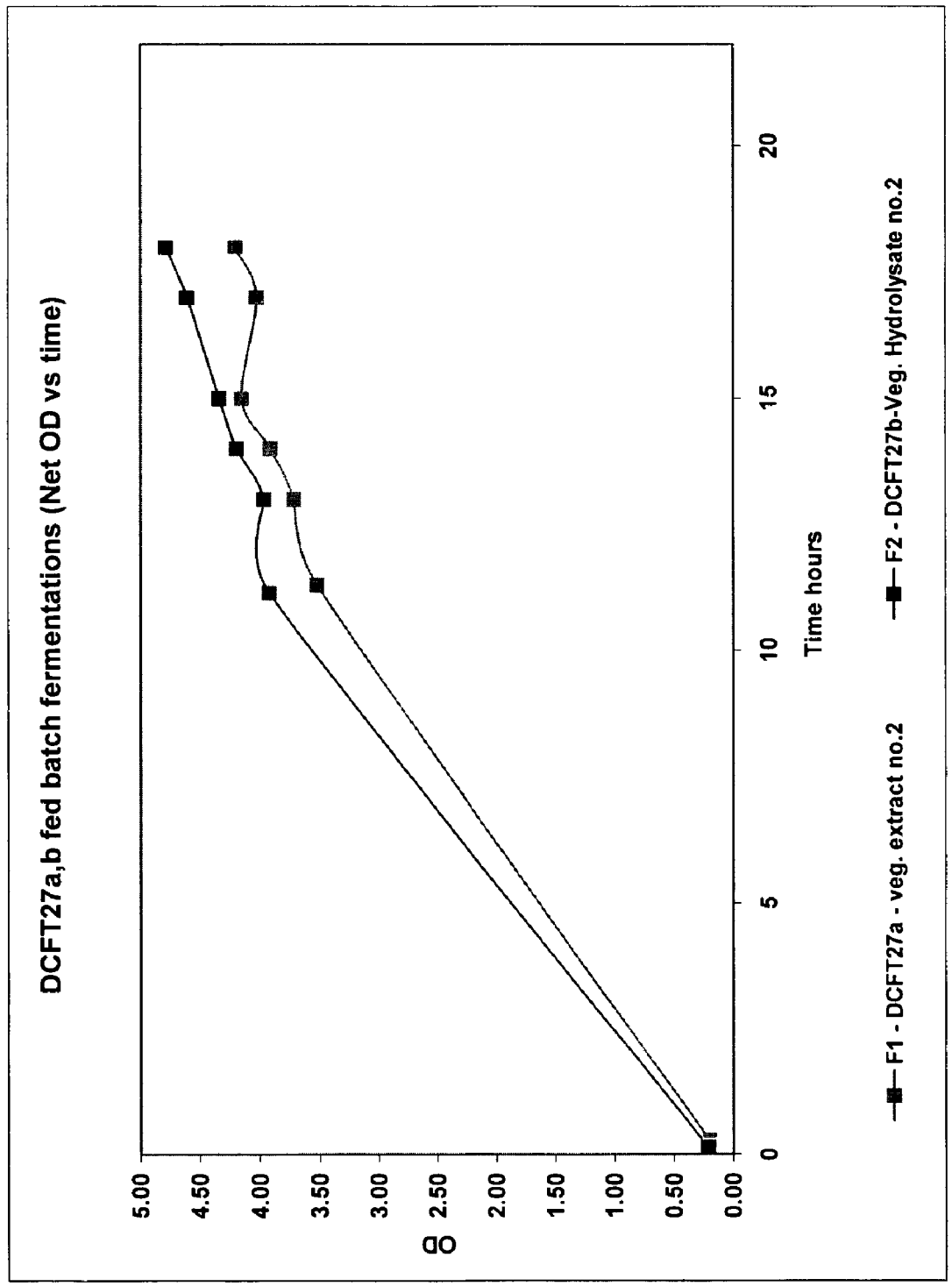
Figure 31:
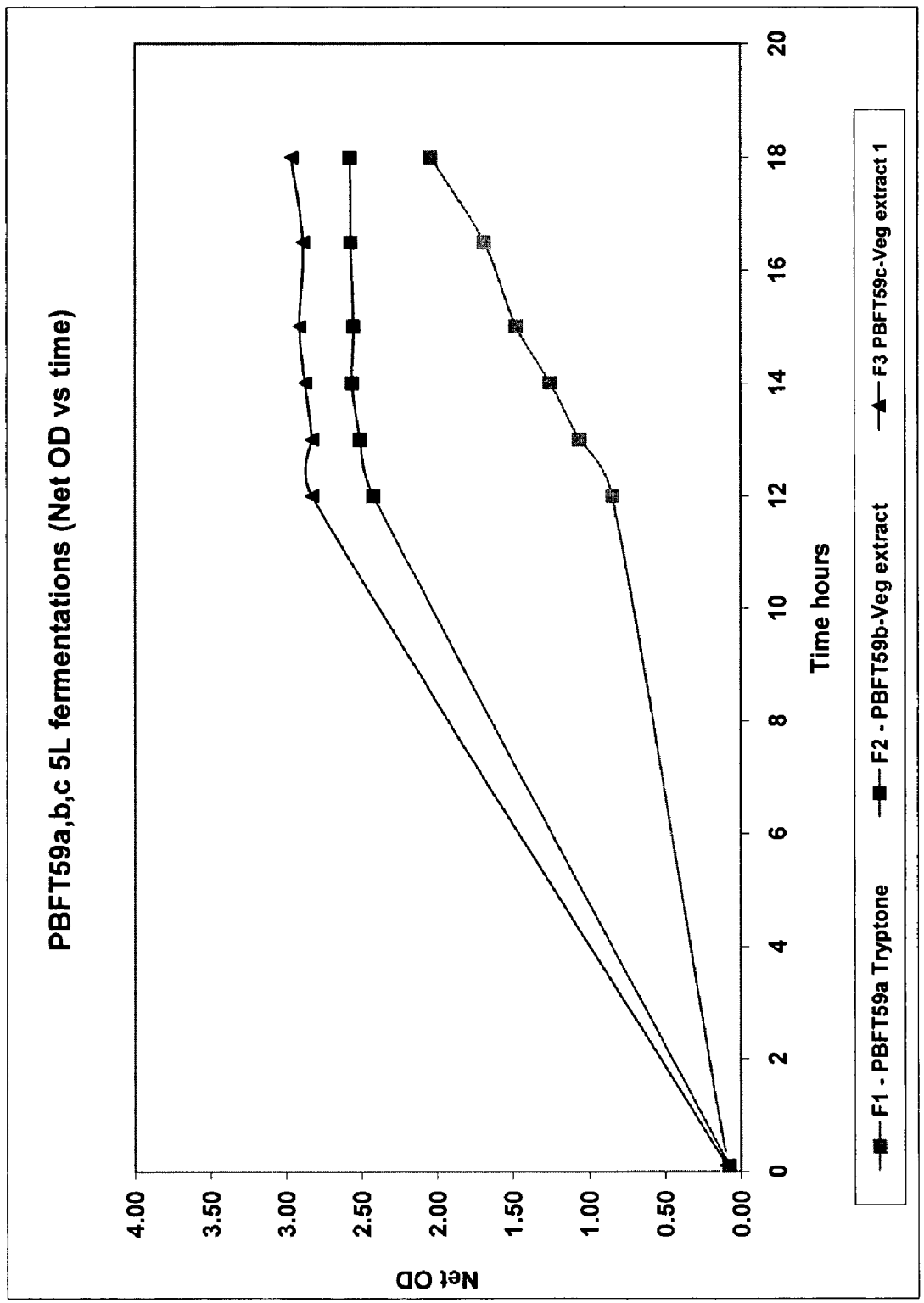
Figure 32:
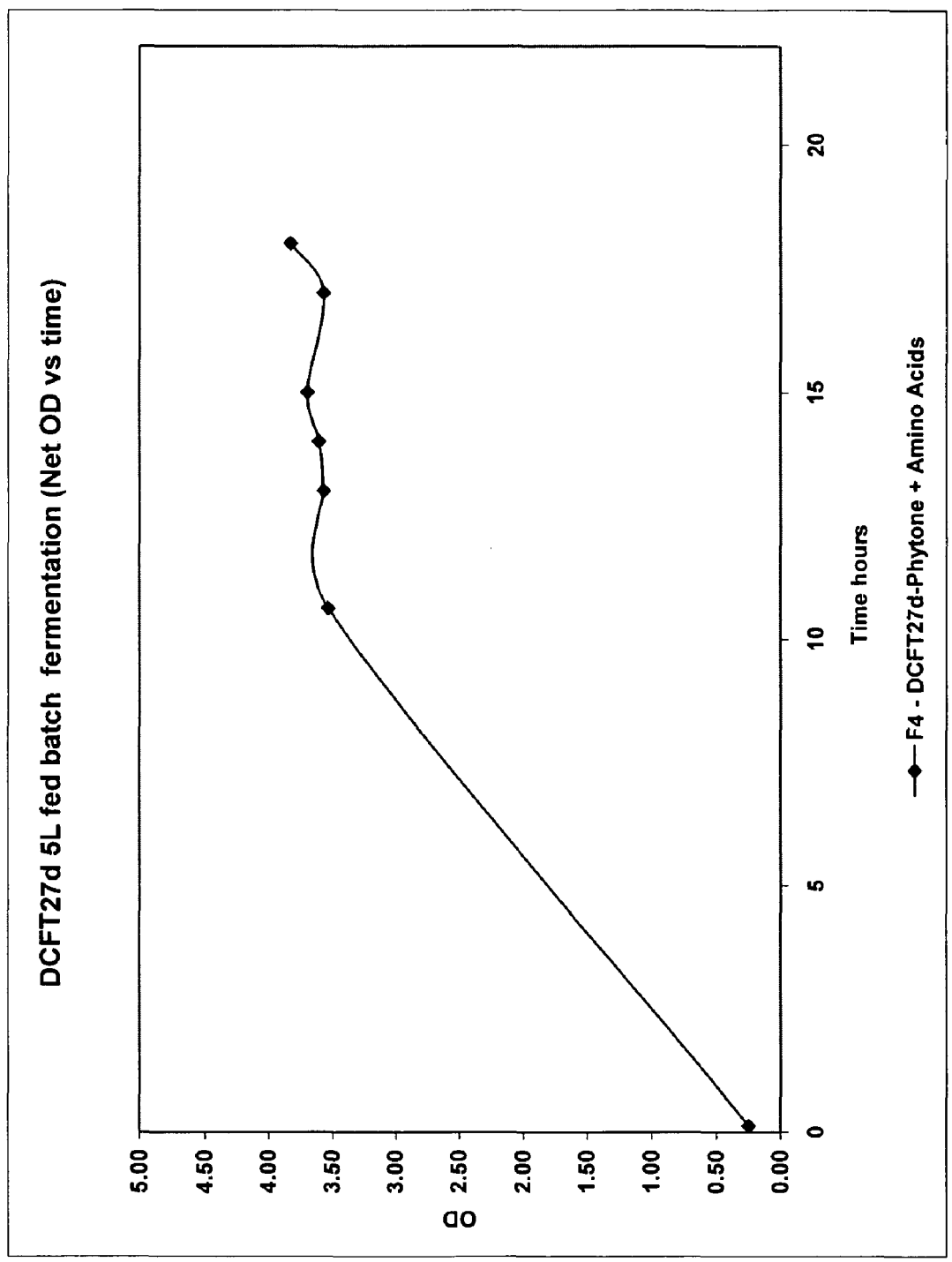
Figure 33A:
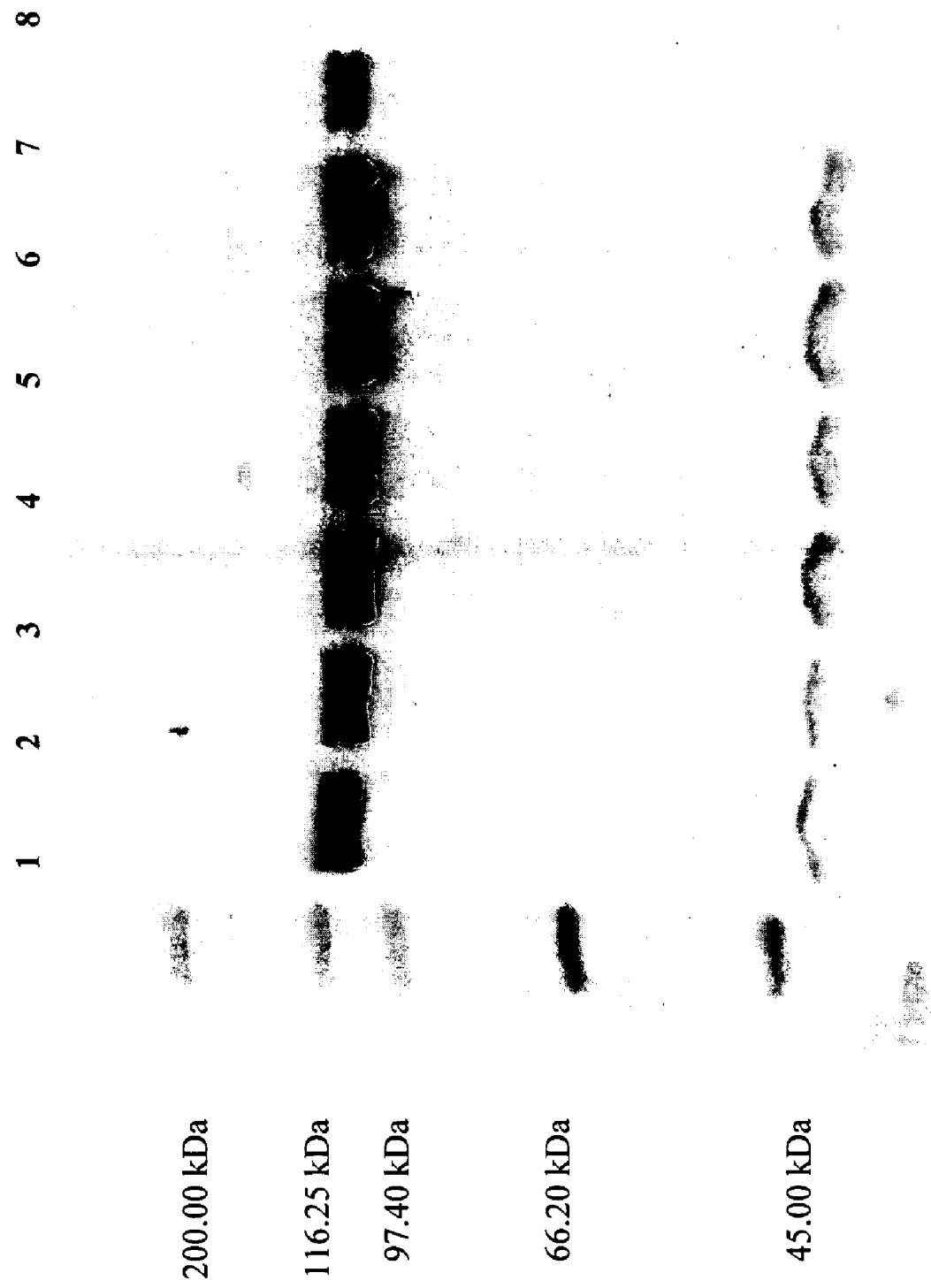
Figure 33B:
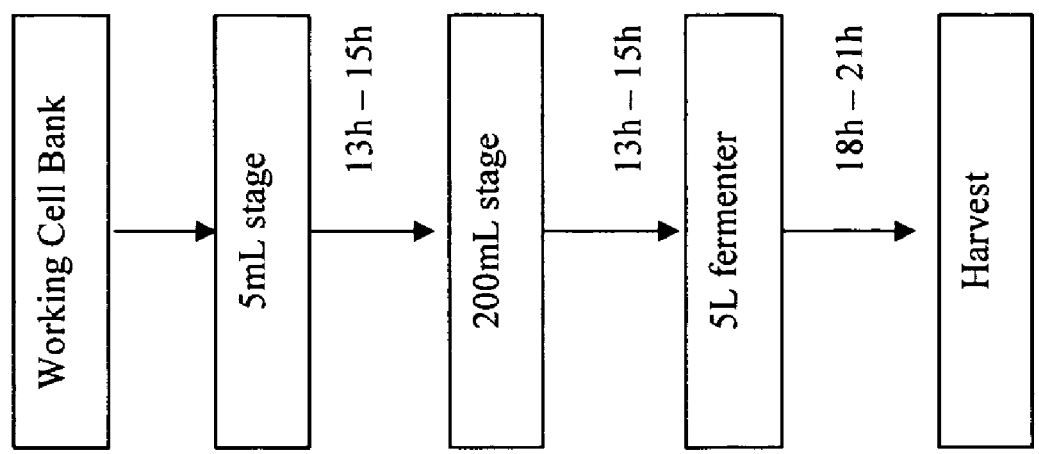
Figure 33C:
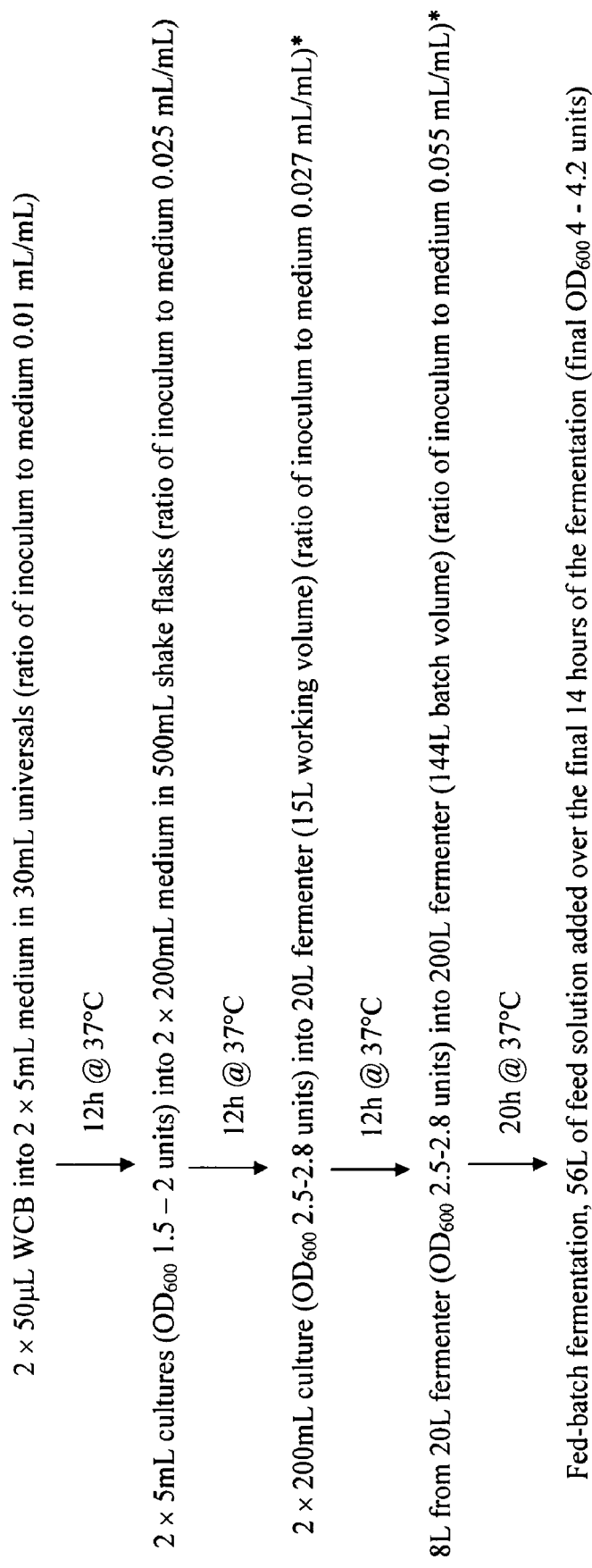
Figure 34:
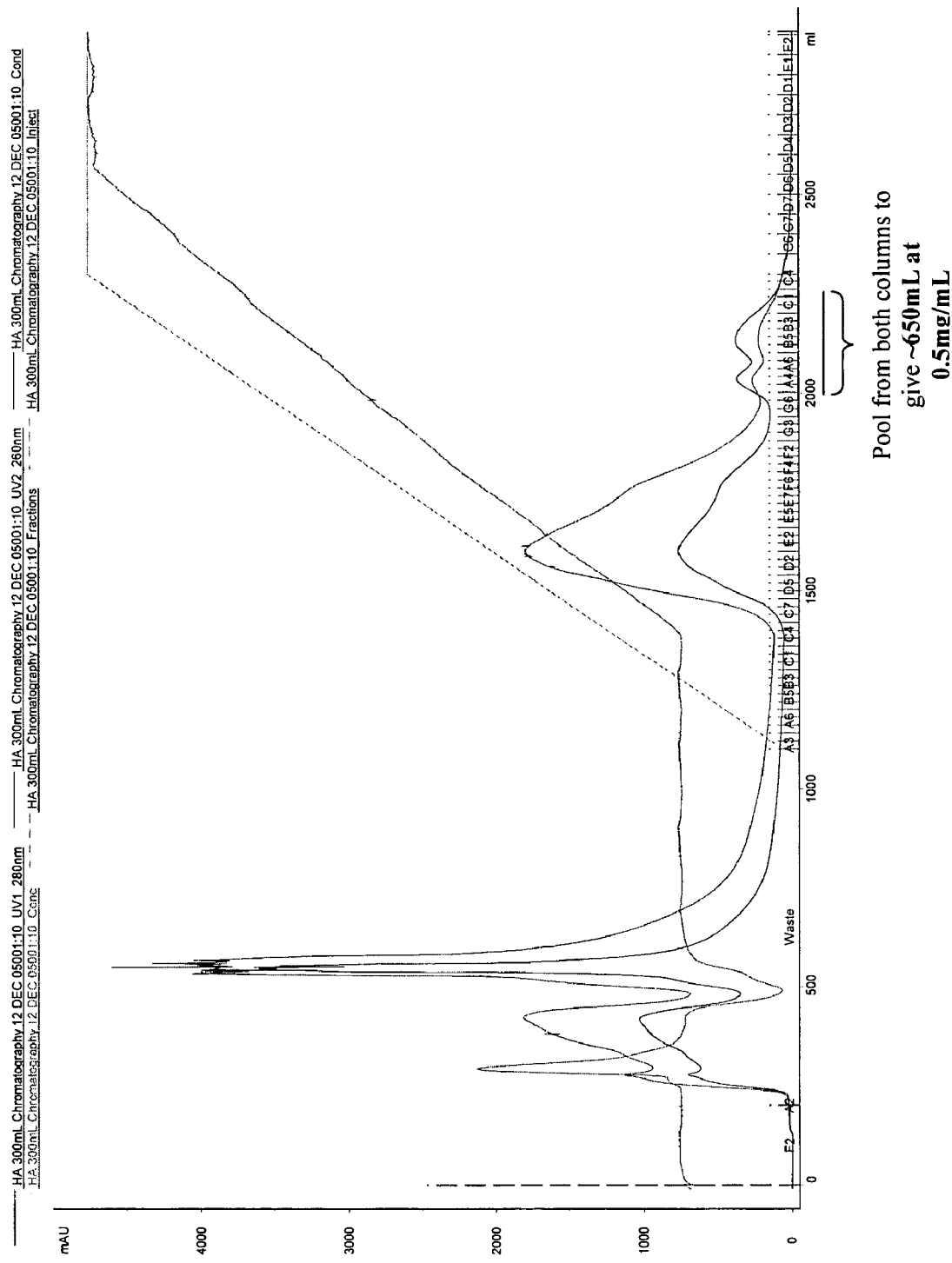
Figure 35:
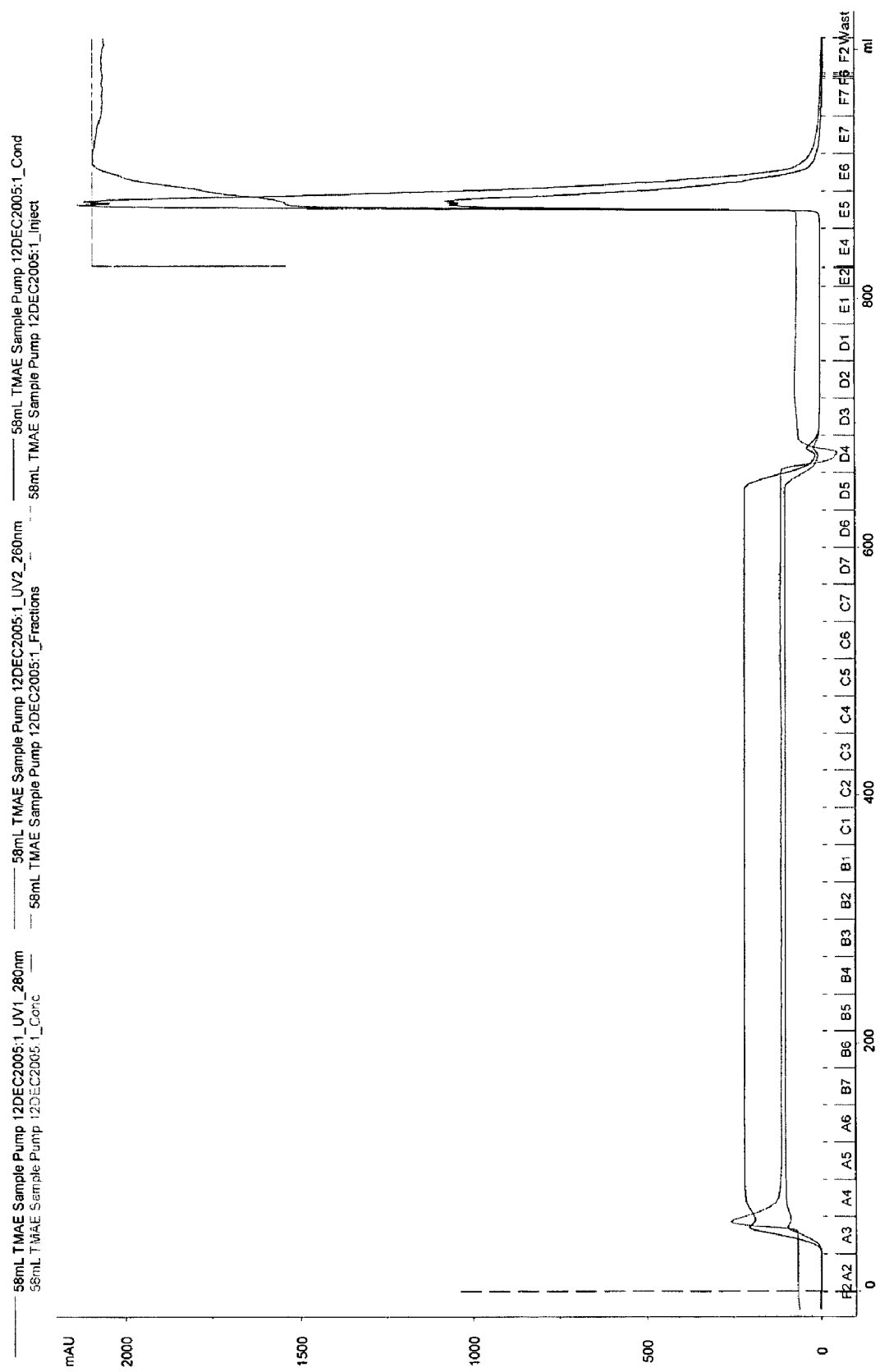
Figure 36:
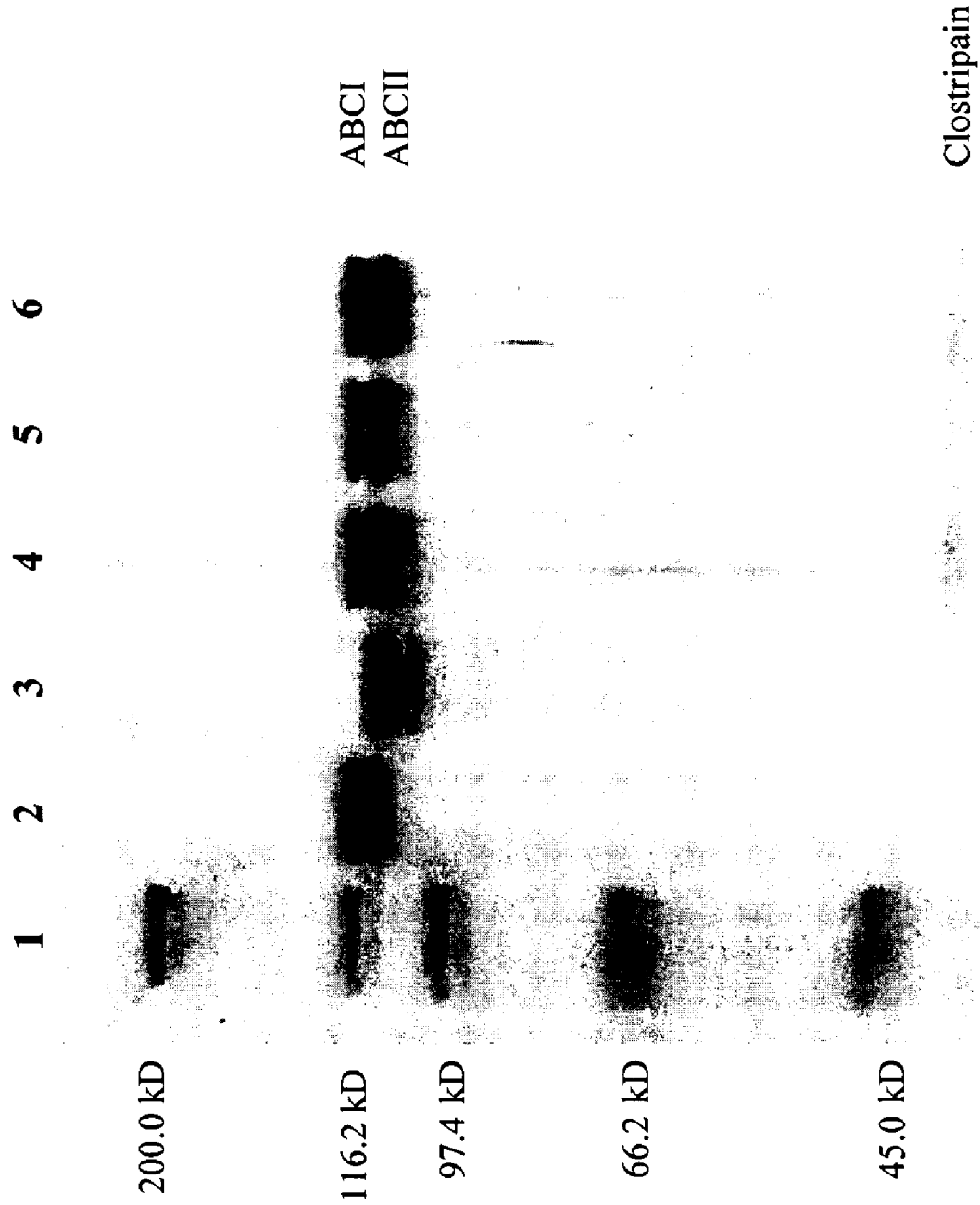

Lane 8: post dialysed harvest point sample—(1/10 dilution)
Lane 9: post dialysed harvest point sample—(1/15 dilution)
Lane 10: post dialysed harvest point sample—(1/20 dilution);

FIG. 27 is a SDS PAGE gel for post-dialysed harvest point sample (400 g/L ammonium sulphate) of PBFT58d fermentation (strain 013):
Lane 1: High Molecular Weight Marker
Lane 2: 0.27 μg collagenase I and 0.29 μg collagenase II
Lane 3: 0.18 μg collagenase I and 0.19 μg collagenase II
Lane 4: 0.135 μg collagenase I and 0.145 μg collagenase II
Lane 5: 0.108 μg collagenase I and 0.1161 g collagenase II
Lane 6: post dialysed harvest point sample—Neat
Lane 7: post dialysed harvest point sample—(1/5 dilution)
Lane 8: post dialysed harvest point sample—(1/10 dilution)
Lane 9: post dialysed harvest point sample—(1/15 dilution)
Lane 10: post dialysed harvest point sample—(1/20 dilution);

FIG. 28 is illustrates a flow chart of the Experimental procedure used for screening the alternative vegetable peptones;

FIG. 29 illustrates a fed-batch strategy for DCFT27a,b fermentations;

FIG. 30 depicts growth curves (Net OD vs time) of *C. histolyticum* in 5 L DCFT27a and DCFT27b fed-batch fermentations;

FIG. 31 depicts growth curves (Net OD vs time) of *C. histolyticum* in 5 L PBFT59a,b,c batch fermentations;

FIG. 32 depicts a growth curve (Net OD vs time) of *C. histolyticum* in 5 L DCFT27d fed-batch fermentation;

FIG. 33*a* is a SDS PAGE gel for DCFT27d (Phytone supplemented with amino acids):
Lane 1: High Molecular Weight Marker
Lane 2: 18 h (6.12 μL of sample)
Lane 3: 17 h (6.12 μL of sample)
Lane 4: 15 h (6.12 μL of sample)
Lane 5: 14 h (6.12 μL of sample)
Lane 6: 13 h (6.12 μL of sample)
Lane 7: 11.3 h (6.12 μL of sample)
Lane 8: 0.27 μg Collagenase I and 0.29 μg Collagenase II;

FIG. 33*b* represents a schematic diagram of the inoculation procedure;

FIG. 33*c* represents a flow chart of an approximately 200 L fed batch inoculation process;

FIG. 34 shows a chromatogram after hydroxyapatite chromatography;

FIG. 35 shows a chromatogram after a fractogel TMAE anion exchange;

FIG. 36 is an 8% Tris-Glycine SDS-PAGE analysis of Pre HA, Post HA and Post TMAE material from 5 L scale process:

| Lane | Sample | Load volume, μl |
|---|---|---|
| 1 | High Molecular Weight Marker | 20 |
| 2 | Collagenase ABC I reference 1 μg | 20 |
| 3 | Collagenase ABC II reference 1 μg | 20 |
| 4 | Pre HA - 1 μg | 20 |
| 5 | Post HA - 1 μg | 20 |
| 6 | Post TMAE - 1 μg | 20 |

FIG. 37 shows a chromatogram after a fractogel TMAE anion exchange;

FIG. 38 is an 8% Tris-Glycine SDS-PAGE analysis of Q Sepharose IEX chromatography of post TMAE material run in the presence leupeptin:

| Lane | Sample | Load volume, μl |
|---|---|---|
| 1 | High Molecular Weight marker | 20 |
| 2 | Collagenase ABC I reference 1 μg | 20 |
| 3 | Collagenase ABC II reference 1 μg | 20 |
| 4 | Post TMAE/Post Dialysis - 1 μg | 20 |
| 5 | Fraction D6 - neat | 20 |
| 6 | Fraction E6 - neat | 20 |
| 7 | Fraction F7 - 1 μg | 20 |
| 8 | Fraction F6 - 1 μg | 20 |
| 9 | Fraction F5 - 1 μg | 20 |
| 10 | Fraction F4 - neat | 20; |

FIG. 39 is an 8% Tris-Glycine SDS-PAGE analysis of Q Sepharose IEX chromatography of post TMAE material run in the presence of leupeptin. Gel 2-Peak 2 (ABCI):

| Lane | SampleLoad volume, μl | Load volume, μl |
|---|---|---|
| 1 | High Molecular Weight marker | 20 |
| 2 | Collagenase ABC I reference 1 μg | 20 |
| 3 | Collagenase ABC II reference 1 μg | 20 |
| 4 | Fraction B2 - neat | 20 |
| 5 | Fraction C1 - 1 μg | 20 |
| 6 | Fraction C2 - 1 μg | 20 |
| 7 | Fraction C3 - 1 μg | 20 |
| 8 | Fraction C4 - 1 μg | 20 |
| 9 | Fraction C5 - neat | 20 |
| 10 | Fraction C6 - neat | 20; |

FIG. 40 shows a chromatogram after a Q Sepharose HP anion exchange with modified gradient;

FIG. 41 shows a chromatogram after a Superdex 75 Gel Permeation chromatography of ABCII;

FIG. 42 is a 12% Bis-Tris SDS-PAGE analysis of Superdex 75 GPC of concentrated ABC II run in the presence of arginine:

| Lane | Sample | Load volume, μl |
|---|---|---|
| 1 | Mark 12 marker | 10 |
| 2 | Collagenase ABC I reference 1 μg | 15 |
| 3 | Collagenase ABC II reference 1 μg | 15 |
| 4 | GPC load 1 μg | 15 |
| 5 | Fraction D4 Neat | 15 |
| 6 | Fraction D3 | 15 |
| 7 | Fraction D2 | 15 |
| 8 | Fraction D1 | 15 |
| 9 | Fraction E1 | 15 |
| 10 | Fraction E2 | 15 |
| 11 | Fraction E3 | 15 |
| 12 | Fraction E4 | 15; |

FIG. 43 shows a chromatogram after a Superdex 75 Gel Permeation chromatography of ABCI;

Figure 44:
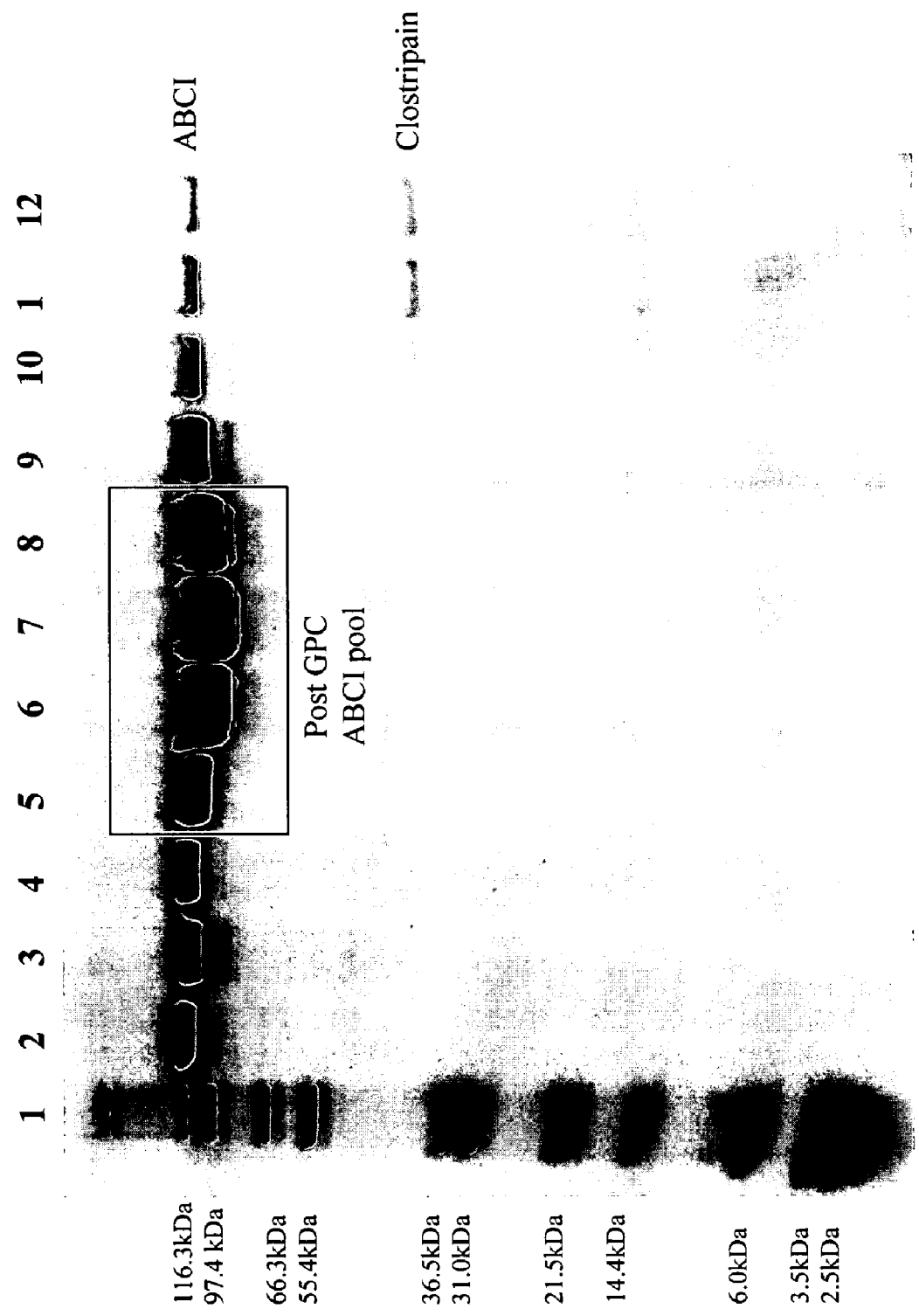

FIG. 44 is a 4-12% Bis-Tris SDS-PAGE analysis of Superdex 75 GPC of concentrated ABC I run in the presence of arginine:

| Lane | Sample | Load volume, µl |
|---|---|---|
| 1 | Mark 12 marker | 10 |
| 2 | Collagenase ABC I reference 1 µg | 15 |
| 3 | Collagenase ABC II reference 1 µg | 15 |
| 4 | GPC load 1 µg | 15 |
| 5 | Fraction D4 | 15 |
| 6 | Fraction D3 | 15 |
| 7 | Fraction D2 | 15 |
| 8 | Fraction D1 | 15 |
| 9 | Fraction E1 | 15 |
| 10 | Fraction E2 | 15 |
| 11 | Fraction E3 | 15 |
| 12 | Fraction E4 | 15; |

Figure 45:
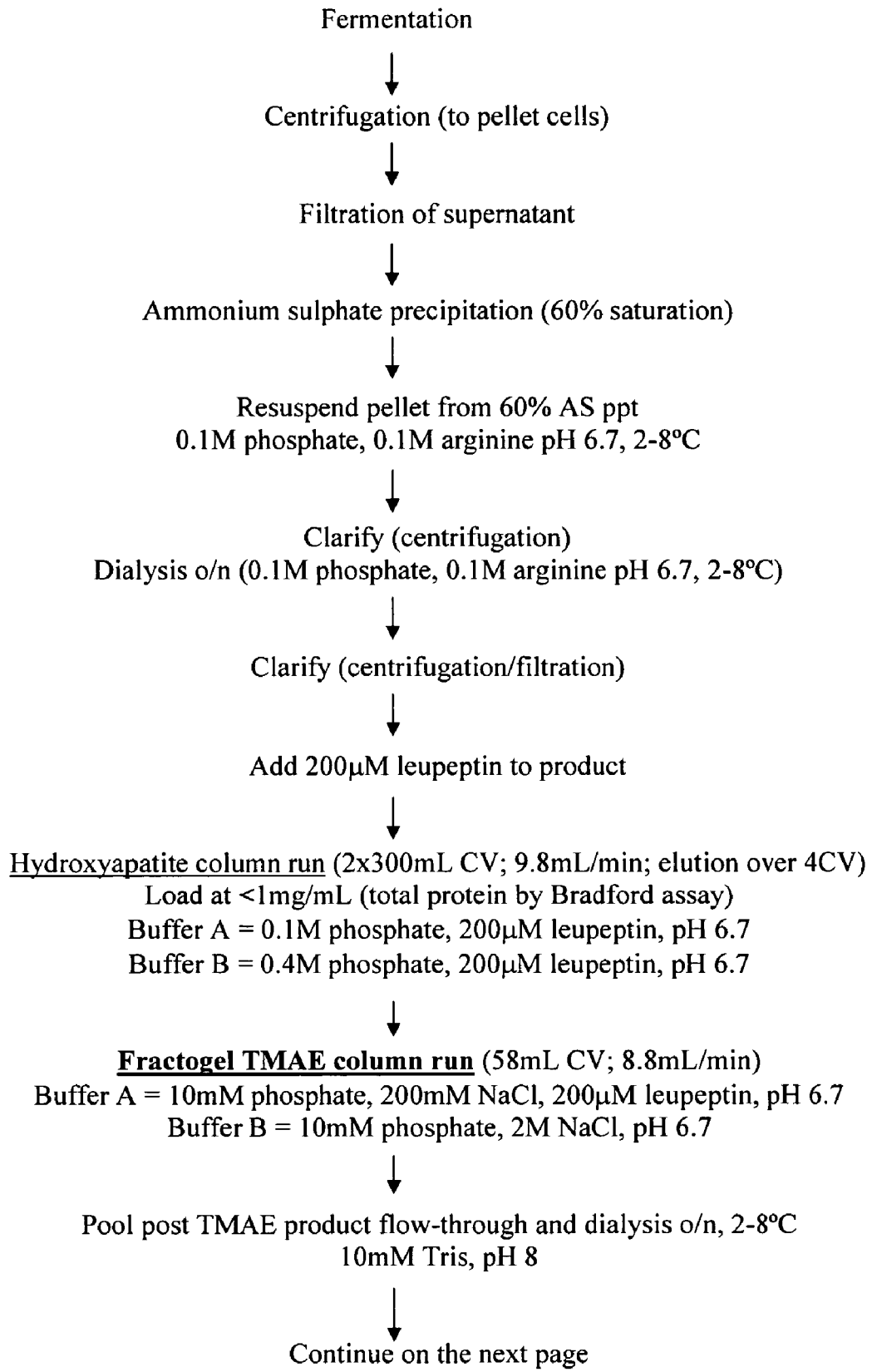
Figure 45:
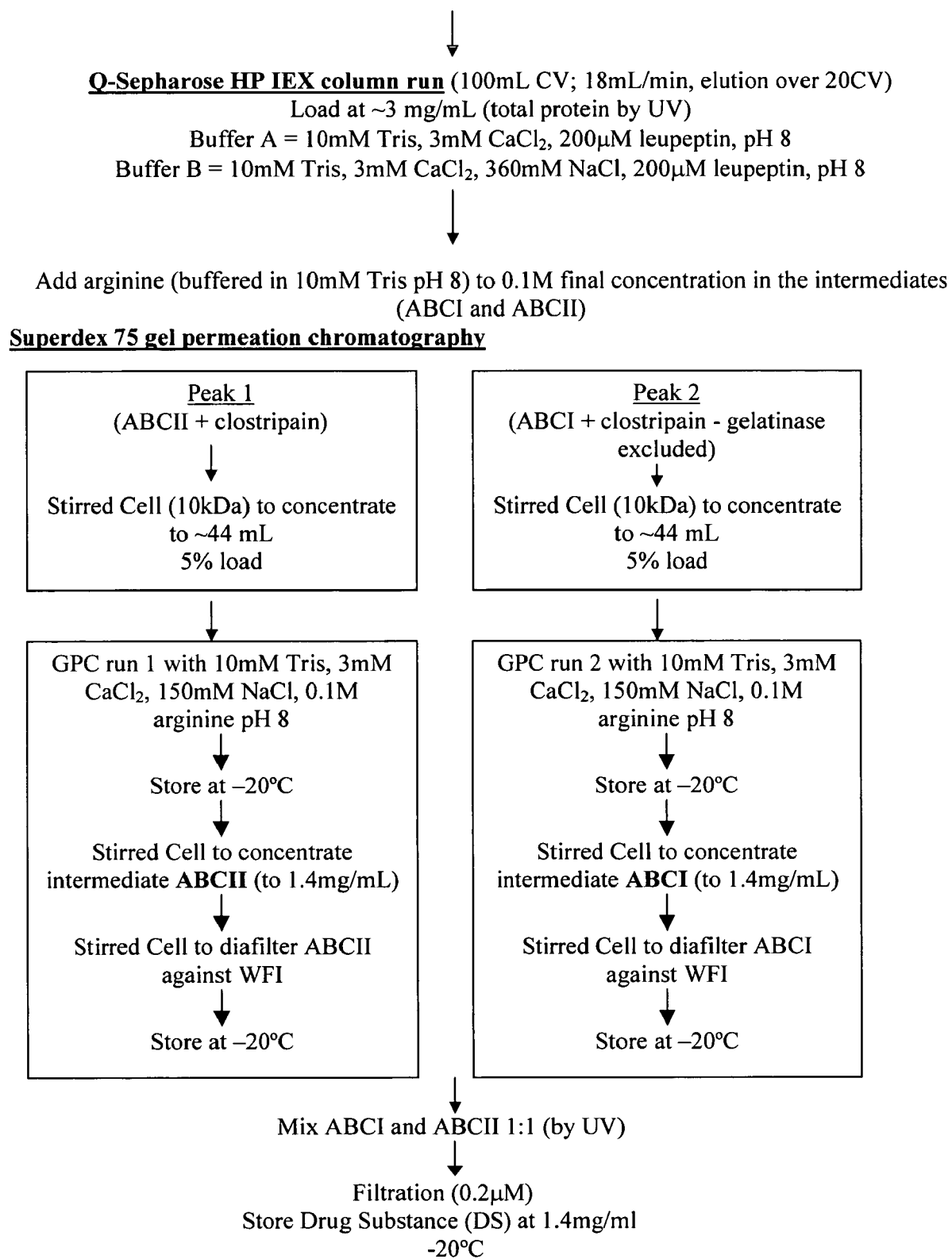
Figure 46:
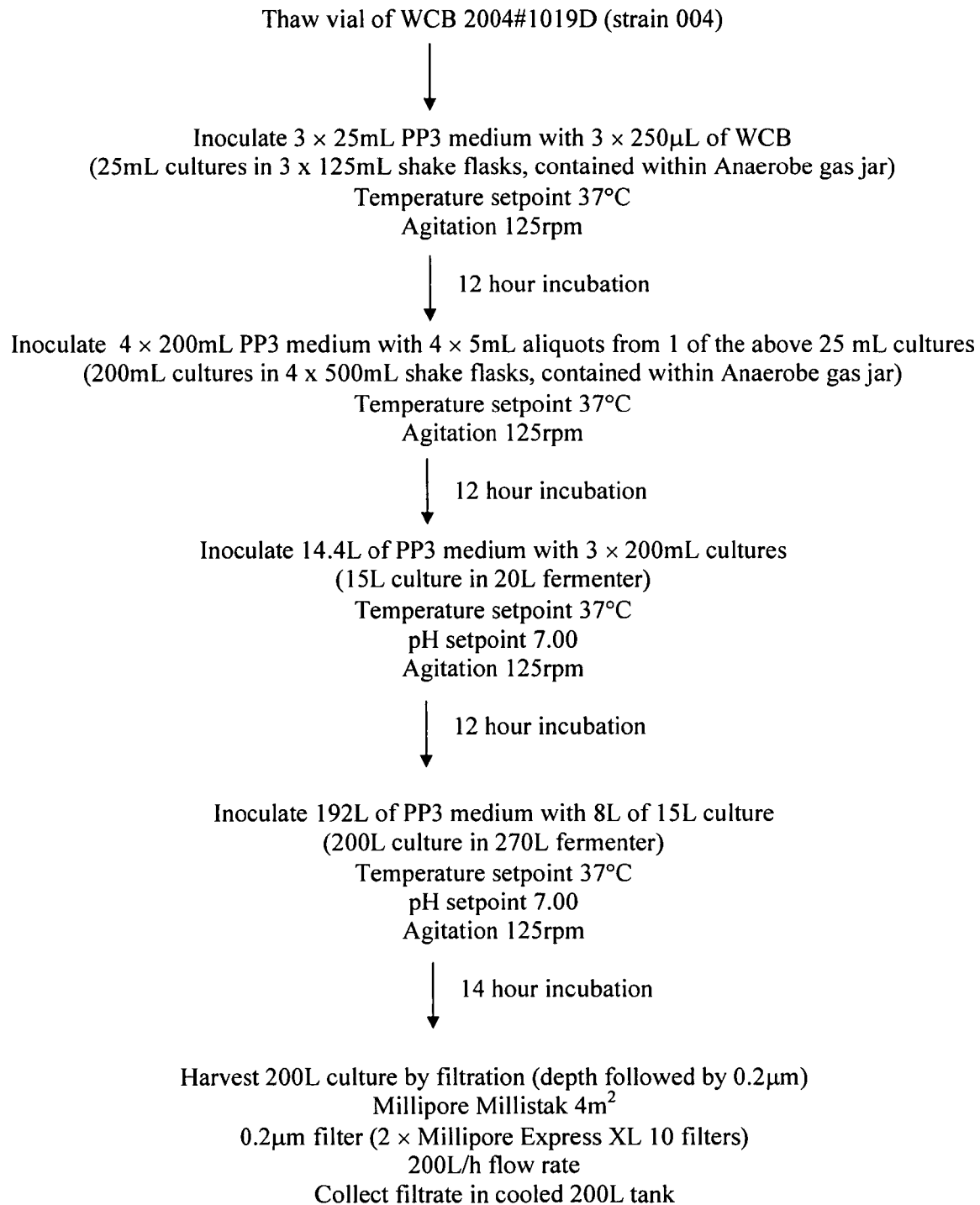
Figure 47:
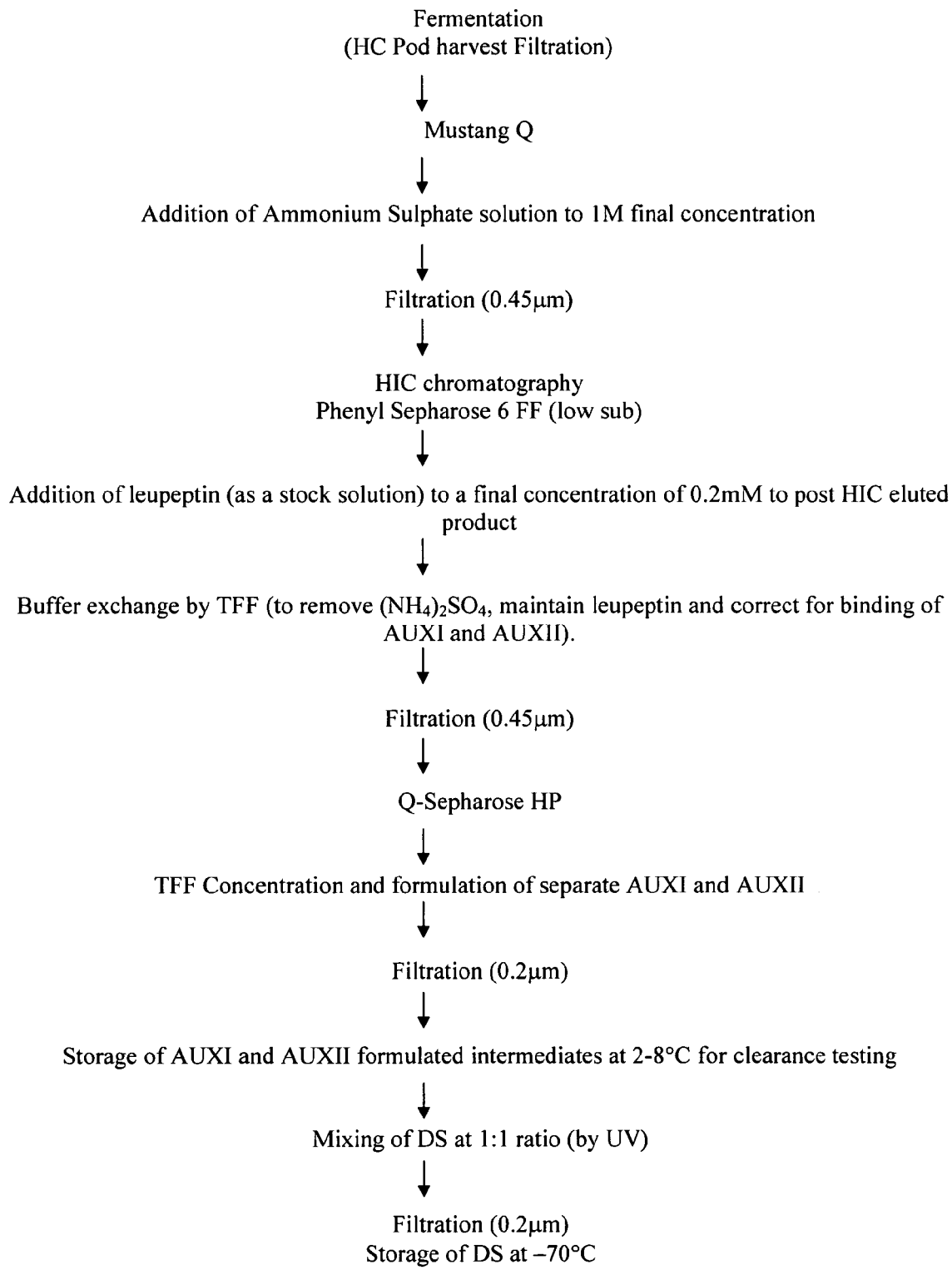
Figure 48:
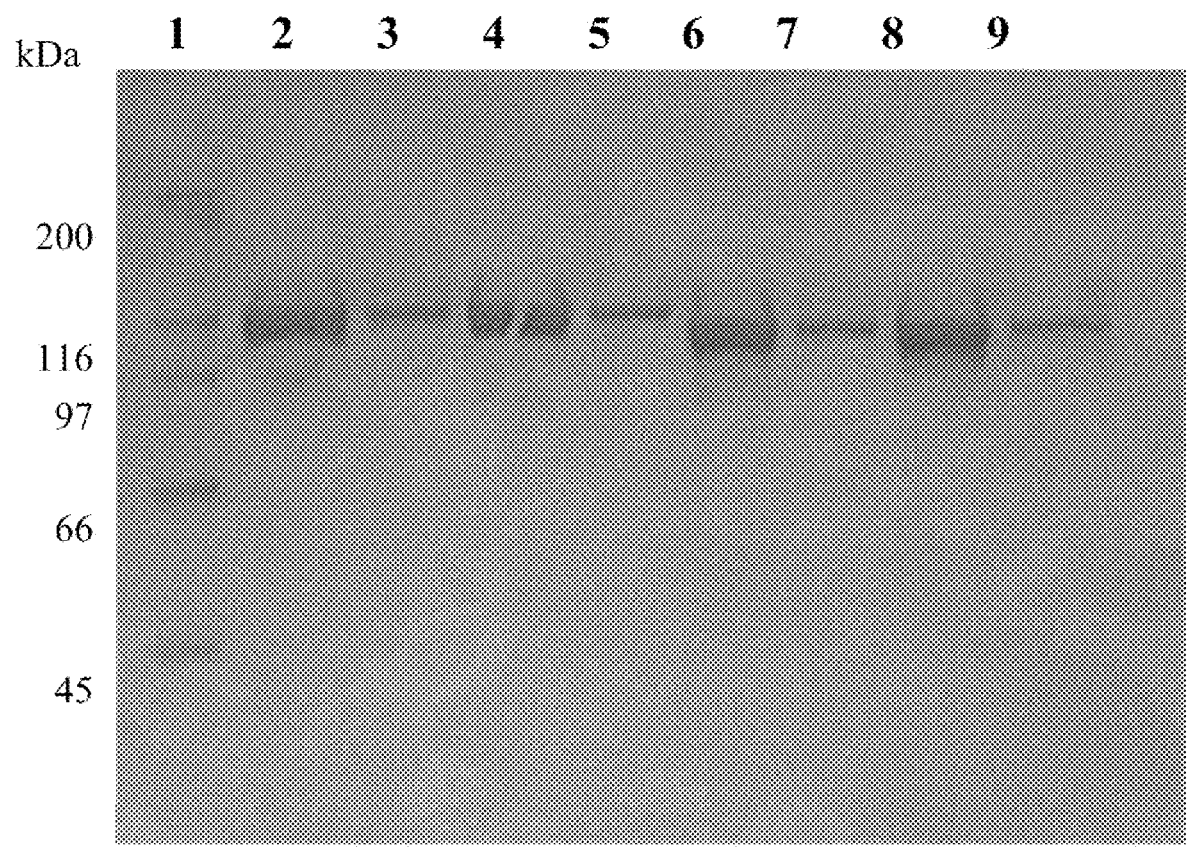

FIG. 45 represents a flow chart of one proposed manufacturing process;

FIG. 46 represents a flow chart of the fermentation procedure for process 3;

FIG. 47 represents a flow chart of the purification procedure for process 3;

FIG. 48 is a SDS-PAGE (reduced) Coomasie stained for Intermediates AUXI and AUXII:

| Lane | |
|---|---|
| 1. | High Molecular Weight Markers |
| 2. | 0.132 mg/ml ABC-I Reference |
| 3. | 0.0265 mg/ml ABC-I Reference |
| 4. | 0.132 mg/ml AUX-I Intermediate |
| 5. | 0.0265 mg/ml AUX-I Intermediate |
| 6. | 0.132 mg/ml ABC-II Reference |
| 7. | 0.0265 mg/ml ABC-II Reference |
| 8. | 0.132 mg/ml AUX-II Intermediate |
| 9. | 0.0265 mg/ml AUX-II Intermediate; |

Figure 49:
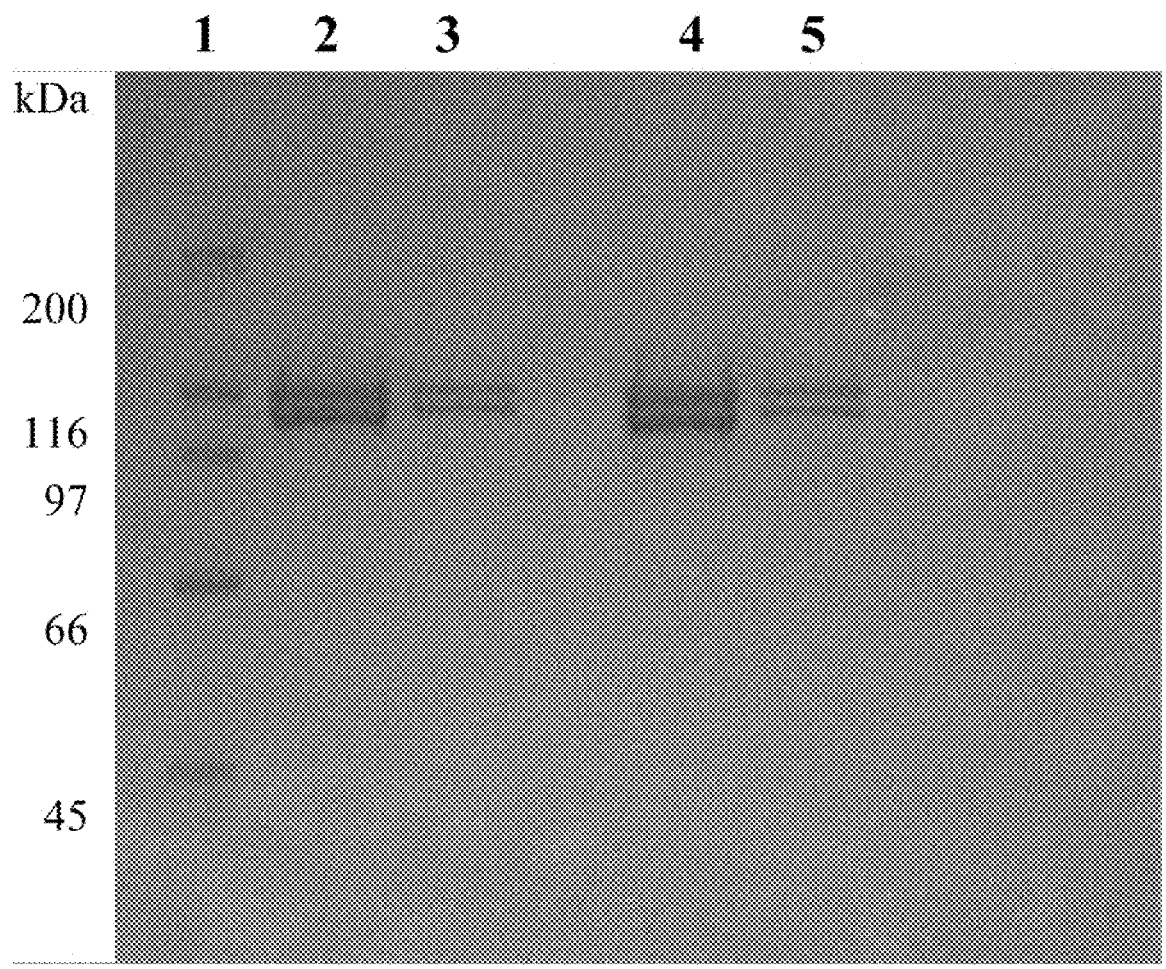

FIG. 49 is a SDS-PAGE (reduced) Coomasie stained for Drug Substance:

| Lane | |
|---|---|
| 1. | High Molecular Weight Markers |
| 2. | 0.132 mg/ml Mixed BTC Reference |
| 3. | 0.0265 mg/ml Mixed BTC Reference |
| 4. | 0.132 mg/ml Drug Substance |
| 5. | 0.0265 mg/ml Drug Substance; |

Figure 50:
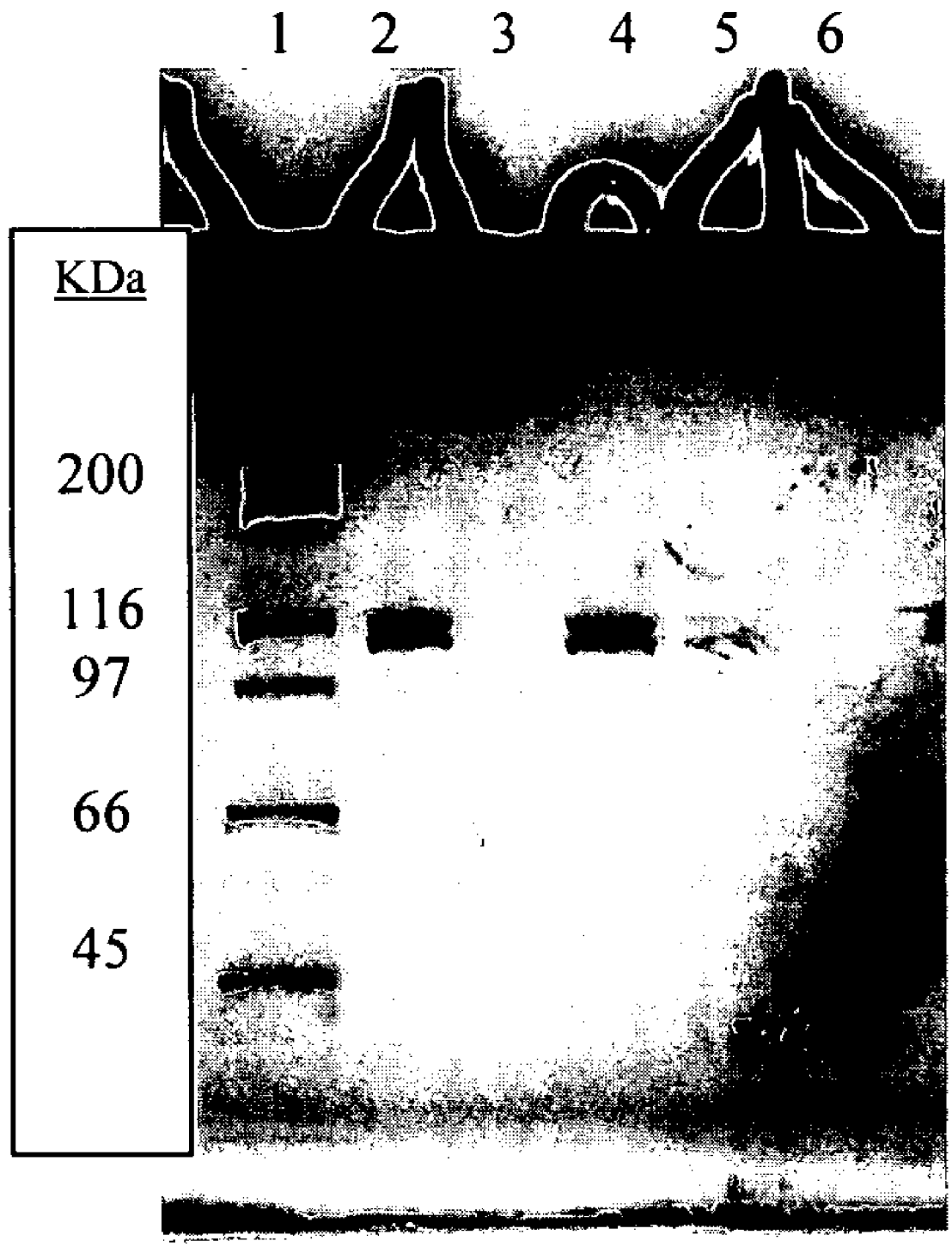

FIG. 50 is DS-PAGE (reduced) Silver stained Drug Substance:

| Lane | |
|---|---|
| 1. | HMW marker |
| 2. | Mixed BTC reference 1.3 µg |
| 3. | Blank |
| 4. | Drug Substance 1.3 µg |
| 5. | Drug Substance 0.27 µg |
| 6. | Drug Substance 0.13 µg. |

Figure 51:
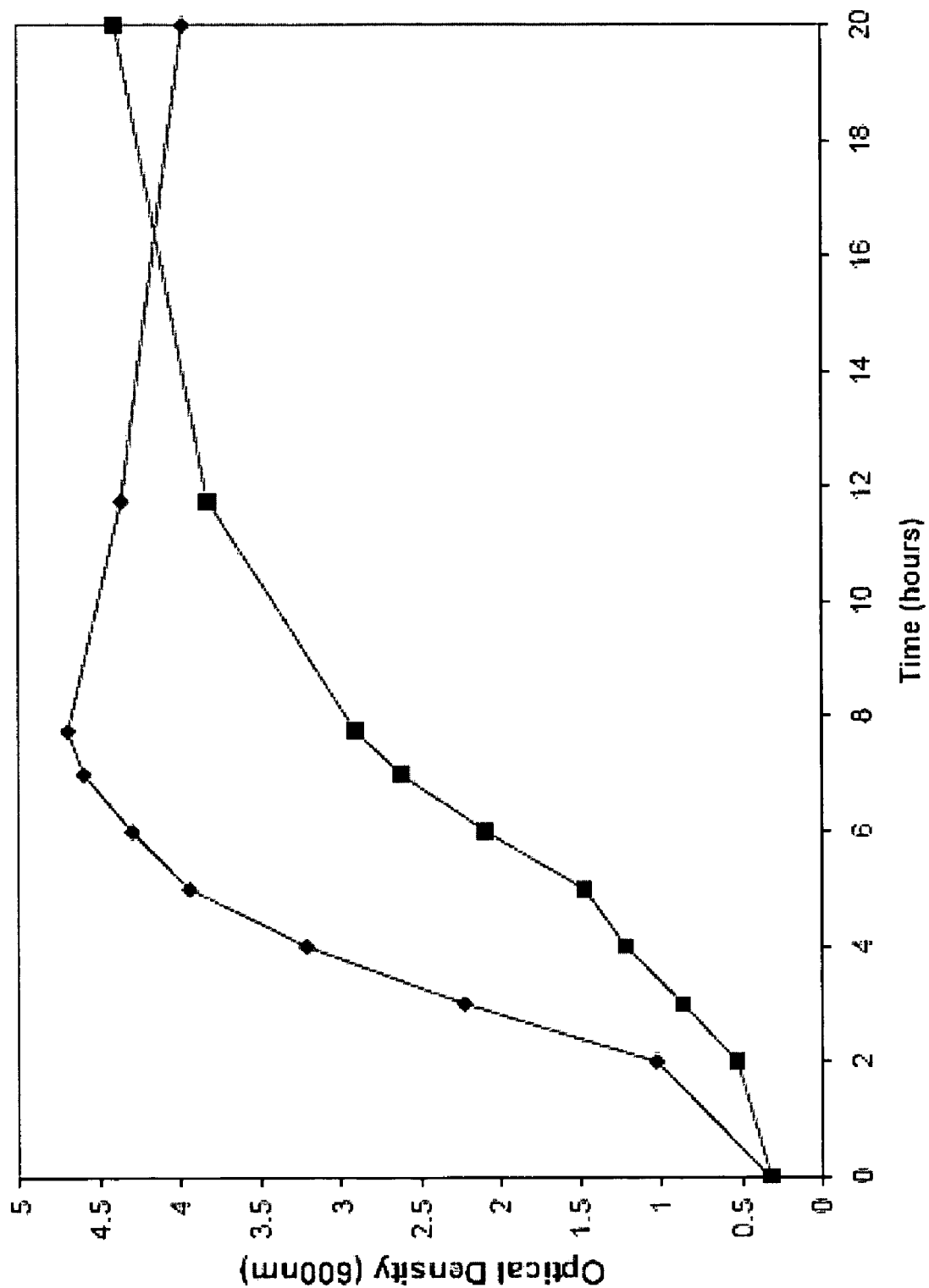

FIG. 51 depicts a comparison of *C. histolyticum* grown on Proteose Peptone #3 in a batch fermentation to the existing fermentation process using Phytone peptone during fed-batch cultivation;

—◆— GCFT03b PP3 batch —■— GCFT03d Phytone fed-batch.

Figure 52:
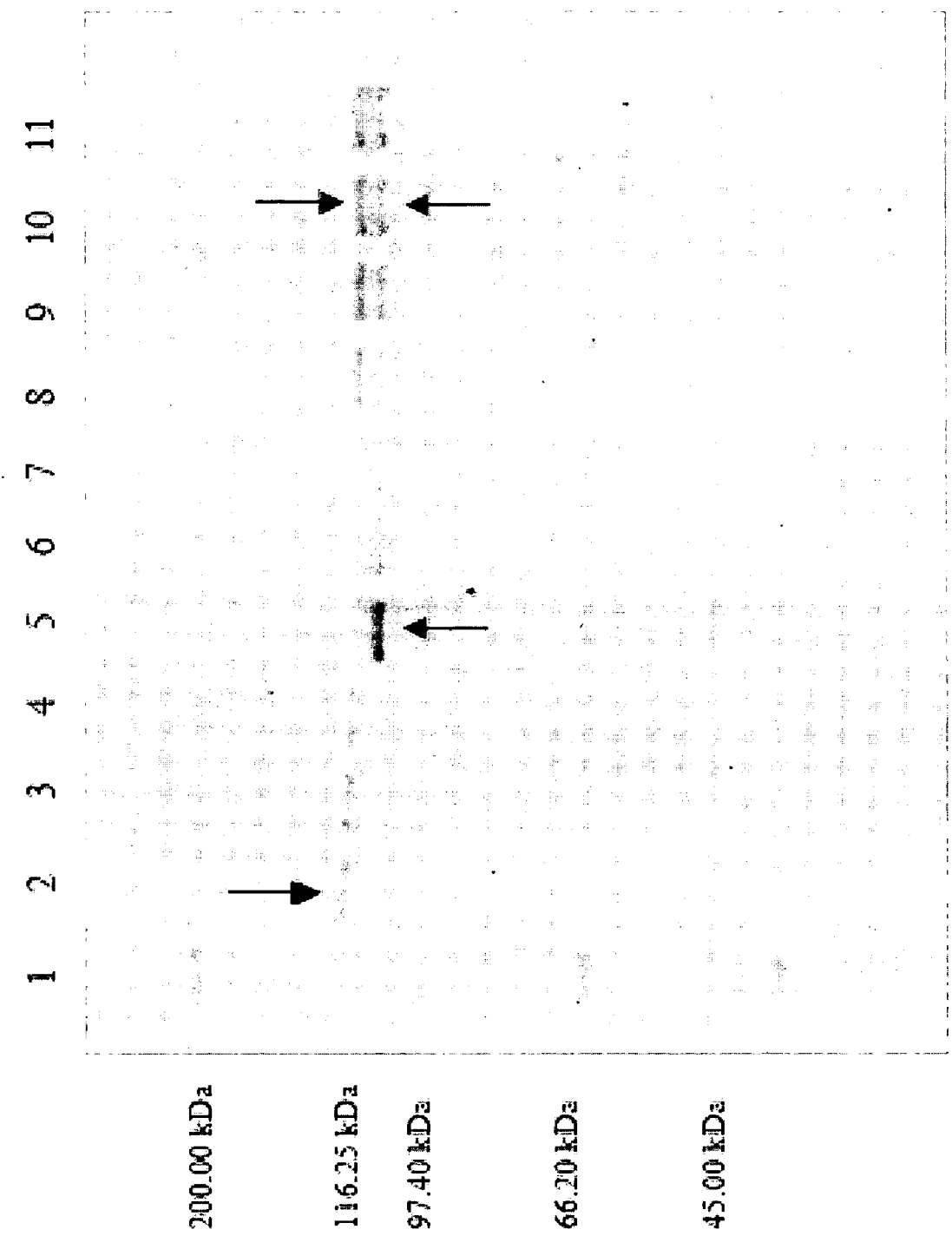

FIG. 52 is a SDS-PAGE analysis of the collagenase product at the harvest point (20 h) of a 5 L Protease Peptone #3 batch fermentation (GCFT03b) (8% Tris-Glycine):

| Lane | Sample |
|---|---|
| 1 | High Molecular Weight Marker |
| 2 | 0.27 µg AUXI |
| 3 | 0.18 µg AUXI |
| 4 | 0.135 µg AUXI |
| 5 | 0.29 µg AUXII |
| 6 | 0.193 µg AUXII |
| 7 | 0.145 µg AUXII |
| 8 | 0.87 µL of sample (1/7 dilution of fermentation sample) |
| 9 | 1.22 µL of sample (1/5 dilution of fermentation sample) |
| 10 | 1.53 µL of sample (1/4 dilution of fermentation sample) |
| 11 | 2.04 µL of sample (1/3 dilution of fermentation sample) |

Estimates
AUXI ~176 mg/L
AUXII ~190 mg/L

Figure 53:
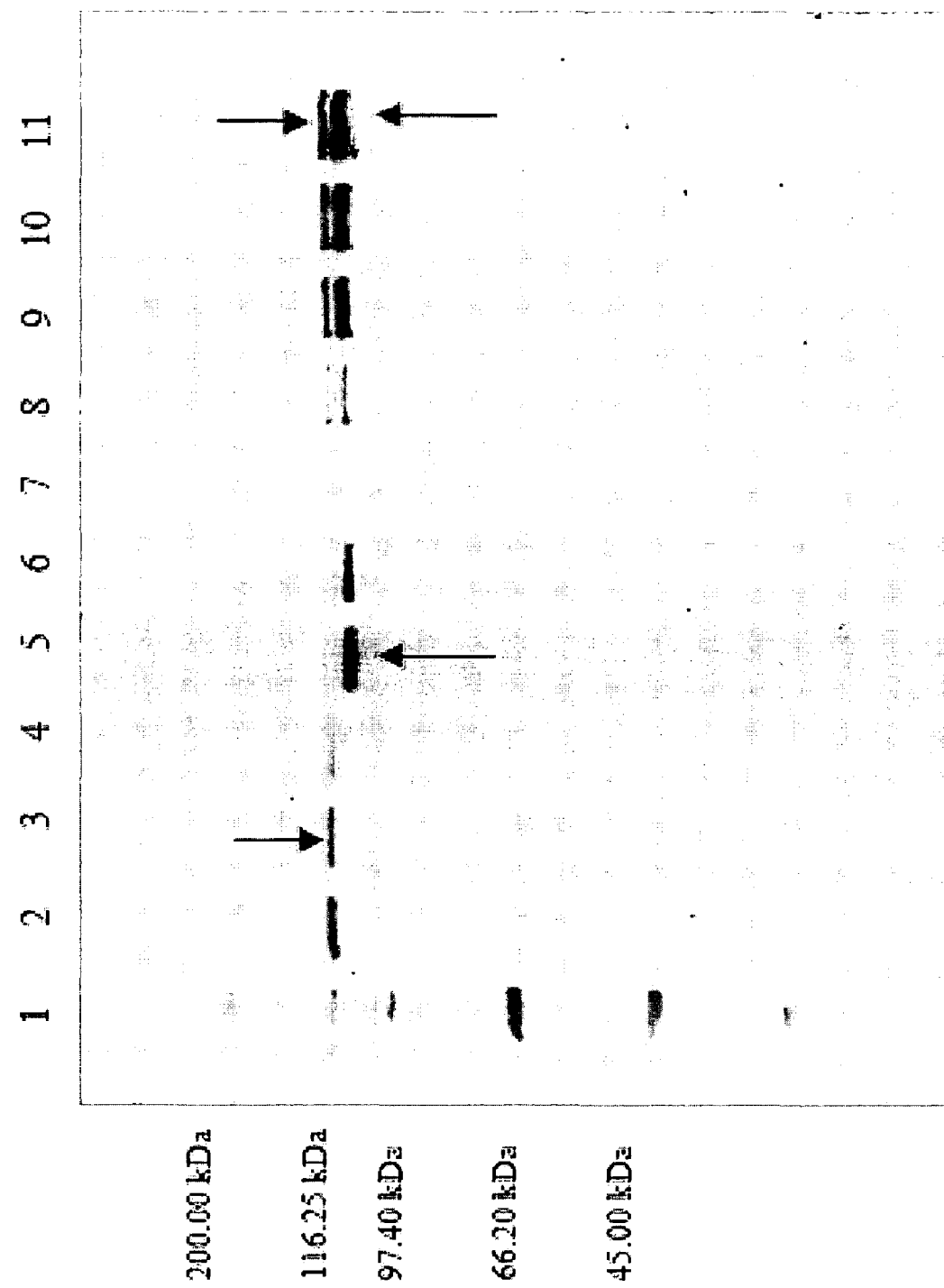

FIG. 53 is a SDS-PAGE analysis of the collagenase product at the harvest point (20 h) of a 5 L Phytone fed-batch fermentation (GCFT03d) (8% Tris-Glycine):

| Lane | Sample |
|---|---|
| 1 | High Molecular Weight Marker |
| 2 | 0.27 µg AUXI |
| 3 | 0.18 µg AUXI |
| 4 | 0.135 µg AUXI |
| 5 | 0.29 µg AUXII |
| 6 | 0.193 µg AUXII |
| 7 | 0.145 µg AUXII |
| 8 | 0.87 µL of sample (1/7 dilution of fermentation sample) |
| 9 | 1.22 µL of sample (1/5 dilution of fermentation sample) |
| 10 | 1.53 µL of sample (1/4 dilution of fermentation sample) |
| 11 | 2.04 µL of sample (1/3 dilution of fermentation sample) |

Estimates
AUXI ~88 mg/L
AUXII ~142 mg/L

Figure 54:
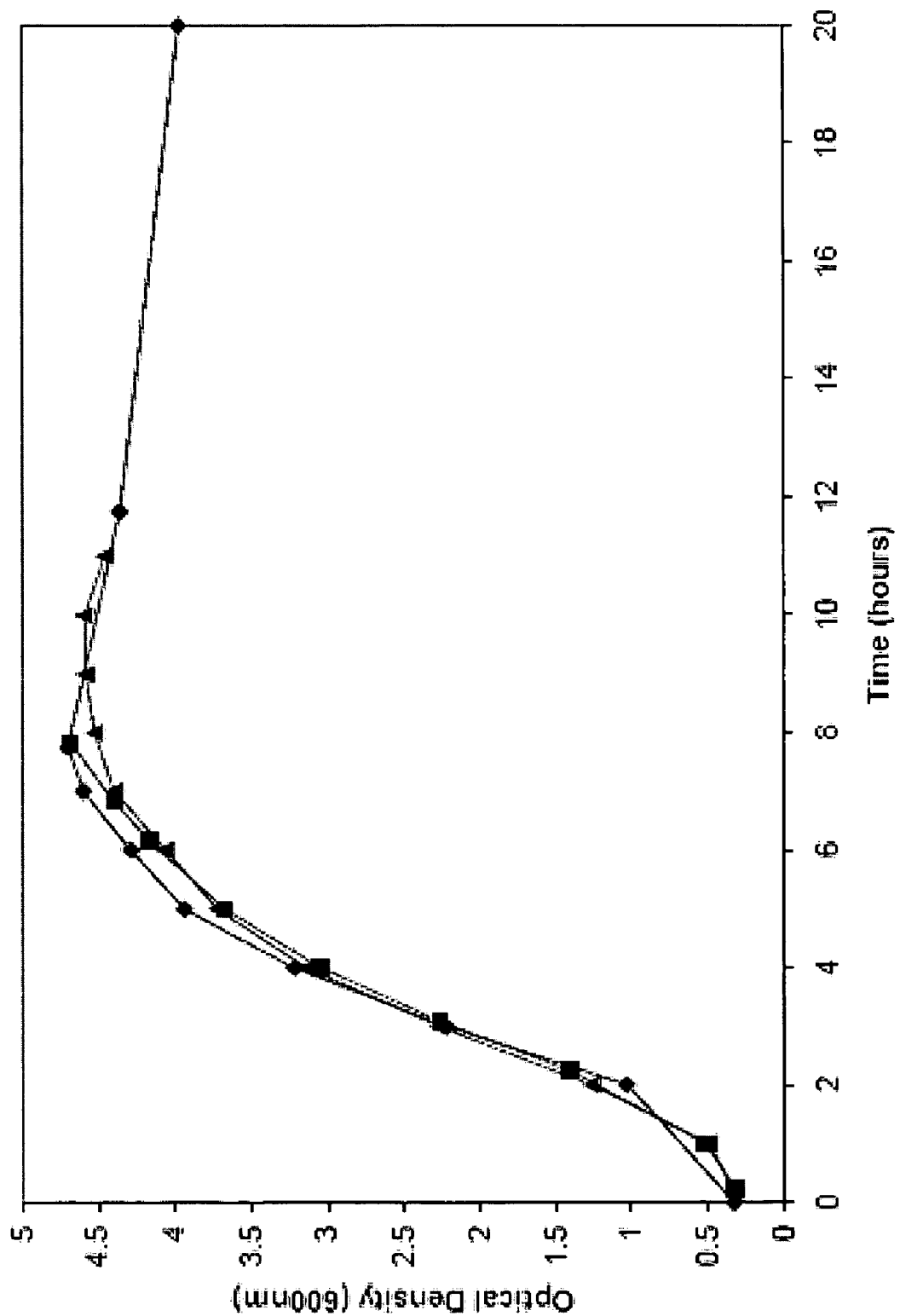

FIG. 54 illustrates three fermentations of *Clostridium histolyticum* grown on 50 g/L PP3 demonstrating a reproducible growth profile:

—◆— GCFT03b —■— GCFT04c —▲— GCFT05d.

FIG. 55 is a SDS-PAGE analysis showing the time course of GCFT05d (batch fermentation with Proteose Peptone #3), 8% Tris Glycine gel, colloidal stained):

| Lane | Sample |
|---|---|
| 1 | High Molecular Weight Marker |
| 2 | Reference, AUXI and AUXII |
| 3 | 3 hours |
| 4 | 4 hours |

-continued

| Lane | Sample |
|---|---|
| 5 | 5 hours |
| 6 | 6 hours |
| 7 | 7 hours |
| 8 | 8 hours |
| 9 | 9 hours |
| 10 | 10 hours |
| 11 | 11 hours |

Figure 56:
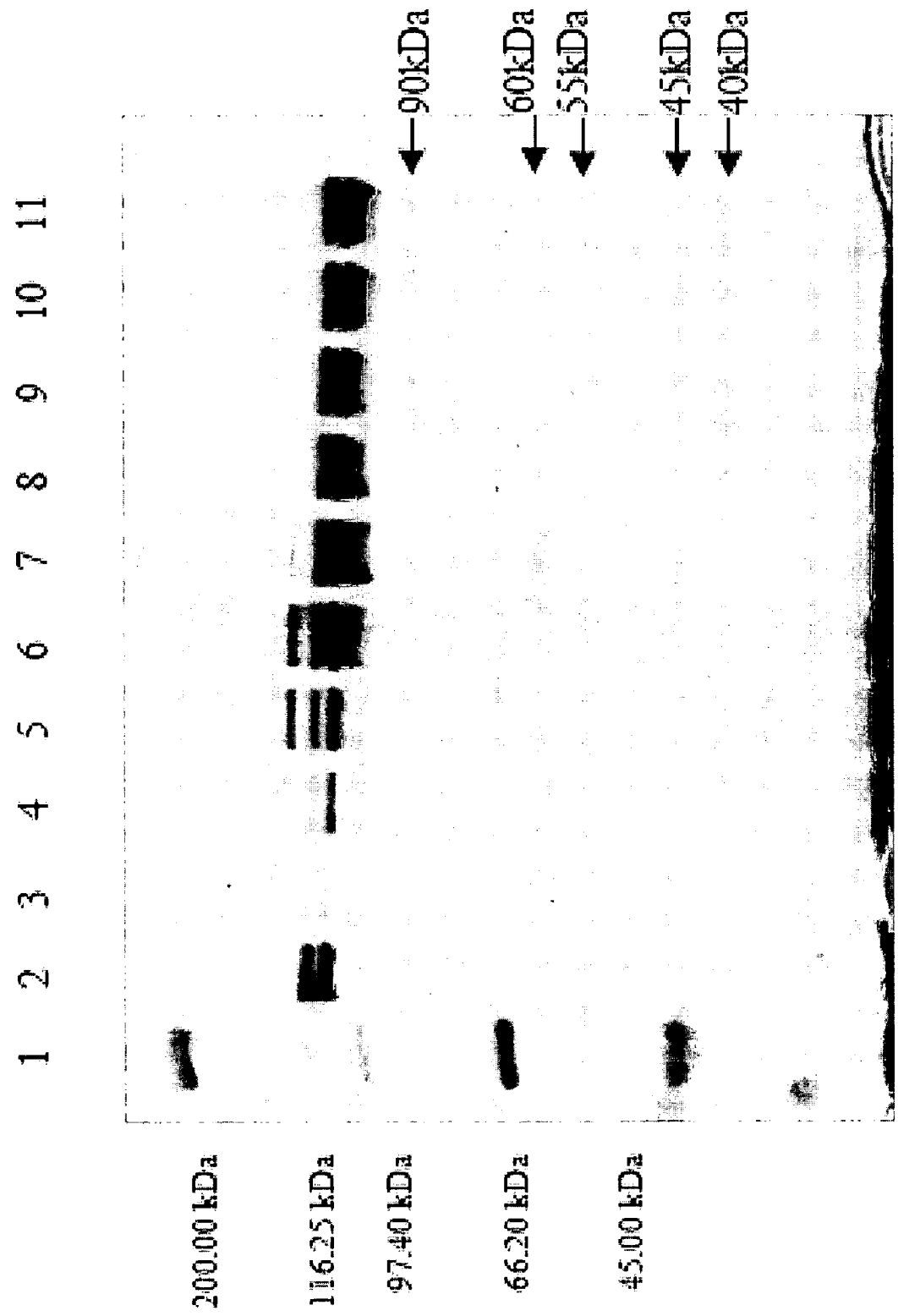

FIG. 56 is a SDS-PAGE analysis showing the time course of GCFT05d (batch fermentation with Proteose Peptone #3), (8% Tris Glycine gel, silver stained):

| Lane | Sample |
|---|---|
| 1 | High Molecular Weight Marker |
| 2 | Reference, AUXI and AUXII |
| 3 | 3 hours |
| 4 | 4 hours |
| 5 | 5 hours |
| 6 | 6 hours |
| 7 | 7 hours |
| 8 | 8 hours |
| 9 | 9 hours |
| 10 | 10 hours |
| 11 | 11 hours |

Figure 57:
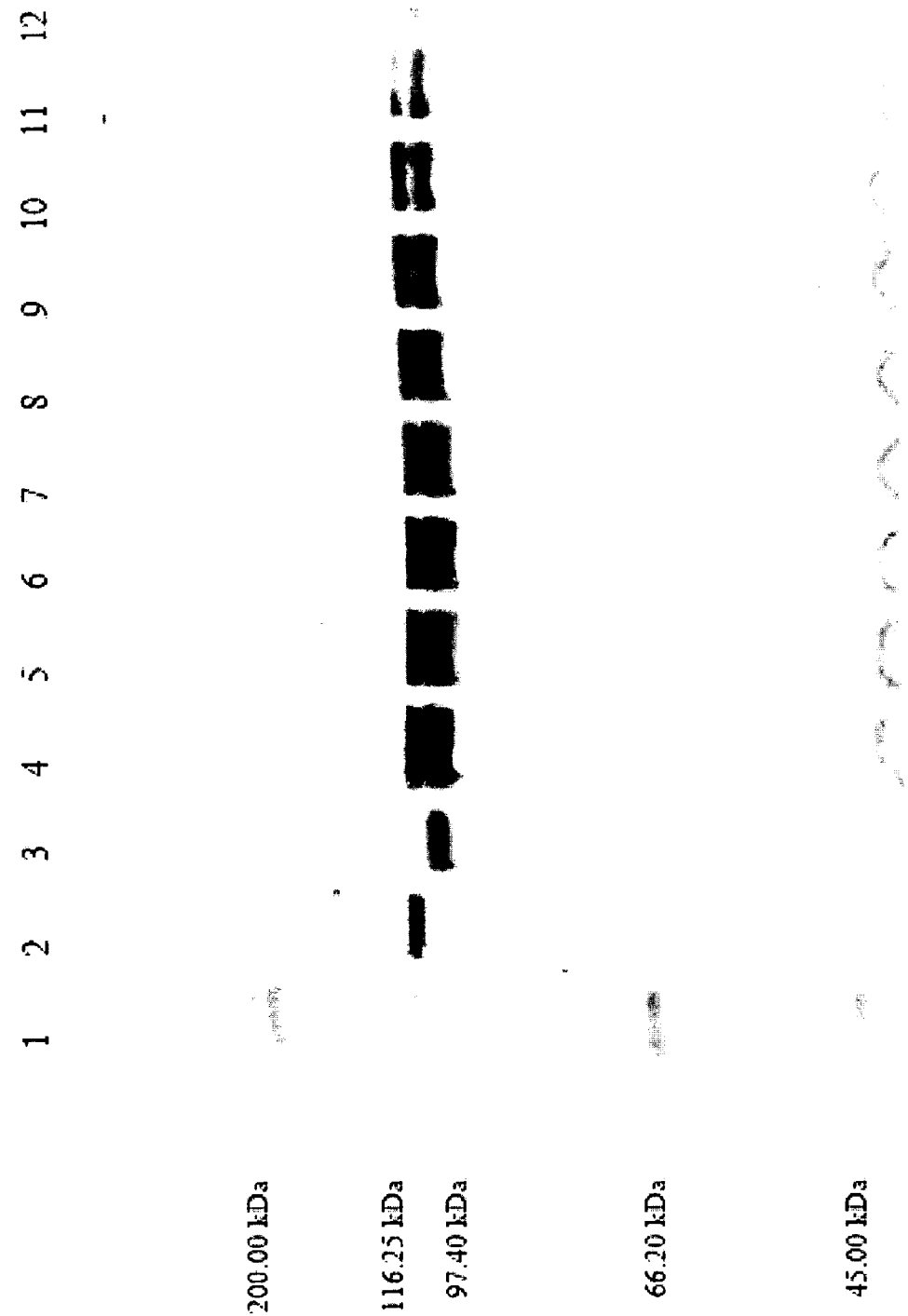

FIG. 57 is a SDS-PAGE analysis showing the time course of DCFT24b (fed-batch fermentation using Phytone peptone), (8% Tris Glycine gel, colloidal stained):

| Lane | Sample |
|---|---|
| 1 | High Molecular Weight Marker |
| 2 | AUXI - 0.27 µg |
| 3 | AUXII - 0.29 µg |
| 4 | 20 hours - Harvest point |
| 5 | 19 hours |
| 6 | 17 hours |
| 7 | 16 hours |
| 8 | 15 hours |
| 9 | 14 hours |
| 10 | 13 hours |
| 11 | 11.6 hours |
| 12 | 10.5 hours |

Figure 58:
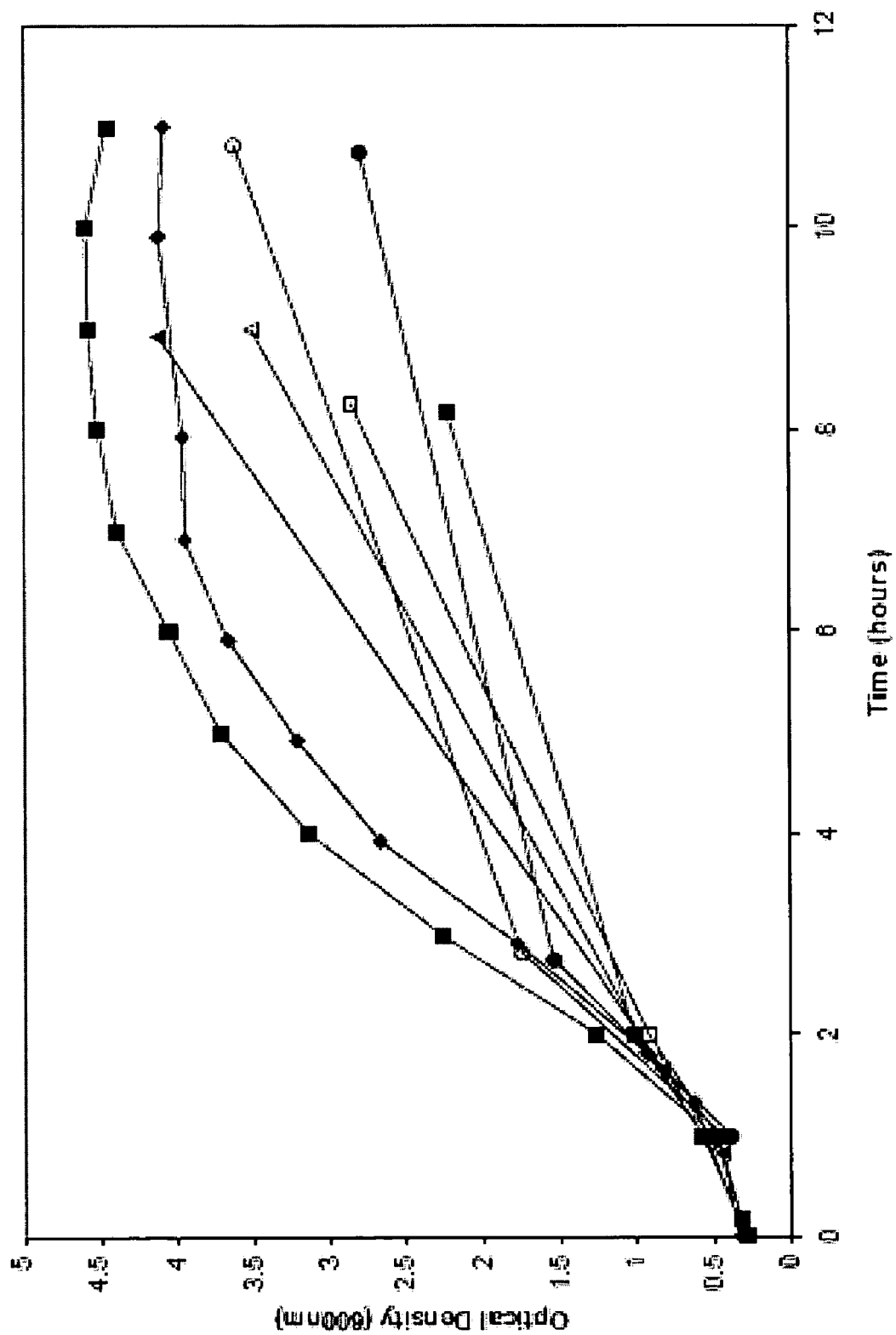

FIG. 58 illustrates a comparison of growth curves from *C. histolyticum* fermentations using different lots of PP3:

─■─GCFT05d  ─●─GCFT06b  ─▲─GCFT07c  ─■─GCFT07d
─▲─GCFT08c  ─▲─GCFT08d  ─●─GCFT09C GCFT09D.

FIG. 59 illustrates a small scale comparison of three lots of PP3 and evaluation of □batch 5354796 (50 g/L) □batch 5332398 (50 gL)

100 g/L PP3: ■batch 5325635 (50 g/L) □batch 5332398 (100 g/L).

FIG. 60 depicts a growth profiles of two 5 L fermentations utilizing PP3 at 100 g/L:

PBFT70c lot # 5354796 PBFT70d lot # 5325635.

FIG. 61 is a SDS-PAGE analysis of the time course of PBFT70c, 100 g/L PP3 (lot # 5354796) fermentation (8% Tris-Glycine):

| Lane | Sample |
|---|---|
| 1 | High Molecular Weight Marker |
| 2 | Reference, 0.4 μg AUXI and AUXII |
| 3 | 3.1 hours |
| 4 | 4.4 hours |
| 5 | 5.5 hours |
| 6 | 6.6 hours |
| 7 | 8.0 hours |
| 8 | 9.1 hours |
| 9 | 10.1 hours |
| 10 | 11.4 hours |
| 11 | 12.0 hours |

FIG. 62 is a SDS-PAGE analysis of the timecourse of PBFT70d, 100 g/L PP3 (lot # 532635) fermentation (8% Tris-Glycine):

| Lane | Sample |
|---|---|
| 1 | High Molecular Weight Marker |
| 2 | Reference, 0.4 μg AUXI and AUXII |
| 3 | 3.1 hours |
| 4 | 4.3 hours |
| 5 | 5.5 hours |
| 6 | 6.6 hours |
| 7 | 7.8 hours |
| 8 | 9.1 hours |
| 9 | 10.1 hours |
| 10 | 11.3 hours |
| 11 | 12.0 hours |

FIG. 63 represents a densitometry analysis of SDS-PAGE to compare cell growth to product formation from 5 L fermentation PBFT70c:

Precursor Aux 1 Aux 2 OD.

FIG. 64 illustrated a Comparison of 100 g/L PP3 process at 5 L and 200 L scale:

PBFT70c PBFT70d 200L scale-up fermentation.

FIG. 65 is a SDS-PAGE analysis of the time course of the 200 L fermentation (8% Tris-Glycine):

| Lane | Sample |
|---|---|
| 1 | High Molecular Weight Marker |
| 2 | AUXI and AUXII mixed reference (1.2 μg) |
| 3 | 4 hours |

-continued

| Lane | Sample |
|------|--------|
| 4 | 6 hours |
| 5 | 8 hours |
| 6 | 9.4 hours |
| 7 | 12 hours |
| 8 | 14 hours |

Figure 66:
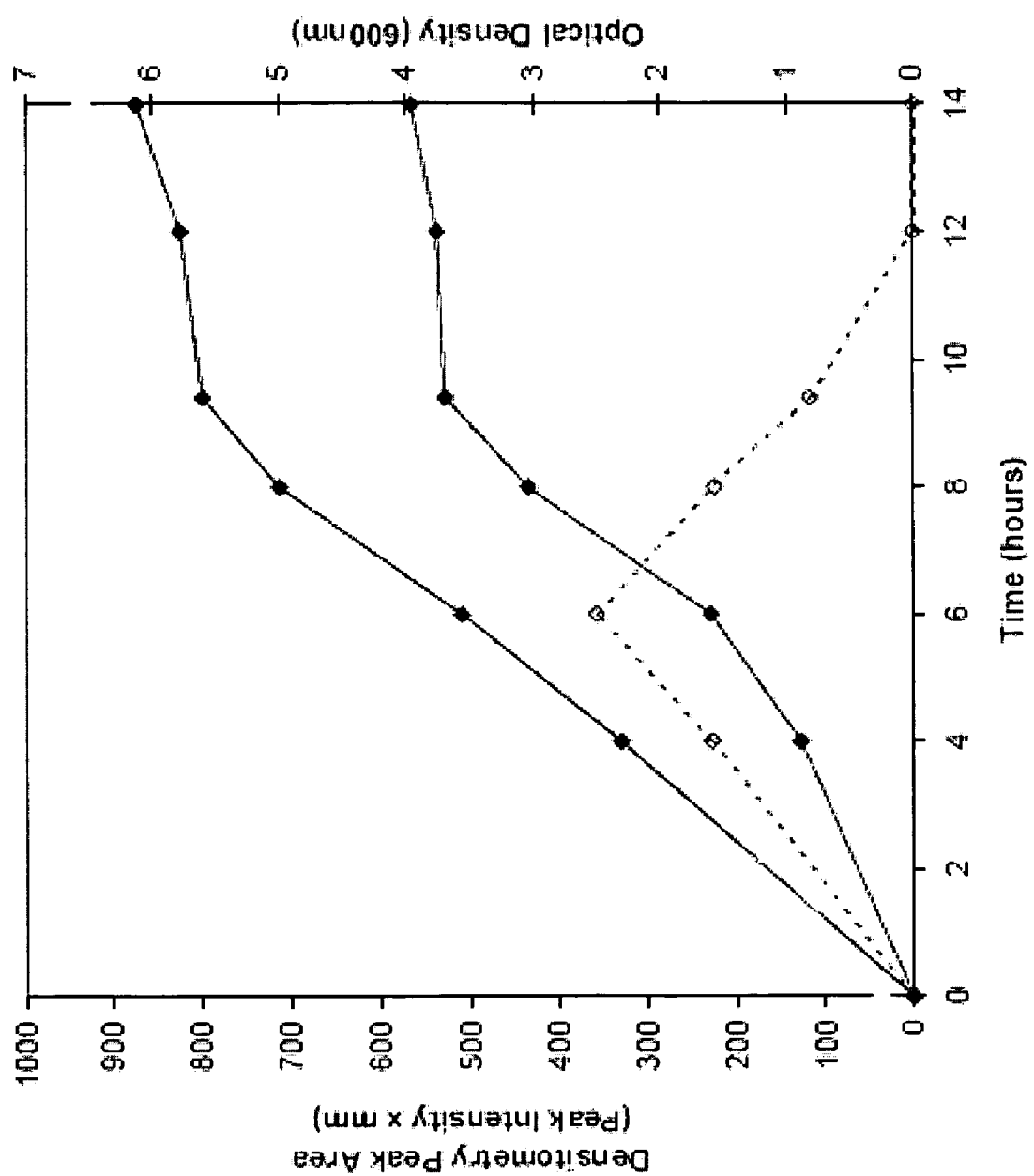

FIG. 66 represents a densitometry analysis of SDS-PAGE to compare cell growth to product formation from 200 L fermentation:

-- ◇ -- Precursor  — ● — Aux 1  — ▲ — Aux 2  OD.

Figure 67:
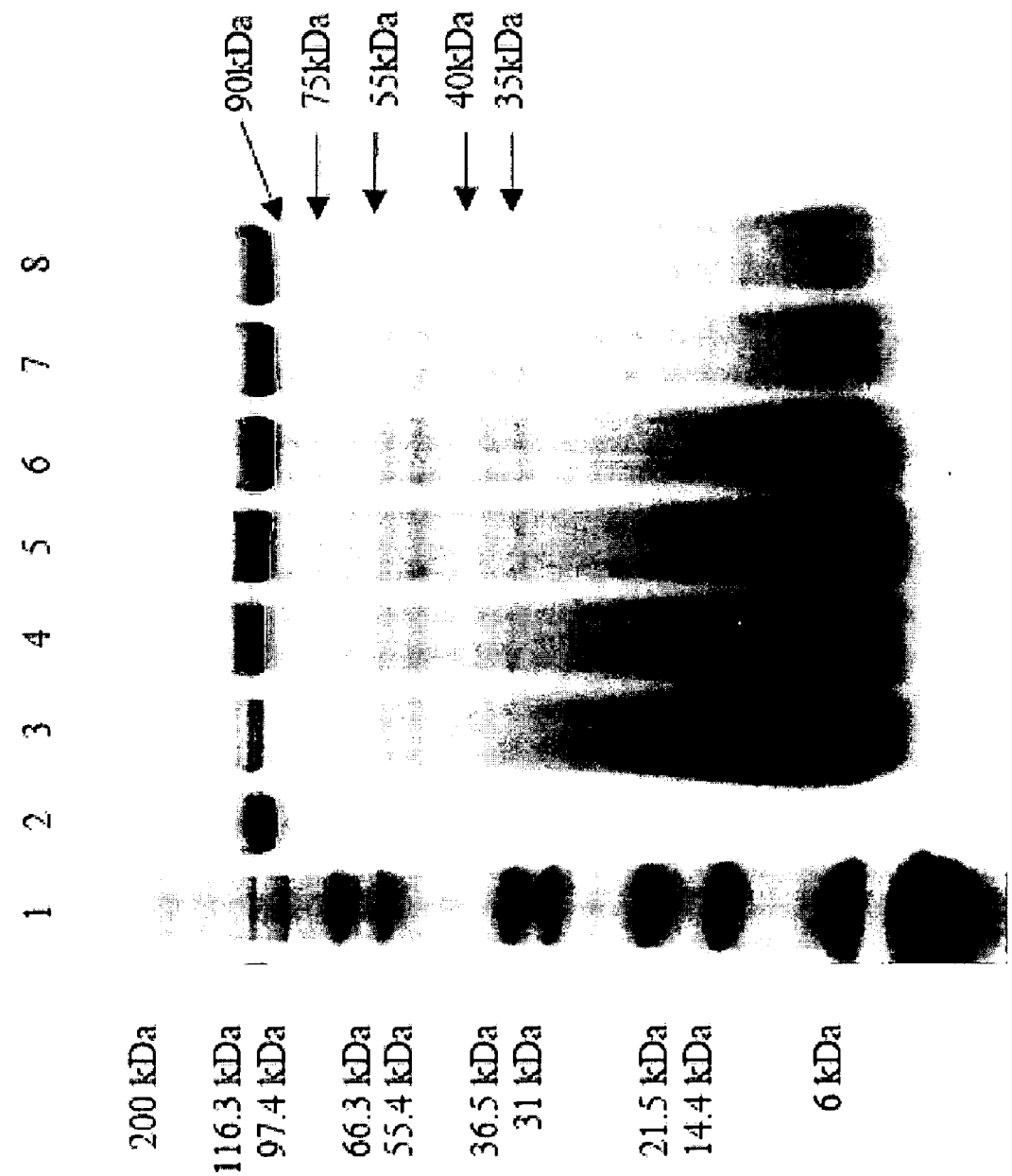

FIG. 67 is a SDS-PAGE analysis of the time course of the 200 L fermentation (4-12% Bis-Tris):

| Lane | Sample |
|------|--------|
| 1 | High Molecular Weight Marker |
| 2 | AUXI and AUXII mixed reference (1.2 μg) |
| 3 | 4 hours |
| 4 | 6 hours |
| 5 | 8 hours |
| 6 | 9.4 hours |
| 7 | 12 hours |
| 8 | 14 hours |

Figure 68:
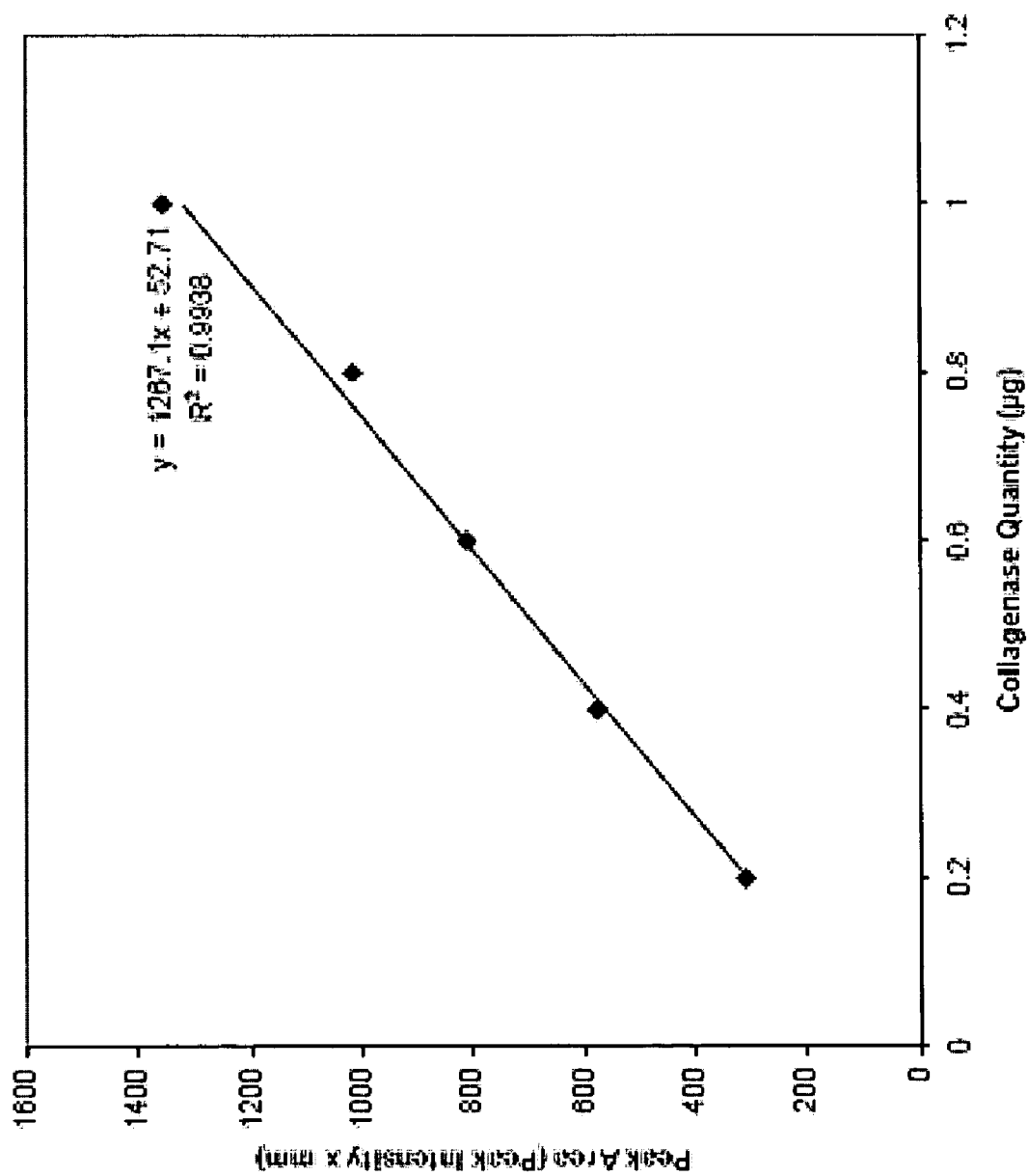

FIG. 68 shows a standard curve for densitometry quantification of collagenase concentration.

Figure 69:
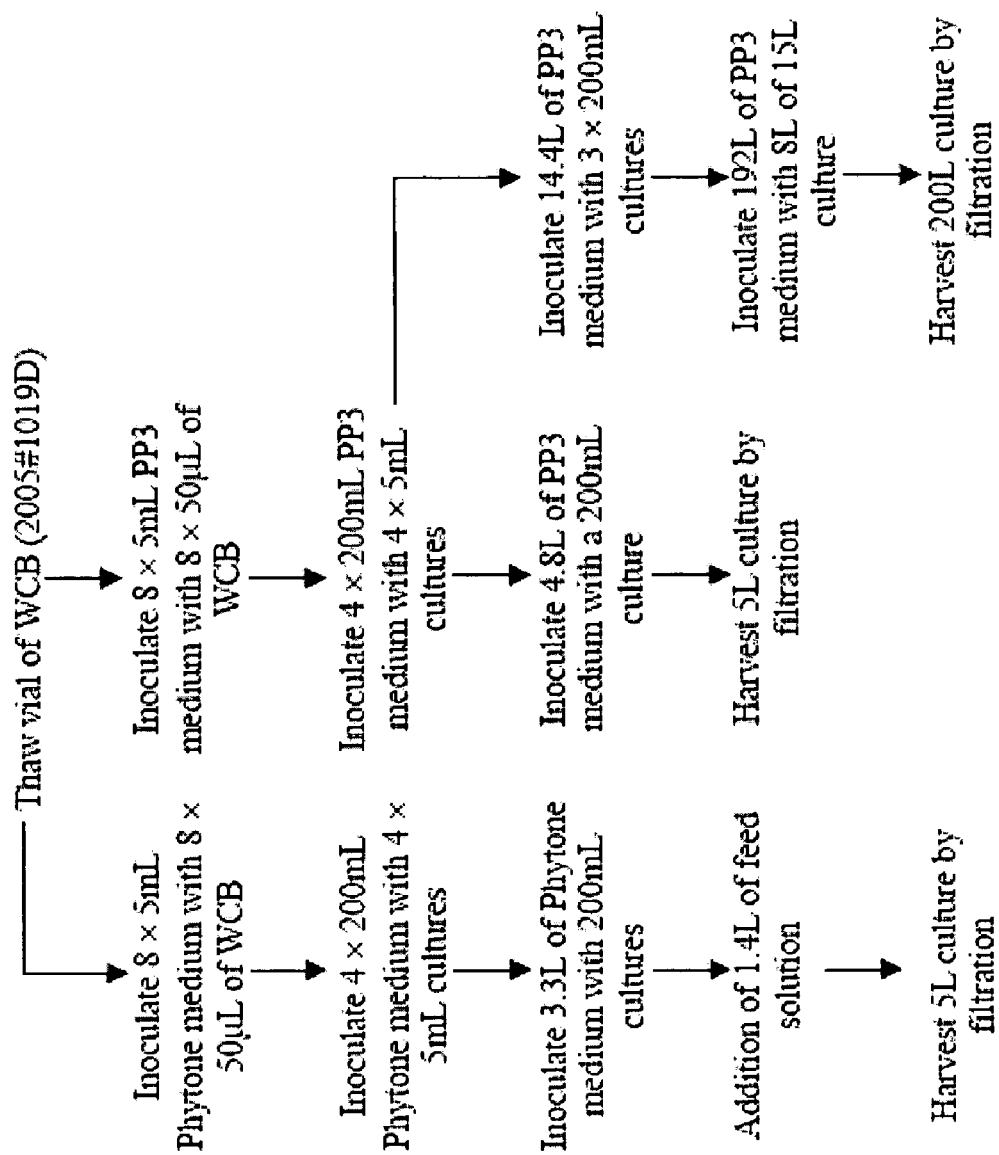

FIG. 69 represents a schematic illustration of the fermentation and harvest of *Clostridium histolyticum*.

FIGS. 70 (*a*) and (*b*) are chromatograms resulting from Hydrophobic interaction chromatography using Phenyl Sepharose FF (low sub): (a) is full scale chromatogram and (b) is an expanded chromatogram showing fraction collection.

Figure 71:
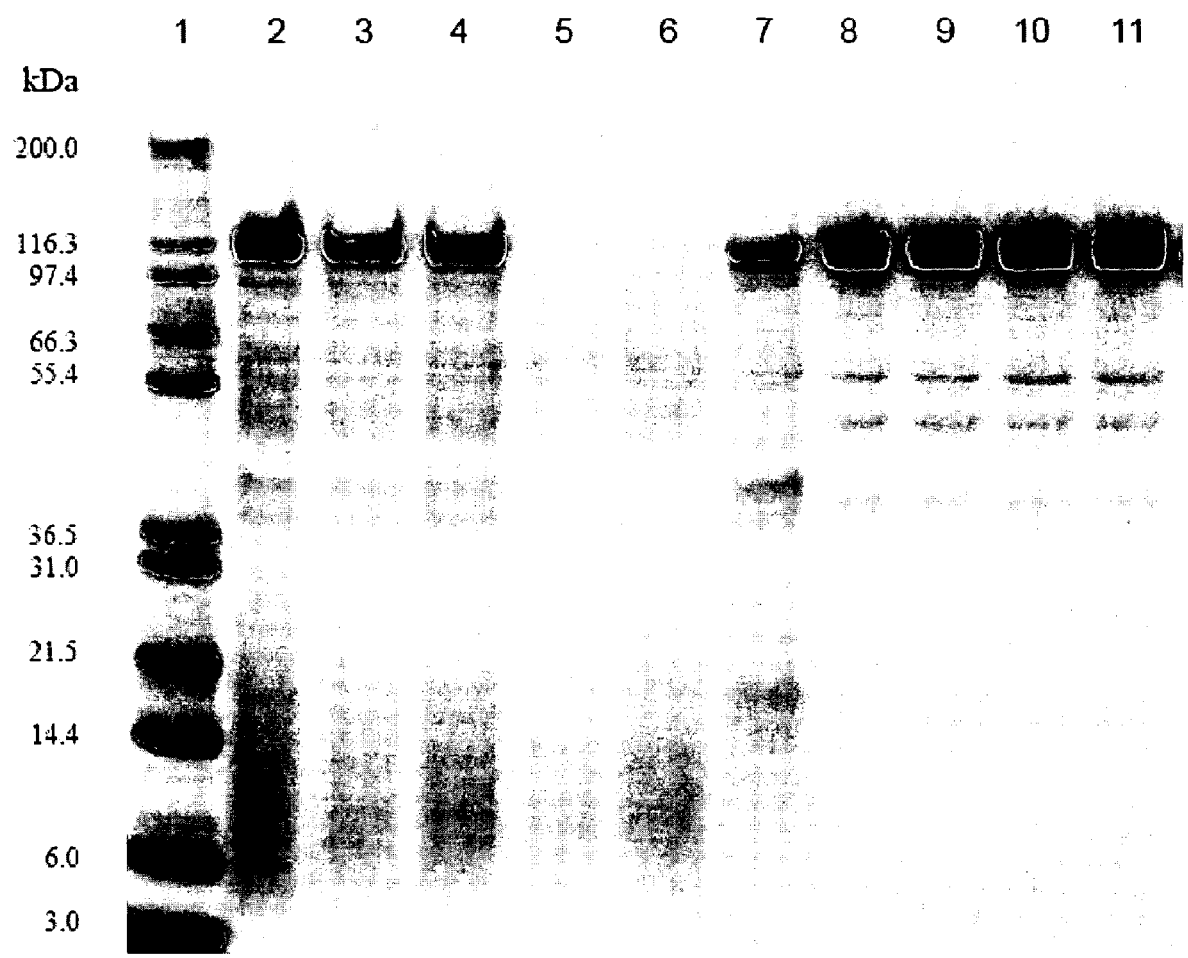

FIG. 71 is a 4-12% Bis-Tris SDS-PAGE analysis of in-process samples from the MUSTANG Q filter step to the TFF1 step. The gel is stained with Colloidal blue and overloaded (2.5 μm total protein/lane) to show contaminant bands:

| Lane | Sample | Load volume, μl |
|------|--------|-----------------|
| 1 | Mark 12 Molecular Weight Marker | 12 |
| 2 | Post Mustang Q filtrate | 15 |
| 3 | Pre HIC Bag 1 | 15 |
| 4 | Pre HIC Bag 2 | 15 |
| 5 | HIC flow-through Bag 1 | 15 |
| 6 | HIC flow-through Bag 2 | 15 |
| 7 | HIC Peak 1 (0.3 M AS wash) | 15 |
| 8 | Post HIC pool (peak 2) | 15 |
| 9 | Pre TFF (post HIC pool + 2 day hold) | 15 |
| 10 | Post TFF | 15 |
| 11 | Pre Q-AEX (post TFF + overnight hold) | 15 |

Figure 72:
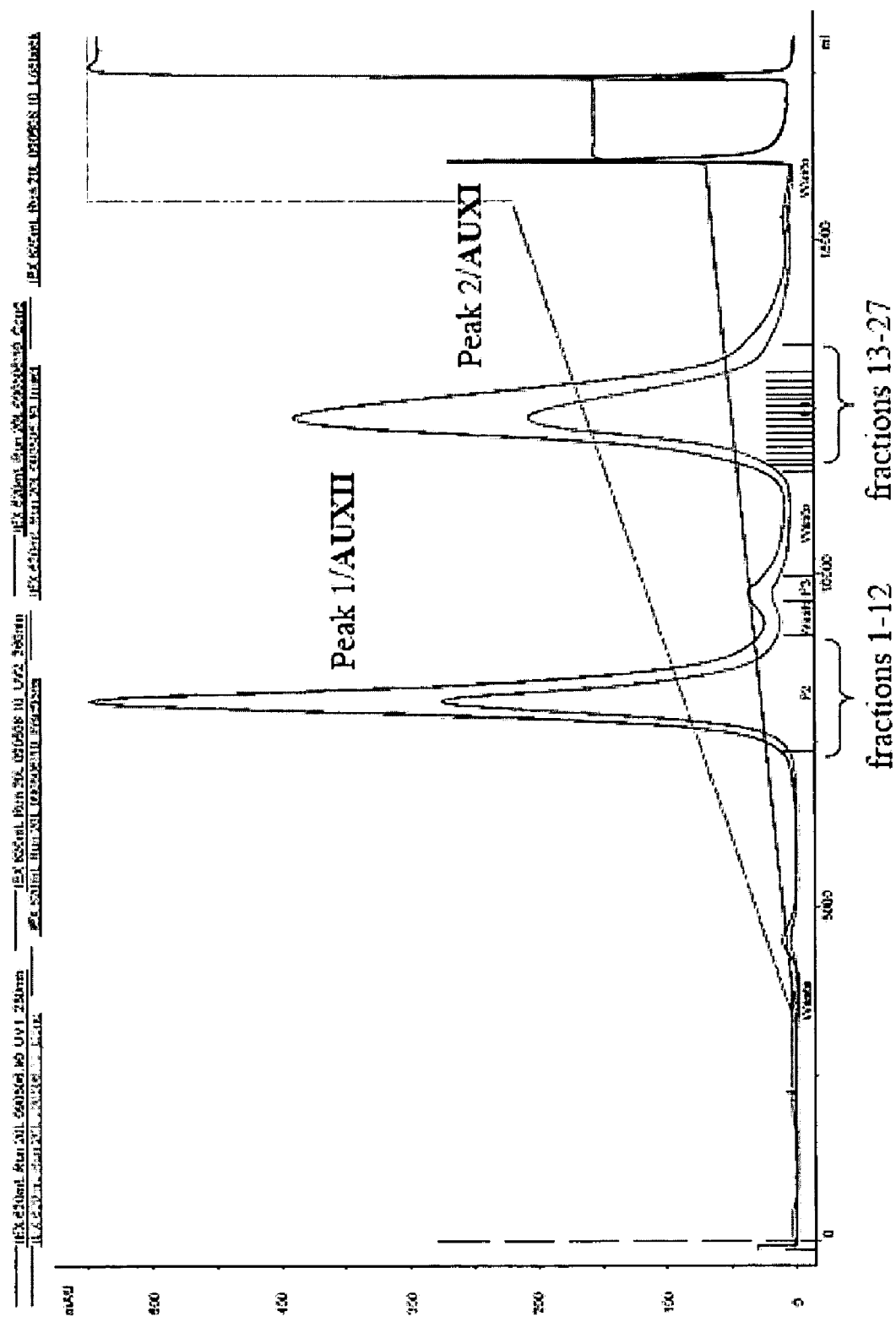

FIG. 72 is an Ion exchange chromatogram (Q Sepharose HP) of the post HIC material after concentration and diafiltration into 10 mM Tris, 200 μM leupeptin pH 8.

Figure 5:
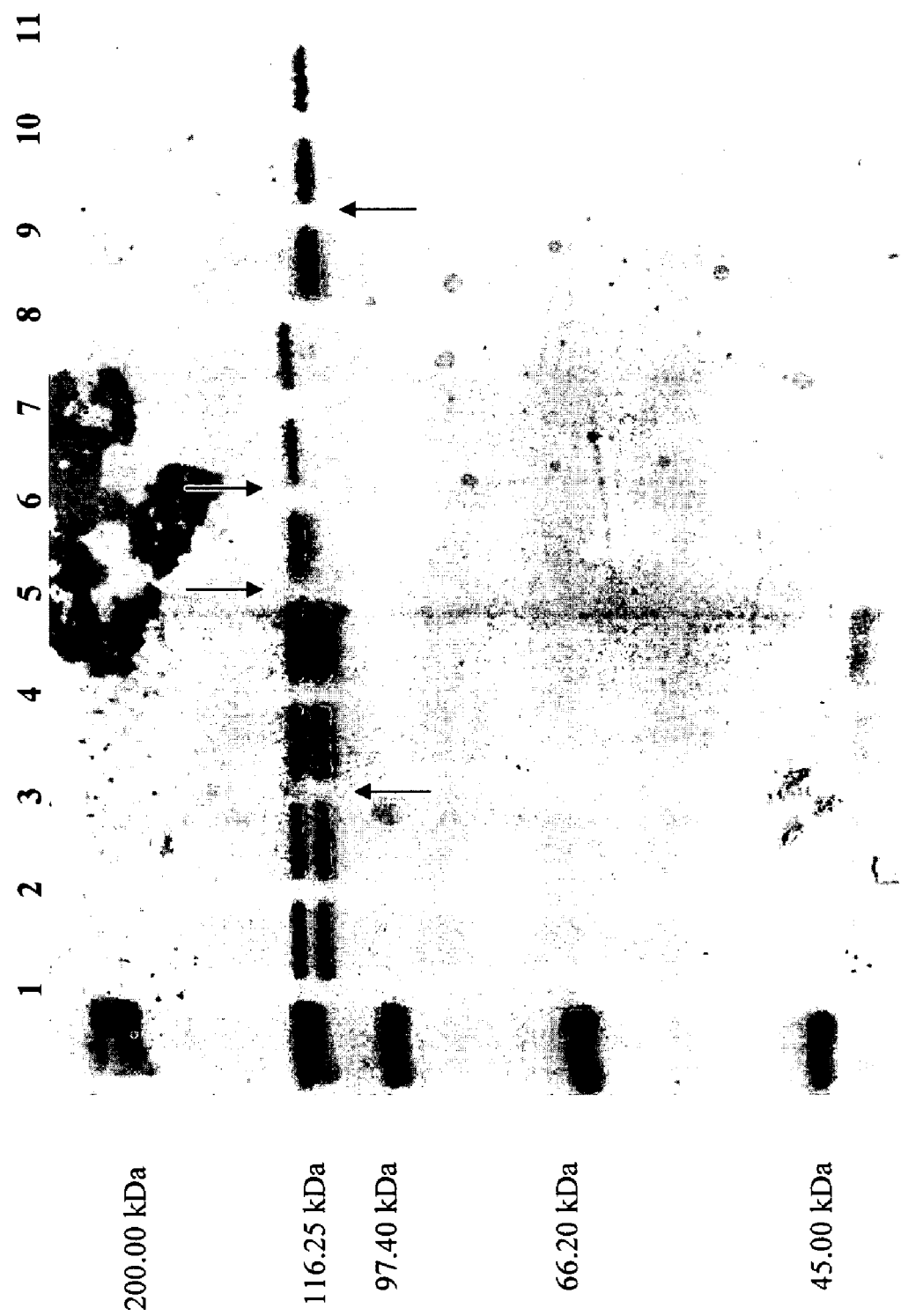
FIG. 5 is a Semi-quantitative SDS PAGE gel for the second fermentation, harvest point sample:
Lane 1: High Molecular Weight Marker
Lane 2: 0.87 µL of sample (1/7 dilution of fermentation sample)
Figure 73:
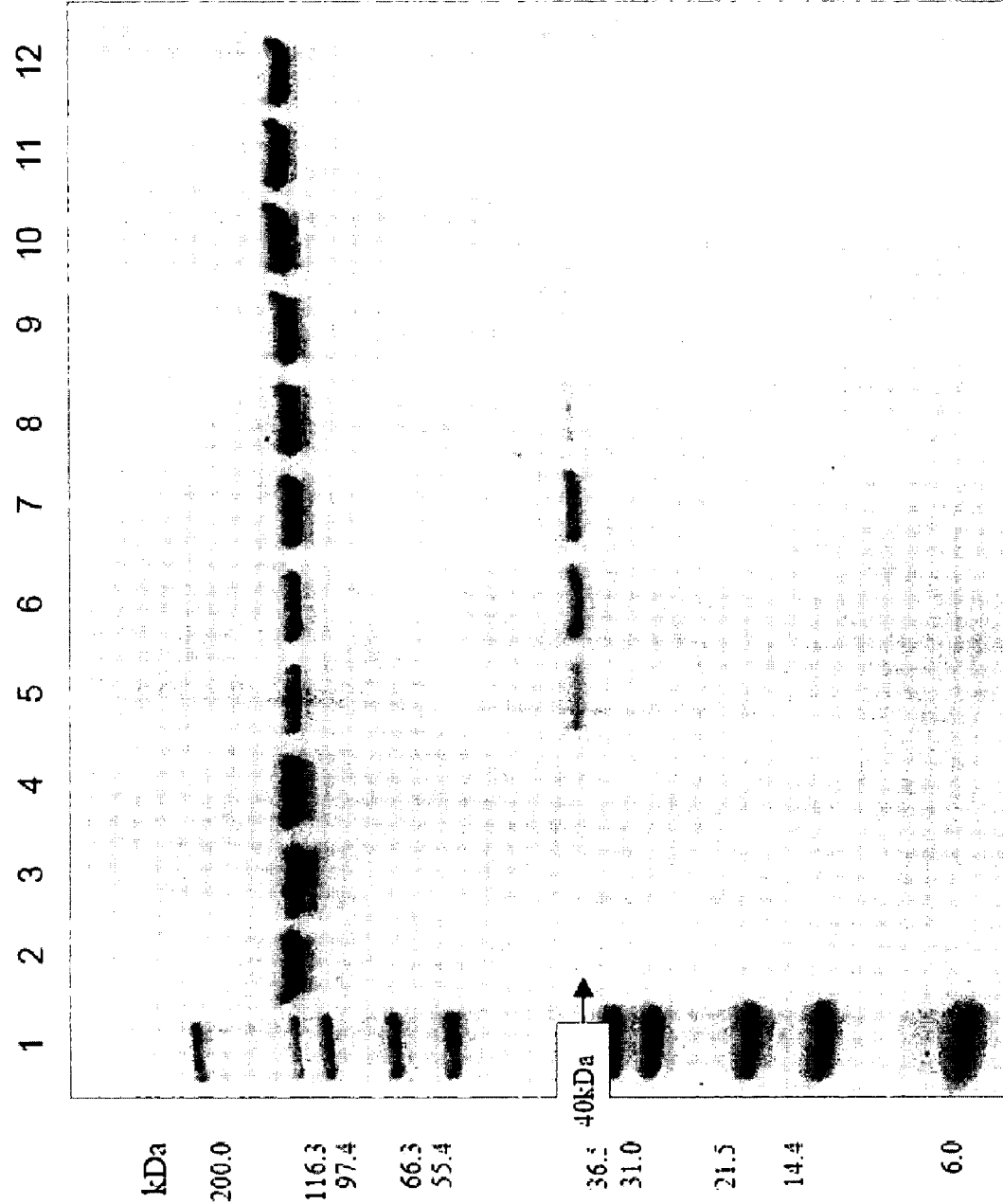

FIG. 73 is a 4-12% Bis Tris SDS-PAGE analysis of fractions from peak I (AUXII) eluted during the ion exchange column (FIG. 5). Gel 1: the gel is stained with Colloidal blue:

| Lane | Sample | | Load volume, μl |
|------|--------|---|-----------------|
| 1 | Mark 12 Molecular Weight Marker | | 10 |
| 2 | Collagenase ABC I reference | 1 μg | 15 |
| 3 | Collagenase ABC II reference | 1 μg | 15 |
| 4 | Load | 1 μg | 15 |
| 5 | Fraction 1 | neat | 15 |
| 6 | Fraction 2 | neat | 15 |
| 7 | Fraction 3 | neat | 15 |
| 8 | Fraction 4 | AUXII fractions, 1 μg | 15 |
| 9 | Fraction 5 | 1 μg | 15 |
| 10 | Fraction 6 | 1 μg | 15 |
| 11 | Fraction 7 | 1 μg | 15 |
| 12 | Fraction 8 | 1 μg | 15 |

Figure 74:
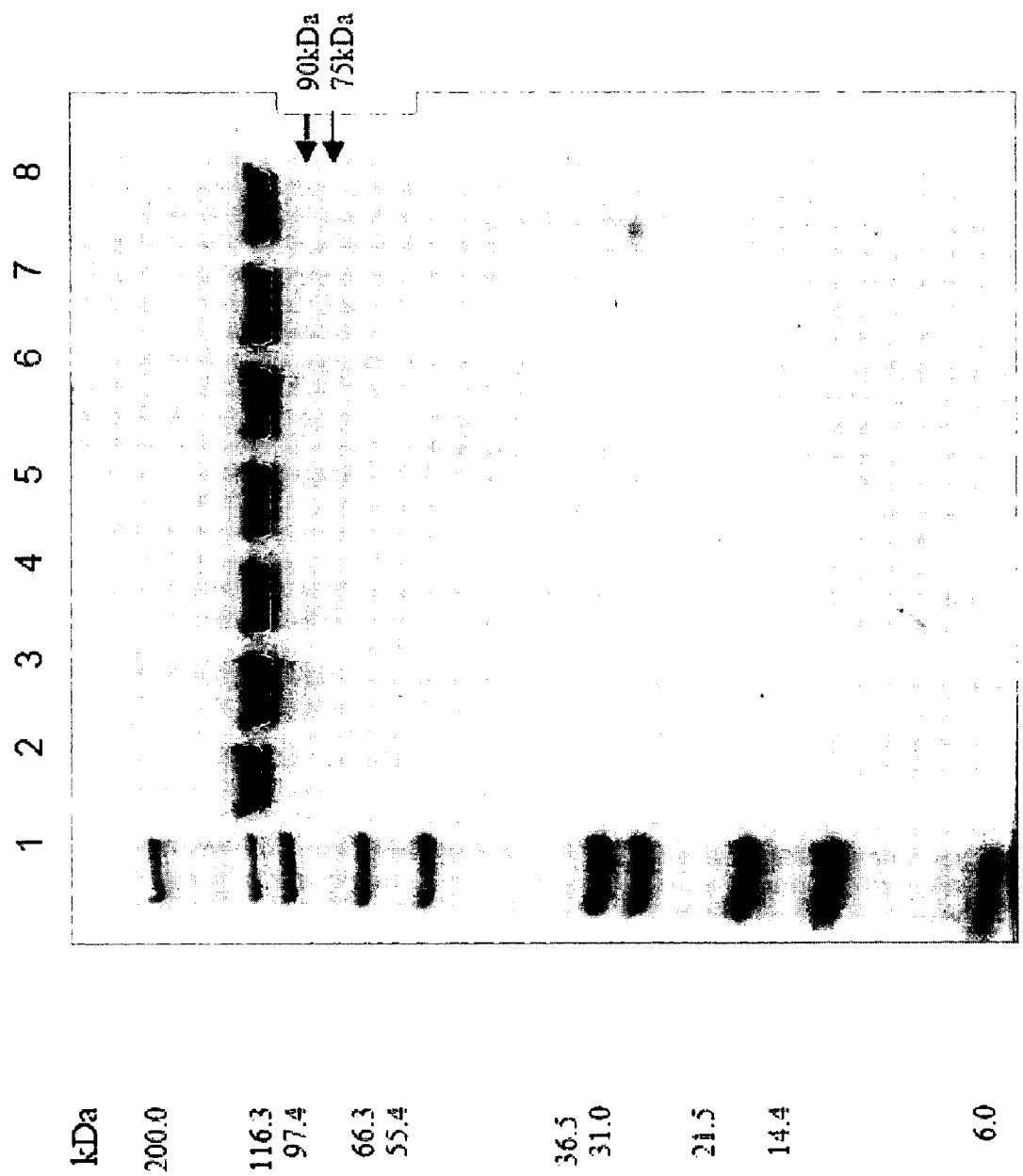

FIG. 74 is a 4-12% Bis Tris SDS-PAGE analysis of fractions from peak 1 (AUXII) eluted during the ion exchange column (FIG. 5). Gel 2: the gel is stained with Colloidal blue:

| Lane | Sample | | Load volume, μl |
|------|--------|---|-----------------|
| 1 | Mark 12 Molecular Weight Marker | | 10 |
| 2 | Collagenase ABC I reference | 1 μg | 15 |
| 3 | Collagenase ABC II reference | 1 μg | 15 |
| 4 | Fraction 9 | 1 μg | 15 |
| 5 | Fraction 10 | 1 μg | 15 |
| 6 | Fraction 11 | AUXII fractions, 1 μg | 15 |
| 7 | Fraction 12 | 1 μg | 15 |
| 8 | Peak 1 Tail | 1 μg | 15 |

Figure 75:
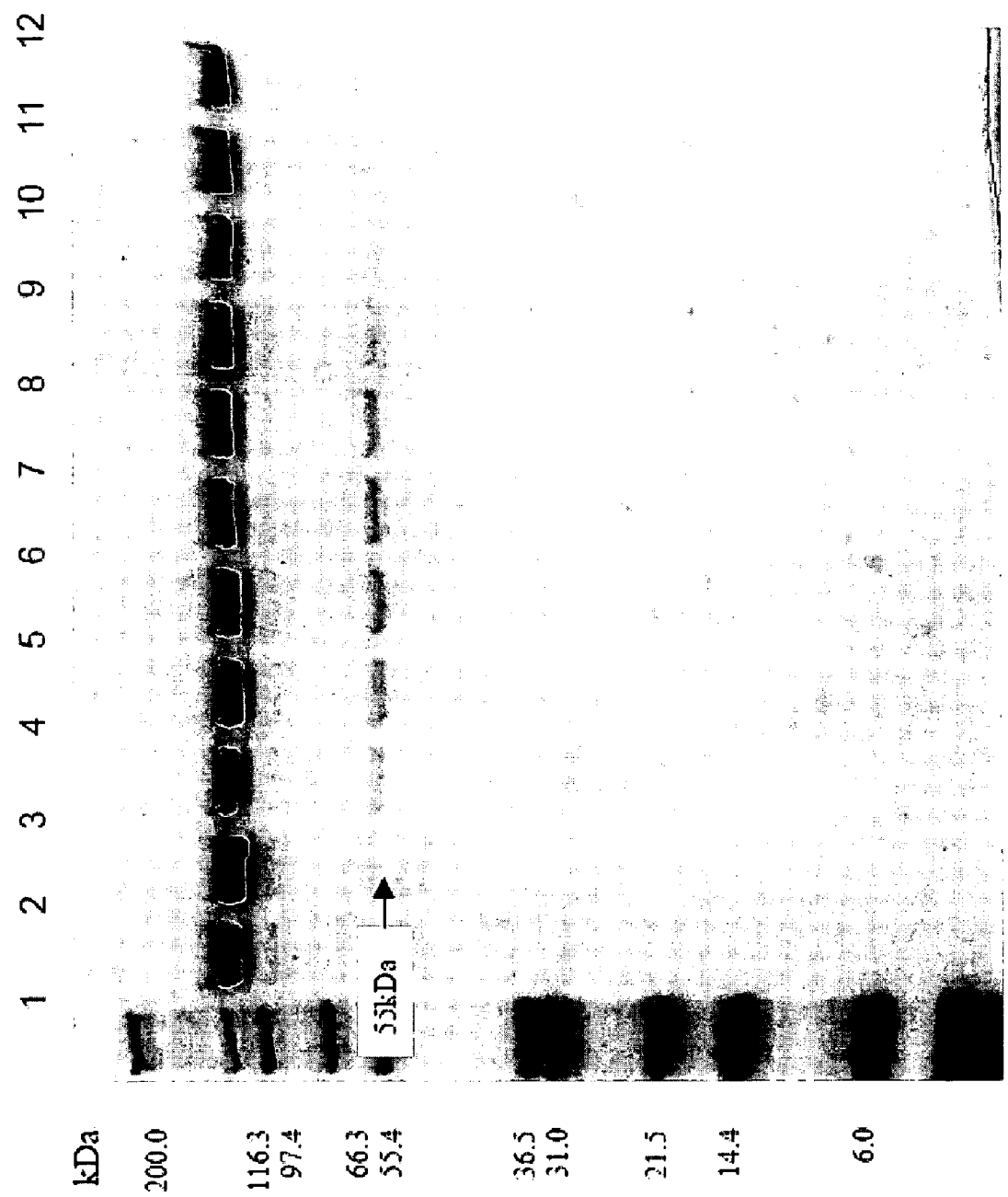

FIG. 75 is a 4-12% Bis Tris SDS-PAGE analysis of fractions from peak 2 (AUXI) eluted during the ion exchange column (FIG. 5). Gel 3: the gel is stained with Colloidal blue:

| Lane | Sample | | Load volume, μl |
|------|--------|---|-----------------|
| 1 | Mark 12 Molecular Weight Marker | | 10 |
| 2 | Collagenase ABC I reference | 1 μg | 15 |
| 3 | Collagenase ABC II reference | 1 μg | 15 |
| 4 | Fraction 13 | neat | 15 |
| 5 | Fraction 14 | 1 μg | 15 |
| 6 | Fraction 15 | 1 μg | 15 |
| 7 | Fraction 16 | AUXI fractions, μg | 15 |
| 8 | Fraction 17 | μg | 15 |
| 9 | Fraction 18 | 1 μg | 15 |
| 10 | Fraction 19 | 1 μg | 15 |
| 11 | Fraction 20 | 1 μg | 15 |
| 12 | Fraction 21 | 1 μg | 15 |

Figure 76:
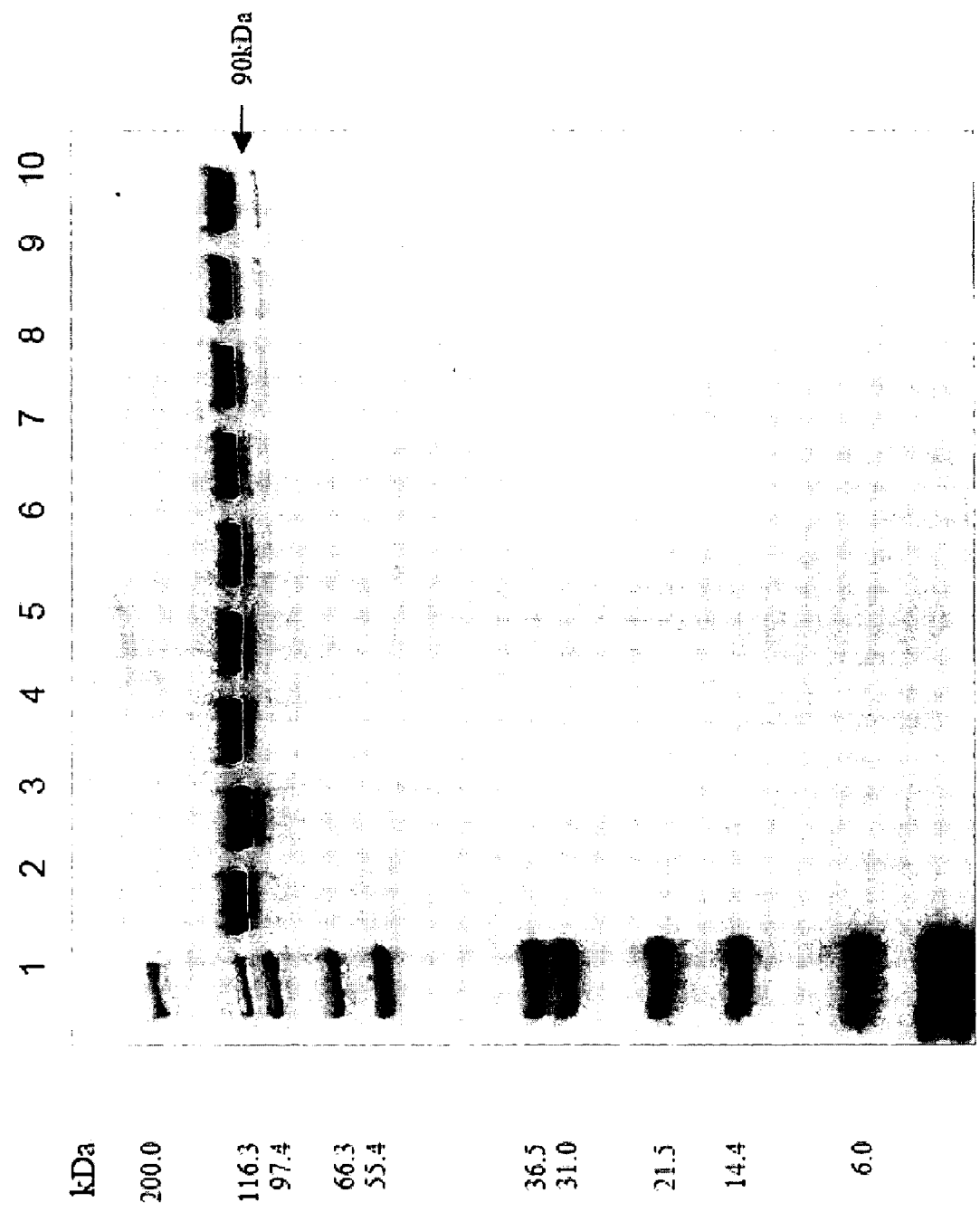

FIG. 76 is a 4-12% Bis Tris SDS-PAGE analysis of fractions from peak 2 (AUXI) eluted during the ion exchange column (FIG. 5). Gel 4: the gel is stained with Colloidal blue:

| Lane | Sample | | Load volume, μl |
|------|--------|---|-----------------|
| 1 | Mark 12 Molecular Weight Marker | | 10 |
| 2 | Collagenase ABC I reference | 1 μg | 15 |
| 3 | Collagenase ABC II reference | 1 μg | 15 |
| 4 | Fraction 22 | 1 μg | 15 |
| 5 | Fraction 23 | 1 μg | 15 |
| 6 | Fraction 24 | AUXI fractions, 1 μg | 15 |
| 7 | Fraction 25 | 1 μg | 15 |
| 8 | Fraction 26 | 1 μg | 15 |
| 9 | Fraction 27 | 1 μg | 15 |
| 10 | Peak 2 Tail | 1 μg | 15 |

Figure 77:
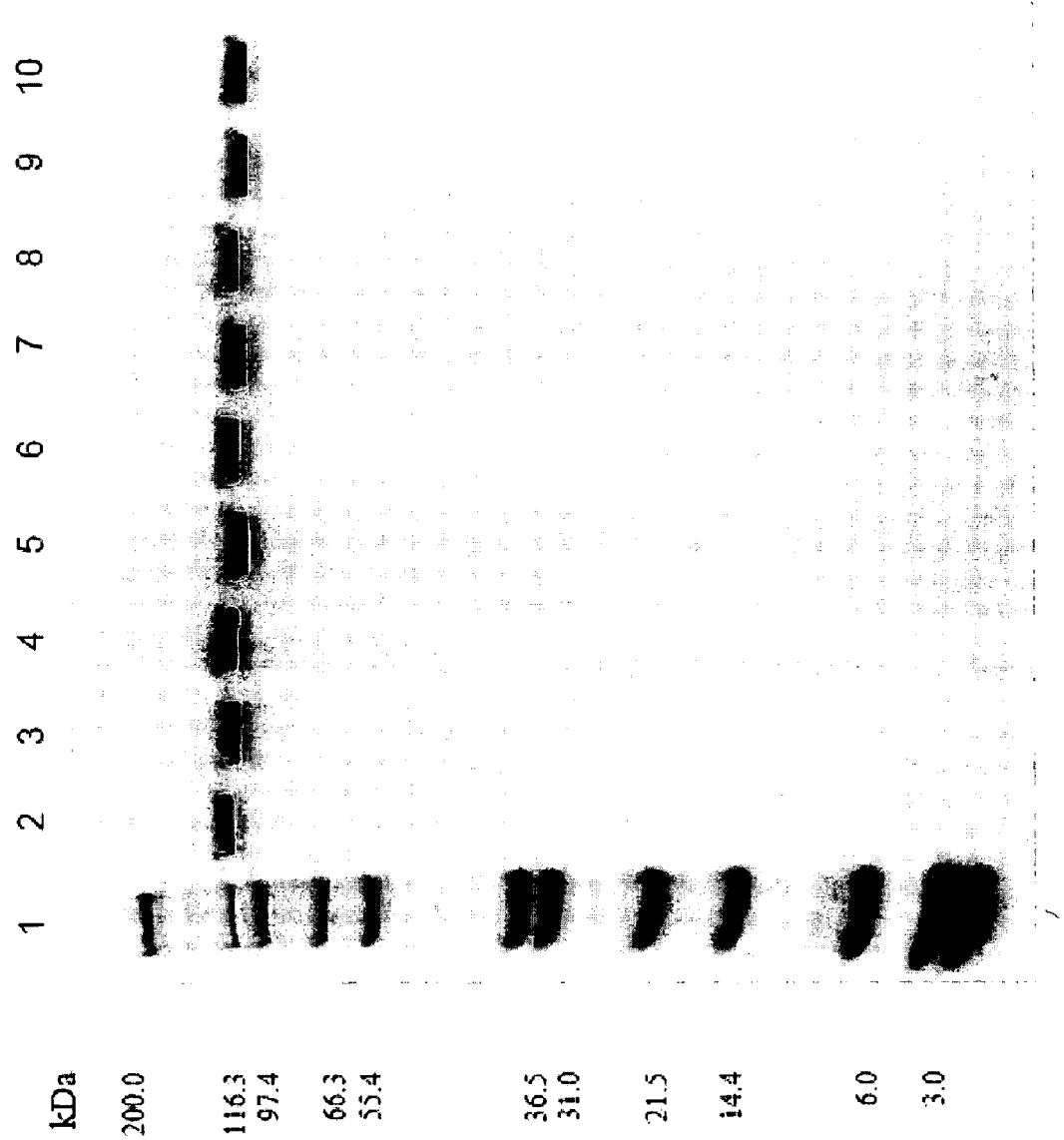

FIG. 77 is a 4-12% Bis-Tris SDS-PAGE analysis of in-process samples from the anion exchange step to final product. The gel is stained with Colloidalblue. Gel 1: 1 μg/lane loading:

| Lane | Sample | Load volume, μl |
|---|---|---|
| 1 | Mark 12 Molecular Weight Marker | 10 |
| 2 | ABC I Reference | 15 |
| 3 | ABC II Reference | 15 |
| 4 | Post IEX AUX I Pool | 15 |
| 5 | Post IEX AUX II Pool | 15 |
| 6 | AUX I Intermediate (DOM: 12 May 2006) | 15 |
| 8 | AUX I Intermediate (Pre Mix) | 15 |
| 9 | AUX II Intermediate (Pre Mix) | 15 |
| 10 | Drug Substance (DOM: 15 May 2006) | 15 |

Figure 78:
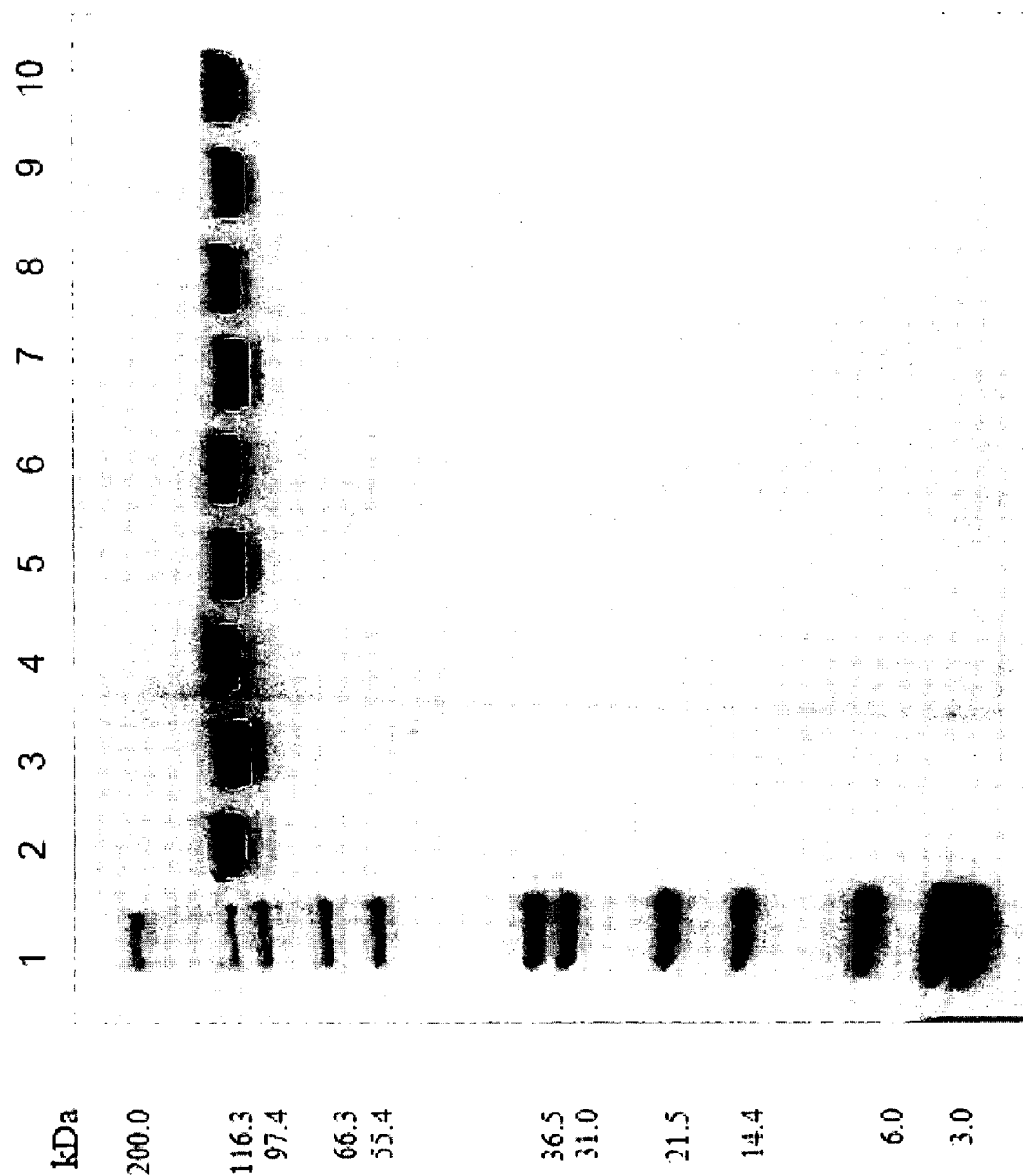

FIG. 78 is a 4-12% Bis-Tris SDS-PAGE analysis of in-process samples from the anion exchange step to final product. The gel is stained with Colloidal blue. Gel 2: 2.5 μg/lane loading:

| Lane | Sample | Load volume, μl |
|---|---|---|
| 1 | Mark 12 Molecular Weight Marker | 10 |
| 2 | ABC I Reference | 15 |
| 3 | ABC II Reference | 15 |
| 4 | Post IEX AUX I Pool | 15 |
| 5 | Post IEX AUX II Pool | 15 |
| 6 | AUX I Intermediate (DOM: 12MAY06) | 15 |
| 7 | AUX II Intermediate (DOM: 10MAY06) | 15 |
| 8 | AUX I Intermediate (Pre Mix) | 15 |
| 9 | AUX II Intermediate (Pre Mix) | 15 |
| 10 | Drug Substance (DOM: 15MAY06) | 15 |

Figure 79:
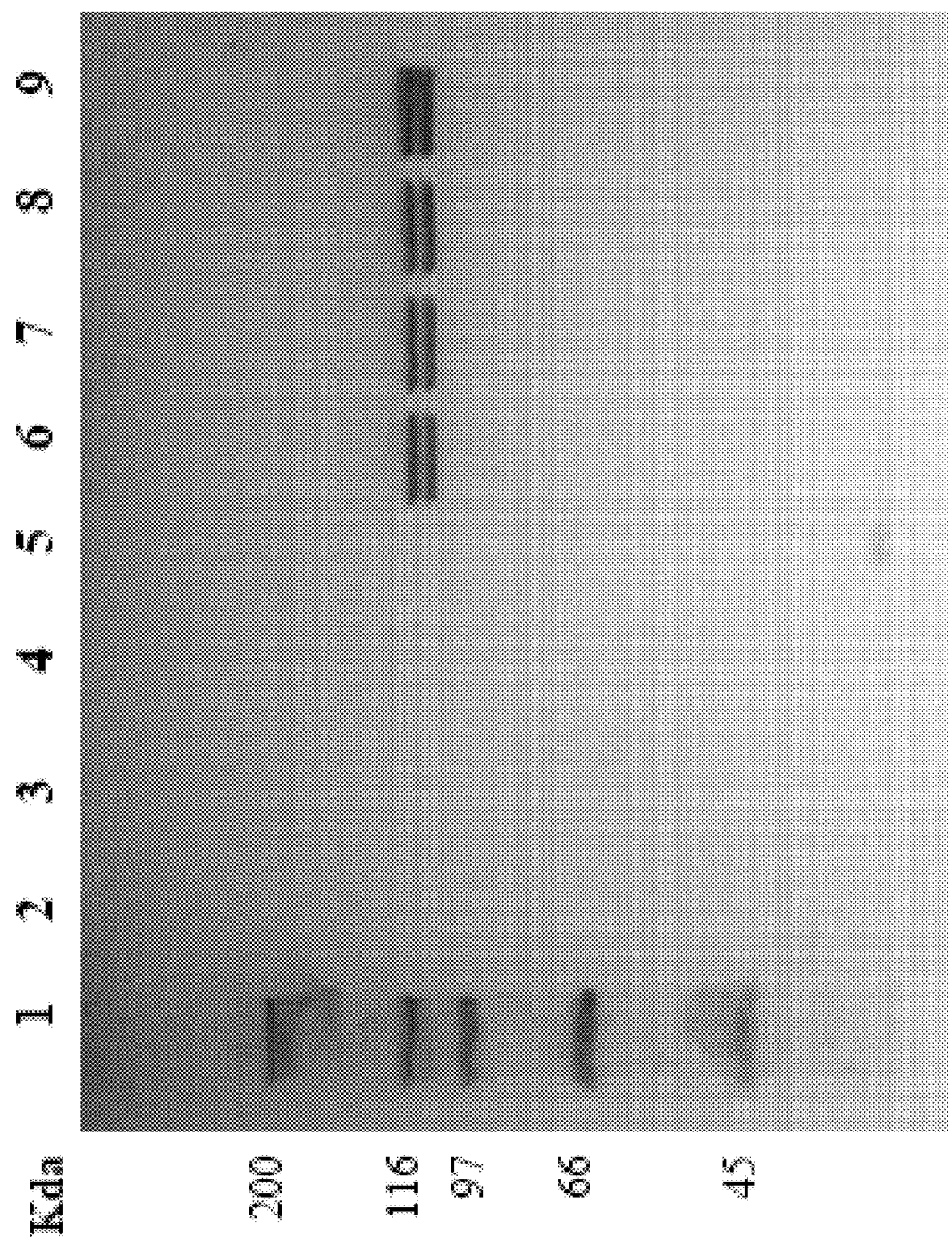

FIG. 79 is a SDS-PAGE with 8% Tris Glycine (NB Ref AS/1640/020):
1. High Molecular Weight Markers
2. Blank Lane
3. 1 μg Fermentation Filtrate Day 4
4. 1 μg Fermentation Filtrate Day 5
5. 1 μg Post Mustang Q Day 4
6. 1 μg Post HIC Day 3
7. 1 μg Post HIC Day 6
8. 1 μg Post TFF Day 2
9. 1 μg Post TFF Day 4

Figure 80:
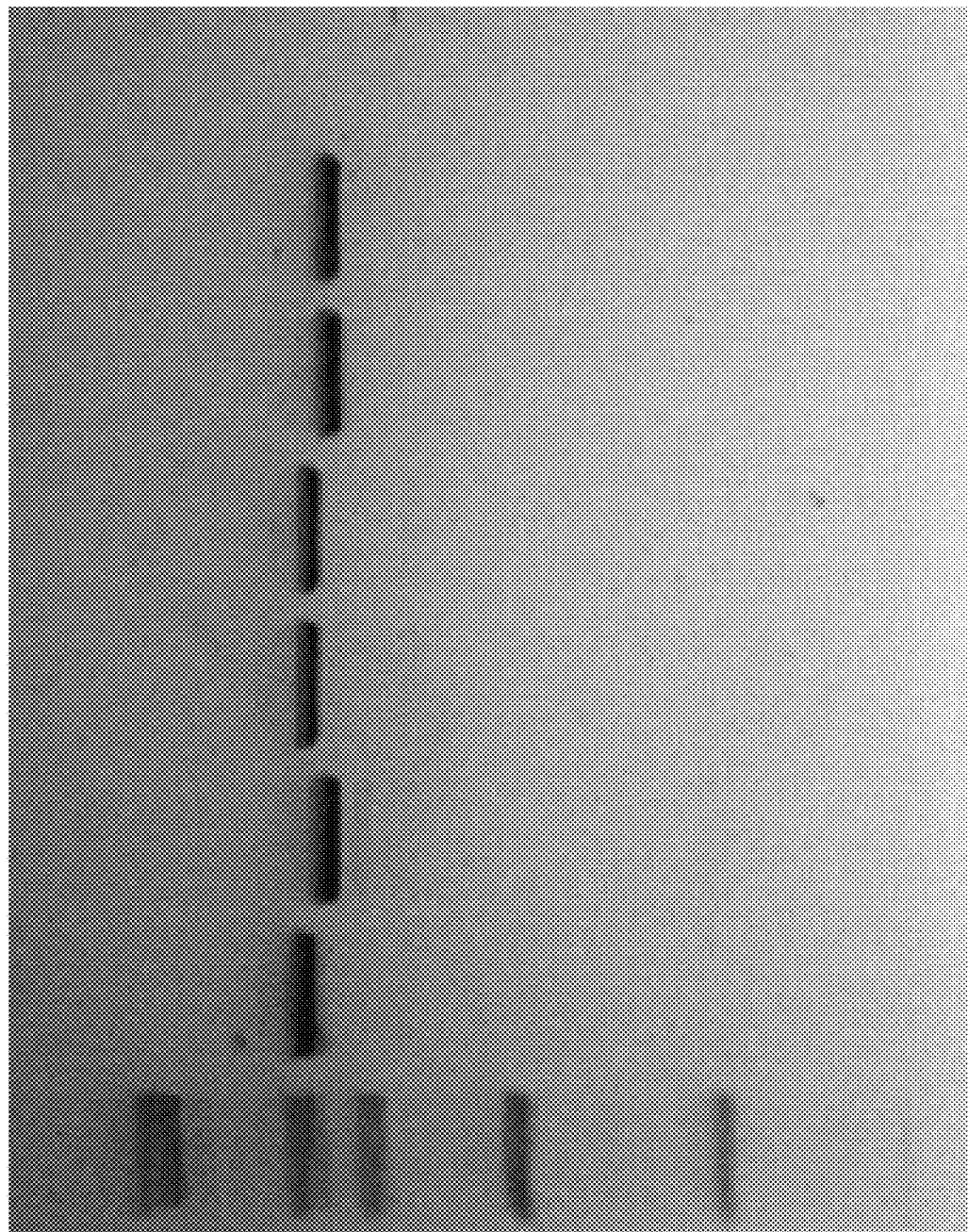

FIG. 80 is a SDS-PAGE with 8% Tris Glycine:
1. High Molecular Weight Markers
2. 1 μg AUX-I Reference
3. 1 μg AUX-II Reference
4. 1 μg Post IEX AUX-I Day D
5. 1 μg Post, IEX AUX-I Day 12
6. 1 μg Post IEX AUX-II Day 5
7. 1 μg Post IEX AUX-II Day 12

Figure 81:
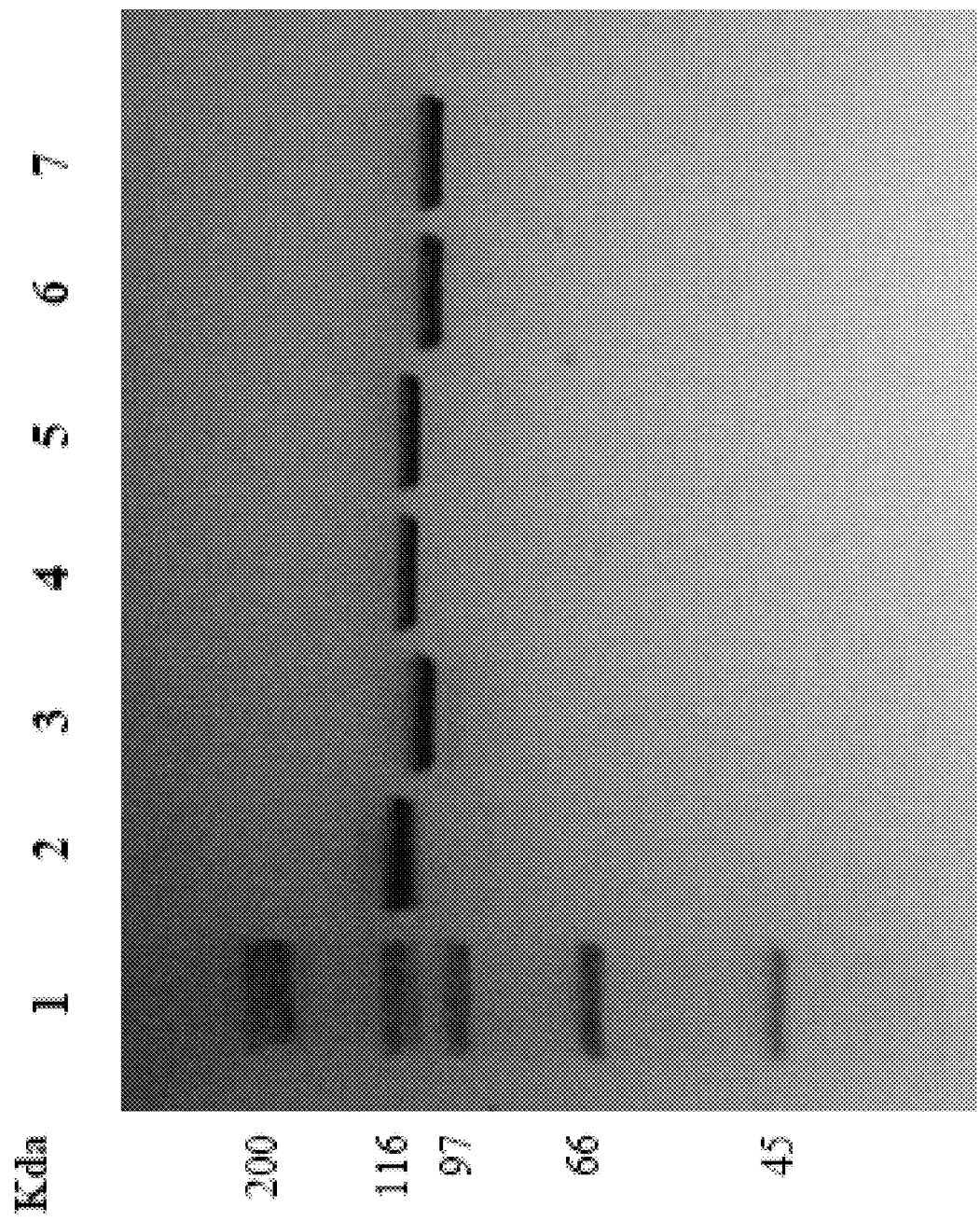

FIG. 81 is a SDS-PAGE gel:
1. High Molecular Weight Markers
2. 1 μg AUX-I Reference
3. 1 μg AUX-II Reference
4. 1 μg AUX-I Intermediate Day 5
5. 1 μg AUX-I Intermediate Day 12
6. 1 μg AUX-I Intermediate Day D
7. 1 μg AUX-II Intermediate Day 12

FIG. 82 represents analytical chromatography analysis.

FIG. 83 shows protein concentration determination by UV.

Figure 84:
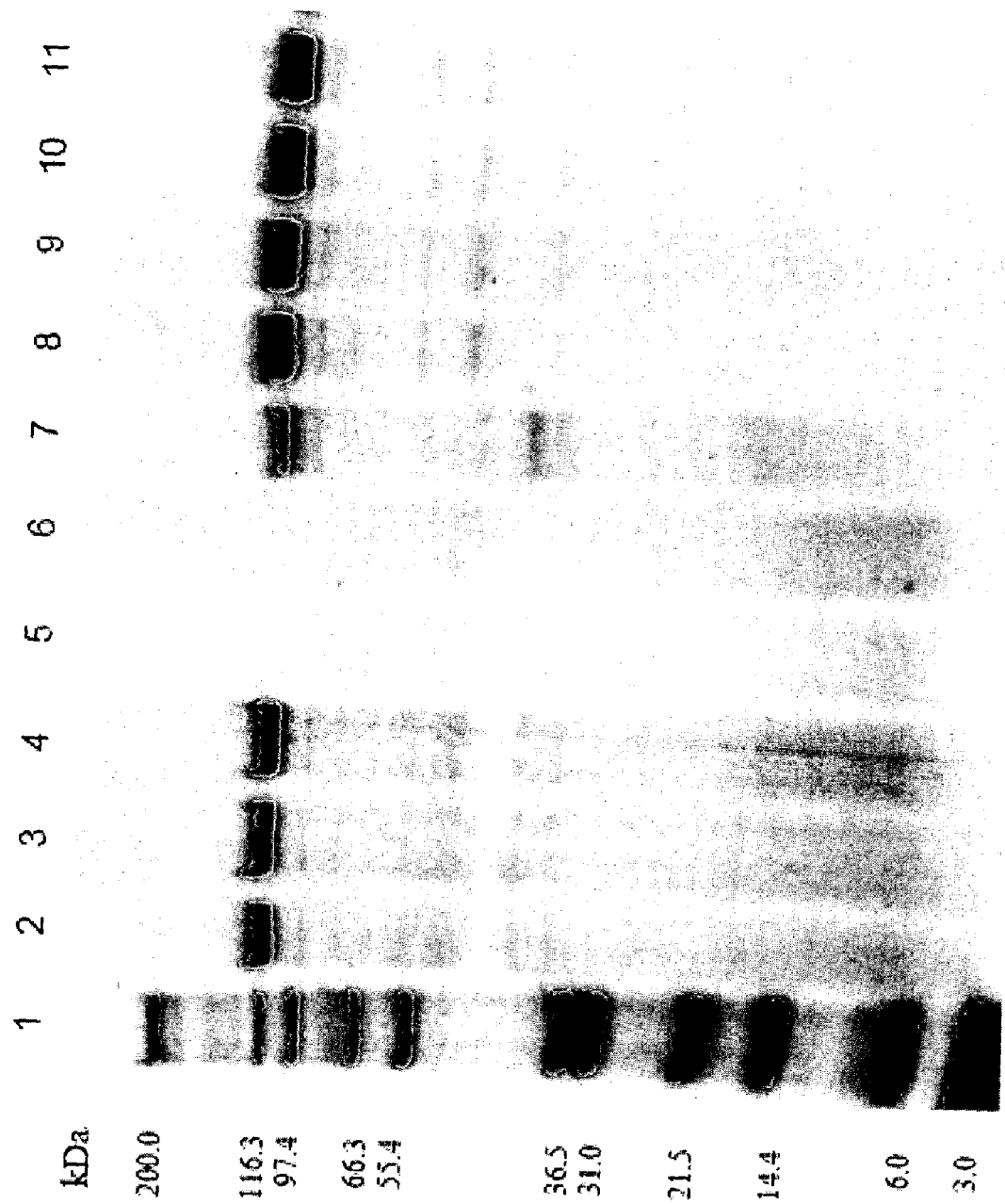

FIG. 84 is a 4-12% Bis-Tris SDS-PAGE analysis of in-process samples from the 20 L demonstration run-through taken at the point of manufacture and stored at −20° C. The gel is stained with Colloidal blue. 1 μg loading:

| Lane | Sample | Load volume, μl |
|---|---|---|
| 1 | Mark 12 Molecular Weight Marker | 12 |
| 2 | Post Mustang Q filtrate | 15 |
| 3 | Pre HIC Bag 1 | 15 |
| 4 | Pre HIC Bag 2 | 15 |
| 5 | HIC flow-through Bag 1 | 15 |
| 6 | HIC flow-through Bag 2 | 15 |
| 7 | HIC Peak 1 (0.3M AS wash) | 15 |
| 8 | Post HIC pool | 15 |
| 9 | Pre TFF1 (post HIC pool + weekend hold) | 15 |
| 10 | Post TFF1 | 15 |
| 11 | Pre Q-AEX (post TFF + overnight hold) | 15 |

Figure 85:
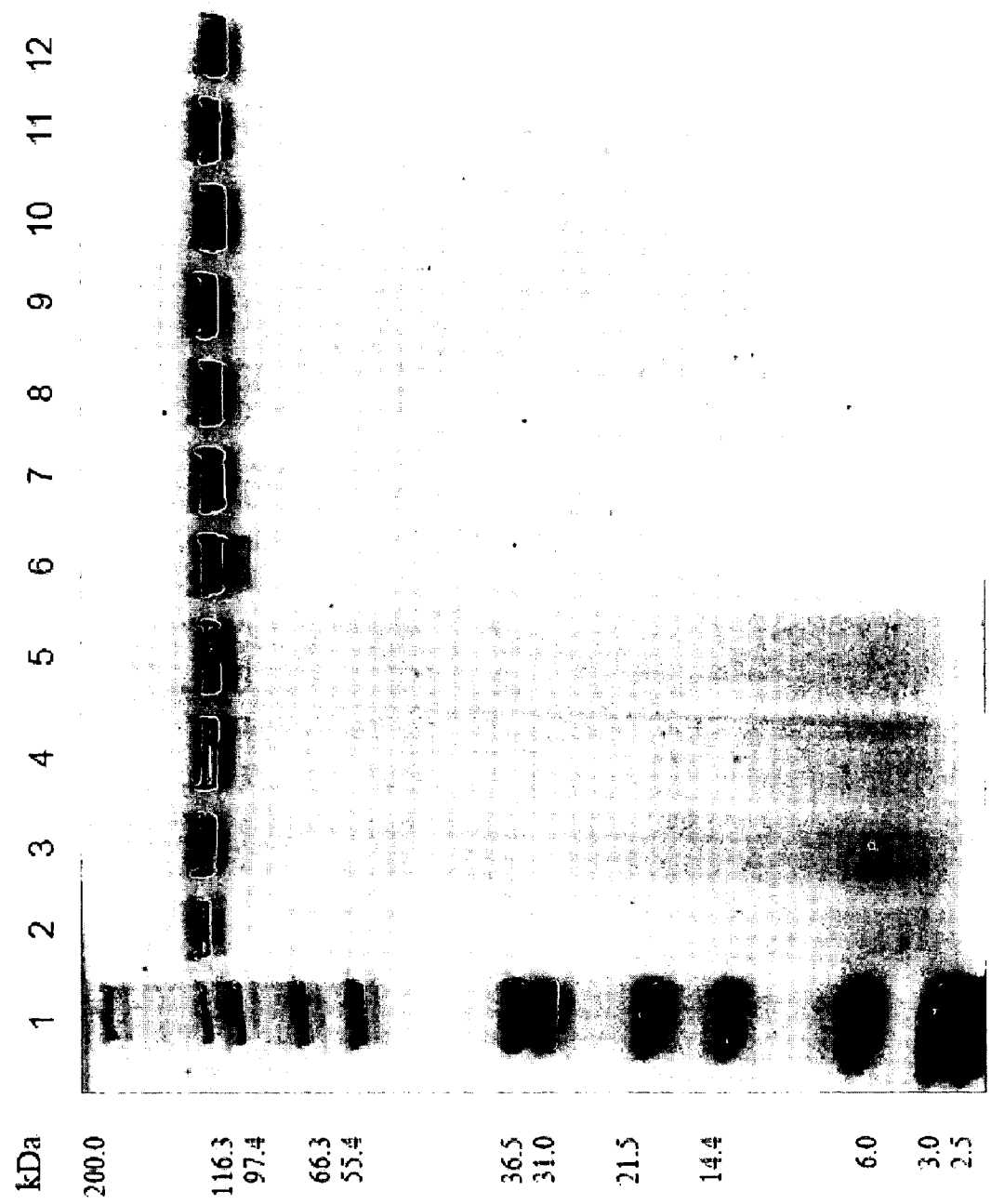

FIG. 85 is a 4-12% Bis-Tris SDS-PAGE analysis of in-process samples from the 20 L demonstration run-through after 22 hrs at Room Temperature. The gel is stained with Colloidal blue:

| Lane | Sample | | Load volume, μl |
|---|---|---|---|
| 1 | Mark 12 Molecular Weight Marker | | 12 |
| 2 | Pre Mustang Q filtrate | | 15 |
| 3 | Post Mustang Q filtrate | | 15 |
| 4 | Pre HIC Bag 1 | | 15 |
| 5 | Pre HIC Bag 2 | | 15 |
| 6 | Post HIC Pool | | 15 |
| 7 | Pre TFF1 | 1 μg loading | 15 |
| 8 | Post TFF1 | | 15 |
| 9 | Post IEX Aux I Pool | | 15 |
| 10 | Post IEX Aux II Pool | | 15 |
| 11 | AUX I Intermediate | | 15 |
| 12 | AUX II Intermediate | | 15 |

Figure 86:
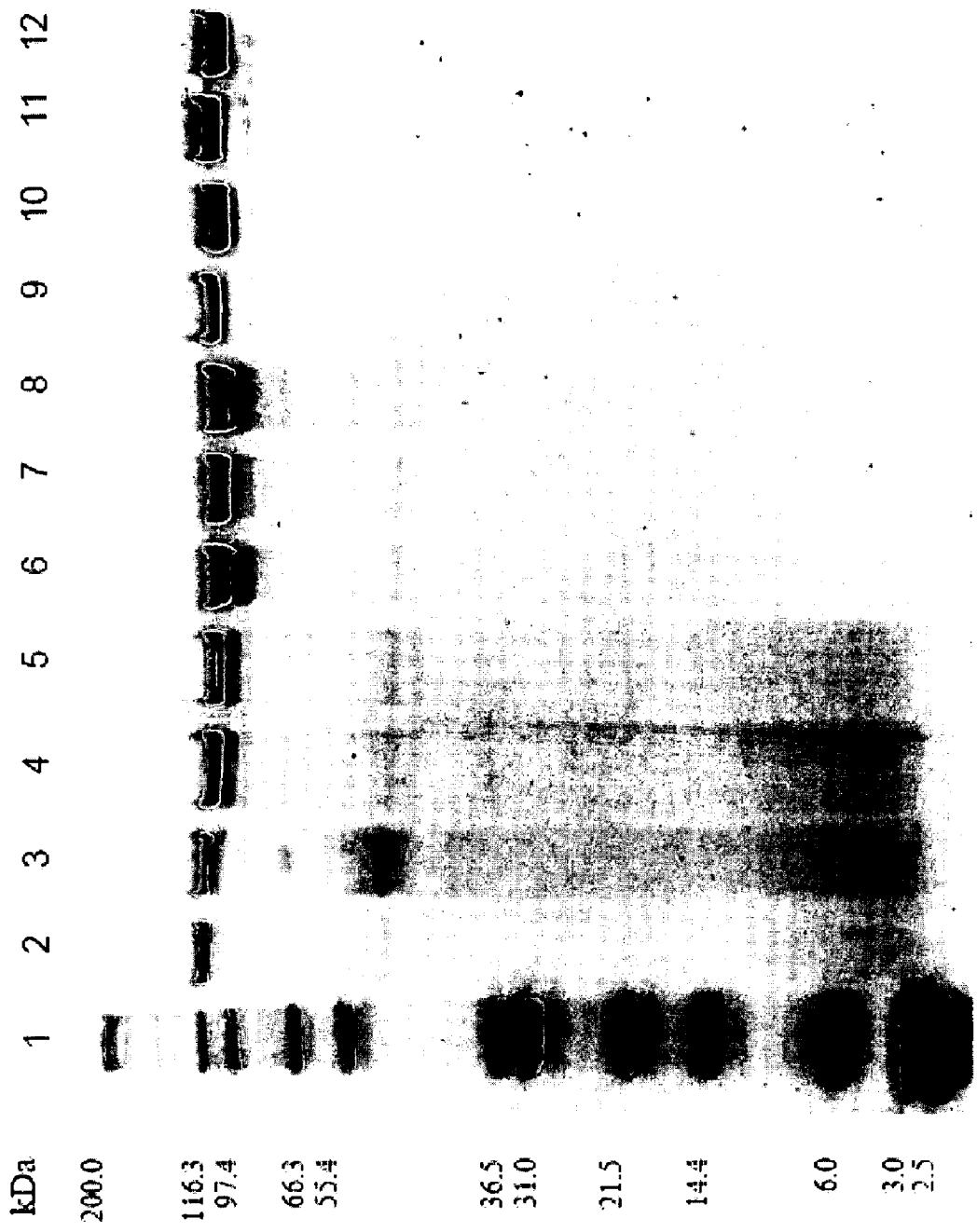

FIG. 86 is a 4-12% Bis-Tris SDS-PAGE analysis of in-process samples from the 20 L demonstration run-through after 22 hrs at 37° C. The gel is stained with Colloidal blue:

| Lane | Sample | | Load volume, μl |
|---|---|---|---|
| 1 | Mark 12 Molecular Weight Marker | | 12 |
| 2 | Pre Mustang Q filtrate | | 15 |
| 3 | Post Mustang Q filtrate | | 15 |
| 4 | Pre HIC Bag 1 | | 15 |
| 5 | Pre HIC Bag 2 | | 15 |
| 6 | Post HIC Pool | | 15 |
| 7 | Pre TFF1 | 1 μg loading | 15 |
| 8 | Post TFF1 | | 15 |
| 9 | Post IEX AUX I Pool | | 15 |
| 10 | Post IEX AUX II Pool | | 15 |
| 11 | AUX I Intermediate | | 15 |
| 12 | AUX II Intermediate | | 15 |

Figure 87:
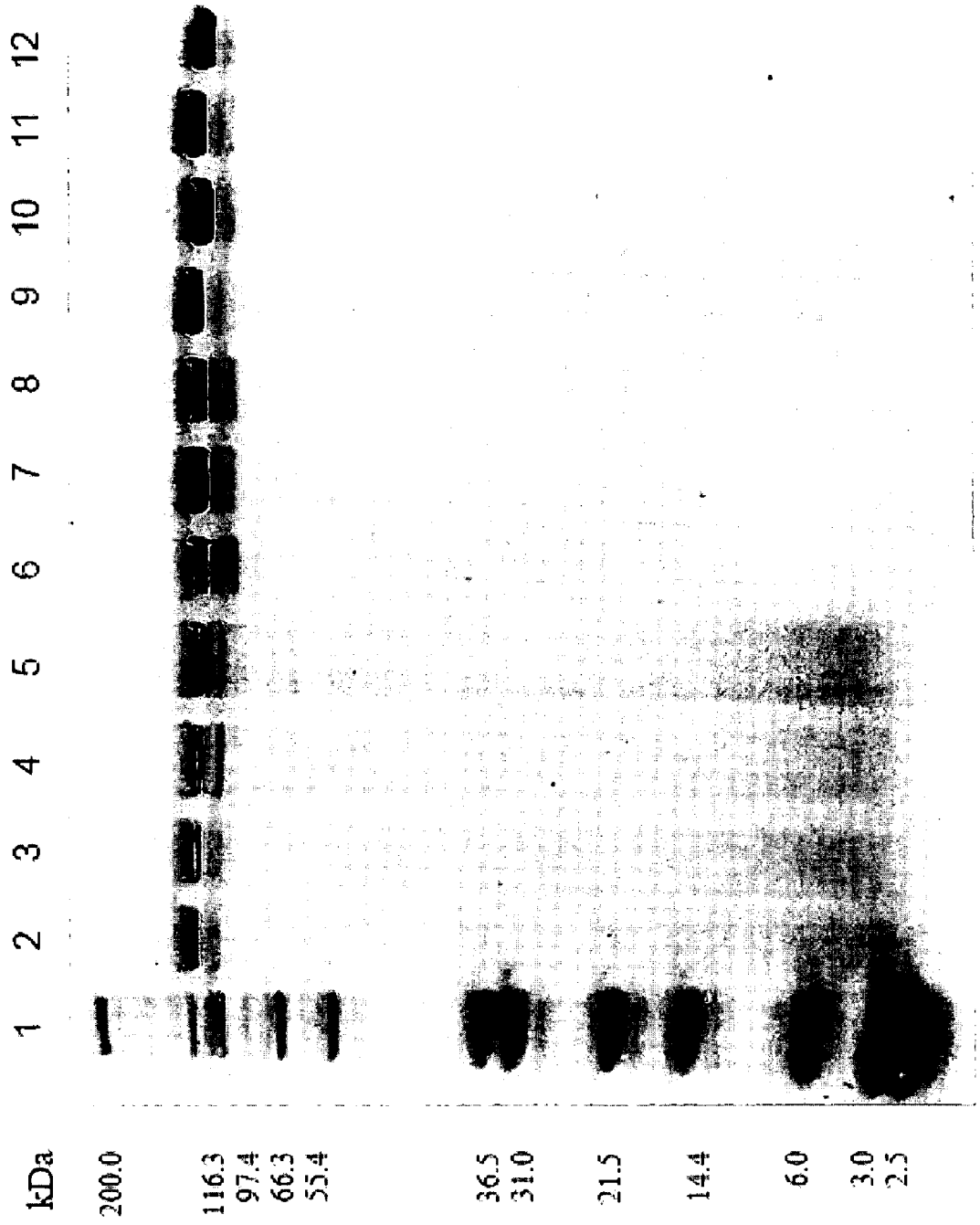

FIG. 87 is a 4-12% Bis-Tris SDS-PAGE analysis of in-process samples from the 20 L demonstration run-through after 94 hrs at Room Temperature. The gel is stained with Colloidal blue:

| Lane | Sample | | Load volume, μl |
|---|---|---|---|
| 1 | Mark 12 Molecular Weight Marker | | 12 |
| 2 | Pre Mustang Q filtrate | | 15 |
| 3 | Post Mustang Q filtrate | | 15 |
| 4 | Pre HIC Bag 1 | | 15 |
| 5 | Pre HIC Bag 2 | | 15 |
| 6 | Post HIC Pool | | 15 |
| 7 | Pre TFF1 | 1 μg loading | 15 |
| 8 | Post TFF1 | | 15 |
| 9 | Post IEX Aux I Pool | | 15 |
| 10 | Post IEX Aux II Pool | | 15 |
| 11 | AUX I Intermediate | | 15 |
| 12 | AUX II Intermediate | | 15 |

Figure 88:
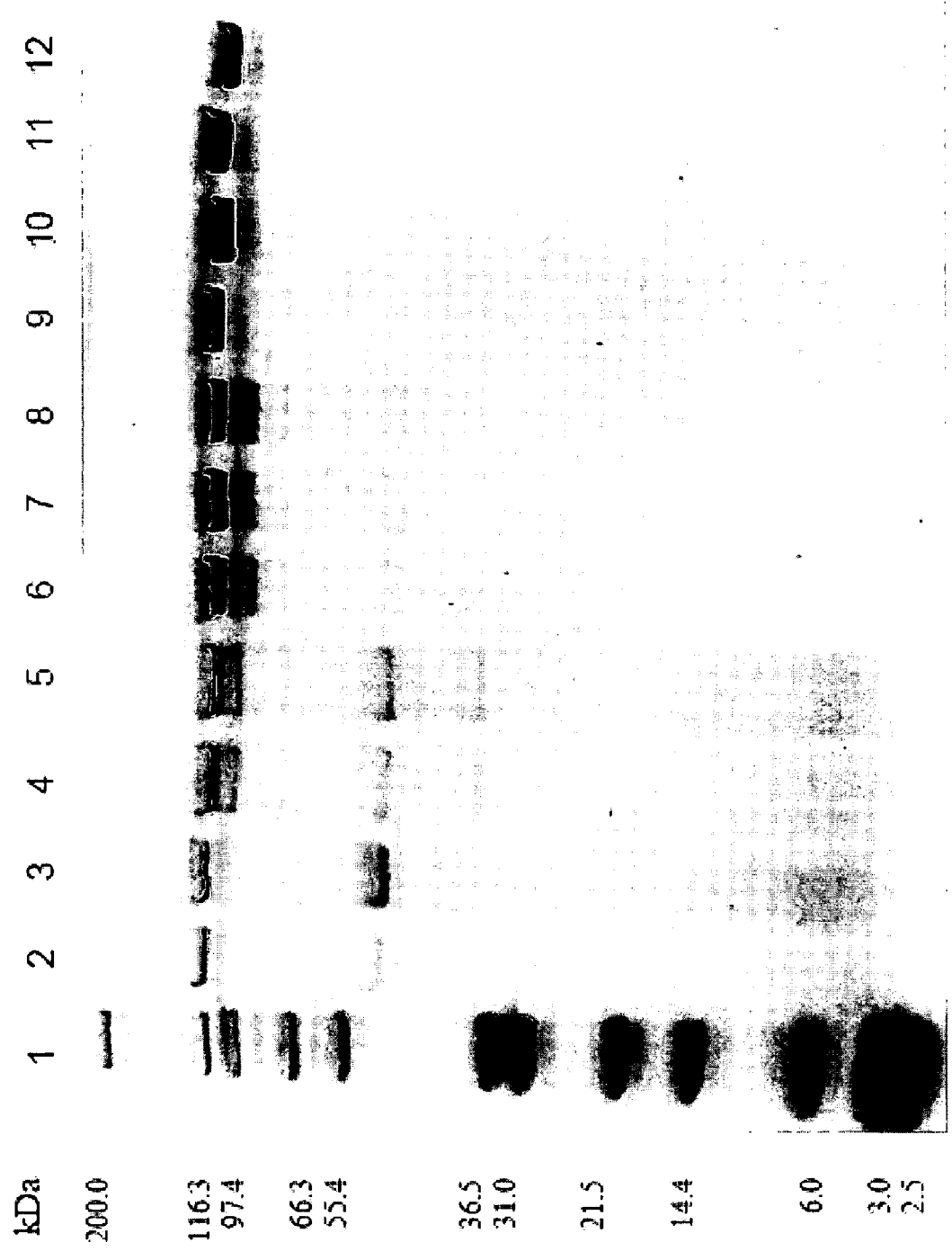

FIG. 88 is a 4-12% Bis-Tris SDS-PAGE analysis of in-process samples from the 20 L demonstration run-through after 94 hrs at 37° C. The gel is stained with Colloidal blue:

| Lane | Sample | | Load volume, μl |
|---|---|---|---|
| 1 | Mark 12 Molecular Weight Marker | | 12 |
| 2 | Pre Mustang Q filtrate | | 15 |
| 3 | Post Mustang Q filtrate | | 15 |
| 4 | Pre HIC Bag 1 | | 15 |
| 5 | Pre HIC Bag 2 | | 15 |
| 6 | Post HIC Pool | | 15 |
| 7 | Pre TFF1 | 1 μg loading | 15 |
| 8 | Post TFF1 | | 15 |
| 9 | Post IEX Aux I Pool | | 15 |
| 10 | Post IEX Aux II Pool | | 15 |
| 11 | AUX I Intermediate | | 15 |
| 12 | AUX II Intermediate | | 15 |

Figure 89:
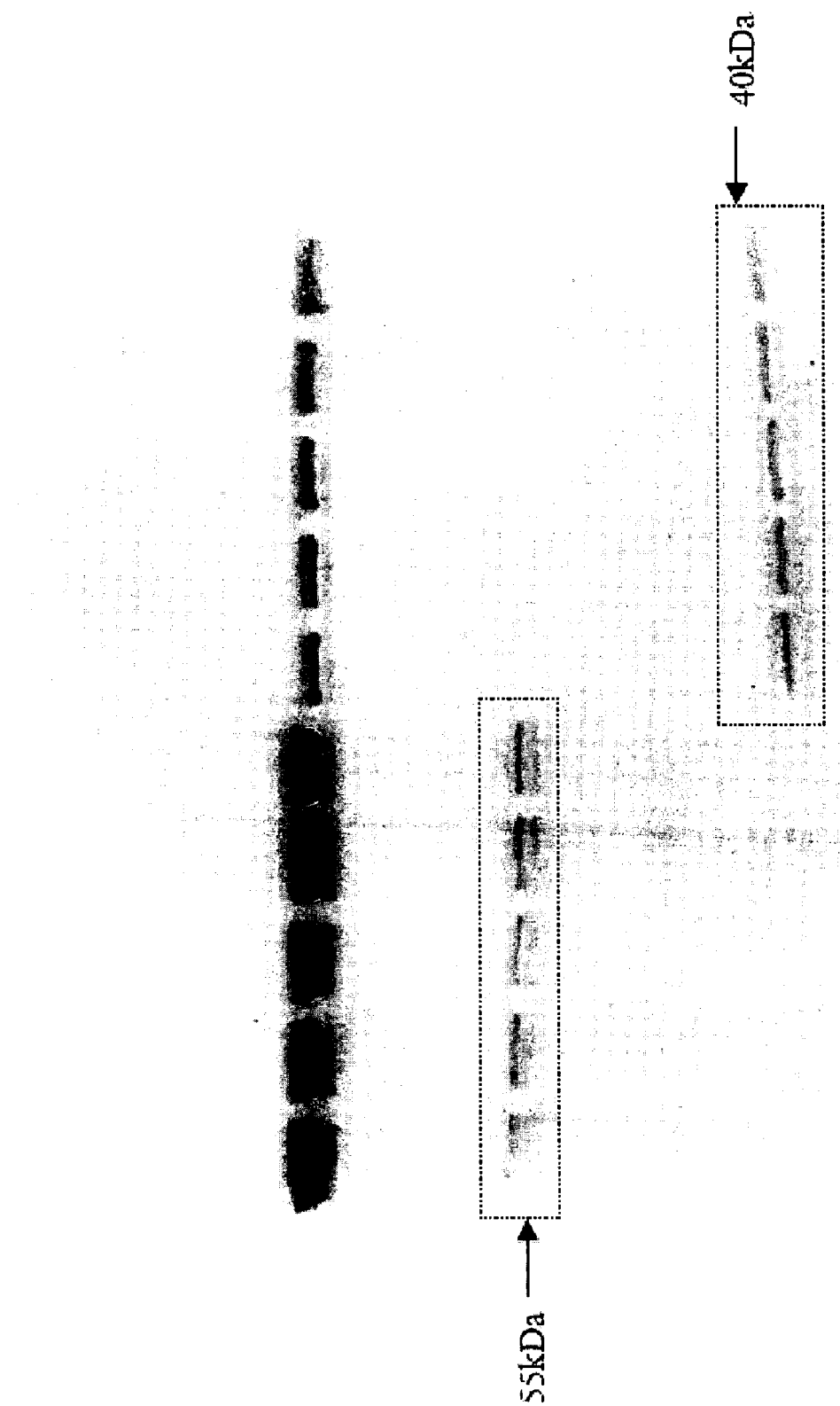

FIG. 89 is a 8% Tris-Glycine SDS-PAGE analysis of selected post IEX AUX I and post IEX AUX II fractions. Fractions were selected from the 20 L demonstration run which were enriched for the required contaminant protein. The gel is stained with Colloidal blue:

| Lane | Sample | | Load volume, μl |
|---|---|---|---|
| 1 | Post IEX AUX I Fraction 16 | | 20 |
| 2 | Post IEX AUX I Fraction 16 | | 20 |
| 3 | Post IEX AUX I Fraction 16 | eluted with | 20 |
| 4 | Post IEX AUX I Fraction 16 | AUXI | 20 |
| 5 | Post IEX AUX I Fraction 16 | | 20 |
| 6 | Post IEX AUX II Fraction 2 | | 20 |
| 7 | Post IEX AUX II Fraction 2 | | 20 |
| 8 | Post IEX AUX II Fraction 2 | eluted with | 20 |
| 9 | Post IEX AUX II Fraction 2 | AUXII | 20 |
| 10 | Post IEX AUX II Fraction 2 | | 20 |

Figure 90:
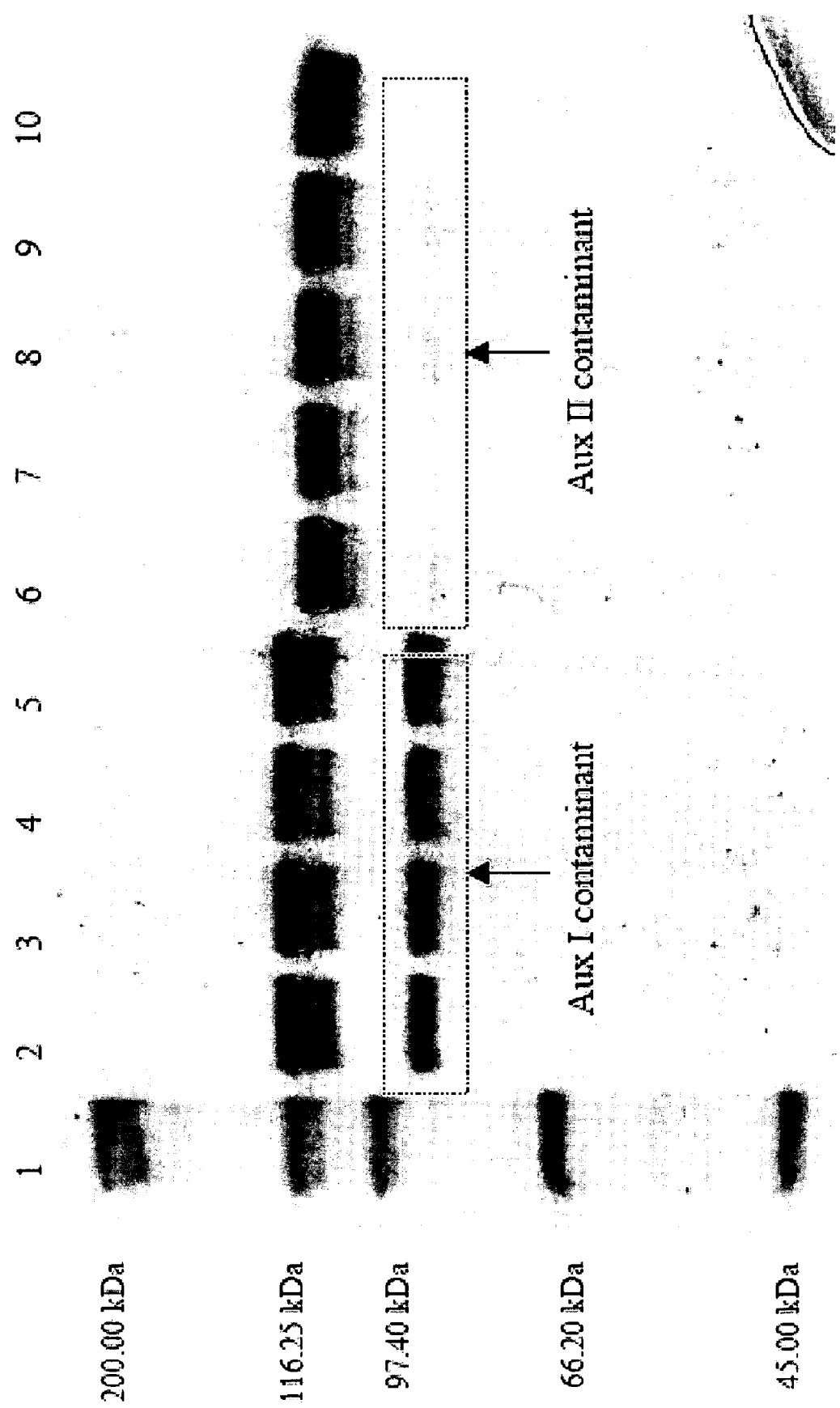

FIG. 90 is a 8% Tris-Glycine SDS-PAGE analysis of selected post IEX AUX I and post IEX AUX II fractions. Fractions were selected from purified material generated from fermentation 20 L PP3 and enriched for the ~90 kDa contaminant protein. The gel is stained with Colloidal blue:

| Lane | Sample | | Load volume, μl |
|---|---|---|---|
| 1 | High Molecular Weight marker | | 20 |
| 2 | Post IEX Fraction B7 R2 | | 20 |
| 3 | Post IEX Fraction B7R2 | | 20 |
| 4 | Post IEX Fraction B7R2 | eluted with | 20 |
| 5 | Post IEX Fraction B7R2 | AUXI | 20 |
| 6 | Post IEX Fraction D1 | | 20 |
| 7 | Post IEX Fraction D1 | | 20 |
| 8 | Post IEX Fraction D1 | eluted with | 20 |
| 9 | Post IEX Fraction D1 | AUXII | 20 |
| 10 | Post IEX Fraction D1 | | 20 |

DETAILED DESCRIPTION OF THE INVENTION

The invention provides a novel collagenase drug substance comprising a mixture of highly purified collagenase I and collagenase II in a mass ratio of about 1 to 1. It has been discovered that a composition comprising a mixture of collagenase I and collagenase II in an artificial mass ratio of 1 to 1 provides highly reproducible and optimal enzymatic activity and imparts superior therapeutic effect while lowering the potential for side effects. It is understood that the terms "drug substance", "drug product" or "collagenase composition" can be used interchangeably.

In one embodiment, the present invention provides a drug substance consisting of collagenase I and collagenase II having the sequence of *Clostridium histolyticum* collagenase I and collagenase II, respectively, having a mass ratio of about 1 to 1 with a purity of at least 95% by area, and preferably a purity of at least 98% by area.

In another embodiment, the present invention provides a drug substance, wherein the drug substance having at least one specification selected from table A below:

TABLE A

| | Specification | |
|---|---|---|
| Test | AUX-I | AUX-II |
| Appearance | Clear colourless and essentially free from particulate matter | |
| Potentiometric Measure of pH of Solution | 7.5 to 8.5 | |
| Endotoxin | <10 EU/mL | |
| Identity (and purity) by SDS-PAGE (Reduced conditions, Coomasie and silver stained) | Major collagenase band between 98-188 kDa MW markers | Major collagenase band between 97-200 kDa; MW markers; major bands comparable to reference standard |

TABLE A-continued

| | Specification | |
|---|---|---|
| Test | AUX-I | AUX-II |
| Total Protein by Absorbance Spectroscopy | 0.8-1.2 mg/mL | |
| SRC assay (AUX-I) | 13 000-23 000 fSRC units/mg | NA |
| GPA assay (AUX-II) | NA | 230 000-430 000 fGPA units/mg |
| Residual host cell protein | Comparable to reference standard; no individual impurity band exhibiting greater intensity than 1% BSA intensity marker | |
| Residual host cell DNA | $\leq$10 pg/dose | |
| Analysis of Proteins using the Agilent 1100 HPLC System (Aggregation by size exclusion chromatography) | $\geq$98% main peak; $\leq$2% aggregates by area | |
| Analysis of Proteins using the Agilent 1100 HPLC System (Identity and purity by reverse phase liquid chromatography) | 2 major peaks (AUX I & AUX II), combined $\geq$97% by area; Retention times of AUX-I and AUX-II within 5% of reference | |
| Analysis of Proteins using the Agilent 1100 HPLC System (Residual clostripain by reverse phase liquid chromatography | $\leq$1% by area | |
| Analysis of Proteins using the Agilent 1100 HPLC System (Residual gelatinase by anion exchange chromatography) | $\leq$1% by area | |
| Residual leupeptin by reverse phase chromatography | $\leq$1 ug/mg w/w | |
| Bioburden | <1 cfu/mL | |

In one aspect, the invention provides a process for producing a drug substance consisting of collagenase I and collagenase II having the sequence of *Clostridium histolyticum* collagenase I and collagenase II, respectively, having a mass ratio of about 1 to 1 with a purity of at least 95% by area, comprising the steps of:
  a) fermenting *Clostridium histolyticum*;
  b) harvesting a crude product comprising collagenase I and collagenase II;
  c) purifying collagenase I and collagenase II from the crude harvest via filtration and column chromatography; and
  d) combining the collagenase I and collagenase II purified from step (c) at a ratio of about 1 to 1.

In one preferred embodiment, the fermentation step is conducted in the presence of a porcine derived, a phytone peptone or a vegetable peptone medium. More preferably, the porcine derived medium is protease peptone #3.

In one embodiment, the invention provides a fermentation procedure comprising the steps of:
  a) inoculating the medium in a first stage with *Clostridium histolyticum* and agitating the mixture;
  b) incubating the mixture from step (a) to obtain an aliquot;
  c) inoculating the medium in a second stage with aliquots resulting from step (b) and agitating the mixture;
  d) incubating mixtures from step (c);
  e) inoculating the medium in a third stage with aliquots resulting from step (d) and agitating;
  f) incubating mixtures from step (e);
  g) inoculating the medium in a fourth stage with an aliquot resulting from step (f) and agitating;
  h) incubating mixtures from step (g); and
  i) harvesting culture resulting from step (h) by filtration.

In a preferred embodiment, the fermentation procedure comprises the steps of:
  a) Inoculating 3×25 mL PP3 (protease peptone) medium with 3×250 μL of WCB (25 mL cultures in 3×125 mL shake flasks, contained within Anaerobe gas jar) at a temperature set point of 37° C., and agitating the mixture at 125 rpm;
  b) incubating the mixture from step (a) for 12 hours;
  c) inoculating Inoculate 4×200 mL PP3 medium with 4×5 mL aliquots from 1 of the above 25 mL cultures (200 mL cultures in 4×500 mL shake flasks, contained within Anaerobe gas jar) at a temperature set point of 37° C., and agitating the mixture at 125 rpm;
  d) incubating mixtures from step (c) for 12 hours;
  e) inoculating 14.4 L of PP3 medium with 3×200 mL culture (15 L culture in 20 L fermenter) at a temperature set point of 37° C. and pH set point of 7.00, and agitating the mixture at 125 rpm;
  f) incubating mixtures from step (e) for 12 hours;
  g) inoculating 192 L of PP3 medium with 8 L of 15 L culture (200 L culture in 270 L fermenter) at a temperature set point of 37° C. and pH set point of 7.00, and agitating the mixture at 125 rpm;
  h) incubating mixtures from step (g) for 14 hours; and
  i) harvesting 200 L culture by filtration (depth followed by 0.2 μm) via Millipore Millistak 4 m² and 0.2 μm filter (2× Millipore Express XL 10 filters) at a flow rate of 200 L/h.

In one embodiment, the invention provides a purification procedure comprising the steps of:
  a) filtering the crude harvest through a MUSTANG Q anion-exchange capsule filter;

b) adding ammonium sulphate; preferably to a final concentration of 1M;
c) filtering the crude harvest; preferably through a 0.45 µm filter;
d) subjecting the filtrate through a HIC column; preferably a phenyl sepharose 6FF (low sub);
e) adding leupeptin to the filtrate; preferably to a final concentration of 0.2 mM to post HIC eluted product;
f) removing the ammonium sulfate and maintaining leupeptin for correct binding of collagenase I and collagenase II with buffer exchange by TFF; preferably with buffer exchange by TFF;
g) filtering the mixture of step (f); preferably through a 0.45 µm filter;
h) separating collagenase I and collagenase II using Q-Sepharose HP;
i) preparing TFF concentration and formulation for collagenase I and collagenase II separately; wherein TFF is a tangential flow filtration using 10 and/or 30 K MWCO (molecular weight cut-off) PES or RC-polyethersulfone or regenerated cellulose filter membranes. Provides means to retain and concentrate select protein and exchange the protein from one buffer solution into another; and
j) filtering through a 0.2 µm filtration system.

The drug substance of the present invention includes both collagenase I and collagenase II. A preferred source of crude collagenase is from a bacterial fermentation process, specifically the fermentation of *C. histolyticum* (*C. his*). In one embodiment of the invention, a fermentation process is described. The crude collagenase obtained from *C. his* may be purified by a variety of methods known to those skilled in the art, including dye ligand affinity chromatography, heparin affinity chromatography, ammonium sulfate precipitation, hydroxylapatite chromatography, size exclusion chromatography, ion exchange chromatography, and metal chelation chromatography. Crude and partially purified collagenase is commercially available from many sources including Advance Biofactures Corp., Lynbrook, N.Y.

Both collagenase I and collagenase II are metalloproteases and require tightly bound zinc and loosely bound calcium for their activity (Eddie L. Angleton and H. E. Van Wart, *Biochemistry* 1988, 27, 7406-7412). Both collagenases have broad specificity toward all types of collagen (Steinbrink, D; Bond, M and Van Wart, H; (1985), *JBC*, 260 p 2771-2776). Collagenase I and Collagenase II digest collagen by hydrolyzing the triple-helical region of collagen under physiological conditions (Steinbrink, D; Bond, M and Van Wart, H; (1985), *JBC*, 260 p 2771-2776). Even though each collagenase shows different specificity (e.g. each have a different preferred amino sequence for cleavage), together, they have synergistic activity toward collagen [Mandl, I., (1964), *Biochemistry*, 3: p. 1737-1741; Vos-Scheperkeuter, G H, (1997), *Cell Transplantation*, 6: p. 403-412]. Collagenase II has a higher activity towards all kinds of synthetic peptide substrates than collagenase I as reported for class II and class I collagenase in the literatures. [Bond, M. D. (1984), *Biochemistry*, 23: p. 3085-3091. Hesse, F, (1995), *Transplantation Proceedings*, 27: p. 3287-3289].

Examples of collagen mediated-diseases that may be treated by the compositions and methods of the invention include but are not limited to: Dupuytren's disease; Peyronie's disease; frozen shoulder (adhesive capsulitis), keloids; hypertrophic scars; depressed scars such as those resulting from inflammatory acne; post-surgical adhesions; acne vulgaris; lipomas, and disfiguring conditions such as wrinkling, cellulite formation and neoplastic fibrosis. U.S. Pat. Nos. 6,086,872 and 5,589,171 incorporated herein by reference disclose the use of collagenase preparations in the treatment of Dupuytren's disease. U.S. Pat. No. 6,022,539 incorporated herein by reference discloses the use of collagenase preparations in the treatment of Peyronie's disease.

In addition its use in treating collagen-mediated diseases, the composition of the invention is also useful for the dissociation of tissue into individual cells and cell clusters as is useful in a wide variety of laboratory, diagnostic and therapeutic applications. These applications involve the isolation of many types of cells for various uses, including microvascular endothelial cells for small diameter synthetic vascular graft seeding, hepatocytes for gene therapy, drug toxicology screening and extracorporeal liver assist devices, chondrocytes for cartilage regeneration, and islets of Langerhans for the treatment of insulin-dependent diabetes mellitus. Enzyme treatment works to fragment extracellular matrix proteins and proteins which maintain cell-to-cell contact. Since collagen is the principle protein component of tissue ultrastructure, the enzyme collagenase has been frequently used to accomplish the desired tissue disintegration. In general, the composition of the present invention is useful for any application where the removal of cells or the modification of an extracellular matrix, are desired.

Collagenase compositions of the invention may also be prepared by mixing either a specific number of activity units or specific masses of the preferably purified enzymes. Collagenase activity can be measured by the enzyme's ability to hydrolyze either synthetic peptide or collagen substrate. Those skilled in the art will recognize that enzyme assays other than those disclosed herein may also be used to define and prepare functionally equivalent enzyme compositions.

Another aspect of the present invention is the reproducible optimization of the 1 to 1 mass ratio of collagenase I to collagenase II in the composition of the invention. The reproducibility of the ratio of collagenase I to collagenase II has previously been a challenge because of several factors. First, commercial fermentation of *Clostridium* generally results in a 1 to 2 ratio of collagenase I and collagenase II. Second, the purification procedures are known to alter this ratio significantly resulting in inconsistent ratios of purified product. The optimized fixed mass ratio of the composition of the present invention maximizes the synergistic activity provided by the two different collagenases resulting in superior therapeutic benefit.

The invention also provides pharmaceutical formulations of the compositions of the invention. The pharmaceutical formulations of the present invention comprise a therapeutically effective amount of a collagenase composition of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, perfuming agents, preservatives and antioxidants can also be present in the composition, according to the judgment of the formulator.

The pharmaceutical compositions of this invention may be administered parenterally, topically, or via an implanted reservoir. The term parenteral as used herein includes subcutaneous, intracutaneous, intravenous, intramuscular, intraarticular, intraarterial, intrasynovial, intrasternal, intrathecal, intralesional and intracranial injection or infusion techniques. In a preferred embodiment, the composition is injected into the disfiguring tissue. In the case of Peyronie's or Duputyren's diseases or adhesive capsulitis, the composition is injected into the cord or plaque. The term "local administration" is defined herein to embrace such direct injection.

Furthermore, particularly good results can be obtained by immobilizing the site of injection after administration. For example, the site of administration can be immobilized for 4 or more hours.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The sterile solutions may also be lyophilized for later use.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In one preferred embodiment, the drug substance of the invention is a lyophilized injectable composition formulated with lactose. In one embodiment each milligram of injectable collagenase is formulated with 1.9 mg of lactose. In another embodiment, each milligram of injection collagenase preferably has approximately 2800 SRC units and 51000 units measured with a potency assay using a synthetic substrate, pzGPGGPA.

In another preferred embodiment, the collagenase composition of the invention is a lyophilized injectable composition formulated with Sucrose, Tris at a pH level of about 8.0. Most preferably, 1.0 mg of the drug substance of the invention is formulated in 60 mM Sucrose, 10 mM Tris, at a pH of about 8.0 (this equates to 20.5 mg/mL of sucrose and 1.21 mg/mL of Tris in the formulation buffer). Examples of some of the formulations include, but not limited to: for a 0.9 mg of the drug substance dose, 18.5 mg of sucrose and 1.1 mg of Tris are added in each vial, where the targeting a vial fill volume is 0.9 mL; and for a 0.58 mg of the drug substance dose, 12.0 mg sucrose (multicompendial) and 0.7 mg of Tris (multicompendial).

In accordance with the invention, methods are provided for treating collagen-mediated diseases comprising the step of administering to a patient in need thereof, a therapeutically effective amount of a composition of the invention, or a therapeutically effective amount of a pharmaceutical formulation of the invention. By a "therapeutically effective amount" of a compound of the invention is meant an amount of the compound which confers a therapeutic effect on the treated subject, at a reasonable benefit/risk ratio applicable to any medical treatment.

The therapeutic effect may be objective (i.e., measurable by some test or marker) or subjective (i.e., subject gives an indication of or feels an effect). Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The drug substance for injectable collagenase consists of two microbial collagenases, referred to as Collagenase AUX I and Collagenase ABC I and Collagenase AUX II and Collagenase ABC II. It is understood that the terms "Collagenase I", "ABC I", "AUX I", "collagenase AUX I", and "collagenase ABC I" mean the same and can be used interchangeably. Similarly, the terms "Collagenase II", "ABC II", "AUX II", "collagenase AUX II", and "collagenase ABC II" refer to the same enzyme and can also be used interchangeably. These collagenases are secreted by bacterial cells. They are isolated and purified from *Clostridium histolyticum* culture supernatant by chromatographic methods. Both collagenases are special proteases and share the same EC number (E.C 3.4.24.3).

Collagenase AUX I has a single polypeptide chain consisting of approximately 1000 amino acids with a molecular weight of 115 kDa. Collagenase AUX II has also a single polypeptide chain consisting of about 1000 amino acids with a molecular weight of 110 kDa.

Even though the literature indicates that there are sequence homologies in regions of collagenase AUX I and AUX II, the two polypeptides do not seem to be immunologically cross reactive as indicated by the western blot analysis.

The drug substance (collagenase concentrate) has an approximately 1 to 1 mass ratio for collagenase AUX I and AUX II. The collagenase concentrate has an extinction coefficient of 1.528.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Process 2:

Fermentation Process

This work was set out to develop a fermentation process that aimed at delivering a target yield of 250 mg/L of total collagenases ABC I & II from the 5 L fermentation scale process in an animal free component growth media. Various potential alternative nitrogen sources were screened to see if they had any affect on collagenase expression over and the above the phytone component currently used in the growth media. An experiment comparing productivities from two strains of C. histolyticum, 004 and 013, was to determine any differences between the two strains with respect to growth kinetics, collagenase productivity and production of contaminating proteases grown in an animal derived media. This comparison highlighted significant differences between growing the C. histolyticum strain in animal derived media as opposed to animal free growth media.

Previous results described that increased concentrations of phytone and yeast extract were shown to support higher biomass concentrations and hence higher levels of total collagenase expression. In an attempt to further increase biomass concentrations and total collagenase productivity of the optimised batch fermentation media, a fed-batch fermentation strategy was designed. Two 5 L fermentations were performed, one with a high concentration of media in the batch phase followed by a low concentration feeding phase, the second with a low concentration of media in the batch phase followed with a high concentration feeding phase. Both fermentations produced high biomass concentrations, however the high concentration batch phase showed relatively low levels of collagenase expression. The low concentration batch fermentation showed very high levels of collagenase expression (~280 mg/L), however this culture also produced significant quantities of the contaminating protease, clostripain.

Although the low concentration batch fermentation gave very good results with respect to expression of the collagenases, the highly concentrated phytone and yeast extract feed solution was very difficult to prepare. Two additional fermentations were performed, the first was a repeat of the previous successful fed-batch fermentation the second had a slightly higher concentration batch phase media composition with a lower concentrated feeding solution. Both fermentations achieved similar biomass concentrations and showed the same expression profile of the collagenases and clostripain. The quantity of collagenase produced was again estimated at approximately 280 mg/L in both fermentations. However, these fermentations produced significant quantities of the contaminating protease clostripain.

A selection of alternative nitrogen sources were assessed for their ability to replace the phytone peptone used in the fed-batch fermentation strategy. The C. histolyticum grew extremely well on the vegetable peptones reaching optical densities (600 nm) of 4 to 5 units. However, SDS-PAGE analysis of these fermentations showed no expression of either collagenase or clostripain. Due to the luxuriant cell growth observed on these peptones it was thought that the concentration of complex nitrogen source was too high resulting in an inhibition of protease expression. A second set of fermentations was therefore carried out using the alternative peptones at 50 g/L in a batch strategy. When the fermentations were analyzed by SDS-PAGE no expression of collagenase or clostripain was seen again. A fed-batch fermentation using phytone peptone was supplemented with three amino acids, glutamine, tryptophan and asparagine. These amino acids were identified as being present in lower amounts in the non-animal media. The growth profile of the fermentation was very similar to that of the fed-batch fermentation without amino acid supplementation. SDS-PAGE analysis showed a similar yield of collagenase but a slightly lower level of clostripain. The clostripain assay showed reduced activity in the amino supplemented when compared to the control fed-batch fermentation. The reduction in clostripain activity whilst still significant was not as great as the difference between animal and non-animal media.

The assessment of the primary recovery step of the collagenases using ammonium sulphate precipitation was carried out on 0.2 μm filtrates of the crude fermentation supernatants. The aim here was to help increase the collagenase yield and ideally decrease the quantity of clostripain that was carried through the process. Initially ammonium sulphate concentrations of 100-400 g/L were assessed. Ammonium sulphate at 400 g/L resulted in significant recovery of collagenase. A further study was carried out with a higher range of ammonium sulphate (400-520 g/L). In addition, the effect of decreasing the pH to 6.0 and oxygenating the media prior to precipitation were also investigated. No difference was observed in either the quantity of the collagenases or clostripain recovered from the supernatant under any of these conditions. The pellet generated from 400 g/L ammonium sulphate was the easiest to resuspend.

The study to compare the two strains of C. histolyticum (004 and 013) showed that the productivity of the collagenases from the animal derived media was lower than that of the optimal non-animal derived media. SDS-PAGE analysis, supported by an enzymatic assay for clostripain activity, highlighted that there were significantly lower quantities of clostripain in the material produced from the animal derived media than the non-animal media. This highlighted the fact that the feedstock produced from the non-animal derived media fermentation was a significantly different feedstock material from the fermentation using animal derived media with respect to the production of contaminating proteases.

$1^{st}$ Set of Fed-Batch Fermentations—DCFT24

The results from the process development work showed that the use of an enriched media (100 g/L phytone peptone and 50 g/L yeast extract) resulted in the expression of higher amounts of collagenases compared to the original media (50 g/L phytone peptone and 8.5 g/L yeast extract). In addition, it initially appeared that it reduced the amounts of clostripain produced.

Two 5 L fermentations were then performed. Firstly the strategy consisted of a long batch phase/short fed-batch phase, whereas the second consisted of a short batch phase/ long fed-batch phase. In both strategies at the end of the fermentation (after 20 h) the concentrations of phytone peptone and yeast extract were 100 g/L and 50 g/L, respectively, as in the case of the batch fermentations. Table 1 and 2 detail the media recipes and strategies used.

TABLE 1

Media recipe and fed-batch strategy

Long batch-short fed-batch

| Component | Batch phase | Feed | Concentrations at harvest point |
|---|---|---|---|
| Phytone Peptone | 100 g/L | 100 g/L | 100 g/L |
| Yeast extract | 50 g/L | 50 g/L | 50 g/L |
| Glucose | 10 g/L | 10 g/L | 10 g/L |
| | | Filtered sterilised | |
| $KH_2PO_4$ | 1.92 g/L | | |
| $K_2HPO_4$ | 1.25 g/L | | |
| $Na_2HPO_4$ | 3.5 g/L | | |
| NaCl | 2.5 g/L | | |
| Magnesium | 0.08 g/L | | |
| Vitamin solution | 10 mL/L | | |
| Volume | 4 L | 1 L | ~5 L |

Inoculation →(Batch Phase 10h)→ (Fed-batch Phase 10h)→ Harvest at 20h

TABLE 2

Media recipe and fed-batch strategy

Short batch-long fed-batch

| Component | Batch phase | Feed | Concentrations at harvest point |
|---|---|---|---|
| Phytone Peptone | 40 g/L | 254 g/L | 100 g/L |
| Yeast extract | 10 g/L | 153 g/L | 50 g/L |
| Glucose | 7.5 g/L | 17.8 g/L | 10 g/L |
| | | Filtered sterilised | |
| $KH_2PO_4$ | 1.92 g/L | | |
| $K_2HPO_4$ | 1.25 g/L | | |
| $Na_2HPO_4$ | 3.5 g/L | | |
| NaCl | 2.5 g/L | | |
| Magnesium | 0.08 g/L | | |
| Vitamin solution | 10 mL/L | | |
| Volume | 4 L | 1 L | ~5 L |

Inoculation →(Batch Phase 6h)→ (Fed-batch Phase 14h)→ Harvest at 20h

Figure 1:
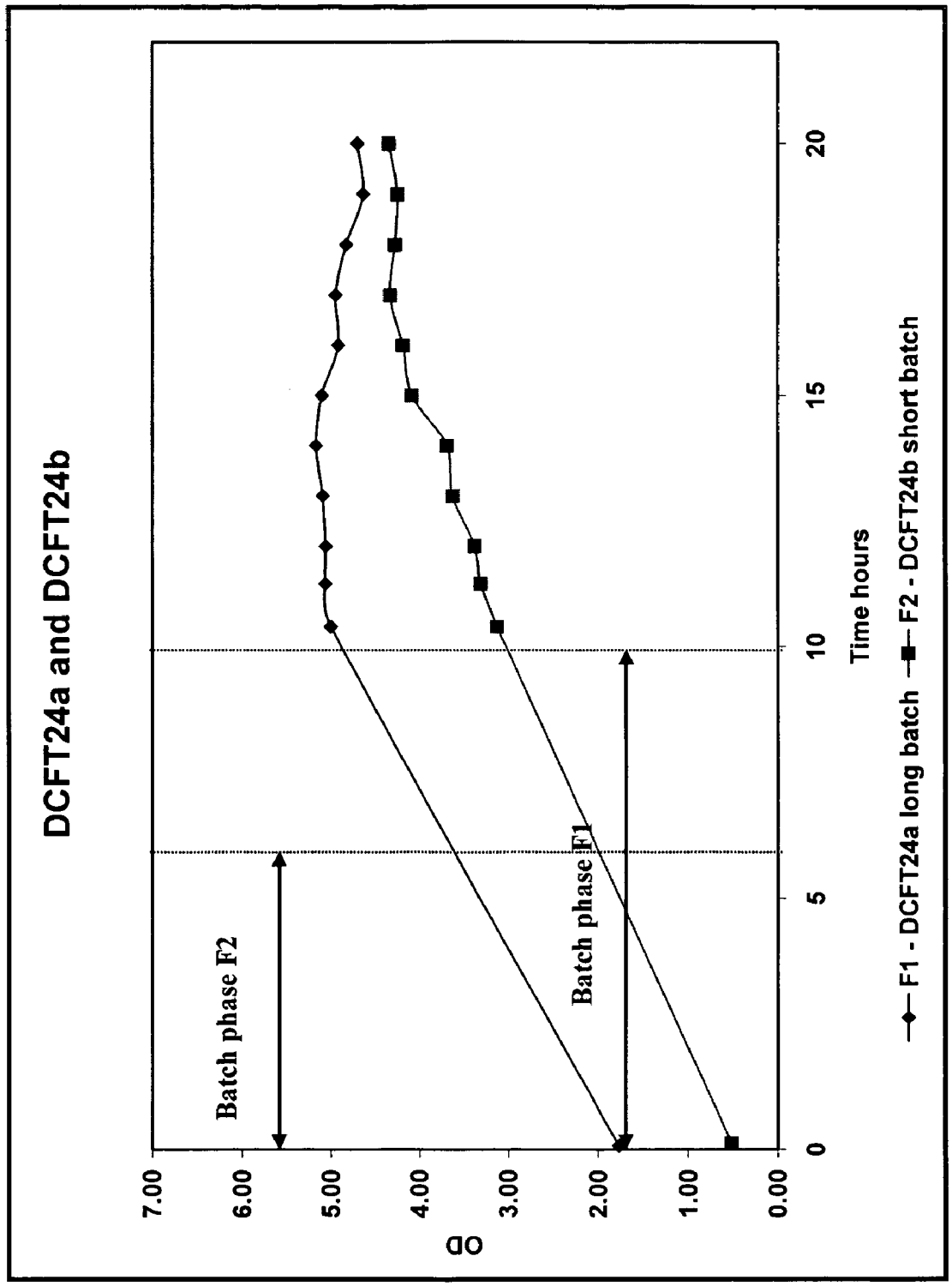
FIG. 1 depicts growth curves (OD vs time) of C. histolyticum in 5 L DCFT24a,b fermentations.
Figure 2:
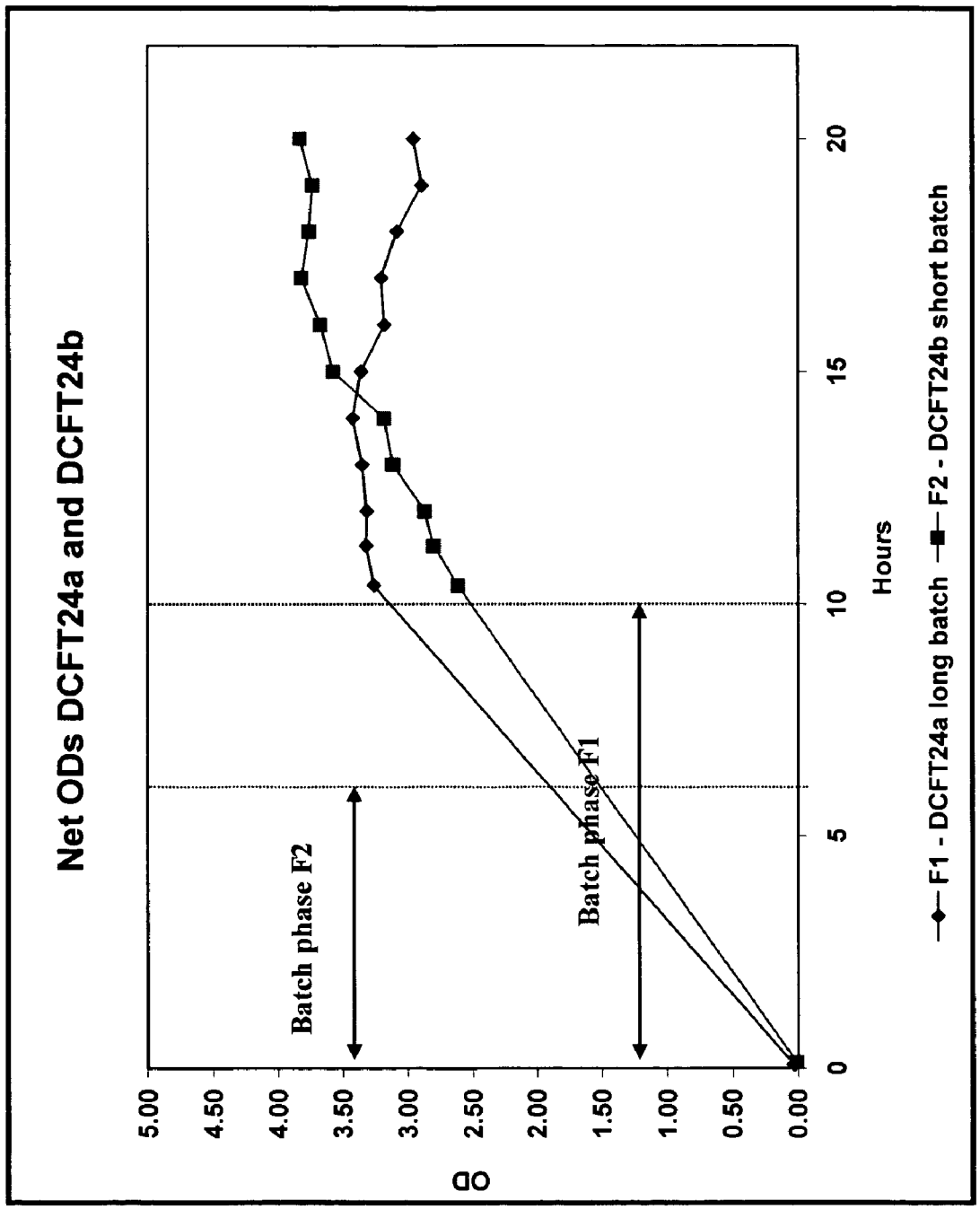
FIG. 2 depicts net growth curves (Net OD vs time) of C. histolyticum in 5 L DCFT24a,b fermentations.

FIG. 1 shows the growth curves ($OD_{600nm}$ vs time) from the two fermentations, whereas FIG. 2 shows the net growth curves (Net $OD_{600nm}$ vs time). It was observed that the cells from the first fermentation grew very fast and reached their maximum OD after approximately 10 hours. This was due to the fact that the media in the batch phase was very rich. During the fed-batch phase the cells did not appear to grow. The OD values decreased slightly, which could be partly attributed to the fact that the cells were dying and to the dilution effect of the feed in to the fermenter.

For the second fermentation, the fed-batch phase was started after 6 hours. At that point the OD value would have been low, as suggested by the growth curve in FIG. 1. The cells continued to grow slowly up to approximately 18 hours.

It was noted that the net growth curves in FIG. 2 suggested that the cell densities in DCFT24b fermentation were higher than in DCFT24a fermentation. The $OD_{600nm}$ of the media prior to inoculation was approximately 1.7, whereas in DCFT24b it was approximately 0.4. These differences are due to the fact when the fermenters are autoclaved a precipitate is formed. For DCFT24a, higher amounts were formed compared to DCFT24b.

Figure 3:
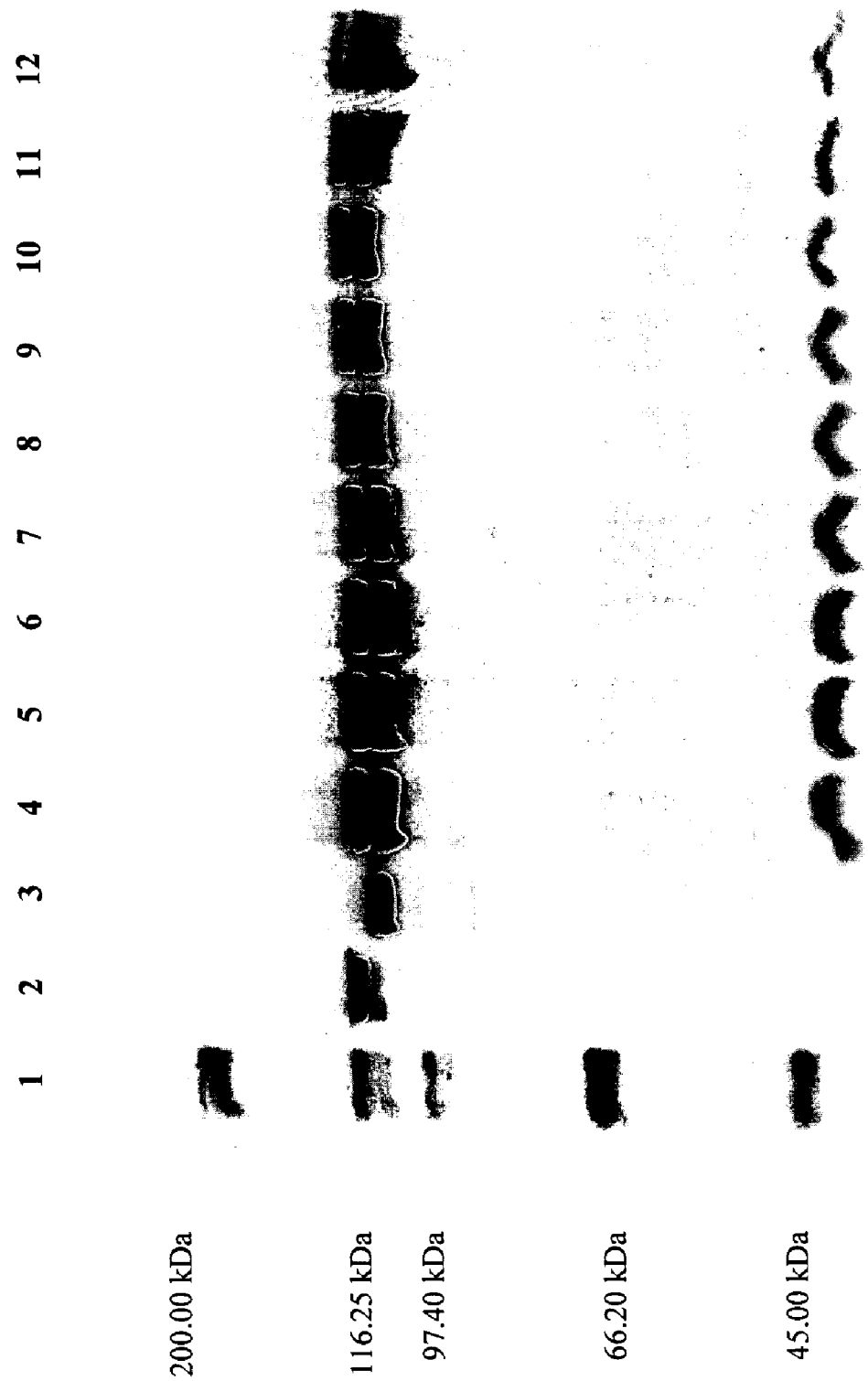
FIG. 3 is a 8% Tris-glycine SDS PAGE gel from the second fermentation:
Lane 1: High Molecular Weight Marker
Lane 2: Collagenase I—0.27 kg
Lane 3: Collagenase II—0.29 µg
Lane 4: 20 h (6.12 µL of sample)—Harvest point
Lane 5: 19 h (6.12 µL of sample)
Lane 6: 17 h (6.12 µL of sample)
Lane 7: 16 h (6.12 µL of sample)
Lane 8: 15 h (6.12 µL of sample)
Lane 9: 14 h (6.12 µL of sample)
Lane 10: 13 h (6.12 µL of sample)
Lane 11: 11.6 h-19 h (6.12 µL of sample)
Lane 12: 10.5 h (6.12 µL of sample)
Figure 4:
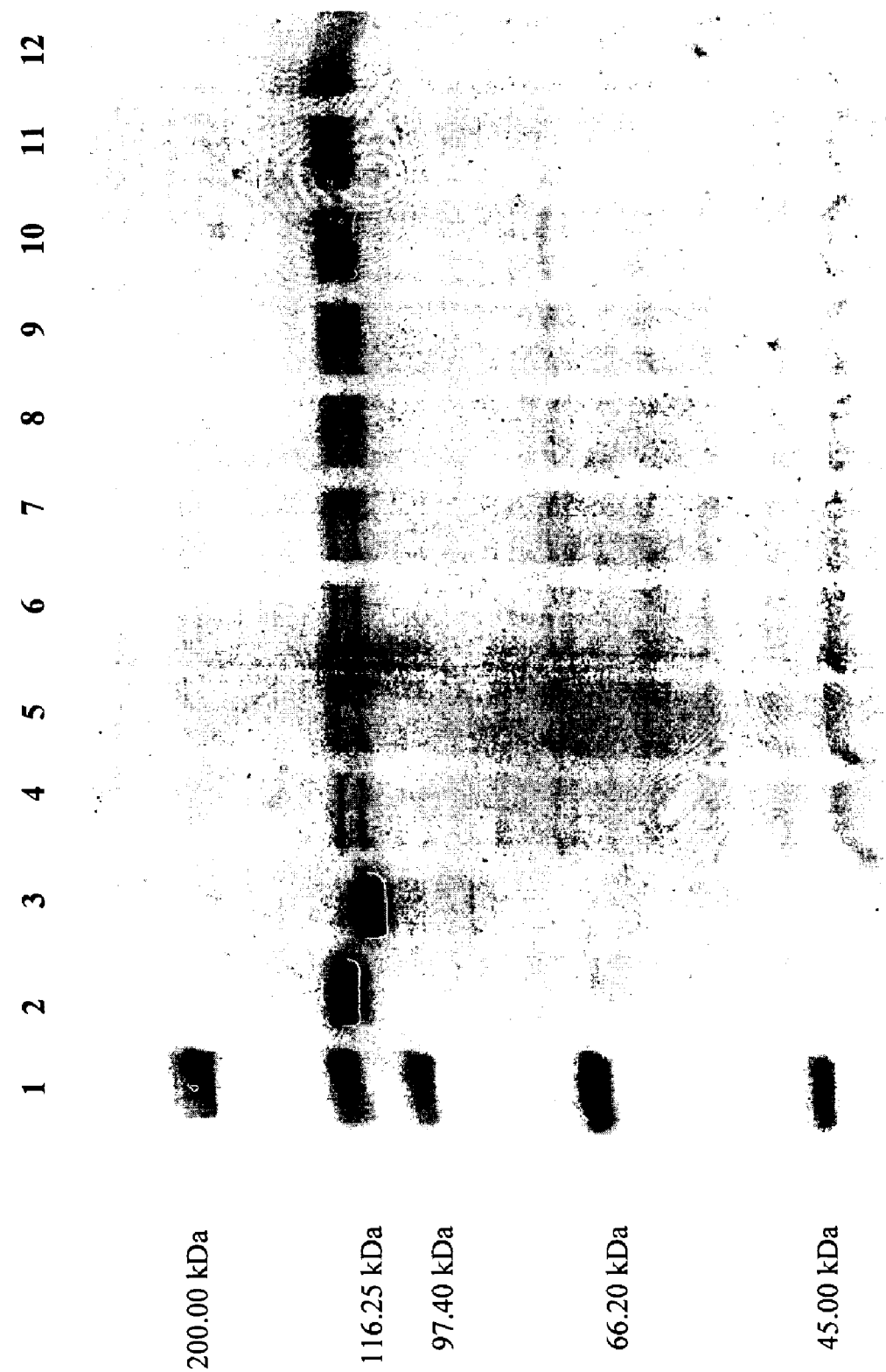
FIG. 4 is a 8% Tris-glycine SDS PAGE gel from the first fermentation:
Lane 1: High Molecular Weight Marker
Lane 2: Collagenase I—0.27 kg
Lane 3: Collagenase II—0.29 kg
Lane 4: 20 h (6.12 µL of sample)—Harvest point
Lane 5: 19 h (6.12 µL of sample)
Lane 6: 17 h (6.12 µL of sample)
Lane 7: 16 h (6.12 µL of sample)
Lane 8: 15 h (6.12 µL of sample)
Lane 9: 14 h (6.12 µL of sample)
Lane 10: 13 h (6.12 µL of sample)
Lane 11: 11.4 h (6.12 µL of sample)
Lane 12: 10.4 h (6.12 µL of sample)

SDS PAGE Gels:

SDS PAGE analysis (8% Tris-Glycine gels) of the supernatant samples were carried out for each for the two fermentations. The gels are shown in FIGS. 3 and 4. A semi-quantitative SDS PAGE gel was also produced for the harvest point sample of the second fermentation.

The SDS PAGE gel analysis in FIG. 4 indicated that very low amounts of the collagenases were expressed. This could be due to the fact that the cells grew very fast during the batch phase and as a result the maximum cell concentration was reached after approximately 10 hours. In contrast, very high level of collagenase expression was observed in the second fermentation, probably due to the fact that the cells grew more slowly during the short batch phase and continued to grow during the fed-batch phase. Thus the invention relates to an improved fermentation method for C. his wherein cell growth is controlled and slow during the short batch phase and continuing growth during the fed-batch phase. Slow growth is defined to mean that the rate of growth during the short batch phase does not result in a maximum cell concentration prior to the fed-batch phase, such as within about 10 hours of the beginning of the fermentation process. In a preferred embodiment, the rate of growth is approximately that resulting from the second fermentation cycle described herein.

Estimated collagenase productivities from the semi-quantitative SDS PAGE gel at the harvest point of the second fermentation cycle (FIG. 5), were 132 mg/L for collagenase ABC I and 158 mg/L for collagenase ABC II. Comparing these values with those previously obtained, there is approximately a 3-fold increase in the expression levels using the fed-batch strategy.

The next step was to perform an additional set of fed-batch fermentations using slightly modified fed-batch strategies and media. The aim was to improve the scalability and robustness of the fermentation process.

The media recipe for this fermentation was the same as above, with the exception that the phytone peptone and the yeast extract in the batch phase were filter sterilised instead of being autoclaved. This was done in order to avoid autoclaving the yeast extract and phytone, which can potentially affect their composition by heat and denaturation of proteins in the media. For fermentation DCFT26b, the amount of yeast extract and phytone peptone was increased. This was done so that the concentration of yeast extract and peptone in the feed was less than that in DCFT26a and thus easier to make up and filter sterilise. For both fermentations the strategy followed was the same, a 6 h batch phase followed by a 14 h fed-batch phase. Tables 3 and 4 present the media recipes, whereas FIG. 6 the strategy used for both fermentations.

TABLE 3

Media recipe and fed-batch strategy for DCFT26a

DCFT26a - (short batch-long fed-batch)

| Component | Batch phase | Feed | Concentrations at harvest point |
|---|---|---|---|
| Phytone Peptone | 40 g/L | 254 g/L | 100 g/L |
| Yeast extract | 10 g/L | 153 g/L | 50 g/L |
| Glucose | 7.5 g/L | 17.8 g/L | 10 g/L |
| | | Filtered sterilised | |
| $KH_2PO_4$ | 1.92 g/L | | |
| $K_2HPO_4$ | 1.25 g/L | | |
| $Na_2HPO_4$ | 3.5 g/L | | |
| NaCl | 2.5 g/L | | |

TABLE 3-continued

Media recipe and fed-batch strategy for DCFT26a

DCFT26a - (short batch-long fed-batch)

| Component | Batch phase | Feed | Concentrations at harvest point |
|---|---|---|---|
| Magnesium | 0.08 g/L | | |
| Vitamin solution | 10 mL/L | | |
| Volume | 3.6 L | 1.4 L | ~5 L |

TABLE 4

Media recipe and fed-batch strategy for DCFT26b

DCFT26b - (short batch-long fed-batch)

| Component | Batch phase | Feed | Concentrations at harvest point |
|---|---|---|---|
| Phytone Peptone | 60 g/L | 151.4 g/L | 100 g/L |
| Yeast extract | 20 g/L | 127.1 g/L | 50 g/L |
| Glucose | 7.5 g/L | 17.8 g/L Filtered sterilised | 10 g/L |
| $KH_2PO_4$ | 1.92 g/L | | |
| $K_2HPO_4$ | 1.25 g/L | | |
| $Na_2HPO_4$ | 3.5 g/L | | |
| NaCl | 2.5 g/L | | |
| Magnesium | 0.08 g/L | | |
| Vitamin solution | 10 mL/L | | |
| Volume | 3.6 L | 1.4 L | ~5 L |

FIG. 7 shows the growth curves ($OD_{600nm}$ vs time) from the two fermentations, whereas FIG. 8 shows the net growth curves (Net $OD_{600nm}$ vs time).

The growth curves for DCFT26a and DCFT26b were very similar to that of DCFT24b shown in FIG. 2. The cells grew slowly during the fed-batch phase and reached a final net $OD_{600nm}$ of approximately 3.5.

SDS PAGE Gels of Fermentation Samples:

SDS PAGE analysis (8% Tris-Glycine gels) of the supernatant samples was carried out for each of the two fermentations (FIG. 9 and FIG. 10). In addition, in order to have a better estimate of the amount of collagenases, a semi-quantitative SDS PAGE gel was conducted for the harvest sample point of DCFT26a (FIG. 11) and DCFT26b (FIG. 12).

In both fermentations the levels of collagenases were similar to those in DCFT24b (FIG. 3). The semi-quantitative SDS PAGE gel shows that very similar levels to DCFT24b (between 280 mg/L to 300 mg/L total collagenase) were obtained for both DCFT26a and DCFT26b. The harvest point of the DCFT26a fermentation cycle (FIG. 11) were ~142 mg/L for collagenase I and ~132 mg/L for collagenase II. The harvest point of the DCFT26b fermentation cycle (FIG. 12) were ~147 mg/L for collagenase I and ~158 mg/L for collagenase II. The levels of clostripain, as in the case of DCFT24b, were still high.

Study of the Ammonium Sulphate Precipitation Step:

The results from these fermentations indicated that although the levels of collagenases were high using the fed-batch strategy, the levels of clostripain were also still significantly high. Therefore a small scale experimental study was set up to investigate the effect of the ammonium sulphate concentration on the recovered amounts of clostripain and collagenases in the precipitated pellet from the filtered fermentation supernatant.

In order to evaluate the efficiency of the ammonium sulphate precipitation step, 6×100 mL supernatant samples were harvested from fermentation DCFT26a. These samples were precipitated with 6 different ammonium sulphate concentrations as detailed in the following table. The pellets were re-suspended in 3.3 mL of WFI and dialysed against 100 mM of $K_2HPO_4$ (pH 6.7).

TABLE 5

Ammonium sulphate concentrations that were used to precipitate 100 mL supernatant samples from DCFT26a.

| Percentage saturation | Ammonium sulphate Concentration (g/L) |
|---|---|
| 15% | 100 g/L |
| 22.5% | 150 g/L |
| 30% | 200 g/L |
| 37.5% | 250 g/L |
| 45% | 300 g/L |
| 60% | 400 g/L |

The post-dialysed samples were then analysed by SDS PAGE analysis.

FIG. 13: post-dialysed harvest point sample precipitated with 15% and 22.5%

FIG. 14: post-dialysed harvest point sample precipitated with 30% and 37.5%

FIG. 15: post-dialysed harvest point sample precipitated with 45% and 60%

The gels show that in the case where the ammonium sulphate used was between 15% to 45% saturation, the levels of collagenases in the post-dialysed samples were very low. The recovery in these cases seemed to be less than 5%.

In the case where 60% saturation of ammonium sulphate was used (400 g/L) the levels of collagenases in the post-dialysed sample were very high (FIG. 15). By comparing the intensity of the bands (sample versus references) it can be estimated that approximately 70 mg/L for each of the collagenases were present in the post-dialysed sample. This suggests a recovery of about 50 to 60%, since according to the semi-quantification gel for DCFT26a (FIG. 11) there were approximately 130 mg/L of each of the collagenases in the harvest point sample.

Thus, the invention relates to the use of the media recipe (of course, amounts set forth therein are approximated) set forth above in DCFT26b and the use of ammonium sulphate to precipitate collagenase wherein about 400 g/liter of ammonium sulfate is added to the collagenase-containing medium.

$3^{rd}$ Set of Fed-Batch Fermentations

Here the primary aim was to assess the reproducibility of the developed fed-batch strategy. A fed-batch fermentation was performed which was a replicate fermentation of DCFT26b. In addition, the ammonium sulphate/precipitation steps were investigated in more detail compared to the previous small-scale study. More specifically, the aim was to examine the effect of various ammonium sulphate concentrations, from 60% (400 g/L) up to 80% (530 g/L) on the recovery of collagenases and clostripain in the post precipitated/dialysed samples. In addition, two methods of treating the harvested supernatant samples were also assessed, i.e., shifting the pH and oxygenating the media.

Growth Curve:

The media and fed-batch strategy used was exactly the same as DCFT26b. FIG. 16 shows the growth curve ($OD_{600nm}$ vs time) and the net growth curve (Net OD$_{600nm}$ vs time) from the fermentation. The growth curve was very similar to that of DCFT26b, indicating the good reproducibility of the process.

SDS PAGE analysis (8% Tris-Glycine gels) of the supernatant samples taken throughout the fermentation indicated that the levels of collagenases and clostripain were very similar to those of DCFT26b (SDS PAGE gel not shown). A semi-quantitative SDS PAGE gel (8% Tris-Glycine gel) was performed for the harvest point sample (FIG. 17). The gel suggests that there is higher than 120 mg/L of each of the collagenases present, similar to the levels observed in DCFT26b.

Ammonium Sulfate Precipitation of Fermentation Harvest Samples:

In order to evaluate the efficiency of the ammonium sulphate precipitation step, 7×500 mL supernatant samples were harvested. These were precipitated using the following six methods.

In all cases, the pellets were re-suspended in 16.5 mL of WFI and dialysed against 100 mM of K$_2$HPO$_4$ (pH 6.7), with the exception of method 4, where the pellet was re-suspended in 16.5 mL of 100 mM of K$_2$HPO$_4$ (pH 6) and dialysed against the same buffer. SDS PAGE gels were then performed in order to estimate the amounts of collagenases in the post-dialysed samples and evaluate the recovery of the precipitation/dialysis steps.

The methods for precipitation/dialysis followed are the following:

1 Precipitation with 400 g/L of ammonium sulphate added all at once into the supernatant sample. Dialysis against 100 mM of K$_2$HPO$_4$, pH 6.7.
2 Precipitation with 400 g/L of ammonium sulphate added slowly (about 30 min) into the supernatant sample. Dialysis against 100 mM of K$_2$HPO$_4$, pH 6.7.
3 Precipitation with 400 g/L of ammonium sulphate added slowly (about 30 min) into the supernatant sample, which was pre-oxygenated. This was done by oxygenating for approximately 10 minutes 500 mL of cell culture harvested from the fermenter. The culture was then filter sterilised. The pellet formed after ammonium sulphate precipitation was dialysed against 100 mM of K$_2$HPO$_4$ pH 6.7.
4 Precipitation with 400 g/L of ammonium sulphate added slowly (about 30 min) into the supernatant sample, the pH of which was changed to pH 6 by adding 5N HCl. The pellet formed after was dialysed against 100 mM of K$_2$HPO$_4$, pH 6.
5 Precipitation with 440 g/L of ammonium sulphate added slowly (about 30 min) into the supernatant sample. Dialysis against 100 mM of K$_2$HPO$_4$, pH 6.7.
6 Precipitation with 480 g/L of ammonium sulphate added slowly (about 30 min) into the supernatant sample. Dialysis against 100 mM of K$_2$HPO$_4$, pH 6.7.
7 Precipitation with 520 g/L of ammonium sulphate added slowly (about 30 min) into the supernatant sample. Dialysis against 100 mM of K$_2$HPO$_4$, pH 6.7.

The ammonium sulphate did not completely dissolve when added at 480 g/L and 520 g/L in the supernatant samples, whereas it completely dissolved when added at 400 g/L and 440 g/L.

The results from the SDS PAGE indicated that the different levels of ammonium sulphate used for the precipitation step (400 g/L, 440 g/L, 480 g/L, 520 g/L) or the other methods used (oxygenation, pH shift) did not seem to have an obvious effect on the amounts of collagenases present in the post dialyzed samples. In all cases, the concentration of each of the collagenases in the post dialyzed samples ranged between 50 mg/L and 60 mg/L. FIG. 18a shows a representative SDS PAGE gel, such as that of the post dialyzed sample precipitated with 400 g/L ammonium sulphate. Since all the gels were very similar the other SDS PAGE gels are not presented in this report.

Taking into account the estimated concentrations of collagenases in the harvest point sample (FIG. 17) and in the post dialyzed samples, the recovery of the collagenase after the precipitation/dialysis steps was approximately 50%. In order to investigate whether the value of 50% recovery was accurate, since the error in the estimation of collagenase concentration by SDS gel is in general high, the following SDS PAGE gels were carried out.

An SDS PAGE gel of all the supernatants after centrifugation of the ammonium sulphate precipitated samples (FIG. 18a). The aim was to assess whether any amount of collagenases is lost into the supernatant.

An SDS PAGE gel in which the harvest point supernatant sample and the post dialysed ammonium sulphate (400 g/L) precipitated sample were appropriately diluted to contain equal amounts of collagenases and loaded on the same gel (FIG. 19).

An SDS PAGE gel in which the harvest point supernatant sample and the post dialysed ammonium sulphate sample (520 g/L) were appropriately diluted to contain equal amounts of collagenases and loaded on the same gel (FIG. 20).

It can be seen from FIG. 18b that the amount of collagenases present in the supernatants after centrifugation of the ammonium sulphate precipitated samples was very low. In FIG. 19 and FIG. 20 that the amount of collagenases after the precipitation/dialysis steps appeared to be very similar to that in the supernatant harvest sample. It was therefore likely that the recovery value that was derived by comparing the semi-quantitative SDS PAGE gels of the supernatant and the post-dialyzed samples was actually higher.

Benchmarking Fermentation Experiments with Animal Derived TSB/Proteose:

Fermentations of *C. histolyticum* 013 and 004 strains in the media containing animal derived components were performed. The aim was to compare strain 013 to strain 004 and evaluate the effect of the animal components on cell growth, collagenase expression and on the levels of contaminants. *C. histolyticum* 013:

The lyophilised strain was re-constituted in PBS and plated out onto TSB/Proteose agar plates (30 g/L TSB, 10 g/L protease peptone, 12 g/L agar. The plates were incubated in an anaerobic jar in the presence of anaerobic gas packs. Single colonies were picked and used to inoculate 5 mL TSB/Proteose media. After 15 hours of incubation at 37° C. the OD$_{600nm}$ of the culture was approximately 1.0 unit. 5 mL of culture was then mixed with 1 mL of sterile and stored below −70° C.

PBFT58 Fermentations

Growth Curves:

Two 5 L batch fermentations were carried out, PBFT58c (strain 004) and PBFT58d (strain 013). Table 6 presents the recipe of the TSB/Proteose media used. FIG. 21 shows the growth curves obtained (Net OD$_{600nm}$ vs time).

TABLE 6

Recipe for TSB/Proteose media

| Component | Concentration |
|---|---|
| Proteose peptone | 50 g/L |
| TSB | 15 g/L |
| $MgSO_4 \cdot 7H_2O$ | 0.08 g/L |
| $KH_2PO_4$ | 1.92 g/L |
| $Na_2HPO_4$ | 3.5 g/L |
| Vitamin solution (Sterile filtered) | 10 mL/L |

It was seen from FIG. 21 that the strain 013 grew to a higher OD than strain 004. In both cases however the final $OD_{600nm}$ was higher than 2.5, indicating that the animal derived media supported good growth for both strains.

It was noted that strain 013 continued to grow slowly up to the harvest point (20 hours) whereas strain 004 grew up to a net $OD_{600nm}$ of approximately 2.7 and then stopped growing. Compared to the fed-batch fermentations presented previously, using the non-animal derived media, the final OD obtained using the animal derived TSB/Proteose media was lower.

SDS PAGE Analysis:

The SDS PAGE gels (8% Tris-Glycine gels) of the supernatant samples taken throughout the fermentations are shown in FIG. 22 and FIG. 23.

There did not seem to be any clostripain in the fermentation supernatants, especially in the case of strain 013. This was a very important finding since it could explain the fact that the originator may not have had issues or reduced issues during the purification of collagenases. In contrast, significant problems with degradation of the collagenases had been previously experienced during the purification process. This could be partly attributed to the presence of clostripain in the fermentation.

In order to obtain a better estimate of the amount of collagenases present in the fermentations, a semi-quantitative SDS PAGE gel was conduced for the harvest point samples (FIG. 24 and FIG. 25). The gels suggest that lower amount of collagenases was produced in the batch fermentations with the TSB/Proteose media (PBFT58c) compared to the fed-batch fermentation with the vegetable media (PBFT57). This could be attributed to the fact that higher cell densities were obtained in the latter case ($OD_{600nm}$~4 to $OD_{600nm}$~2.7). Table 7 summarizes the results from the semi-quantitative gels.

TABLE 7

Results from semi-quantitative SDS PAGE gels for PBFT57 and PBFT58c, d

| | PBFT57 (Animal-free, strain 004) | PBFT58c (Animal-derived, strain 004) | PBFT58d (Animal-derived, strain 013) |
|---|---|---|---|
| AUX I (mg/L) | 132 | 88 | 59 |
| AUX II (mg/L) | 142 | 95 | 95 |
| Total | 274 | 183 | 154 |

Ammonium Sulphate Precipitation of Fermentation Harvest Samples:

For each fermentation, 2×500 mL harvest point samples were precipitated with 400 g/L (60%) and 520 g/L (80%) ammonium sulphate. The pellets were re-suspended in 16.5 mL of WFI and dialyzed against 100 mM of $K_2HPO_4$ (pH 6.7). SDS PAGE analysis (8% Tris-Glycine gels) of the post-dialyzed samples was then performed (FIG. 26 and FIG. 27).

The results from these gels indicated that the levels of clostripain, even in the very concentrated post-dialyzed samples (lanes 6 and 7 of FIGS. 26 and 27) were extremely low. This is more evident in the case of strain 013 compared to strain 004.

Thus the invention relates to collagenase compositions which are free of clostripain, such as those produced by the fermentation processes described herein.

Measurement of Clostripain Activity:

In order to investigate further the role of clostripain an enzymatic assay was set up to measure the clostripain activity of post dialyzed samples. The following method was used:

Enzymatic assay of clostripain:

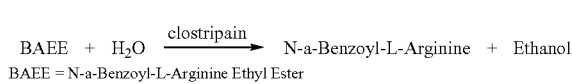

BAEE = N-a-Benzoyl-L-Arginine Ethyl Ester

Conditions: T=25° C., pH=7.6, $A_{253}$ nm, Light path=1 cm

Method: Continuous Spectrophotometric Rate Determination

Unit definition: One unit will hydrolyze 1.0 μmole of BAEE per minute at pH 7.6 at 25° C. in the presence of 2.5 mM DTT.

Analysis of Post Dialysed Samples for Clostripain Activity:

The clostripain activity assay was used to analyze the post-dialyzed samples from the fermentations with the TSB/Proteose (PBFT58) and the vegetable based fed-batch fermentation (PBFT57). Table 8 summarizes the results.

The results demonstrate that there was very low clostripain activity in the case of TSB/Proteose fermentations. In contrast the clostripain activity in the case of the fed-batch PBFT58 was very high.

TABLE 8

Enzymatic activities of post-dialyzed samples

| | PBFT57 (Animal-free, strain 004) | PBFT58c (Animal-derived, strain 004) | PBFT58d (Animal-derived, strain 013) |
|---|---|---|---|
| Clostripain activity (U/mL) | 56.4* | 1.0* | 0.1* |
| Specific clostripain activity (U per mg total collagenase) | 205.8 | 5.5 | 0.7 |

*Clostripain activity determined in the post precipitated/dialyzed sample

Investigation of Alternative Peptones

Screening Experiments in Shake Flask:

In this work various vegetable peptones were used as alternatives to the phytone peptone. The aim was to evaluate their effect on the levels of expression of the collagenases and clostripain. All the peptones tested are derived from vegetable sources and are marketed by Sigma.

The experimental procedure used is described in FIG. 28. The media recipes are detailed in Table 9, whereas a list of the peptones used is shown in Table 10. A control shake flask was also conducted, containing phytone peptone. In all cases, 50 g/L of yeast extract and 100 g/L of each peptone were used in an effort to mimic the concentrations of these components at the harvest point of the developed fed-batch fermentation (see Table 4).

TABLE 9

Composition of media used in shake flask experiment.
All media were filter sterilised.
Vegetable media

| Component | Concentration |
|---|---|
| Alternative Peptone | 100 g/L |
| Yeast extract | 50 g/L |
| $KH_2PO_4$ | 1.92 g/L |
| $K_2HPO_4$ | 1.25 g/L |
| $Na_2HPO_4$ | 3.5 g/L |
| NaCl | 2.5 g/L |
| Magnesium | 0.08 g/L |
| Vitamin solution | 10 mL/L |
| Glucose | 0.9 g/L |

The shake flasks were incubated for 18 hours. The cultures were analysed for $OD_{600nm}$ and viable cell counts. The cultures were filtered and the supernatants analysed by SDS PAGE. The results from the $OD_{600nm}$ measurements and viable cell counts are summarised in Table 10.

Most of the vegetable peptones resulted in higher net OD values compared to the phytone peptone. However the OD values did not correlate to the viable cell counts. This could be partly attributed to the variability of the viable cell count method or to the fact that the cells had already started to lyse before the pre-selected harvest point (18 hours).

Interestingly, the SDS-PAGE gel indicated that there was no expression of collagenase (gel not shown) in all the flasks, including that of the control (phytone peptone). A possible reason for this could be the fact that the concentrations of the phytone peptone and yeast extract used were very high and as a result they repressed the expression of collagenases.

TABLE 10

Results from 1$^{st}$ screening experiment

| Type of peptone | Net $OD_{600\ nm}$ after 18 h growth | CFU/mL |
|---|---|---|
| Phytone peptone (control) | 2.65 | $1.2 \times 10^9$ |
| Proteose peptone (vegetable) | 2.58 | $7.4 \times 10^8$ |
| Tryptone (vegetable) | 3.05 | $4.8 \times 10^8$ |
| Vegetable extract | 3.22 | $1.0 \times 10^9$ |
| Vegetable extract 1 | 3.11 | $9.6 \times 10^9$ |
| Vegetable extract 2 | 3.05 | $7.8 \times 10^9$ |
| Vegetable hydrolysate 2 | 3.01 | $8.4 \times 10^9$ |

Fed-Batch Fermentations Using Alternative Peptones—DCFT27a b:

Based on information from the previous shake flasks experiments that no expression of collagenases was observed, it was decided to evaluate the alternative peptones using the developed fed-batch strategy.

Two fed-batch fermentations were conducted, DCFT27a (vegetable extract 2) and DCFT27b (vegetable hydrolyzate 2). In both fermentations the fed-batch strategy that was developed for the media containing phytone peptone was used. Table 11 describes the media recipes, whereas FIG. 29 the strategy used.

TABLE 11

Media recipe for fed-batch fermentations DCFT27a and DCFT27b

| | DCFT27a, b | | |
|---|---|---|---|
| Component | Batch phase | Feed | Concentrations at harvest point |
| Alternative Peptone | 60 g/L | 151.4 g/L | 100 g/L |
| Yeast extract | 20 g/L | 127.1 g/L | 50 g/L |
| Glucose | 7.5 g/L | 17.8 g/L Filtered sterilized | 10 g/L |
| $KH_2PO_4$ | 1.92 g/L | | |
| $K_2HPO_4$ | 1.25 g/L | | |
| $Na_2HPO_4$ | 3.5 g/L | | |
| NaCl | 2.5 g/L | | |
| Magnesium | 0.08 g/L | | |
| Vitamin solution | 10 mL/L | | |
| Volume | 3.6 L | 1.4 L | ~5 L |

Growth Curves:

The growth curves (Net $OD_{600nm}$ vs. time) for DCFT27a and DCFT27b are depicted in FIG. 30. In both fermentations, the cells grew to a slightly higher $OD_{600nm}$ compared to the media containing phytone peptone (fermentation PBFT57, FIG. 16). This was in accordance with the viable cell counts (approximately $2 \times 10^9$ CFU/mL for DCFT27a,b compared to $1.5 \times 10^9$ CFU/mL for PBFT57).

SDS PAGE Gels:

As with the shake flask experiments the SDS PAGE analysis indicated that there was no expression of collagenases in both DCFT27a and DCFT27b (gels not shown).

This could be attributed to the fact that the media, which consists of high amounts of peptone, supports the expression of collagenases when phytone peptone is used, but is too rich when an alternative peptone is used and thus represses the expression of any metabolite, including collagenase and clostripain. It seems that the cells experience luxurious growth conditions in the media containing the alternative peptones and do not need to produce any proteases.

Batch Fermentations Using Alternative Peptones—Pbft59a, b,c:

The results from DCFT27a and DCFT27b fed-batch fermentations, led to further work to investigate three additional alternative peptones, however using lower concentrations than previously used.

Three 5 L batch fermentations were conducted, PBFT59a (vegetable tryptone), PBFT59b (vegetable extract) and PBFT59c (vegetable extract no. 1). The fermentations were harvested after 18 hours.

All peptones were used at concentrations of 50 g/L in an effort to mimic the concentration of the protease peptone in the animal media (Proteose/Peptone) and the concentration of phytone peptone that was used previously. The media recipe is shown in Table 12.

TABLE 12

Media recipe and fermentation strategy for 5 L fermentations PBFT59a, b, c

| Component | Concentration |
|---|---|
| Alternative Peptone | 50 g/L |
| Yeast extract | 8.5 g/L |
| Glucose | 5 g/L |
| $KH_2PO_4$ | 1.92 g/L |
| $K_2HPO_4$ | 1.25 g/L |
| $Na_2HPO_4$ | 3.5 g/L |
| NaCl | 2.5 g/L |
| Magnesium | 0.08 g/L |
| Vitamin solution | 10 mL/L |
| Volume | 5 L |

Growth Curves:

The growth curves obtained from PBFT59a,b,c fermentations are depicted in FIG. 31. In all cases the cells grew to a lower $OD_{600nm}$ (between 1.8 and 2.8) compared to the DCFT27 fed-batch fermentations. This was also in accordance with the viable cell counts (between $0.7 \times 10^9$ CFU/mL to $1.2 \times 10^9$ CFU/mL for PBFT59a,b,c compared to $2 \times 10^9$ CFU/mL for DCFT27a,b). In the media containing tryptone the cells demonstrated the slowest growth rate and achieved the lowest cell density after 18 hours.

SDS PAGE Gels:

As for the shake flask experiment and the DCFT27a,b fed-batch fermentations no collagenase expression was seen in the SDS PAGE gels (gels not shown).

These results show that the alternative peptones, although they support the cell growth, they do not allow the expression of collagenases. As suggested before this could be due to the fact these peptones are very rich in nutrients, e.g., free amino acids, small peptides.

$4^{th}$ Set of Fed-Batch Fermentations—DCFT27d

As the results from the experiments using the alternative vegetable peptones were not successful the next aim of this work was to investigate the possibility of decreasing the levels of clostripain in the developed fed-batch fermentation using the phytone peptone media. As described previously, the clostripain was probably causing the degradation of collagenases during the purification process.

A fed-batch fermentation was carried out using the standard phytone peptone media supplemented with three amino acids, i.e., glutamine, tryptophan and asparagine. This fermentation was performed as the concentrations of these particular amino acids were lower in the phytone peptone compared to the animal TSB/Proteose media, based on the amino acid composition of these components, provided by the manufacturers.

The aim here was to investigate whether addition of these amino acids could reduce any nutrient limitation that may be a contributing factor for the expression of clostripain. The media recipe is shown in Table 13. The fermentation strategy used was the standard fed-batch strategy used for DCFT26 and PBFT57 fermentations (see FIG. 6).

TABLE 13

Media recipe for fed-batch fermentation DCFT27d

| | DCFT27d | | |
|---|---|---|---|
| Component | Batch phase | Feed | Concentrations at harvest point |
| PhytonePeptone | 80 g/L | 151.4 g/L | 100 g/L |
| Yeast extract | 20 g/L | 127.1 g/L | 50 g/L |
| Glucose | 7.5 g/L | 17.8 g/L | 10 g/L |
| Amino acids | | | |
| Glutamine | 2.8 g/L | Filtered | |
| Tryptophan | 0.35 g/L | sterilised | |
| Asparginine | 0.18 g/L | | |
| $KH_2PO_4$ | 1.92 g/L | | |
| $K_2HPO_4$ | 1.25 g/L | | |
| $Na_2HPO_4$ | 3.5 g/L | | |
| NaCl | 2.5 g/L | | |
| Magnesium | 0.08 g/L | | |
| Vitamin solution | 10 mL/L | | |
| Volume | 3.6 L | 1.4 L | ~5 L |

Growth Curve:

The growth curve obtained from DCFT27d fermentation is depicted in FIG. 32. The growth profile obtained was very similar to that obtained for the standard fed-batch fermentation in the absence of amino acids (DCFT26b and PBFT57) shown previously.

SDS PAGE Gel:

FIG. 33a shows the SDS PAGE gel of the supernatant samples taken throughout the fermentation. The level of collagenases is similar to that seen for the standard fed-batch fermentation (see FIG. 10 for SDS PAGE gel from DCFT26b). Although clostripain is still present in the fermentation, it did seem that its level was lower than that in DCFT26b.

In order to investigate this further, the clostripain activity of the post-dialysed harvest point sample was estimated using the clostripain activity assay. In addition, the clostripain activity of the post-dialysed harvest point sample taken from the 20 L lyophilization batch was also estimated. Since this particular batch was purified without showing significant collagenase degradation, knowledge of its clostripain activity would be informative. Table 14 summarizes the enzymatic activities of the post-dialyzed samples. It also includes the enzymatic activities for the standard fed-batch fermentation PBFT57 and the animal TSB/Proteose peptone presented in Table 8, for comparative purposes.

TABLE 14

Enzymatic activities of post-dialyzed samples

| | PBFT57 Standard fed-batch | DCFT27d Fed-batch plus amino acids | 20 L Lyo batch | PBFT58c Animal TSB/ Proteose |
|---|---|---|---|---|
| Clostripain activity (U/mL) | 56.4 | 15.2 | 16.6 | 1.0 |
| Specific clostripain activity (U per mg total collagenase) | 205.8 | 55.3 | 184.4 | 5.5 |

The results from DCFT27d indicate that the addition of the amino acids reduces the activity of clostripain produced by the strain. The ratio of clostripain to collagenase is approximately four fold lower in the amino acid supplemented fermentation compared to the control fed-batch fermentation. The ratio of clostripain to collagenase in the animal-derived fermentation was ten fold lower than the amino acid supplemented fed-batch fermentation. It is possible that the reduction of clostripain activity may result in significant reduction on the degradation of collagenases during purification.

A series of 5 L fermentations were conducted to assess several fed-batch fermentation strategies. The strategies were assessed based on their yield of collagenase, quantity of contaminants and scalability. Based on these results an optimum fed-batch strategy was identified that resulted in a productivity of total collagenases of approximately 280 mg/L. The fermentation strategy was modified by slightly increasing the batch media concentration and reducing the fed-batch media concentration to improve its scalability. This change to the fermentation strategy had no effect on the productivity or levels of contaminants.

The second objective was to optimize the primary recovery step of the collagenases. Optimization of this step involved improvement in the yield of the process step or a reduction in the quantity of contaminants recovered or an increase in scalability. A range of ammonium sulphate concentrations from 100 to 520 g/L were assessed. The effect of lowering the pH to 6.0 and oxygenating the media were also assessed. All ammonium sulphate concentrations below 400 g/L showed very low recoveries of collagenase. No difference in the recovery of collagenase or clostripain was observed in any of the ammonium sulphate concentrations between 400 and 520 g/L. The pellet from the 400 g/L precipitation was the easiest to re-suspend and this concentration was therefore defined as the optimum level.

A benchmarking experiment was carried out in order to determine and compare the growth and production of collagenases and clostripain in an animal-derived media with *C. histolyticum* strains 013 and 004. The animal-derived media recipe was taken from the Process 1 fermentation media, utilizing TSB and protease peptone. This experiment also allowed a comparison of strain 004 grown in animal and non-animal media. The results from SDS-PAGE analysis showed that much lower quantities of clostripain from *C. histolyticum* grown in the animal-derived media. These results were confirmed using an enzymatic assay for clostripain activity. The assay demonstrated a significant reduction in the activity of clostripain in fermentations using the animal-derived media. When the two strains were compared 004 showed a higher clostripain activity than 013.

Selections of alternative nitrogen sources were assessed for their ability to replace the Phytone peptone in the fed-batch fermentation strategy. These peptones were Vegetable Extract No. 2 (Sigma, 49869) and Vegetable Hydrolysate No. 2 (Sigma, 07436). The *C. histolyticum* grew extremely well on the vegetable peptones reaching optical densities (600 nm) of 4 to 5 units. SDS-PAGE analysis of these fermentations showed no expression of either collagenase or clostripain. Due to the luxuriant cell growth observed on these peptones it was thought that the concentration of complex nitrogen source was too high resulting in an inhibition of protease expression. A second set of fermentations was therefore carried out using the alternative peptones at 50 g/L in a batch strategy. Vegetable Tryptone (Sigma, 16922) Vegetable Extract (Sigma, 05138) and Vegetable Extract No. 1 (Sigma, 04316) were used as alternative peptones for these experiments. When the fermentations were analyzed by SDS-PAGE no expression of collagenase or clostripain was seen. A fed-batch fermentation using Phytone peptone was supplemented with three amino acids, glutamine, tryptophan and asparagine. These amino acids were identified as being present in lower amounts in the non-animal media. The growth profile of the fermentation was very similar to that of the fed-batch fermentation without amino acid supplementation. SDS-PAGE analysis showed a similar yield of collagenase but a slightly lower level of clostripain. The clostripain assay showed reduced activity in the amino supplemented when compared to the control fed-batch fermentation. The reduction in clostripain activity whilst still significant was not as great as the difference between animal and non-animal media.

Materials and Methods:

Inoculum Media for Fermentations Using Vegetable Media

Throughout this development work the following recipes for the inoculum media were used.

Inoculum media—Vegetable

| Component | Concentration |
|---|---|
| Vegetable Peptone | 50 g/L |
| Yeast extract | 8.5 g/L |
| Glucose | 0.9 g/L |
| $KH_2PO_4$ | 1.92 g/L |
| $K_2HPO_4$ | 1.25 g/L |
| $Na_2HPO_4$ | 3.5 g/L |
| NaCl | 2.5 g/L |
| Magnesium | 0.08 g/L |
| Vitamin solution | 10 mL/L |

The media was filter sterilized

Inoculation Procedure

A vial from the internal cell bank was thawed and 0.025 mL was used to inoculate 5 mL of the inoculum media in a 30 mL universal. The 5 mL culture was incubated at 37° C. in an anaerobic jar in the presence of anaerobic gas generators. After approximately 13 to 15 hours of incubation, 4 mL of the culture was used to inoculate 200 mL of the inoculum media in a 500 mL flask. As previously the flask was placed in an anaerobic jar in the presence of anaerobic gas generators. After approximately 13 to 15 hours of incubation at 37° C. and 75 rpm, the whole content of the flask was used to inoculate the fermenter.

The pH and the temperature of the fermenters were controlled at 7.0 and 37° C., respectively. The nitrogen flow rate was set at 1 L/min (~0.2 vvm) and the stirrer speed at 100 rpm. The fermenter was sampled at regular time intervals for $OD_{600nm}$ measurements and viable cell counts. Samples were filtered through a 0.22 μm filter. The filtrates were stored at −20° C. and were frozen at −20° C. for SDS PAGE analysis. FIG. 33*b* depicts a schematic diagram the inoculation procedure.

A preferred recipe for the fed-batch fermentation is set forth below.

| Component | Quantity |
|---|---|
| Batch Phase | |
| $KH_2PO_4$ | 2.91 g/L |
| $K_2HPO_4$ | 1.89 g/L |
| $Na_2HPO_4$ | 5.30 g/L |
| NaCl | 3.79 g/L |
| Phytone | 65.45 g/L |
| Bacto Yeast Extract | 21.80 g/L |
| $MgSO_4$ | 0.12 g/L |
| $FeSO_4x7H_2O$ | 18.18 mg/L |

-continued

| Component | Quantity |
|---|---|
| Riboflavin | 0.758 mg/L |
| Niacin | 1.52 mg/L |
| Calcium Pantothenate | 1.52 mg/L |
| Pimelic acid | 1.52 mg/L |
| Pyridoxine | 1.52 mg/L |
| Thiamine | 1.52 mg/L |
| Volume for 5 L fermentation | 3.3 L |
| Fed-batch Phase | |
| Glucose | 17.86 g/L |
| Phytone | 151.43 g/L |
| Bacto Yeast Extract | 127.14 g/L |
| Volume for 5 L fermentation | 1.4 L |

It is also desirable to scale-up the fermentation process further without detracting from the quality or yields of the collagenase products. Thus, the invention further relates to an approximately 200 liter fed batch process as described in the flow chart in FIG. 33c.

Viable Cell Counting Method

Samples taken from the shake flasks were diluted by a factor of $10^{-4}$ to $10^{-7}$ and plated out onto TB agar plates. Plates were incubated at 37° C. for approximately 48 hours in a Genbox Jar. An Anaerobic Gas Generator Pack was used in order to create anaerobic conditions within the Jar. The number of colonies was then counted.

Ammonium Sulphate Precipitation:

Materials: Sorvall Evolution centrifuge

Chemicals: Ammonium Sulphate, GPR grade (BDH)

Supernatant samples (100 mL to 500 mL) were filtered through a 0.22 μm filter. Depending on the experiment various amounts of ammonium sulphate were added (from 15% to 80% saturation). The solution was mixed slowly in a magnetic stirrer for approximately 15 minutes, until all the ammonium sulphate had dissolved. It was then held without mixing for ~3.5 hours at +2-8° C. Following the hold step, significant amount of precipitate was formed. The solution was then centrifuged at 7,200×g for 20 minutes at 4° C. The supernatant was decanted and the pellet stored at −20° C.

Dialysis

Materials: 10 kDa MWCO SnakeSkin Dialysis Tubing (68100, Pierce)

Magnetic Stirrer

Chemicals: Potassium Dihydrogen Orthophosphate AnalaR (BDH)

Water for Injection (WFI)

The pellets obtained from a 100 mL ammonium sulphate sample were re-suspended in 3.3 mL of WFI. The re-constituted pellet was transferred into a pre-wetted 10 kDa MWCO SnakeSkin dialysis tubing and dialyzed against 100 mM of $K_2HPO_4$ (pH 6.7) for ~12 to 16 hours at 2-8° C. The WFI was then changed and dialysis continued for 2 to 4 hours. The dialyzed material was recovered and the volume determined. The post-dialyzed sample was stored at −20° C.

SDS-PAGE Analysis (8% Tris-Glycine Gels)

Materials: Xcell SureLock Mini-Cell

Chemicals:

SDS-PAGE Standards High Molecular Weight (161-0303, Bio Rad)

Novex 8% Tris-Glycine gels, 1.5 mm, 10 well (EC6018BOX, Invitrogen)

Novex 8% Tris-Glycine gels, 1.5 mm, 15 well (EC60185BOX, Invitrogen)

Novex Tris-Glycine SDS Running Buffer (10×) (LC2675, Invitrogen)

Novex Tris-Glycine SDS Sample Buffer (2×) (LC2676, Invitrogen)

NuPAGE Sample Reducing Agent (10×) (NP0009, Invitrogen)

Collodial Blue Staining kit (LC6025, Invitrogen)

Ethylenediaminetetra-acetic acid disodium salt Analar R (BDH)

Samples were prepared for reducing SDS-PAGE by adding 110 μl of sample to 10 μl sample Buffer (2×), 2.5 μl reducing agent (10×) and 2 μl of 0.1M EDTA (to achieve final concentration of 10 mM). The high molecular weight (HMW) marker was prepared by adding 10 μl of concentrated stock to 80 μl reducing agent (10×), 310 μl WFI and 400 μl sample buffer (2×). The diluted HMW standard was then heated at 95° C. for 5 minutes before aliquoting and storage at −20° C. for use in subsequent gels. Samples (15 μl) containing collagenases were run directly (i.e. with no prior heat treatment) on 8% Tris-Glycine gels using Tris-Glycine running buffer at 130 V for ~1 hour 50 mins. After electrophoresis, the gels were stained with colloidal blue stain reagent as per the manufacturer's instructions.

Purification Process

Method Summary for 5 L Process of Purification:

Step 1. Ammonium sulfate precipitation of culture media supernatant (secreted protein).
  Reconstitution and dialysis into 0.1M potassium phosphate, 0.1M arginine pH6.7

Step 2. Hydroxyapatite chromatography (in presence of 200 μM leupeptin)
  Elute with 0-100% gradient of 0.264M potassium phosphate pH6.7 over 4CV
  Pool 2 late-eluting peaks where $A_{280}>A_{260}$, load straight onto TMAE Step 3. Fractogel TMAE ion exchange (in presence of 200 μM leupeptin) Nucleic acid removal (a Pall MUSTANG Q filter can also be used) Collect and pool unbound flowthrough Step 4. Dialysis into 10 mM Tris pH8.0

Step 5. Q Sepharose HP ion exchange (in presence of 200 μM leupeptin)
  Separates AUXI from AUXII
  Elute with 0-40% gradient of 10 mM Tris, 3 mM $CaCl_2$, 360 mM NaCl pH8.0 over 20 CV
  2 peaks collected: Peak 1=AUXII
    Peak 2=AUXI
  Arginine added to 0.1M to AUXI and AUXII containing fractions Step 6. AUXI and AUXII pools concentrated by pressurized stirred-cell Step 7. Superdex 75 Gel Filtration
  Removal of clostripain and gelatinase from AUXI and AUXII
  AUXI and AUXII run individually on separate columns
  Samples loaded at 5% CV
  Buffer: 10 mM Tris, 3 mM $CaCl_2$, 150 mM NaCl, 0.1M Arginine pH8

Step 8. The AUXI and AUXII are pooled and concentrated individually, diafiltered into water and then pooled to form the final drug product.

Column Details:

TABLE 15

Column specifications for 5 L process

| Media | Volume (mL) | Column | Bed height (cm) | Asymmetry | Plates/meter |
|---|---|---|---|---|---|
| HA | 300 | XK50/30 | 15 | 1.85 | 9227 |
| Fractogel TMAE | 58 | XK26/40 | 10 | 1.02 | 5368 |
| Q Sepharose | 100 | XK50/20 | 5 | 1.35 | 19,367 |
| Superdex 75-1 | 880 | XK50/60 | 45 | 1.24 | 18,644 |
| Superdex 75-2 | 880 | XK50/60 | 45 | 1.85 | 13,576 |

Column Packing
Columns were packed as manufacturer's instructions where possible.
TMAE column - no issues were encountered.
Q Sepharose and Superdex 75 - difficulties were encountered in packing to correct pressure due to size of the column. However, the columns could be run at the recommended pressure.
HA - packed as a 50% slurry and run at 10 mL/min.

Yields/Recoveries from 5 L Process:

TABLE 16

Purification from AS ppt to Q-Sepharose IEX
Chromatography step yields in bold

| Process Step | Protein Concentration (mg/mL) | Method | Volume (g) | Total Protein (mg) | Step Yield (%) |
|---|---|---|---|---|---|
| Post AS ppt and dialysis | 1.12 | Bradford | 346.45 | 388.02 | — |
| Pre HA (post-leupeptin addition) | 1.08 | Bradford | 359.85 | 388.64 | — |
| Post HA | 0.51 | Bradford | 646.85 | 329.89 | 84.88 |
| Pre-TMAE | 0.51 | Bradford | 646.85 | 329.89 | — |
| Post-TMAE | 0.51 | UV | 647.2 | 330.07 | 100.05 |
| Post dialysis | 0.404 | UV | 715.0 | 288.86 | 87.51 |
| Pre-IEX | 0.388 | UV | 744.0 | 288.67 | — |
| Post IEX ABC I (peak 2) | 0.454 | UV | 188.1 | 85.40 | 29.58 |
| Post IEX ABC II (peak 1) | 0.536 | UV | 220.7 | 118.29 | 40.98 |

TABLE 17

Purification from Q-Sepharose IEX to post Superdex 75 GPC.

| Process Step | Protein Concentration (mg/mL) | Method | Volume (g) | Total Protein (mg) | Step Yield (%) |
|---|---|---|---|---|---|
| Pre-stirred cell ABC I | 0.454 | UV | 188.1 | 85.40 | — |
| Post-stirred cell ABC I | 1.901 | UV | 41.6 | 79.08 | 92.6 |
| Pre GPC ABC I | 1.901 | UV | 40.6 | 77.18 | — |
| Post GPC ABC I | 1.12 | UV | 60.0 | 67.2 | 87.07 |
| Pre-stirred cell ABC II | 0.536 | UV | 220.7 | 118.29 | — |
| Post-stirred cell ABC II | 2.76 | UV | 45.5 | 125.58 | 106.16 |
| Pre GPC ABC II | 2.46 | UV | 44.0 | 108.24 | — |
| Post GPC ABC II | 1.192 | UV | 59.3 | 70.68 | 65.3 |

Yields from a 5 L process are approximately 60-75 mg each of ABCI and ABCII

For the scale up, depending on fermentation, yields of 250-300 mg for 20 L and 2500-3000 mg for 200 L could be expected.

Individual Chromatography steps of 5 L scale process:

Hydroxyapatite Chromatography

| | |
|---|---|
| Column size: | 2 × 300 mL in XK50/30 (15 cm bed height each) |
| Buffer A: | 0.1M potassium phosphate, 200 μM leupeptin, pH6.7 |
| Buffer B: | 0.264M potassium phosphate, 200 μM leupeptin, pH6.7 |
| Sample: | ~350 mL (in 0.1 M potassium phosphate, 0.1M Arginine pH6.7) loaded at <1.0 mg/mL media* |
| Flow rate: | 9.8 mL/min |
| Elution: | 0-100% B over 4 CV |

FIG. 34 shows a chromatogram after hydroxyapatite with a loading of 1.0 mg/L media, wherein a considerable loss of resolution and target degradation occurs.

Fractogel TMAE Anion Exchange

| | |
|---|---|
| Column size: | 58 mL in XK26/20 (10 cm bed height) |
| Buffer A: | 10 mM Potassium Phosphate, 0.2M NaCl, 200 μM leupeptin, pH6.7 |
| Buffer B: | 10 mM Potassium Phosphate, 2M NaCl, pH6.7 |
| Sample: | ~650 mL @ 0.5 mg/mL (in Potassium Phosphate pH6.7, straight from HA column) loaded at ~5.5 mg/mL media |
| Flow rate: | 8.8 mL/min |
| Elution: | (100% B to elute nucleic acid) |

FIG. 35 illustrates a chromatogram after Fractogel TMAE anion exchange. The unbound fraction pooled to give ~650 mL at 0.5 mg/mL. Dialysed into 10 mM Tris at pH8.

FIG. 36 shows a SDS-PAGE gel of Pre HA, Post HA and Post TMAE material from 5 L scale process. The gel is stained with Colloidal blue.

Q Sepharose HP Anion Exchange with Original Elution Gradient

| | |
|---|---|
| Column size: | 100 mL in XK50/20 (5.0 cm bed height) |
| Buffer A: | 10 mM Tris, 3 mM CaCl$_2$, 200 μM leupeptin, pH8.0 |
| Buffer B: | 10 mM Tris, 3 mM CaCl$_2$, 360 mM NaCl, 200 μM leupeptin, pH8.0 |

-continued

| | |
|---|---|
| Sample: | ~650 mL at 0.5 mg/mL (in 10 mM Tris, pH8.0 + 200 µM leupeptin) loaded at ~3.0 mg/mL media |
| Flow rate: | 18.0 mL/min |
| Elution: | 0-40% B over 20 CV |

Figure 37:
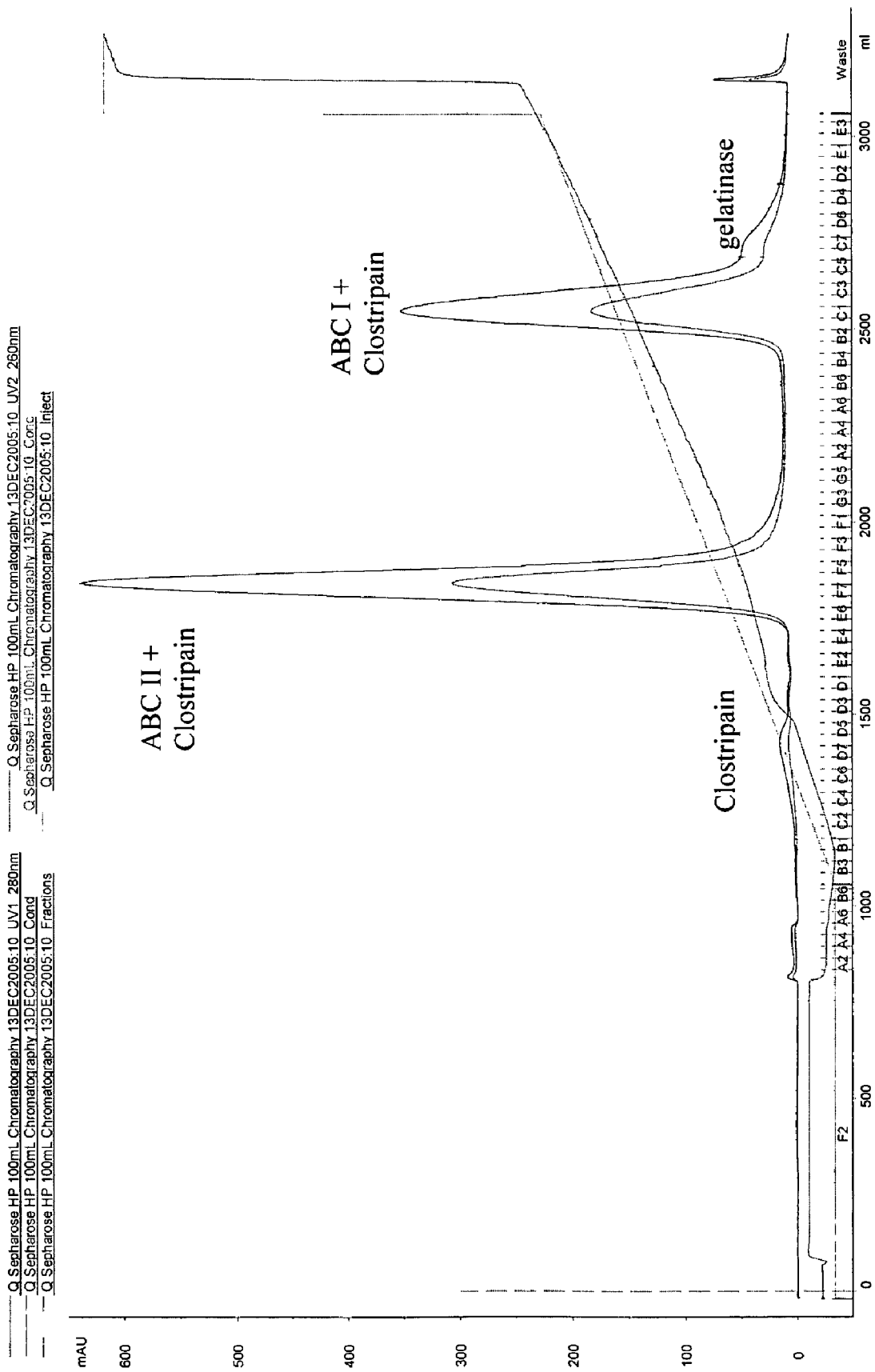

FIG. 37 illustrates a chromatogram after Q Sepharose HP anion exchange with original elution gradient. Arginine is added to 0.1M to ABCI and ABCII containing fractions. Peak 1 fraction (ABCII) pooled to give ~220 mL at 0.55 mg/mL which was concentrated by stirred-cell to give ~45 mL at 2.8 mg/mL. Peak 2 fractions (ABCI, excluding gelatinase shoulder) pooled to give ~190 mL at 0.45 mg/mL, which was concentrated by stirred-cell to give ~42 mL at 2 mg/mL.

Figure 38:
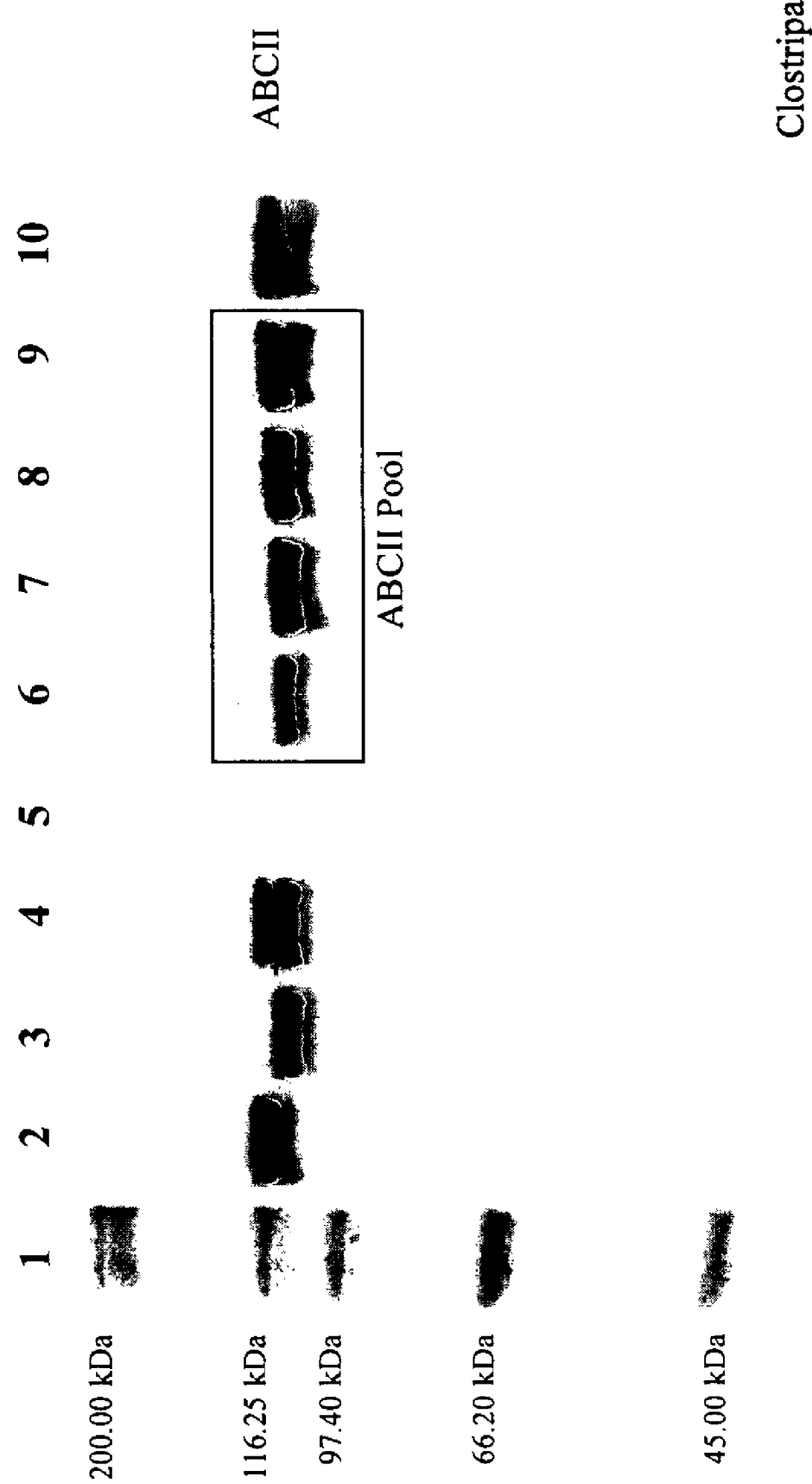

FIG. 38 shows a SDS-PAGE gel of Q Sepharose IEX chromatography of post TMAE material run in the presence of leupeptin for Peak 1 (ABCII). The gel is stained with Colloidal blue.

Figure 39:
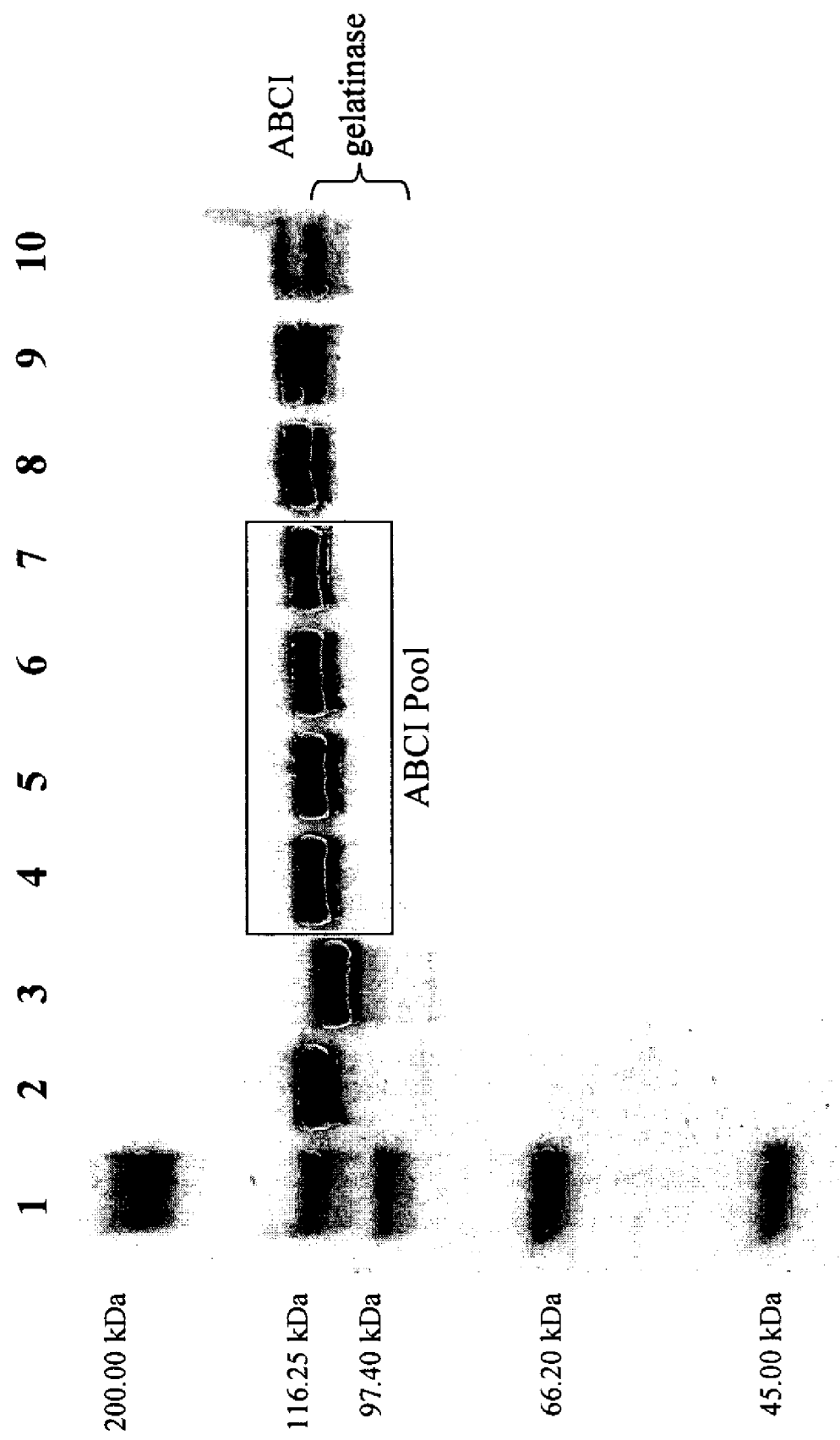

FIG. 39 shows a SDS-PAGE gel of Q Sepharose IEX chromatography of post TMAE material run in the presence of leupeptin for Peak 2 (ABCI). The gel is stained with Colloidal blue.

Q Sepharose HP Anion Exchange with Modified Gradient

Small scale test of NaCl addition to Buffer A and using a steeper/faster gradient.

Sample was from a ⅓ 5 L process, post TMAE, previously frozen (−20° C.).

| | |
|---|---|
| Column size: | 1 mL |
| Buffer A: | 10 mM Tris, 30 mM NaCl, 3 mM CaCl$_2$, 200 µM leupeptin, pH8.0 |
| Buffer B: | 10 mM Tris, 3 mM CaCl$_2$, 360 mM NaCl, 200 µM leupeptin, pH8.0 |
| Sample: | 3 mg post TMAE, post dialysis into 10 mM Tris, 30 mM NaCl, 200 µM leupeptin, pH 8.0. Loaded at 3 mg/mL media |
| Gradient: | 0-25% B over 2CV, 25% B for 2CV, 25-40% B over 7.5CV |

Figure 40:
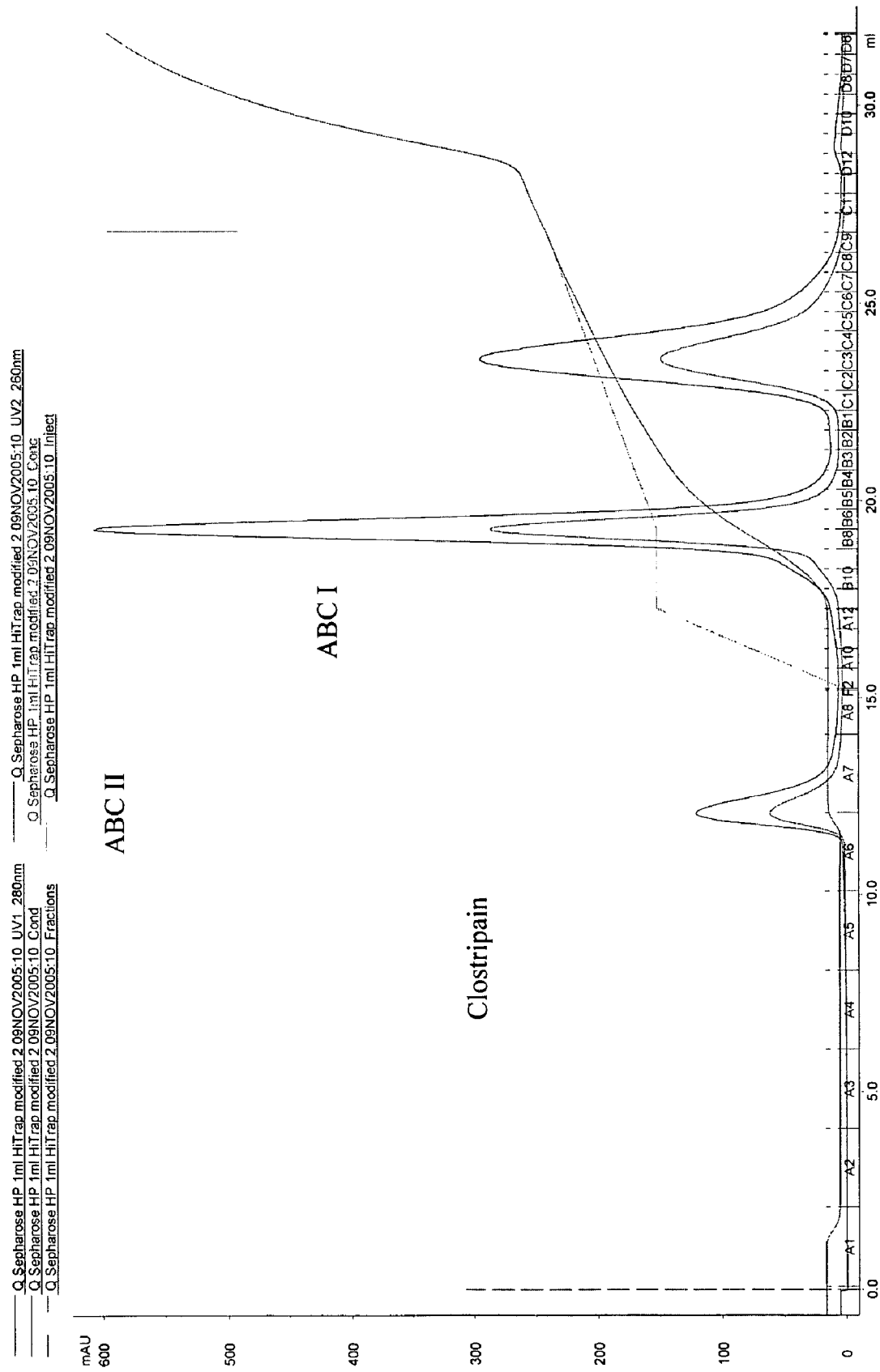

FIG. 40 illustrates a chromatogram after Q Sepharose HP anion exchange with modified elution gradient. Good separation of ABCI and ABCII is observed. The second part of the gradient can be made steeper to sharpen ABCI peak. Improvement of the peak can also be made using 5 mL CV loaded at 3 and 10 mg/mL media.

Superdex 75 Gel Permeation Chromatography of ABCII (Peak 1 from IEX)

| | |
|---|---|
| Column size: | 880 mL in XK50/60 (54 cm bed height) |
| Buffer: | 10 mM Tris, 3 mM CaCl$_2$, 150 mM NaCl, 0.1M arginine, pH 8.0 |
| Sample: | ~44 mL (5% CV) at 2.5 mg/mL (in 10 mM Tris, 3 mM CaCl$_2$, ~60 mM NaCl, 0.1M arginine, pH 8.0) |
| Flow rate: | 8.8 mL/min |

Figure 41:
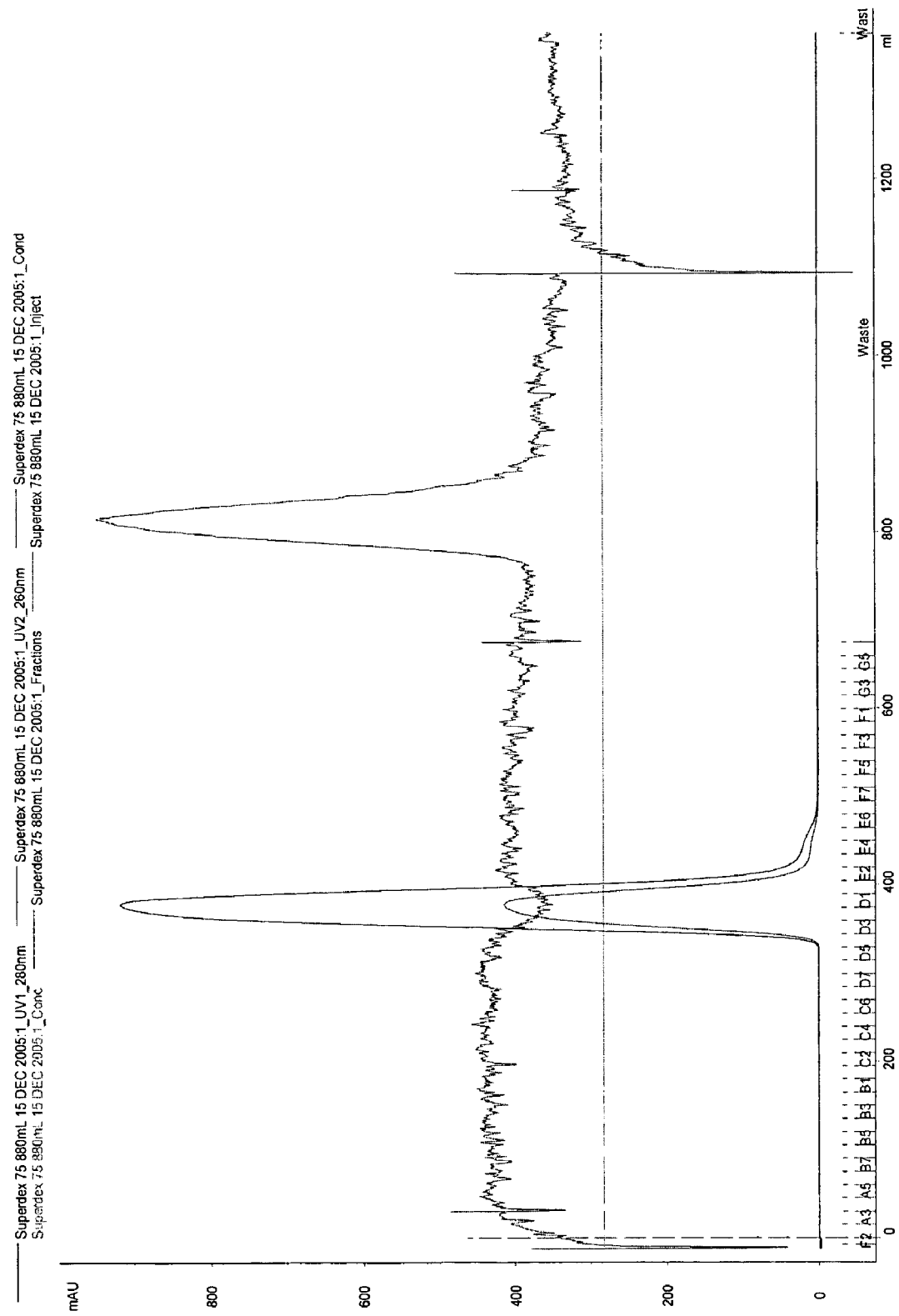

FIG. 41 illustrates a chromatogram after superdex 75 gel permeation chromatography of ABCII (Peak 1 from IEX). Peak pooled to give ~60 mL ABC II at 1.2 mg/mL.

Figure 42:
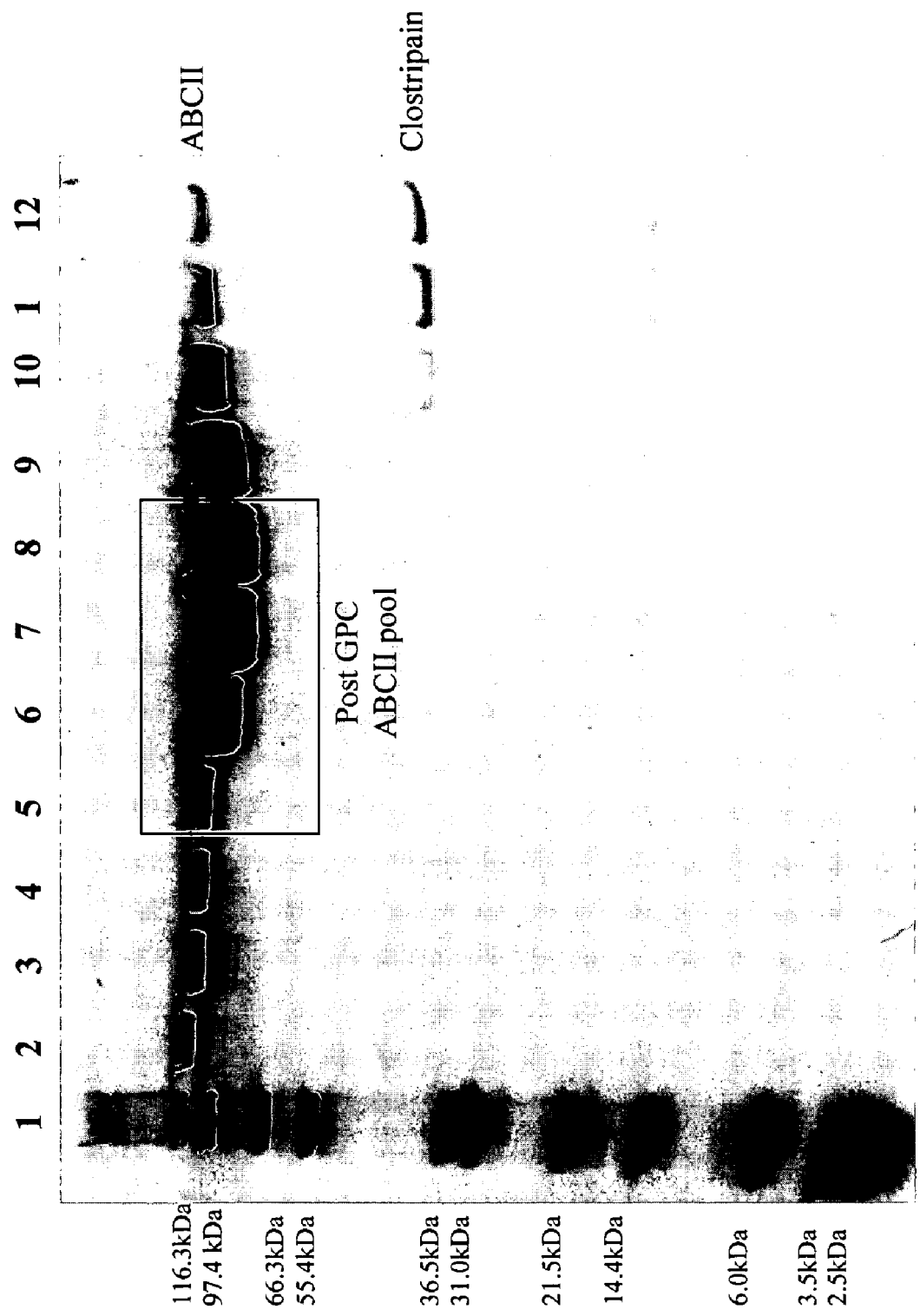

FIG. 42 shows a SDS-PAGE gel of superdex 75 gel permeation chromatography of concentrated ABC II run in the presence of arginine. The gel is stained with Colloidal blue.

Superdex 75 Gel Permeation Chromatography of ABCI (Peak 2 from IEX):

| | |
|---|---|
| Column size: | 880 mL in XK50/60 (54 cm bed height) |
| Buffer: | 10 mM Tris, 3 mM CaCl$_2$, 150 mM NaCl, 0.1M arginine, pH 8.0 |
| Sample: | ~42 mL (5% CV) at 2.0 mg/mL (in 10 mM Tris, 3 mM CaCl$_2$, ~60 mM NaCl, 0.1M arginine, pH 8.0) |
| Flow rate: | 8.8 mL/min |

Figure 43:
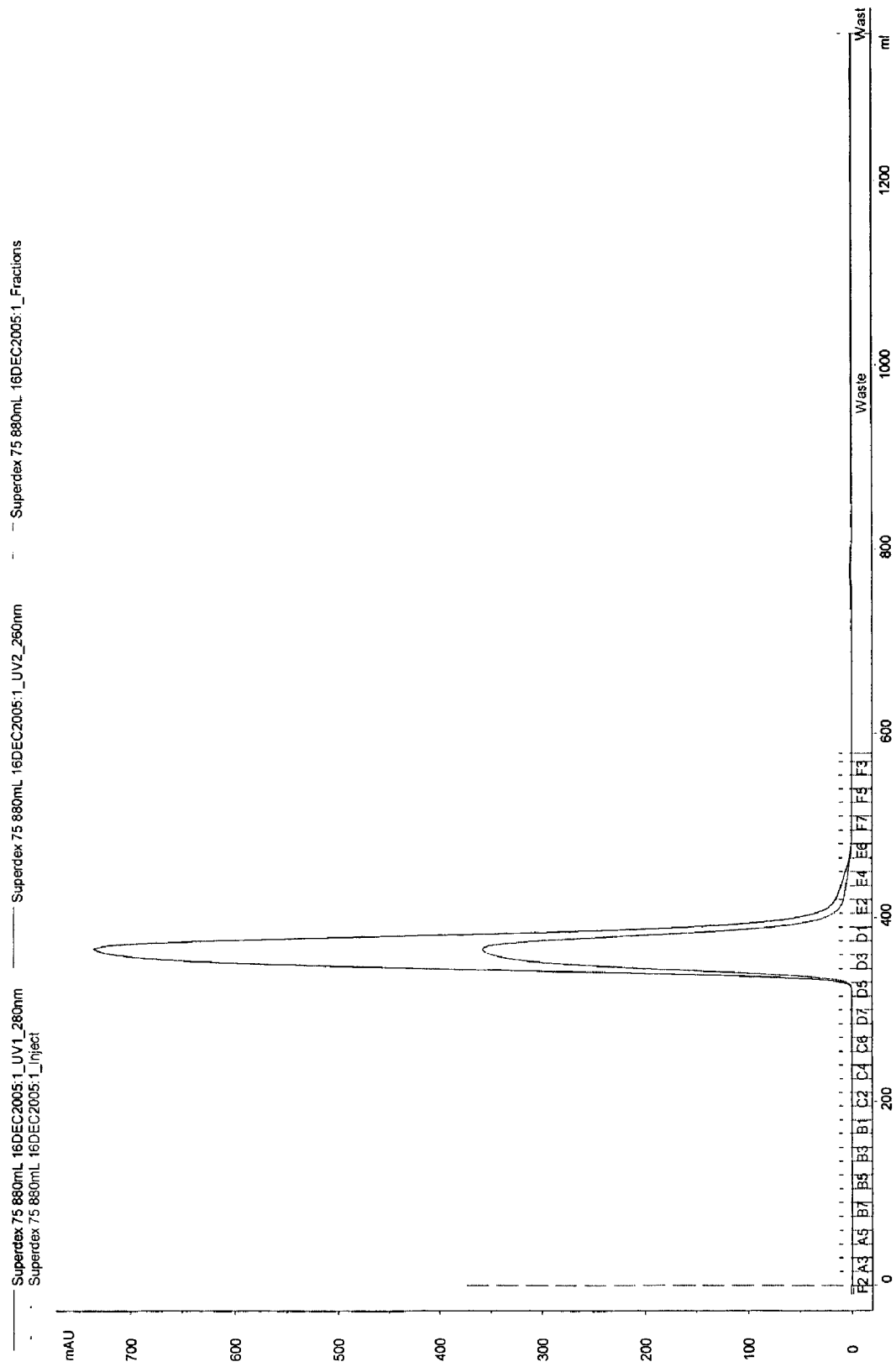

FIG. 43 illustrates a chromatogram after superdex 75 gel permeation chromatography of ABCI (Peak 2 from IEX). Peak pooled to give ~60 mL ABC I at 1.1 mg/mL.

FIG. 44 shows a SDS-PAGE gel of superdex 75 gel permeation chromatography of concentrated ABC I run in the presence of arginine. The gel is stained with Colloidal blue.

Scale Up Column Sizing

TABLE 18

| Process Scale | Media volume | Column type | Bed height | Media volume | Column type | Bed height |
|---|---|---|---|---|---|---|
| | Hydroxyapatite | | | Fractogel TMAE | | |
| ⅓ | 220 mL | XK50/30 | ~11 cm | 18 mL | XK16/20 | ~9 cm |
| 5 L | 2 × 300 mL | XK50/30 | ~15 cm | 54 mL | XK26/40 | ~10 cm |
| 20 L | 2.4 L (at 1 mg/mL load) | * | * | 216 mL | XK50/20 | ~11 cm |
| 200 L | 24 L | * | * | 2.2 L | * | * |
| | Q Sepharose HP | | | Superdex 75 | | |
| ⅓ | 65 mL | XK26/20 | ~12 cm | 300 mL | XK26/70 | ~57 cm |
| 5 L | 100 mL | XK50/20 | ~5 cm | 880 mL | XK50/60 | ~45 cm |
| 20 L | 400 mL (at 3 mg/mL load) | * | * | 4 L | * | * |
| 200 L | 4 L (at 3 mg/mL load) | * | * | 40 L | * | * |

* Column type and resulting bed height to be further optimized. Media volumes are linear scale up from 5 L scale.

In yet other embodiments of the invention, the dialysis steps of the purification process described above can be substituted with ultrafiltration/diafiltration (UF/DF) operations using dialysis and stirred cells will be replaced by TFF, tangential flow filtration. The TMAE step discussed above is optional.

The invention includes the collagenase products that are produced by (or can be produced by) the above purification processes. Such collagenase products possess exceptional high degrees of purity and retained enzymatic activity. For example, the compositions are free of clostripain (e.g., possess negligible or undetectable levels of clostripain).

Optimization of the Manufacturing Process:

In order to support clinical studies and provide a commercial-scale process, optimization of the manufacturing process earlier developed was completed. The process changes are described briefly below, and are outlined in Table 19.

TABLE 19

Summary of Process Changes between BTC (Process 1) and Auxilium Supplies (Process 2 and 3)

| Stage | | Process 1 | Process 2 | Process 3 |
|---|---|---|---|---|
| Fermentation and Primary Recovery | Cell line | 013 and 004 | 004 | 004 |
| | Cell line storage form | Lyophilized | Frozen liquid culture | Frozen liquid culture |
| | Cell bank medium | Bovine-derived | Non animal-derived | Non animal-derived |
| | Seed medium | Bovine-derived | Non animal-derived | Proteose peptone (porcine-derived) |
| | Seed scale-up strategy | 1 WCB vial →1 × 500 mL bottle → 45 L fermentor | 2 WCB vials→2 × 30 mL → 2 × 500 mL flasks→ 1 × 20 L fermentor | 1 WCB vials→3 × 25 mL → 4 × 200 mL flasks→ 1 × 20 L fermentor→200 L fermentor |
| | Production medium | Bovine-derived | Non animal-derived | Proteose peptone (porcine-derived) |
| | Production medium sterilization | Autoclaved | Sartoclear maxicap and 0.2 μm filters | In situ media sterilization and 0.2 micron filtration |
| | Production strategy | Batch | Fed-batch | Batch |
| | Production scale | 45 L | 20 L | 200 L |
| | Harvest method | 10 μm and 1 μm filter train | Millipore Millistak HC Pod | Millipore Millistak HC Pod filter |
| | Ammonium Sulfate precipitation (AS ppt) | 95% saturation | 60% saturation | Capture proteins using Phenyl Sepharose FF Low Substitution chromatography media |
| | Resuspended AS ppt buffer exchange | Dialysis | Dialysis | N/A |
| | Temperature control | None | 2-8° C. solutions | 2-8° C. solutions |
| Purification | New chromatography/filtration step | NA | Mustang Q filter | Mustang Q filter |
| | New chromatography step | NA | Superdex 75 GPC | Elimination of Hydroxyapatite (HA) and GPC |
| | HA and Q HP buffer systems | minus leupeptin | 200 μM leupeptin | 200 μM leupeptin |
| | Temperature control | None | 2-8° C. buffers and column packings | 2-8° C. buffers and column packings |
| | Buffer exchange Pre-Q HP | Dialysis | Dialysis | TFF |
| | Buffer exchange Post-Q HP | Dialysis | Dialysis | NA |
| | Concentrate/diafilter into final formulation | Dialysis | Dialysis | TFF |
| | Scale-up all steps for 200 L fermentation | NA | NA | 4.5 times |
| Formulation | Formulation of Drug Substance (DS) | DS in WFI dilute w/Lactose | DS in WFI dilute w/Lactose | DS in 10 mM Tris, 60 mM Sucrose, pH 8.0 |

Fermentation Optimization

Removal of the bovine-derived raw materials from the original cell bank and fermentation process was carried out. Strain 004 of *Clostridium histolyticum* was propagated for use as the master cell bank based on passage viability required for scale-up. The specifications and analytical results for the master cell bank are captured in Table 20. In order to increase biomass and production of collagenase, a fed-batch fermentation strategy was developed utilizing animal-free raw materials in the growth medium at a 20 Liter fermentation scale. Further fermentation scale-up to 200 Liter was observed to require the use of a porcine-derived media component (i.e., Proteose Peptone #3, infra) to assure consistent cell growth, collagenase expression, and an improved impurity profile. Subsequent changes were made to increase the yield and purity of collagenase over the downstream process. These changes include the addition of new separation and filtration strategies, as well as scale-up of the production equipment to support the 200 Liter batch fermentation scale. FIG. 45 depicts a flow chart of the fermentation for process 3.

TABLE 20

| Analytical Specifications and Test Results for Master Cell Bank | | |
|---|---|---|
| Test | Specification | Result |
| Identity | Expected profile, >95% ID | Expected profile, 99.9% ID |
| Viable Count | ≧1 × $10^6$ cfu/mL on TB agar | 1.3 × $10^7$ cfu/mL on TB agar |
| Purity Test | No extraneous organisms observed | No extraneous organisms observed |
| Colony Morphology (anaerobic at 37° C.) | Irregular shape, 1-2 mm in size, grey to white color | Irregular, flat elevation, undulate margin 1-2 mm diameter (48 hr), grey, white color |
| Gram Stain | Gram positive rods | Gram positive rods |
| Phenol Red Dextrose fermentation | Negative | Negative |
| Hydrogen Sulfide production | Positive | Positive |

TABLE 20-continued

Analytical Specifications and Test Results for Master Cell Bank

| Test | Specification | Result |
| --- | --- | --- |
| Gelatinase Test | Positive | Positive |
| Spore Test | Negative | Negative on all media |
| Growth in cooked meat media | Positive | Positive |
| Growth in thioglycollate media | Growth as finger-like projection | Growth as finger-like projection |
| Motility Test (MIO media) | Non-motile | Non-motile |
| Bacteriophage | None detected | No confirmed evidence of phage |

Primary Recovery and Purification Optimization

Further development to optimize the primary recovery and downstream purification process is being undertaken. Substitution of the ammonium sulfate precipitation with phenyl sepharose fast flow low sub column chromatography to capture the collagenases has been implemented to improve yields, eliminate the use of bulk ammonium sulfate and to improve aseptic processing.

With regards to purification, the Pall MUSTANG Q filter has been implemented for residual DNA and impurity clearance to further enhance yields and simplify the production process train and validation requirements. The Quaternary Amine Sepharose High Performance (Q HP) operating parameters have been optimized to eliminate the Gel Permeation Chromatography (GPC) step. In addition to the process changes cited above, the drug substance formulation has been modified to include 10 mM Tris, 60 mM Sucrose, pH 8.0, improving both product solubility and drug substance and drug product stability.

The optimization process took place in two stages. The initial process (Process 2) utilizes an animal-free medium for all cell banking and fermentation stages with the fed-batch fermentation performed at the 20 Liter scale. The downstream process has been adapted from Process 1 to include MUSTANG Q filtration for residual DNA removal and Superdex 75 GPC for additional host cell contaminant clearance. Leupeptin has also been added to the chromatography buffer systems to prevent proteolytic degradation. Process 2 material has been bridged analytically with Process 1 material (Table 21A), and was tested in a side-by-side pre-clinical study outlined herein. Process 2 material has been proposed for use in the early stage of the Phase 3 clinical program. The specifications for Process 2 intermediates and drug substance are detailed in Tables 22 and 23 respectively. Further process, formulation and lyophilization development provided an optimized manufacturing process (Process 3). These changes include the addition of new separation and filtration strategies, as well as scale-up of the production equipment to support the 200 Liter batch fermentation scale as outlined in Table 19. FIG. 46 depicts a flow chart of the purification for process 3.

Declaration of dose: The initial in vitro potency assay was a bovine collagenase assay and did not differentiate collagenase types I and II. This assay was utilized for the material used in the open label, DUPY101 and DUPY 202 clinical studies only, with the 0.58 mg dose typically resulting in a potency of 10,000 Units. Analysis of Process I material utilizing the current separate in vitro potency assays for type I collagenase and type II collagenase typically results in 1,700 to 3,500 Units/dose (0.58 mg dose) for type I collagenase and 43,000 to 69,000 Units/dose (0.58 mg dose) for type II collagenase. Analysis of Process 2 material utilizing the current in vitro potency assays has confirmed that similar relative potency values compared to Process 1 material are typically achieved.

Demonstration of analytical comparability between Process 1 and Process 2: In order to support the changes between Process 1 and Process 2, comparability data have been submitted in the form of release testing and analytical characterization. These data are presented in Table 21.

Comparison of the intermediates, described as AUX-I and AUX-II, and drug substance from the previous process (Process 1; Reference) with a process of the invention (Process 2). This analytical comparison shows that material manufactured from Process 2 is comparable to that made with Process 1 (Table 21). In particular, the identity, potency and purity between these materials are comparable.

The purity level of Process 2 intermediates is shown in FIG. 47, a reduced SDS-PAGE Coomasie stained gel. The gel shows a single band for each intermediate with no other minor bands evident. AUX-I has an apparent MW of 115 kDa and compares with the reference (ABC I), while AUX-II has an apparent MW of 110 kDa and compares with the reference (ABC II). FIG. 48 shows a reduced SDS-PAGE Coomasie stained gel depicting drug substance. As with the intermediates, drug substance manufactured by Process 2 compares with the reference (Process 1). A silver stained SDS-PAGE gel is depicted in FIG. 49 further substantiating the high purity level of the Process 2 drug substance. In summary, the release testing and analytical characterization for the intermediates (AUX-I and AUX-II) and drug substance manufactured using Process 2 clearly demonstrates comparability with Process 1 (Reference) materials. Additionally, further release testing was performed on Process 2 material and is listed in Table 21B. In conclusion, the direct analytical comparison between Process 1 and Process 2 materials (Table 21), and the further intermediate and release testing (Table 22) indicate that Process 2 material is suitable for use in the human studies. Tables 23 and 24 further list the analytical specifications resulting from Process 2 manufacturing process.

TABLE 21

Analytical comparability between (Process 1) and Auxilium (Process 2) intermediates and drug substance.

| Test | Intermediate AUX-I | Intermediate AUX-II | Drug Substance | Drug Substance Specification | |
|---|---|---|---|---|---|
| Identity by SDS-PAGE | Conforms to reference (see attached) | Conforms to reference (see attached) | Conforms to reference (see attached) | Major collagenase band between 100-115 kDa; no minor bands | Major collagenase band between 107-110 kDa; no minor bands |
| Rat Tail Tendon Collagen Assay for Potency (AUX-I) | 2310 units/mg | — | 2866 units/mg | 1700-3500 units/mg | |
| Process 1 Reference | 2704 units/mg | — | 2018 units/mg | * | |
| Potency for Class II Collagenases (AUX-II) | — | 179704 units/mg | 50955 units/mg | 43000-69000 units/mg | |
| Process 1 Reference | — | 174045 units/mg | 58491 units/mg | * | |
| Analysis of proteins using the Agilent 1100 HPLC System (Purity and aggregation by size exclusion chromatography) | 100% main peak; 0% aggregates | 100% main peak; 0% aggregates | 100% main peak; 0% aggregates | ≧99% main peak; ≦1% aggregates by area | |
| Process 1 Reference | 87% main peak; 13% aggregates | 90% main peak; 10% aggregates | Intermediates used** | * | |
| Analysis of proteins using the Agilent 1100 HPLC System (Identity and purity by reverse phase liquid chromatography) | 99% AUX-I; 1% AUX-II | 100% AUX-II | 100% AUX-I and AUX-II | 2 major peaks (AUX I & AUX II), combined ≧97% by area; Retention times of AUX-I and AUX-II within 5% of reference | |
| Process 1 Reference | 89.4% ABC-I; 5.4% ABC-II; 5.2% other | 93% ABC-II; 0.5% ABC-I; 6.5% other | Intermediates used** | * | |
| Analysis of proteins using the Agilent 1100 HPLC System (Gelatinase by anion exchange chromatography) | <1% | <1% | <1% | <1% by area | |
| Process 1 Reference | <1% | <1% | <1% | * | |
| Peptide Mapping by Tryptic Digest and Reverse Phase HPLC | Peak pattern conforms to Reference | N/A | Peak pattern conforms to Reference | Conforms to reference | |
| N- & C-terminal sequencing | Sequence identical to Reference*** | Sequence identical to Reference | Not required | Conforms to reference | |

* Process 1 preliminary specifications not included here
**Drug Substance not available for these tests, limited supplies on hand
***N-terminal sequencing completed for AUX-I (identical to reference), but further development required for AUX-II as N-terminus appears to be blocked.

TABLE 22

Analytical results for Process 2 intermediates and drug substance

| Test | Intermediate AUX-I | Intermediate AUX-II | Drug Substance |
|---|---|---|---|
| pH of Solution | Not required | Not required | 6.8 |
| Protein Concentration by Bradford Assay | Not required | 1.54 mg/mL | Not required |
| Total Protein by Absorbance Spectrophotometry | 1.36 mg/mL | 1.39 mg/mL | 1.41 mg/mL |
| Residual Host Protein | Not required | Not required | Band pattern similar to Reference |
| Residual Host DNA | Not required | Not required | 2.9 ng/mL* |
| Endotoxin | Not required | Not required | 8.7 EU/mg |
| Residual Leupeptin | Not required | Not required | <1 µg/mL |

*Result is at the LOQ of the previous residual DNA method

TABLE 23

Analytical Specifications for Process 2 AUX-I and AUX-II Intermediates

| Test | Specification AUX-I | AUX-II |
|---|---|---|
| Appearance | Clear colorless and free from particulate matter | Clear colorless and free from particulate matter |
| *Endotoxin | <10 EU/mL | <10 EU/mL |
| Identity (and purity) by SDS-PAGE (Reduced conditions, Coomasie and silver stained) | Major band between 110-115 kDa, and no minor bands | Major band between 107-110 kDa, and no minor bands |
| *Total Protein by Absorbance Spectroscopy | 1.0-1.5 mg/mL | 1.0-1.5 mg/mL |
| SRC assay (AUX-I) | 1900-3300 units/mg | Not applicable |
| GPA assay (AUX-II) | Not applicable | 4300-6400 units/mg |
| Analysis of Proteins using the Agilent 1100 HPLC System (Aggregation by size exclusion chromatography) | ≧99% main peak; ≦1% aggregates by area | ≧99% main peak; ≦1% aggregates by area |
| *Analysis of Proteins using the Agilent 1100 HPLC System (Purity by reverse phase liquid chromatography) | ≧97% by area | ≧97% by area |
| Analysis of Proteins using the Agilent 1100 HPLC System (Residual gelatinase by anion exchange chromatography) | <1% by area | <1% by area |
| Analysis of Proteins using the Agilent 1100 HPLC System (Residual clostripain by reverse phase liquid chromatography) | <1% by area | <1% by area |
| Identity by Peptide Mapping | Conforms to reference | Conforms to reference |
| Bioburden | <100 CFU/mL | <100 CFU/mL |

*Tests required for provisional release of intermediates for further manufacturing

TABLE 24

Analytical Specifications for Process 2 Drug Substance

| Test | Specification AUX-I | AUX-II |
|---|---|---|
| Appearance | Clear colorless and essentially free from particulate matter | |
| Potentiometric Measure of pH of Solution | 6.0 to 7.0 | |
| Endotoxin | <10 EU/mL | |
| Identity (and purity) by SDS-PAGE (Reduced conditions, Coomasie and silver stained) | Major collagenase band between 100-115 kDa; no minor bands | Major collagenase band between 107-110 kDa; no minor bands |
| *Total Protein by Absorbance Spectroscopy | 1.1-1.5 mg/mL | |
| *SRC assay (AUX-I) | 1700-3500 units/mg | NA |
| *GPA assay (AUX-II) | NA | 43000-69000 units/mg |
| Residual host cell protein | <10 ppm | |
| Residual host cell DNA | <10 pg/dose | |
| Analysis of Proteins using the Agilent 1100 HPLC System (Aggregation by size exclusion chromatography) | ≧99% main peak; ≦1% aggregates by area | |
| *Analysis of Proteins using the Agilent 1100 HPLC System (Identity and purity by reverse phase liquid chromatography) | 2 major peaks (AUX I & AUX II), combined ≧97% by area; Retention times of AUX-I and AUX-II within 5% of AA4500 reference | |
| Analysis of Proteins using the Agilent 1100 HPLC System (Residual clostripain by reverse phase liquid chromatography | <1% by area | |

TABLE 24-continued

Analytical Specifications for Process 2 Drug Substance

| Test | Specification | |
|---|---|---|
| | AUX-I | AUX-II |
| Analysis of Proteins using the Agilent 1100 HPLC System (Residual gelatinase by anion exchange chromatography) | | <1% by area |
| Residual leupeptin by reverse phase chromatography | | <1% by area |
| *Bioburden | | <1 CFU/mL |

*Tests required for provisional release of Drug Substance for further manufacturing Detailed Experimental for Process 3:

Process 3 Fermentation:

The fermentation process using Phytone peptone employed during Process 2 had shown significant variability during both supplies for DSP development and GMP manufacture.

During previous work an animal derived Proteose Peptone had been shown to support the growth of *C. histolyticum* very well. The animal derived Proteose Peptone culture produced significantly less clostripain than observed during Process 2 and expressed AUXI and AUXII at a 1:1 ratio. As a result a regulatory acceptable animal derived peptone, Proteose Peptone #3 from Becton Dickinson (PP3), was evaluated in 5 L fermenters. Initial comparison to the existing Phytone based process (Process 2) showed that using the PP3 at 50 g/L generated a high biomass concentration with a rapid exponential growth rate. The fermentation resulted in a higher product yield of >350 mg/L total collagenase opposed to ~230 mg/L from Process 2 (by semi quantitative SDS-PAGE analysis). Further fermentations using PP3 demonstrated that significantly less clostripain was produced using the animal derived fermentation medium. The first three fermentations (using one batch of PP3) demonstrated very consistent growth profiles. When the product was analysed by SDS-PAGE the yield and purity of collagenase was found to be very reproducible between the three fermentations.

To supply DSP with material for process development several fermentations were conducted using PP3. For this supply material three different batches of PP3 were used. It was noted that when two of these batches were used the growth profiles of the cultivations were not consistent with previous PP3 fermentations and demonstrated variability in the growth profile between fermentations. A small scale investigation showed that batch to batch variability in the PP3 caused this variation. The small scale study also demonstrated that an increase in the PP3 concentration to 100 g/L would prevent this variation.

Two 5 L fermentations were conducted with 100 g/L PP3 using two batches of the peptone, one that resulted in the typical growth profile and one which did not (as demonstrated during the small scale experiment). The experiment showed that the increase in concentration ensured that the two fermentations with different batches of PP3 were reproducible. The growth profiles were highly similar and the product was expressed at a similar yield and purity.

The optimized fermentation process utilizing 100 g/L PP3 was finally scaled to 200 L. The 200 L growth profile was very similar to that seen at 5 L scale. SDS-PAGE analysis of the fermentation filtrate showed a high yield from the 200 L fermentation, ~320 mg/L total collagenase (by quantitative densitometry analysis). The purity of the collagenase product (post fermentation) was similar at both 5 L and 200 L scale. 20 L of the 200 L fermentation filtrate was processed by the DSP group to represent a partial scale-up for the downstream process (infra).

The Proteose Peptone #3 fermentation process (Process 3) generated collagenase with a higher yield and with less clostripain than the existing Phytone process. At 100 g/L PP3 was shown to yield *C. histolyticum* cultivations with reproducible growth curves despite using various batches of PP3. Both the yield and purity of collagenase were also shown to be reproducible when using various lots of PP3.

Evaluation of Proteose Peptone #3 as a Raw Material for Production of Collagenase from *Clostridium histolyticum.*

Due to the variability observed in fermentations utilising Phytone peptone as a complex nitrogen source the suitability of Proteose Peptone #3 (Becton Dickinson, 212230) (PP3) was evaluated in 5 L fermentations. A simple batch strategy with 50 g/L PP3 was used. The exact medium composition can be found in the materials and methods section.

FIG. 51 compares the growth curve of the 50 g/L PP3 (a lower concentration than the Phytone concentration in Process 2) fermentation to the Phytone fed-batch fermentation. The PP3 cultivation demonstrates a very rapid specific growth rate during exponential growth before entering stationary phase approximately 8 hours after inoculation. The PP3 fermentation reached a maximum optical density (600 nm) of 4.7 units. The culture was left for a further 12 hours in stationary phase to monitor product formation/degradation.

FIG. 52 shows SDS-PAGE semi-quantitative analysis of the concentration of the collagenase products from the 20 hour point of the PP3 cultivation. FIG. 53 shows the same analysis for the Phytone fed-batch process. It can be observed that the PP3 fermentation generates more product than the Phytone based process (an increase from 230 mg/L to 360 mg/L total collagenase, based on the semi-quantitative analysis in FIGS. 52 and 53). The PP3 culture also expressed AUXI and AUXII at a 1:1 ratio, whereas the Process 2 produced the two proteins at a 1:1.6 ratio.

Reproducibility of Proteose Peptone #3 Batch Fermentation.

The reproducibility of the PP3 batch process was further examined using lot # 5354796 of Proteose Peptone #3. All three runs illustrated in FIG. 54 demonstrate consistent growth profiles with a maximal optical density (600 nm) of approximately 4.5 obtained after 8 hours.

Semi-quantitative SDS-PAGE analysis of the harvest points of the fermentation showed that yield of total collagenase to be ~350-400 mg/L.

Figure 55:
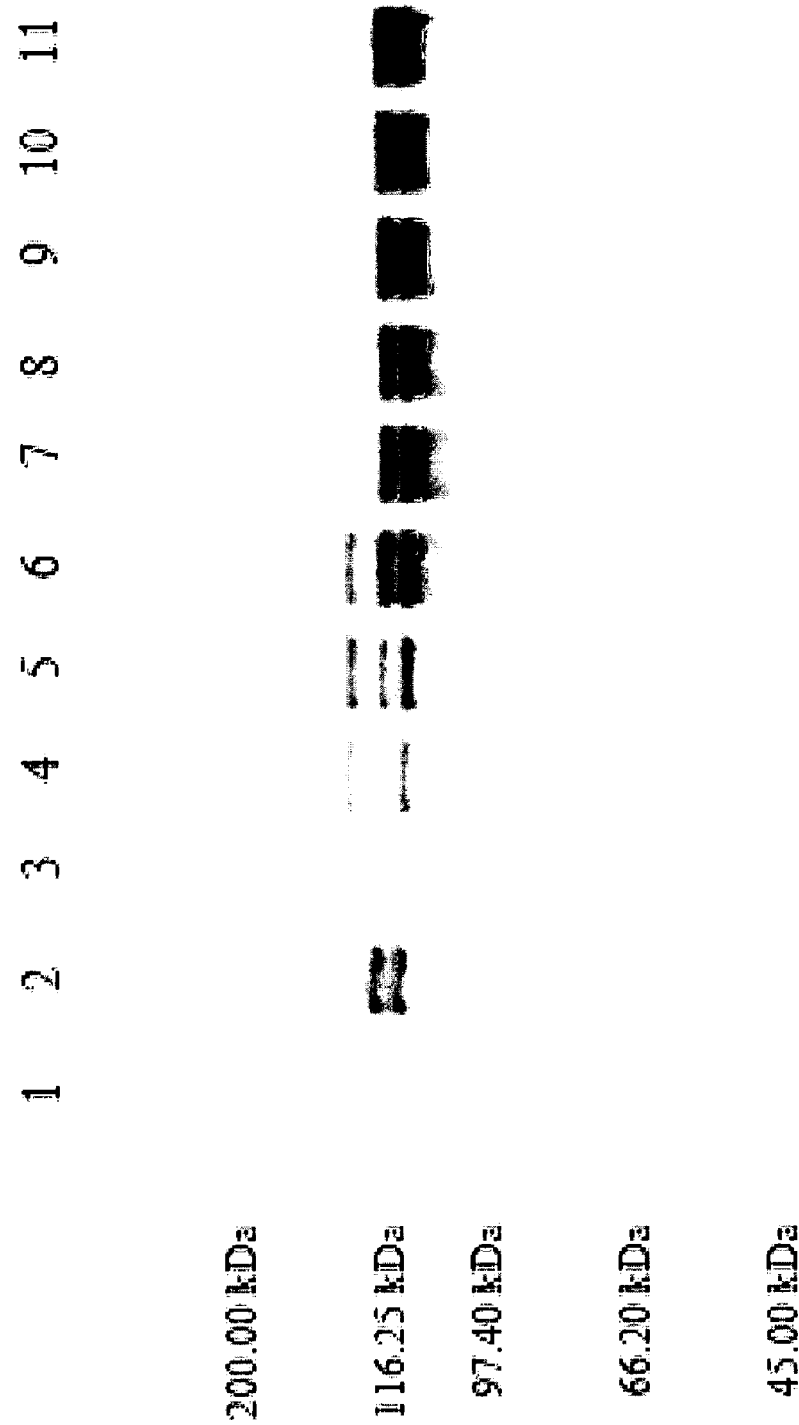

The harvest point of the fermentation was also evaluated during this study. The fermentations were harvested at 8, 11 and 20 hours. FIGS. 55 and 56 show SDS-PAGE analysis of the time course of PP3 fermentation GCFT05d (harvested at 11 hours). The gel depicted in FIG. 55 has been stained with colloidal blue and the gel in FIG. 56 has been silver stained. A third higher molecular weight band can be observed above the two collagenase bands on the gels in FIGS. 55 and 56. It is thought that this band corresponds to an AUXI precursor protein reported in the literature. The precursor band is present during the exponential growth phase. At the end of exponential growth the precursor band decreases in intensity and is not present after 11 hours (in GCFT05d). The main lower molecular weight contaminants can be seen on the silver stained gel at approximately 90, 60, 55, 45 and 40 kDa. It must be noted that these contaminants are present at a low level and are only clearly detected on the silver stained gel. The optimal harvest point for the fermentation was determined to be ~11 hours at this stage of development. FIG. 57 shows SDS-PAGE analysis of samples from the time course of a standard Phytone fed-batch fermentation. A 40 kDa contaminant can be observed on the gel in FIG. 57. This 40 kDa contaminant band from the Phytone fed-batch process was identified as the protease clostripain. By comparing the gels in FIGS. 55 and 57 it is possible to determine that the quantity of clostripain produced using the PP3 fermentation process is significantly lower than the Phytone based fermentation.

Generation of Supply Material for Downstream Process Development

To support downstream process (DSP) development several fermentations were conducted using 50 g/L PP3. During these fermentations two different lots of PP3 were used (5332398 and 5325635). FIG. 58 depicts the growth curves of these fermentations (shown in diamond) compared to a fermentation (shown in square) using lot # 5354796 (GCFT05d). The fermentations with the new batches of PP3 display highly varied growth profiles. Although the initial growth rates of the cultures are all very similar, the point at which they enter stationary phase and therefore the maximum biomass concentrations differ considerably. The optical densities (600 nm) in the inoculum cultures showed very little variation (OD600 of 5 mL stage; 2.9-3.6 units, OD600 of 200 mL stage; 4.5-5.9 units) and no reduction from previous inoculate using PP3 lot # 5354796. The variation and reduced optical density (600 nm) only manifested itself in the final (fermentation) stage of the cultivation. This suggests that reason for the variation was a nutrient limitation in the PP3 and the quantity of the limiting nutrient varied between batches of PP3.

Although these fermentations were successfully used for DSP development and SDS-PAGE analysis showed that there was not a huge variation in the quantity of collagenase produced (350-400 mg/L total collagenase based on semi-quantitative SDS-PAGE analysis, data not shown) it was decided that it was still critical to investigate the reason for the variation. The variation in the growth profile would make it very difficult to predict a harvest point of the fermentation. There were also concerns that nutrient limitation may induce expression of other proteases as seen with the Phytone fed-batch process and specifically the protease, clostripain.

Investigation into the Variation Between Batches of Proteose Peptone #3.

Initial work with PP3 had demonstrated a highly robust process with a higher product yield and lower levels of the protease clostripain. When new batches of PP3 were employed it was observed that the process robustness decreased significantly with highly variable growth profiles. A shake flask experiment was conducted to directly compare the three batches of PP3 used so far (lots 5354796, 5325635 and 5332398). The experiment replicated the two stage inoculum process from the 5 L process but replaced the final fermentation phase with another 200 mL culture. Having this third stage was critical, as the variation was only observed in the final fermentation stage of the process in previous experiments. The optical densities (600 nm) of the cultures were measured at each transfer stage and the cultures were used to inoculate the next stage. Media was prepared using the three batches of PP3 at 50 g/L. One of the two batches that had resulted in lower biomass concentrations of C. histolyticum during 5 L experiments (lot# 5332398) was also prepared at 100 g/L.

Figure 59:
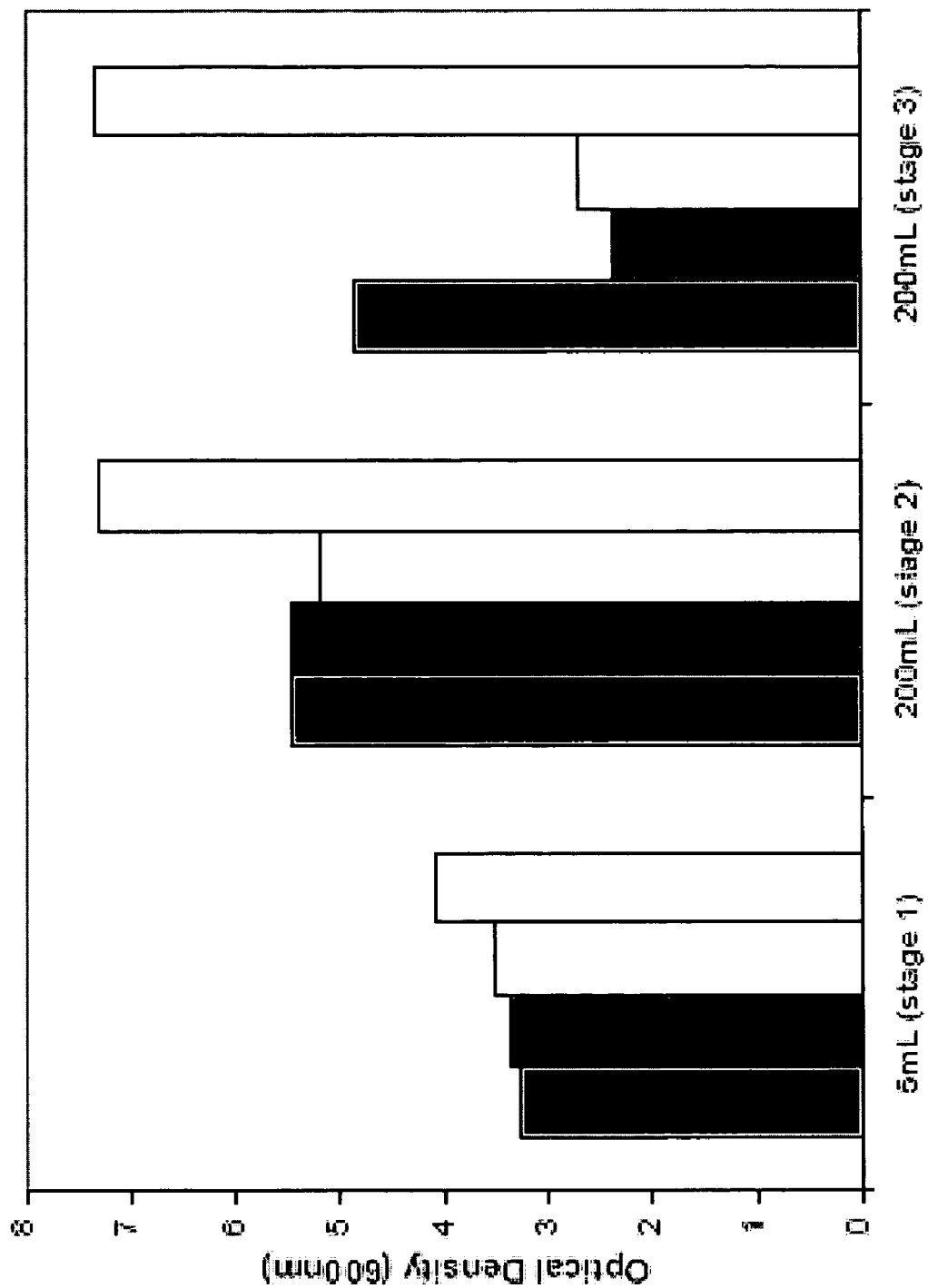

FIG. 59 shows the results from the small scale experiment. It can be observed that lot 5325635 and 5332398 showed reduced optical densities (600 nm) in the third stage of approximately 2.5 units, these were deemed to be "poor" batches of PP3. Lot 5354796 maintains an optical density (600 nm) of 5 units in the third stage of cultivation, this was deemed to be a "good" batch of PP3. Interestingly when the concentration of a "poor" batch of PP3 (5332398) was increased to 100 g/L the same optical density (600 nm) was achieved in the second and third stage of the cultivation. This data does support the theory that the deviations in growth profiles are caused by variation in the quantity of a limiting nutrient between batches of PP3. It was not possible to identify this nutrient by analytical testing of the batches of PP3.

Evaluation of Proteose Peptone #3 at 100 g/L in 5 L Fermentation

Figure 60:
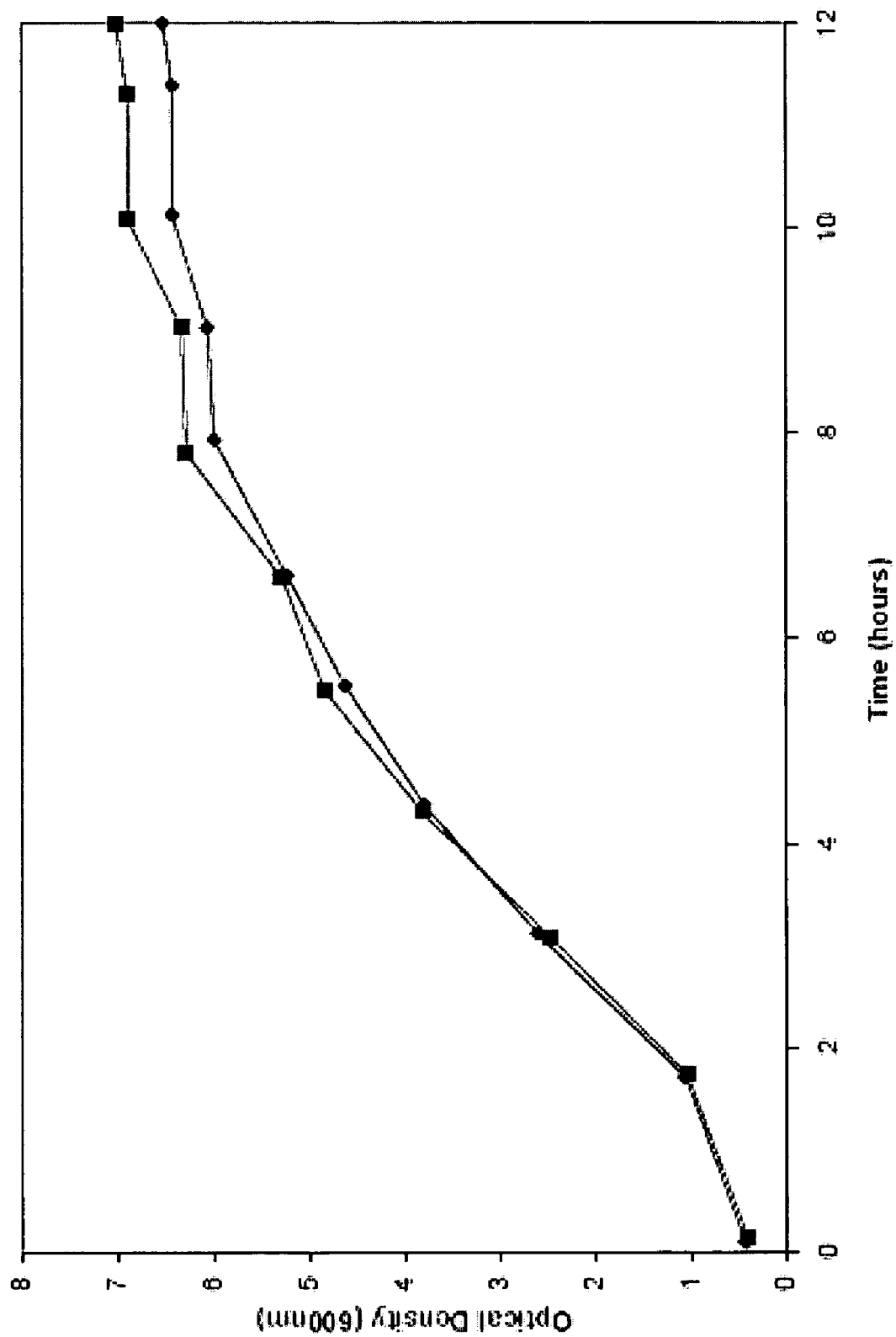

The results of the small scale study demonstrated that increasing the concentration of PP3 from 50 to 100 g/L removed the issue of batch to batch variability. This process change was tested at 5 L scale using a "good" and "poor" batch of PP3 (lot 5354796 and 5325635, respectively) as determined during the small scale investigation into PP3 variability. FIG. 60 shows the growth profiles of the two fermentations. The two cultures show identical specific growth rates during the exponential phase. The fermentation enter stationary phase and reach very similar maximal optical densities (600 nm) of approximately 6.5 units. This data demonstrates that increasing the concentration of PP3 alleviates the issue of batch to batch variability of the PP3. Due to the higher biomass concentration achieved and longer exponential phase in the fermentation harvest point was extended to 12 hours.

Figure 61:
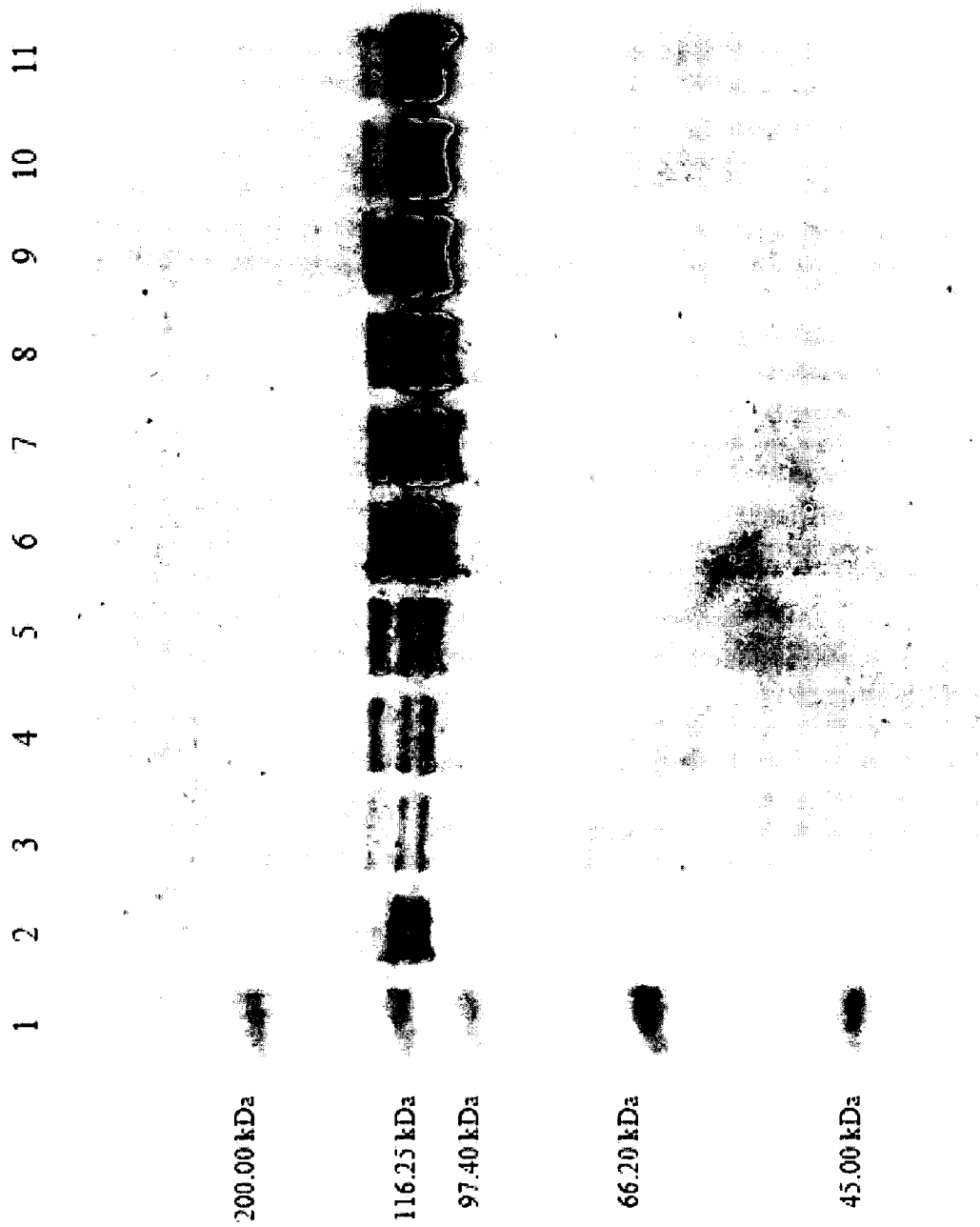
Figure 62:
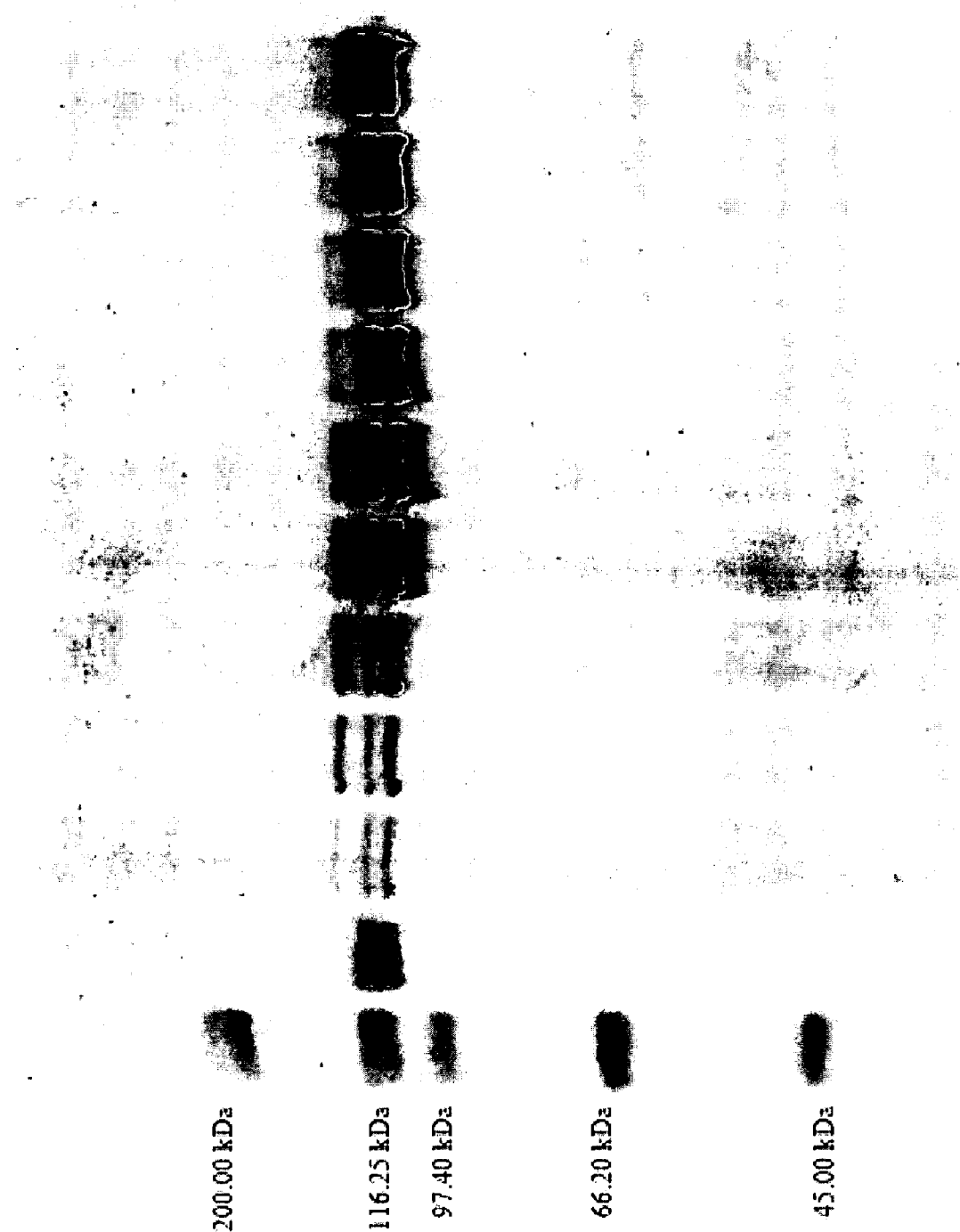

FIGS. 61 and 62 show SDS-PAGE analysis of the two fermentations utilising 100 g/L PP3. The gels demonstrate consistent expression of collagenase in both fermentations. The samples from both fermentations appear to contain similar levels of contaminant described in FIG. 56, although PBFT70d appears contain slightly more of the 40 kDa band (clostripain). It is possible that these small differences are due to staining or loading differences. Again the quantity of clostripain produced using the PP3 process is significantly lower than the Phytone process. The precursor band appears to persist longer into the time course of the fermentation. It was recommended that future fermentations at 100 g/L should be extended to a 14 hour harvest. The presence of the precursor band highlights the importance of the harvest point definition and its qualification during process validation.

Figure 63:
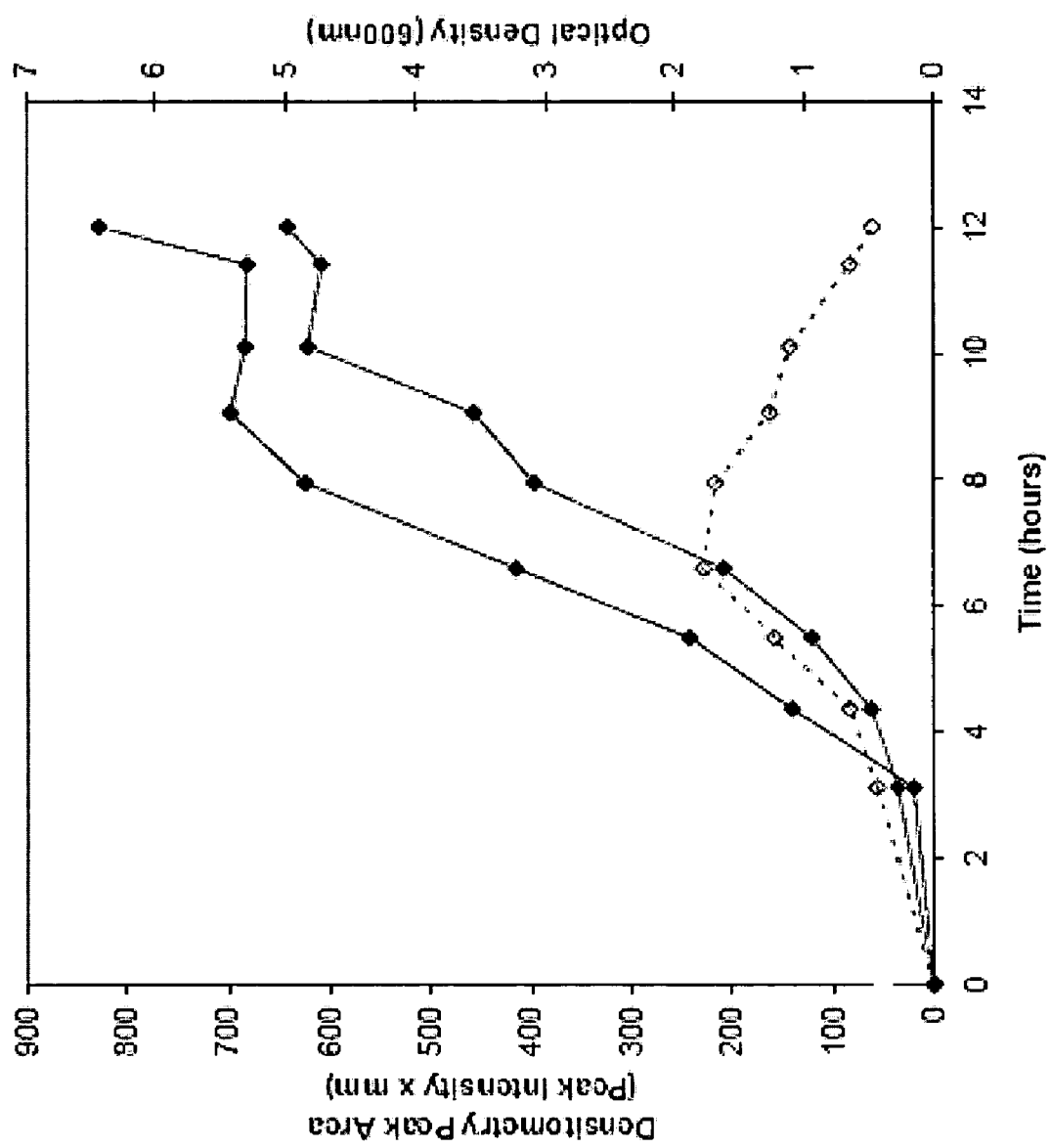

FIG. 63 displays data from densitometry analysis of the gel in FIG. 61. The chart compares product and precursor formation (densitometry peak area) to cell growth (OD600). Product formation appears to be consistent with cell growth and the rate of production decreases as the cultivation enters stationary phase. The precursor band decreases in intensity as exponential growth ends but is still present at the harvest point of the fermentation.

Scale-Up of 100 g/L Proteose Peptone #3 Fermentation to 200 L.

Figure 64:
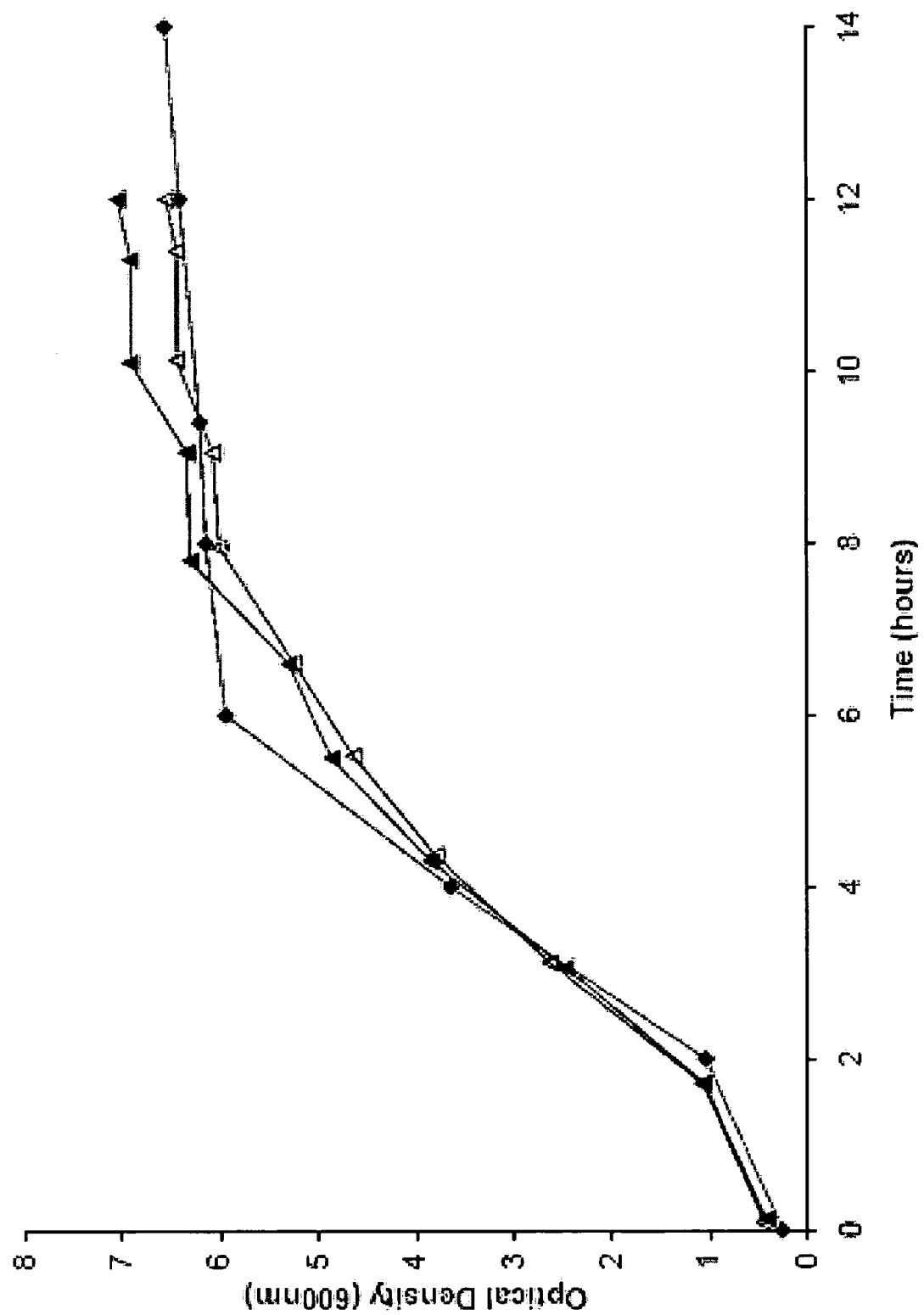

Following the increase in the PP3 concentration to 100 g/L the process was scaled to 200 L. To generate the required quantity of inoculum for the 200 L vessel a third inoculum stage was introduced using a 15 L working volume fermenter. 3×200 mL cultures were used to inoculate the 15 L fermenter and following 12 hours of growth 8 L of the 15 L were inoculated into the 200 L vessel. FIG. 64 compares the growth curve of the 200 L fermentation to the two 5 L fermentation using 100 g/L PP3. As recommended the growth profile was extended to 14 hours to ensure that the precursor band had completely disappeared before processing began. The growth profile of the 200 L fermentation is very similar to the fermentation at 5 L scale, demonstrating successful scale up of the cultivation.

Figure 65:
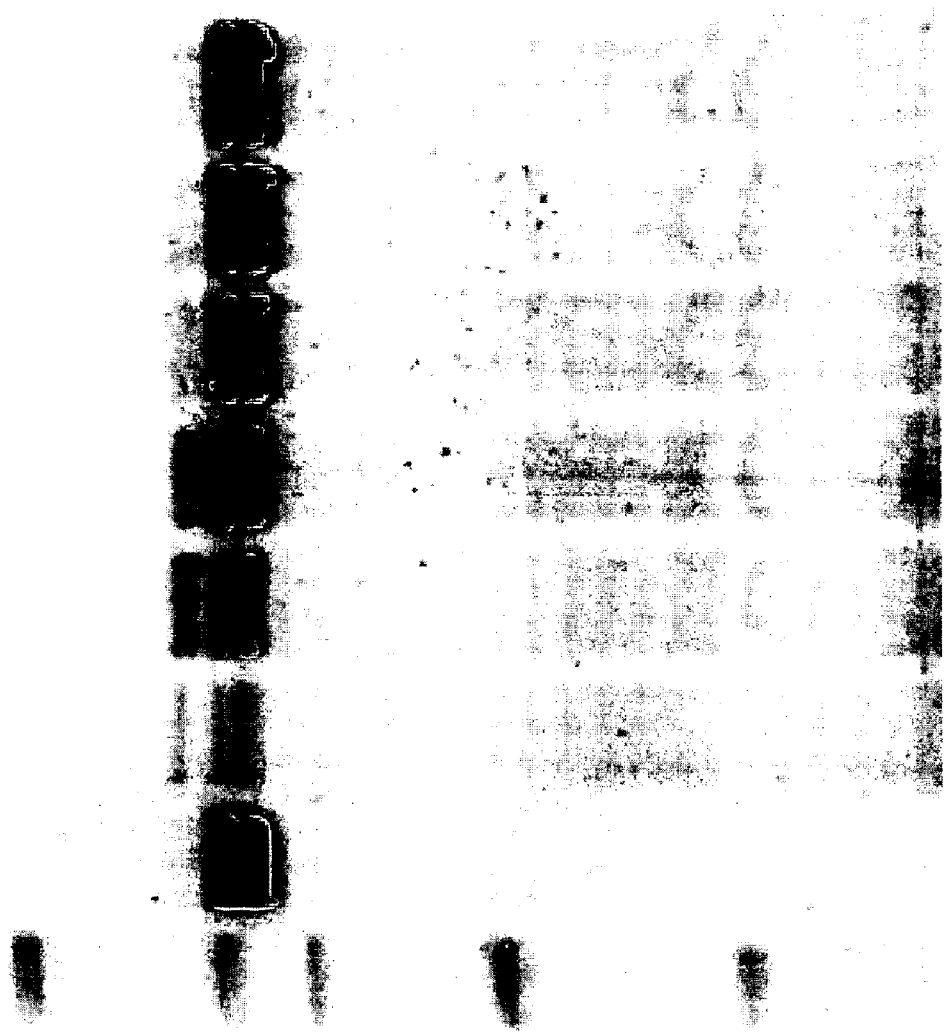

FIG. 65 shows SDS-PAGE analysis of the time course of the 200 L fermentation. The gel shows product formation during the course of the fermentation. The material at the 14 hour harvest point contains no detectable pre-cursor and very low levels of contaminants. The product generated from the 200 L fermentation appears very similar to that produced from the 5 L process, indicating that the increased generation number of the 200 L process has not had a detrimental effect. FIG. 66 displays data from densitometry analysis of the gel in FIG. 64.

The chart compares product and precursor formation (densitometry peak area) to cell growth (OD600). Product formation appears to be consistent with cell growth and the rate of production decreases as the cultivation enters stationary phase. The precursor band decreases in intensity as exponential growth ends. The precursor band decreases in intensity more rapidly in the 200 L fermentation than the 5 L cultivation, PBFT70c (FIG. 63). FIG. 67 shows SDS-PAGE analysis using a 4-12% Bis-Tris gel on the 200 L fermentation time course. The approximate molecular weights of the detected contaminants are annotated on the gel.

The harvest process (clarification by filtration) developed for Process 2 was evaluated during the 200 L scale up fermentation. The cell culture was successfully clarified using the existing process with no blockage of the filter train. The harvest process is described in the materials and methods section. 20 L of filtrate from the 200 L fermentation was processed by DSP to demonstrate a partial scale up of the downstream Process 3 (infra).

Quantification of Product Yield by Densitometry Analysis

A more accurate and quantifiable method was required to determine product concentration during the upstream process step than the semi-quantitative SDS-PAGE analysis (FIGS. 62 and 63). The fermentation filtrate has a high quantity of pigment and peptides from the growth medium that makes standard protein quantification techniques such as UV and the Bradford assay unusable. The semi-quantitative analysis carried out previously was modified and updated by carrying out densitometry analysis of the Coomassie stained gels. The method involved loading a range of quantities (0.2-1.2 μg/lane) of mixed AUXI and AUXII reference material and dilutions of the sample to be quantified onto a Tris Glycine gel. The scanned image was then analysed and the peak area for estimated for the standards and the samples. A standard curve was then constructed (total collagenase) and used to quantify the amount of total collagenase in the sample dilutions. FIG. 68 shows an example of a collagenase standard curve and highlights the linearity of the quantification method within the anticipated range of the samples. The Tris Glycine gels did not completely resolve AUXI and AUXII therefore the total collagenase was quantified rather than attempting to separately quantitate the two proteins.

The quantity of collagenase was analysed for PBFT70c, PBFT70d and the 200 L scale-up fermentations. The quantity was found to be ~280-350 mg/L total collagenase for all three fermentations.

Materials and Methods

Media Preparation:

1 L Media Preparation

The phosphates for the inoculum preparation (table 25) were autoclaved in a 1 L bottle at 121° C. for 20 minutes. The bulk media (table 26) was initially heated in a microwave to 60° C. to fully dissolve components before autoclaving in a 1 L bottle at 121° C. for 20 minutes. The PSA 1 (table 27) was filtered through a 0.2 μm Sartopore 2 150 cm$^2$ filter into a 250 mL sterile bottle. The 300 mL autoclaved phosphates, 600 mL autoclaved bulk media and 100 mL sterile filtered PSA 1 were pooled before aliquoting into 30 mL gamma irradiated universals (8×5 mL) and 500 mL Erlenmeyer flasks (4×200 mL).

TABLE 25

Phosphate composition for inoculum preparation

| Component | Quantity Required |
|---|---|
| $KH_2PO_4$ | 1.92 g |
| $K_2HPO_4$ | 1.25 g |
| $Na_2HPO_4$ | 3.5 g |
| NaCl | 2.5 g |
| Deionised Water | Up to 300 mL |

TABLE 26

Bulk medium composition for inoculum preparation

| Component | Quantity Required |
|---|---|
| Proteose Peptone # 3 | 50 g or 100 g* |
| Yeast Extract | 8.5 g |
| Deionised Water | Up to 600 mL |

*Medium recipe includes PP3 at 50 and 100 g/L.

TABLE 27

PSA 1 Magnesium/Glucose composition for inoculum preparation

| Component | Quantity Required |
|---|---|
| $MgSO_4 \cdot 7H_2O$ | 0.08 |
| Glucose | 5 g |
| Vitamin solution | 10 mL |
| Deionised Water | Up to 100 mL |

TABLE 28

| Component | Quantity Required |
|---|---|
| $FeSO_4 \cdot 7H_2O$ | 1.2 g |
| Riboflavin | 50 mg |

TABLE 28-continued

| Component | Quantity Required |
| --- | --- |
| Niacin | 100 mg |
| Calcium Pantothenate | 100 mg |
| Pimelic acid | 100 mg |
| Pyridoxine | 100 mg |
| Thiamine | 100 mg |
| Deionised Water | Up to 1 litre |

5 L Media Preparation

The phosphate solution for the 5 L scale (table 29) was autoclaved in a 1 L bottle at 121° C. for 20 minutes. The bulk medium (table 30) was added directly to the 5 L vessel and autoclaved at 121° C. for 20 minutes. The PSA 1 (table 31) was filtered through a 0.2 μm Sartopore 2 150 cm² filter into a 500 mL sterile bottle. The 250 mL phosphate solution and 200 mL PSA 1 was separately pumped into the 5 L vessel on completion of autoclaving and cooling of the vessel.

TABLE 29

Phosphate composition for 5 L fermentation

| Component | Quantity Required |
| --- | --- |
| $KH_2PO_4$ | 9.22 g |
| $K_2HPO_4$ | 6 g |
| $Na_2HPO_4$ | 16.8 g |
| NaCl | 12 g |
| Deionised Water | Up to 250 mL/278.35 g |

TABLE 30

Bulk medium composition for 5 L fermentation

| Component | Quantity Required |
| --- | --- |
| Proteose Peptone #3 | 240 g or 480 g* |
| Bacto Yeast Extract | 40.8 g |
| Deionised Water | Up to 4.35 L |

*Medium recipe includes PP3 at 50 and 100 g/L.

TABLE 31

PSA 1 Magnesium/Glucose composition for 5 L fermentation

| Component | Quantity Required |
| --- | --- |
| $MgSO_4 x 7H_2O$ | 0.38 g |
| Glucose | 24 g |
| Vitamin solution | 48 mL |
| Deionised Water | Up to 200 mL/200 g |

TABLE 32

Vitamin solution for 5 L fermentation

| Component | Quantity Required |
| --- | --- |
| $FeSO_4 x 7H2O$ | 1.2 g |
| Riboflavin | 50 mg |
| Niacin | 100 mg |
| Calcium Pantothenate | 100 mg |
| Pimelic acid | 100 mg |
| Pyridoxine | 100 mg |
| Thiamine | 100 mg |
| Deionised Water | Up to 1 litre |

15 L Media Preparation

The phosphate solution (table 33) was filtered through a 0.21 μm Sartopore 2 300 cm² filter into a sterile 2 L bottle. The bulk medium (table 34) was added directly to the 20 L vessel prior to Steam-In-Place (SIP) sterilisation of the vessel. The PSA I (table 35) was filtered through a 0.2 μm Sartopore 2 300 cm² filter into a 1 L sterile bottle. The 750 mL phosphates and 600 mL PSA I were separately pumped into the 20 L vessel on completion of SIP and cooling of the vessel.

TABLE 33

Phosphate composition for 15 L fermentation

| Component | Quantity Required |
| --- | --- |
| $KH_2PO_4$ | 27.66 g |
| $K_2HPO_4$ | 18 g |
| $Na_2HPO_4$ | 50.4 g |
| NaCl | 36 g |
| Deionised Water | Up to 750 mL/835.05 g |

TABLE 34

Bulk medium composition for 15 L fermentation

| Component | Quantity Required |
| --- | --- |
| Proteose Peptone #3 | 1.44 kg |
| Bacto Yeast Extract | 122.4 g |
| Deionised Water | Up to 13.05 L |

TABLE 35

PSA 1 Magnesium/Glucose composition for 15 L fermentation

| Component | Quantity Required |
| --- | --- |
| $MgSO_4 x 7H_2O$ | 1.14 g |
| Glucose | 72 g |
| Vitamins solution | 144 mL |
| Deionised Water | Up to 600 mL/600 g |

TABLE 36

Vitamin solution for 15 L fermentation

| Component | Quantity Required |
| --- | --- |
| $FeSO_4 x 7H2O$ | 1.2 g |
| Riboflavin | 50 mg |
| Niacin | 100 mg |
| Calcium Pantothenate | 100 mg |
| Pimelic acid | 100 mg |
| Pyridoxine | 100 mg |
| Thiamine | 100 mg |
| Deionised Water | Up to 1 litre |

200 L Media Preparation

The phosphate solution (table 37) was filtered through a 0.2 μm Sartopore 2 300 cm² filter into a Gammasart Biosystem SA10 10 L bag. The bulk media (table 38) was added directly to the 200 L vessel prior to SIP sterilisation of the vessel. The PSA 1 solution (table 39) was filtered through a 0.2 μm 300 cm² filter into a Gammasart Biosystem SA10 10 L bag. The 10 L phosphates and 8 L PSA 1 were separately pumped into the 200 L vessel on completion of SIP and cooling of the vessel.

TABLE 37

Phosphate composition for 200 L fermentation

| Component | 4 × Fermenters |
|---|---|
| $KH_2PO_4$ | 368.8 g |
| $K_2HPO_4$ | 240 g |
| $Na_2HPO_4$ | 672 g |
| NaCl | 480 g |
| Deionised Water | Up to 10 L/11.134 kg |

TABLE 38

Bulk medium composition for 200 L fermentation

| Component | Quantity Required |
|---|---|
| Proteose Peptone #3 | 19.2 kg |
| Bacto Yeast Extract | 1.632 kg |
| Deionised Water | Up to 174 L |

TABLE 39

PSA 1 Magnesium/Glucose composition for 200 L fermentation

| Component | Quantity Required |
|---|---|
| $MgSO_4 x7H_2O$ | 15.2 g |
| Glucose | 960 g |
| Vitamins solution | 1.92 L |
| Deionised Water | Up to 8 L/8 kg |

TABLE 40

Vitamin solution for 200 L fermentation

| Component | Quantity Required |
|---|---|
| $FeSO4x7H2O$ | 2.4 g |
| Riboflavin | 100 mg |
| Niacin | 200 mg |
| Calcium Pantothenate | 200 mg |
| Pimelic acid | 200 mg |
| Pyridoxine | 200 mg |
| Thiamine | 200 mg |
| Deionised Water | Up to 2 L/2 kg |

Fermentation

FIG. 69 illustrates overviews of the process flows for the Phytone and PP3 fermentation processes at 5 and 200 L scale.

5 L Scale Fermentation

A vial of the WCB (2005#1019D) was thawed and 50 μL aliquots were used to binoculate 8×5 mL of inoculum media in 30 mL gamma irradiated universals. The 5 mL cultures were incubated at 37° C. in an anaerobic jar in the presence of 3 anaerobic gas packs. After approximately 12 hours of incubation (OD600 3.0-4.0) 2×5 mL cultures were selected and used to inoculate 2×200 mL inoculum media in 500 mL Erlenmeyer flasks. The two flasks were placed together in an anaerobic jar with 3 gas packs and were incubated at 37° C. in a shaking incubator (70 rpm) for 12 hours. After 12 hours of incubation (OD600 6.0-7.0) each 200 mL inoculum was used to inoculate a 5 L vessel.

The working volume of the 5/7 L vessels FT Applikon vessels was 5 L of which 4% (v/v) was inoculum from the 200 mL stage. The agitation rate was set at 100 rpm. The pH, dO2 and temperature were controlled at 7.00 units, 0% of saturation and 37° C. respectively. The pH was controlled with additions of either HCl (5M) or NaOH (5M). The dO2 concentration was maintained at 0% by continuous sparging of nitrogen, with a flowrate of 1 L/min. Samples were taken during the fermentation and filtered through 0.2 μm filters before storing at −20° C. for analytical purposes. The fermentations began to enter stationary phase at an OD600 of 6.0-7.0. After 12 hours the fermenter was cooled to 10-20° C. before commencing harvest recovery.

200 L Scale Fermentation

A vial of the WCB (2005#1019D) was thawed and 50 μL aliquots were used to inoculate 8×5 mL of inoculum media in 30 mL gamma irradiated universals. The 5 mL cultures were incubated at 37° C. in an anaerobic jar in the presence of 3 anaerobic gas packs. After approximately 12 hours of incubation (OD600 3.0-4.0), 4×5 mL cultures were selected and used to inoculate 4×200 mL inoculum media in 500 mL Erlenmeyer flasks. Two flasks were placed together in anaerobic gas jars with 3 gas packs and left to incubate at 37° C. in a shaking incubator (70 rpm) for 12 hours. After 12 hours of incubation (OD600 6.0-7.0) three of the four flasks were pooled together and used to inoculate the 20 L vessel.

The working volume of the 20 L vessels was 15 L of which 4% (v/v) was inoculum from the 200 mL stage. The agitation rate was set at 100 rpm. The pH, dO2 and temperature were set at 7.00 units, 0% and 37° C. respectively. The pH was controlled with additions of either HCl (5M) or NaOH (5M). The dO2 concentration was maintained at 0% by continuous headspace sparging of nitrogen, with a flowrate of 20 L/min.

After 12 hours of growth in the 20 L vessel (OD600 6.0-7.0), 8 L of culture were used to inoculate the 200 L vessel. The running conditions were identical to the 20 L scale. The final optical density (600 nm) at harvest was 6.0-7.0. After 14 hours the fermenter was cooled to 10-20° C. before commencing harvest recovery.

Harvest

5 L Harvest

The 5 L cultures were pumped with a flow rate of 5 L/h through a Millistak+10" Opticap depth filter (Millipore, KCOHC10FFI) and 0.2 μm Sartopore 2 300 $cm^2$ filter into sterile 250 mL bio-containers. The processed material was either stored at −20° C. or stored at 4° C. overnight before processing by DSP.

200 L Harvest

The 200 L harvest was performed using a filtration harvest train. The culture was pumped with a flow rate of 200 L/h through a Milistak+(MC0HC10FS1) disposable depth filter with a filtration area of 4×1m2 followed by two 0.2 μm Express Opticap XL filters, 2×0.49 m2 (Millipore, KHGES10TT1). The process time for primary clarification was 1 hour. An additional 10 min was allowed at the end of the harvest to retrieve residual product held up in the filters. The clarified supernatant was collected in a 200 L Stedim Palletank with the filtrate weight recorded. 20 L of filtrate was passed through a MUSTANG Q high affinity DNA column with a flowrate ~6 L/min and collected into two sterile 20 L stedim bags, prior to storage at 4° C. overnight.

Analysis

Optical Density Measurements

The spectrophotometer was blanked using PBS at wavelength 600 nm. Fermentation samples were diluted by factors of 10, 20 or 100 (dependent on cell density) using PBS. 1 mL of each diluted sample was transferred into a 1 mL cuvette; the top was sealed and inverted 5 times before recording triplicate optical density readings at a wavelength of 600 nm.

Tris-Glycine Gels

Fermentation samples were filtered through 0.2 μm filters before preparing them for SDS-PAGE analysis. 10 μl of filtered sample was added to 10 μl sample buffer (2×), 2.5 μl reducing agent (10×) and 2 μl of 0.1M EDTA (to achieve final concentration of 10 mM). The high molecular weight (HMW) marker was prepared by adding 10 μl of concentrated stock to 80 μl reducing agent (10×), 310 μl WFI and 400 μl sample buffer (2×). The diluted HMW standard was then heated to 95oC for 5 minutes before aliquoting and storage at −20oC for use in subsequent gels. 15 μL of fermentation sample and 10 μL of HMW marker were run on 8% Tris-Glycine gel using pre-cooled (4° C.) Tris-Glycine running buffer at 130 V, 400 mA and 100 W for ~1 hour and 50 minutes. After electrophoresis, the gels were immersed in 100 mL colloidal blue stain reagent (55 mL WFI, 20 mL methanol, 5 mL stainer A, 20 mL stainer B) and left to stain for 5 h on an orbital shaker at 60 rpm. Gels were de-stained with 200 mL WFI. The gel was left in WFI for 15-20 h until excess stain was removed after which the gel was scanned and dried according to the manufactures instructions Bis-Tris Gels The fermentation samples were prepared for SDS-PAGE analysis by adding 10 μl of 0.2 μm filtered sample to 4 μl sample buffer (4×), 1.5 μl reducing agent (10×) and 1.7 μl of 0.1M EDTA (to achieve final concentration of 10 mM). 15 μL of fermentation sample and 10 μL of Mark 12 marker were run on a 4-12% Bis-Tris gel and run using MES running buffer at 200 V, 400 mA and 100 W for ~40 mins. After electrophoresis, the gels were immersed in a 100 mL fixing solution (40 mL dH$_2$O, 50 mL methanol, 10 mL acetic acid) for 10 minutes before replacing with a 95 mL staining solution (55 mL dH$_2$O, 20 mL methanol, 20 mL stainer A) for a further 10 minutes. 5 mL of stainer B was added to the staining solution and the gels were left to stain for 5 h on an orbital shaker at 60 rpm before de-staining with 200 mL WFI. The gel was left in WFI for 15-20 h until excess stain was removed after which the gel was scanned and dried according to the manufactures instructions.

Process 3 Purification:

The first 20 L scale run-through of a newly developed process (Process 3) for the purification of collagenases from *Clostridium histolyticum*, which was modified from Process 2 performed to GMP at 20 L scale. Significant process changes were introduced in the development of Process 3 in order to make the purification more robust and more amendable to scale up and subsequent process validation. One significant factor in facilitating this process change was in the choice of fermentation component. Process 2 had been based on the requirement to maintain a phytone based fermentation media whereas for process 3 protease peptone No. 3 was use. The process run-through is split into the key steps of the down stream purification and the collagenases AUXI and AUXII. These include the treatment of the fermentation filtrate using a MUSTANG Q capsule, hydrophobic interaction chromatography, tangential flow filtration step 1 (denoted TFF1), anion exchange chromatography and tangential flow filtration step 2 (denoted TFF2). AUXI and AUXII co-purify in the initial steps of the purification and are only separated during the anion exchange chromatography step (performed using Q-Sepharose HP media). AUXI and AUXII are then processed separately and formulated. The intermediates are then mixed in a 1:1 ratio (based on protein content determined by UV) and filtered to form the drug substance. In developing process 3, key steps associated with process 2 were removed. Notably the ammonium sulphate precipitation step, two chromatography steps (hydroxyapatite and gel permeation chromatography) and all −20° C. hold steps were eliminated. The use of un-scaleable steps such as stirred cells and dialysis were also removed and replaced with tangential flow filtration (TFF).

The issue of product instability, which was evident in process 2 (and eliminated the use of TFF), was not apparent in the 20 L scale run of process 3. The contaminant profile associated with process 3 was however different to process 2 in which clostripain and gelatinase had been major components. Most notably a 40 kDa, 55 kDa and two 90 kDa contaminants (one co-purifying with AUXI and the other with AUXII) were detected by SDS-PAGE. As a result of these new contaminants, some of the QC assays (such as RPHPLC and SEC-HPLC) were of limited use since they did not resolve all process 3 impurities. The inability to utilize established QC assays for in-process purity determination, resulted in the need to define a method for establishing which material form the QSepharose column was suitable for further purification. This was required since the contaminants were not clearly resolved from the AUXI and AUXII products on the QSepharose column and it was therefore necessary to collect eluted material in discrete fractions, which could be analyzed retrospectively. Analysis was performed by SDS PAGE and the pooling decision for the 20 L run-through was based on experience of the relative staining intensity of impurity to product using a standardized 1 μg load. Retrospective densitometry analysis of SDS-PAGE enabled the pooling criteria to be described based on relative percent product purity. Further densitometry analysis using material from the 200 L demonstration run enabled a standardised method to be established as well as an approximation of assay variation. This led to an agreed procedure for the pooling of in-process fractions to be implemented in the first GMP campaign.

In addition to the process description, preliminary work describing a buffer stability and in-process sample stability study is presented along with initial characterization of some of the impurities associated with Process 3.

Process 3 differed from process 2 in three main areas. Firstly, the ammonium sulphate precipitation step and hydroxyapatite chromatography steps were removed; secondly, the gel permeation chromatography (GPC) step was eliminated and thirdly, all buffer exchange steps were performed by tangential flow filtration. The precipitation step was replaced by the use of hydrophobic interaction chromatography (HIC) at the client's recommendation. Development of this step resulted in the successful implementation of HIC for (i) product capture (thereby serving as a concentration step) and (ii) some protein and pigment contaminant removal. The HIC step was also subsequently shown to reduce levels of dsDNA. As a result of the process development program, the introduction of HIC and inclusion of a MUSTANG Q filter step removed the need for both the ammonium sulphate precipitation step and the hydroxyapatite chromatography step. The overall effect was to simplify the up front capture of product and to remove a potential hold step associated with Process 2. This latter point had significance in that previously the fermentation could be assessed prior to down stream purification since the pellets resulting from the precipitation step could be held at −20° C. prior to processing.

Following the HIC step, product was buffer exchanged using tangential flow filtration (TFF). This was performed using 30 kDa molecular weight cut off (MWCO) membranes and replaced the dialysis procedure used for Process 2. Aggregate contamination, which when present was detected as AUXII-derived, appeared to be removed during the anion exchange chromatography step (IEX). As a result, the GPC step was eliminated since both AUXI and AUXII intermediates were within specification for aggregates following IEX. Finally, the final concentration and formulation of the AUXI and AUXII intermediates was performed using TFF instead of the previous method of utilising stirred cells.

Overall, Process 3 represented a simpler process that was more amenable to scale up and validation than Process 2. In addition, the reduction in consumable cost was apparent by the elimination of the need for hydroxyapaptite and gel permeation media and by the reduced number of steps requiring leupeptin. An overview of the purification scheme for Process 3 is given in FIG. 46.

Non-GMP Demonstration Run at 20 L Scale

Process 3 was performed at 20 L scale in the process development laboratories in order to demonstrate if material of suitable quality could be generated using this modified process at 20 L scale. A key requirement for processing was the ability to limit potential protease activity by performing steps chilled wherever possible and by the inclusion of the cysteine protease inhibitor leupeptin at key stages in the procedure. A full 20 L of fermentation filtrate was processed since the feedstock was generated from 200 L fermentation PP3. Details of the fermentation and subsequent harvest and filtration are documented in a separate report.

MUSTANG Q Filter Treatment of Fermentation Filtrate

Following 0.2 μm filtration, approximately 22 L of fermentation supernatant was loaded onto a MUSTANG Q chromatography capsule as described previously. Some visible pigment contamination (green/brown) appeared to be removed by the MUSTANG Q capsule during the filtration of the first 10 L since the contents of the first 10 L Stedim bag appeared visibly less pigmented than the second. The ability of the MUSTANG Q capsule to remove dsDNA was monitored across this step by pico green analysis of pre and post MUSTANG Q filter samples (Table 41). In process analysis indicated that unlike previous data generated at small-scale, bulk nucleic acid removal was not evident at the MUSTANG Q filter step. The robustness and application of this step therefore requires further investigation.

TABLE 41

| Sample description | Result ng/ml |
| --- | --- |
| Fermentation filtrate | 230.65 |
| Post Mustang Q | 216.53 |
| Post HIC | 1.02 |
| Post TFF | 6.34 |
| Post IEX Aux I | 2.33 |
| Post IEX Aux II | 3.41 |

Hydrophobic Interaction Chromatography (HIC)

The use of HIC served three functions in the purification. Firstly, the product was reduced in volume since conditions were identified in which collagenases bound to the resin. Secondly, some pigment and protein contaminant was removed at this stage and thirdly, pico green analysis from this run indicated reduction of dsDNA. The HIC step was performed using supernatant processed directly from the fermentation (after MUSTANG Q treatment) and, as a result a hold step, (evident in Process 2 as the ammonium sulphate pellet) was no longer present for Process 3.

In order to provide conditions for collagenases to bind to the HIC column, product (20 L) from the MUSTANG Q filter step was diluted with a 3M-ammonium sulphate solution to a final concentration of 1M. After filtration, product was loaded onto the column and eluted using a 2-step isocratic elution.

The protein concentration of the HIC load material was difficult to determine accurately and was estimated in two ways. Firstly, a Bradford assay was performed on the material prior to ammonium sulphate addition. This was performed with undiluted material in order to standardise the contribution from pigment present in the fermentation media, which was known to interfere with the assay. Secondly, the estimate was based on volume of fermentation media loaded per mL of column resin. The column load was estimated to be 5.9 mg of total protein/mL resin by Bradford assay or alternatively ~13 mL of fermentation media per mL of resin. An estimate of the total amount of target protein eluted from the column was determined as 3.4 g using UV (see Table 42). Assuming that the total protein present in the HIC load was 9 g (Bradford assay), this equated to a 38% recovery. This value was only regarded as a relative measure, however, due to the inaccuracy of the assay for the samples containing fermentation media components.

An alternative method for estimating the HIC load concentration was determined using densitometry although it was recognised that this estimation would give a collagenase content rather than estimate of total protein (which could vary between fermentations). Using this approach, the total collagenases were estimated as 360 mg/L with an approximate ratio of AUXI to AUXII estimated as 40:60. Using this data, the total collagenase expected in the HIC load would be 7.2 g giving a step yield of 47%.

The chromatogram resulting from the HIC step is shown in FIG. 70. Visible pigment was apparent in the flow-through as well as bound to the column. After washing the column with equilibration buffer to remove the flow-through contamination, peak 1 was eluted using an intermediate concentration ammonium sulphate solution (0.3M).

This peak was shown to contain protein contaminants although some AUXII was also eluted at this stage (FIG. 71). This loss in product was expected and had been noted previously. In order to minimise the amount of product lost, without compromising purity, the elution volume for peak 1 removal was set at 5 column volumes. Peak 2, containing the majority of the product, was then eluted using buffer with no ammonium sulphate. Peak 2 was collected as a single pool with the chromatography method programmed so that collection began after ¾ of a column volume of elution buffer had been applied to the column. Collection was then terminated after a total of 4 column volumes had been collected. In order to minimise potential proteolysis in the product at this stage in the process, leupeptin was added to the post HIC eluate and the material held at 2-8° C. The hold time for the post HIC eluate was of 2 day duration.

Tangential Flow Filtration 1 (TFF1)

TFF using 30 kDa membranes was introduced following the HIC in order to reduce the volume of product (5-fold) and to exchange the buffer into conditions suitable for binding to the anion exchange column. Of particular importance was the sufficient reduction in ammonium sulphate such that the conductivity of the IEX load sample was <1.8 mS. The diafiltration buffer was chilled and leupeptin added prior to use to reduce the likelihood of proteolysis. No loss in protein was estimated over the course of this step (>100% recovery) although this may reflect the inaccuracy in protein concentration estimation at this stage in the process due to the presence of pigment in the pre TFF1 material. Approximately 97.5% of the total protein (3325 mg) was recovered in the retentate with an additional 204.8 mg recovered in the first membrane rinse (infra). Filtration of the total protein from the combined retentate and rinse was performed at the end of the TFF step prior to holding the material overnight at 2-8° C. SDS-PAGE analysis indicated no significant differences were detected before and after the TFF step (FIG. 71).

Q-Sepharose Chromatography

The Q-Sepharose column was loaded at a maximum capacity of 5 mg total protein per mL resin. As a result, not all of the available material from the TFF step was utilized in this step (see Table 421). The Q-Sepharose column resolved AUXI and AUXII collagenases as expected (FIG. 72). The start of AUXII elution began at approximately 13.6% B (where buffer A=10 mM Tris, 0.2 mM leupeptin pH 8 and buffer B=Buffer A+360 mM NaCl) which equated to a post column conductivity of 5.7 mS. Fractions (100 mL) were collected throughout the elution of AUXII until the absorbance value dropped to 25% of the peak height (550 mAU). A small peak was eluted at approximately 8 mS (20.3% B) following AUXII elution. In-process analysis of this peak from previous small-scale experiments indicated this to be AUXII derived aggregate material. The start of AUXI elution was at approximately 27% B (which equated to 10.4 mS). As before, 100 mL fractions were collected until the absorbance dropped to the required 25% value (190 mAU).

Each AUXI and AUXII fraction collected was analysed by SDS-PAGE and subjected to densitometry (FIGS. 73-76). Densitometry was performed retrospectively, so the decision on fraction pooling was based on experience of the levels of contaminant visible by Colloidal blue staining. In consultation with Auxilium, fractions 6-12 were pooled for the AUXII product and fractions 19-26 pooled for AUXI. The step yields and protein concentrations present in the material pooled from the Q-Sepharose run are included in table 42.

SDS-PAGE analysis of the post IEX AUXI and AUXII products from the 20 L demonstration run (FIGS. 77 and 78) showed few contaminants visible by SDSPAGE. In addition, the contaminants detected were in accordance with previous small-scale experiments although there were noted differences in the resolution of the contaminants, which appeared to be more defined (i.e. separate peaks or shoulders) in the small-scale model. These contaminants were also different to those identified for Process 2 in which clostripain and gelatinase had been major components. As a result, the QC protocols developed for Process 2 were not optimised for the detection of the new contaminants associated with Process 3.

Retrospective densitometry of the pooled material estimated the purity at 95.1% for AUXI and 99.4% for AUXII. Currently, however the purity specification of ≧97% is specified by RP-HPLC and no final product specification has been established using densitometry.

Concentration and Buffer Exchange of AUXI and AUXII

The separated AUXI and AUXII products from the Q Sepharose column were processed separately by TFF using a 30 kDa membrane. This step was required to; (i) remove/reduce leupeptin in the final product (ii) formulate the intermediates into the correct buffer (10 mM Tris, 60 mM sucrose pH 8) and (iii) to achieve the required target protein concentration of 0.9-1.1 mg/mL. A total of 799 mg (~683 mL at 1.17 mg/mL) of AUXII and 860 mg (796 mL at 1.08 mg/mL) of AUXI was concentrated to a target concentration of 1.75 mg/mL. This theoretical concentration was based on the calculated reduction in volume required assuming no loss of product during the concentration step. Diafiltration was then performed into the required formulation buffer, the membranes washed with the minimum volume of the TFF system (~250 mL) and the full amount combined with the concentrate to achieve the required target concentration of 0.9-1.1 mg/mL. A total of 819.5 mg AUXII (at 1.03 mg/mL) and 797.0 mg of AUXI (at 1.09 mg/mL) were available after filtration. In both cases, the majority of product was recovered in the retentate and was estimated as 95.4% (762 mg) for AUXII and 83.1% (715 mg) for AUXI. The additional material provided by the membrane rinse was estimated as 153 mg and 89.6 mg for AUXII and AUXI respectively.

Mixing of Intermediates to Drug Substance

Approximately 200 mg of each intermediate was combined to give 400 mg of the drug substance. This was then filtered and approximately 26 mg provided to QC for testing. The QC results for AUXI, AUXII intermediates and the drug substance are provided in Table 43. All tests on the drug substance and AUXII intermediate passed the required specification. The test for potency of the intermediate AUXI however, was not within the specified range although all other tests passed. With the exception of the AUXI potency result, these data indicated that Process 3 was capable of generating material of the required specification when purified at the 20 L scale.

As well as QC testing, material from the 20 L demonstration run was utilized for method validation at KBI BioPharma, Inc. At the client's request, 200 mg of drug substance was shipped on dry ice to KBI for drug substance and drug product methods validation. The latter testing was performed after lyophilisation of the drug substance at KBI. In addition, 25 mg of each intermediate was supplied to KBI for validation of analytical methods.

The individual step yields for the 20 L demonstration run are given in table 42. An extrapolation of the data in which all the available material had been loaded onto the Q-Sepharose column indicated that the maximum total amount of available drug substance from this process run-through was 1.6 g (assuming no loss of material through retains). This equates to an approximate overall process yield of 17.8% based on the initial estimate of 9 g (using the Bradford assay) for the amount of total protein available to load onto the HIC column. With the limitation on the load for the Q-Sepharose column, a maximum of 1.4 g of drug substance was available from the current run-through if all the available intermediate had been mixed to form the drug substance.

TABLE 42

| Process step | Protein conc. (mg/mL) | Amount (weight/ volume) | Total protein (mg) | Step yield |
| --- | --- | --- | --- | --- |
| Fermentation | — | 200 L | — | — |
| Pre Mustang Q | — | 22 L | — | — |
| Post Mustang Q | 0.45 (Bradford) | 22 L | 9000 | — |
| HIC load | 0.30* (theoretical) | 30 L | 9000 | 100 |
| HIC peak 2 (after leupeptin) | 0.56 | 6101.7 mL | 3416.95 | 38 |
| Pre-TFF1 | 0.54 | 6317.7 mL | 3411.6 | 100 |
| Post TFF1 (with wash 1 and post | 2.55 | 1378.5 g | 3515.2 | >100% |

TABLE 42-continued

| Process step | Protein conc. (mg/mL) | Amount (weight/volume) | Total protein (mg) | Step yield |
|---|---|---|---|---|
| filtration) | | | | |
| Q load (5 mg/mL resin) | 2.55 | 1216 mL | 3100.8 | 100 |
| Q AUXII pool | 1.17 | 682.8 mL | 798.88 | 25.8 |
| Q AUXI pool | 1.08 | 796.4 mL | 860.11 | 27.7 |
| Pre TFF2 AUXII | 1.17 | 682.80 mL | 798.88 | 100 |
| Intermediate AUXII (post filtration) | 1.03 | 795.6 g | 819.47 | >100 |
| Pre TFF2 AUXI | 1.08 | 796.40 mL | 860.11 | 100 |
| Intermediate AUXI (post filtration) | 1.09 | 731.2 g | 797.01 | 92.7 |

*calculated based on dilution factor after ammonium sulphate addition

TABLE 43

| Test | Method | Drug substance (AXS2006A0754H) | Intermediate AUXI (AXS2006A0745H) | Intermediate AUXII (AXS2006A0737H) |
|---|---|---|---|---|
| Appearance of Solution | QC SOP 001 | Clear, colourless with 2-3 small exogenous fibres 1 mm in length (AK/1573/121) | Clear, colourless and free from Particulate matter (AK/1573/121) | Clear, colourless with 2-3 small exogenous fibres 1 mm in length (AK/1573/121) |
| Potentiometric measurement of pH | QCSOP 002 | 7.6 (FR/1598/098) | Not required | Not required |
| Endotoxin Determination | QCSIO 018 | <0.5 EU/mL (AS/1597/128) | <0.5 EU/mL (AS/1597/128) | 0.136 EU/mL (AS/1597/128) |
| Identity by SDS-PAGE Coomassie Stained | QC SOP 103 | Major collagenase bands between 107 and 110 kDa and 110 and 115 kDa (AS/1597/133) | Major collagenase bands between 110 and 115 kDa (AS/1597/133) | Major collagenase bands between 107 and 110 kDa (AS/1597/133) |
| Total Protein by Absorbance Spectrophotometry | QC SOP 144 | 1.04 mg/mL (AS/1597/106) | 1.11 mg/mL (AS/1597/106) | 0.90 mg/mL (AS/1597/106) |
| Rat Tail Tendon Collagen Assay for Potency | QC SOP 105 | 2326 (1700-3500) (AS/1597/124) | 1483 (1900-3300) (AS/1597/124) (OOS/Keele/2006/0038) | Not Required |
| Reference | | 2097 (2014-3440) | 2097 (2014-3440) | |
| Potency for Class II Collagenases | QC SOP 106 | 57677 GPA units/mg (50000-90000) (AS/1597/111) | Not Required | 119552 GPA units/mg (79000-170000) (AS/1597/111) |
| Reference | | 69523 GPA units/mg (58000-95000) | | 69523 GPA units/mg (58000-95000) |
| Host Cell Protein Assay | QCSOP 107 | <LOD (FR/1589/108) | Not Required | Not Required |
| Host Cell DNA Assay | External | NewLab | Not Required | Not Required |
| Analysis of proteins using the Agilent 1100 HPLC System (Identity and purity by size exclusion chromatography) | QC SOP 109 | 100% main peaks (47.70% AUX-I, 52.30% AUX-II) (AK/1573/122) | 100% main peak 0% aggregates (AK/1573/122) | 100% main peak 0% aggregates (AK/1573/122) |
| Reference | | AUX-I 100% AUX-II 100% | AUX-I 100% | AUX-II 100% |
| Analysis of proteins using the Agilent 1100 HPLC System (Identity and purity by reverse phase liquid chromatography) | QC SOP 109 | 48.89% AUX-I 50.99% AUX-II 0.12% Others (AK/1573/125) | 99.14% AUX-I 0.37% AUX-II 0.49% Others (AK/1573/125) | 0.39% AUX-I 99.35% AUX-II 0.26% Others (AK/1573/125) |
| Reference | | AUX-I 93.92%, AUX-II 4.96%, Others 1.13% AUX-II 100% | AUX-I 93.92%, AUX-II 4.96%, Others 1.13% | AUX-II 100% |
| Analysis of proteins using the Agilent 1100 HPLC System (Gelatinase by anion exchange chromatography) | QC SOP 109 | 0.3% Gelatinase (AK/1573/131) | 0.4% Gelatinase (AK/1573/131) | 0% Gelatinase (AK/1573/131) |
| Reference | | AUX-I 0% Gelatinase AUX-II 0% Gelatinase | AUX-I 0% Gelatinase AUX-II 0% Gelatinase | AUX-I 0% Gelatinase AUX-II 0% Gelatinase |

TABLE 43-continued

| Test | Method | Drug substance (AXS2006A0754H) | Intermediate AUXI (AXS2006A0745H) | Intermediate AUXII (AXS2006A0737H) |
|---|---|---|---|---|
| Peptide Mapping by Tryptic Digest and Reverse Phase HPLC | QC SOP 110 | Not Required | Tuesday | Tuesday |
| Residual Leupeptin | QCSOP 141 | Not detected <0.5% w/w (AK1573/136) | Not required | Not required |
| Bioburden | QCSOP 223 | 0 cfu/5 mL (JM/1505/115) | 0 cfu/5 mL (JM/1505/114) | 0 cfu/5 mL (JM/1505/112) |

Sample Stability Study

During the 20 L demonstration run, samples were taken at key process points. As the demonstration run was performed as a continuous process (with no hold steps) an attempt was made to assess the stability of in-process material during the hold times anticipated for GMP batches. The extended run duration expected for GMP was recognised due to the requirement to obtain equipment clearance data between process steps. In-process material was held at 2-8° C. for approximately the duration expected for the GMP manufacture. In addition samples were held for an extended time representing twice that expected for the GMP campaign. A description of the samples taken, along with the respective hold times is given in table 44. The processing times for the 20 L demonstration run are represented in table 45. All samples were submitted to QC for SDS-PAGE, RP-HPLC, SEC-HPLC and UV analysis (FIGS. 79-83).

Overall, the results showed no detectable deterioration in the product over the first hold point with respect to purity (as determined by RP-HPLC), degradation (as detected by 8% Tris-Glycine SDS-PAGE) and aggregation (as determined by SECHPLC). Some of the assays, however, were recognised to be limiting since low molecular mass components would not be detected by 8% SDS-PAGE and the RPHPLC assay had not been developed to detected the 40 kDa, 55 kDa and 90 kDa contaminants associated with Process 3. Some assays were also less relevant for crude samples such as the use of UV and SEC-HPLC in the fermentation samples. Despite these limitations, the only detected change in product profile was identified for the second hold point (day 12) for the AUXII in-process sample taken from the Q-Sepharose column. This showed an increase in aggregate level between day 5 and day 12 although this increase was only from 0 to 0.62%.

A second stability study was performed on the in-process retains which were taken at the point of manufacture during the 20 L demonstration run and stored at −20° C. In this study, samples were thawed and incubated at room temperature and at 37° C. and monitored by 4-12% SDS-PAGE analysis to allow the full molecular mass range of contaminants to be evaluated (FIGS. 84-88). These data demonstrated that the samples prior to Q-Sepharose anion exchange were vulnerable to degradation. Following separation of the collagenases AUXI and AUXII (by the Q-Sepharose column), the samples appeared to be relatively stable and looked comparable to the time zero samples by SDS-PAGE.

Taken together, both studies indicate that providing the temperature is maintained between 2-8° C., in-process material is not expected to deteriorate during processing over the hold times investigated. This gives a level of confidence that the use of leupeptin and temperature control is sufficient to restrict levels of product degradation during processing over the durations anticipated in GMP.

TABLE 44

| Sample | Duration held at 2-8° C. before freezing | Volume | Storage, Retain Container |
|---|---|---|---|
| Fermentation Filtrate | DAY 4 | 1 × 2 mL | −70° C. Bag |
| | DAY 5 | 1 × 2 mL | |
| Post Mustang Q | DAY 4 | 1 × 2 mL | −70° C. Bag |
| Post HIC | DAY 3 | 1 × 2 mL | −70° C. Bag |
| | DAY 6 | 1 × 2 mL | |
| Post TFF | DAY 2 | 1 × 2 mL | −70° C. Bag |
| | DAY 4 | 1 × 2 mL | |
| Post IEX AUX I | DAY 5 | 2 × 1 mL | −70° C. Biotainer |
| | DAY 12 | 2 × 1 mL | |
| Post IEX AUX II | DAY 5 | 2 × 1 mL | −70° C. Biotainer |
| | DAY 12 | 2 × 1 mL | |
| AUX I Intermediate | DAY 6 | 2 × 1 mL | −70° C. Biotainer |
| | DAY 12 | 2 × 1 mL | |
| AUX II Intermediate | DAY 6 | 2 × 1 mL | −70° C. Biotainer |
| | DAY 12 | 2 × 1 mL | |

TABLE 45

| Process step | 20 L demonstration run |
|---|---|
| Fermentation harvest | Day 1 |
| Mustang Q | Day 1 |
| HIC | Day 2 |
| TFF1 | Day 5 |
| IEX (Q-Sepharose) | Day 6 |
| TFF2 (AUXI) | Day 7 |
| TFF2 (AUXII) | Day 9 |
| DS mixing | Day 12 |

Buffer Stability Study

Buffer samples illustrated in table 46 were reserved from the 20 L demonstration and retested after storage at 2-8° C. The pH, conductivity, temperature and appearance of the buffers were noted at the time of completion and after 12-13 days storage. The results of this study are given in table 47. Small differences were observed in the values for pH and conductivity but this may be due to differences in temperature between the original buffers and the tested retains. In particular, the HIC buffers showed the largest variation in conductivity and temperature. As a result, future studies on buffer stability should include specification of an accepted temperature range for recording all parameters. In all cases, the buffer retains were clear in appearance at time zero and after the required hold time.

TABLE 46

| BUFFER | CONSTITUENTS |
| --- | --- |
| HIC A | 10 mM Tris, 1.0M Ammonium Sulphate, pH 8.0 |
| HIC A2 | 10 mM Tris, 0.3M Ammonium Sulphate, pH 8.0 |
| HIC B | 10 mM Tris, pH 8.0 |
| DIAFILTRATION | 10 mM Tris, 200 µm Leupeptin, pH 8.0 |
| IEX A | 10 mM Tris, 3 mM CaCl$_2$, 200 µm Leupeptin, pH 8.0 |
| IEX B | 10 mM Tris, 3 mM CaCl$_2$, 200 µm Leupeptin, 360 mM NaCl pH 8.0 |
| IEX SCRUB | 10 mM Tris, 3 mM CaCl$_2$, 1.5M NaCl pH 8.0 |
| FORMULATION | 10 mM Tris, 60 mM Sucrose pH 8.0 |
| 3.0M AMMONIUM SULPHATE STOCK | 10 mM Tris, 3.0M Ammonium Sulphate pH 8.0 | region of the Col G sequence for collagenase AUXI whereas the 40 kDa contaminant band from AUXII (Lanes 6-10; FIG. 89) was identical to a region of the Col H sequence for collagenase AUXII. A previous attempt was made to sequence the 90 kDa band associated with both the AUXI and AUXII products (FIG. 90). Sequencing of the 90 kDa contaminant associated with the AUXI product was successful in that identity was correlated with the N-terminus of the AUXI sequence. In contrast, it was not possible to obtain a complete sequence for the 90 kDa contaminant associated with AUXII, which suggested that the two 90 kDa contaminants were different products.

The main contaminants associated with Process 3 appeared to be product related and were either identified as N-terminally cleaved products of AUXI (55 kDa) and AUXII (40 kDa) or a C-terminally cleaved product of AUXI (90 kDa). As these contaminants were different to those identified in Process 2, the QC assays utilized for the specification of the

TABLE 47

| Buffer | Date prepared | Date of testing | Number of days elapsed | Original buffer pH and cond. | pH and conductivity of retain samples | Repeat testing of pH and cond. Of retain samples | Buffer appearance |
| --- | --- | --- | --- | --- | --- | --- | --- |
| HIC A | 2 May 2006 | 15 May 2006 | 13 days | pH 7.98 127.6 mS @17.8° C. | pH 8.10 137.5 mS @15.8° C. | pH 7.89 134.9 mS@ 22.0° C. | Clear |
| HIC A2 | 2 May 2006 | 15 May 2006 | 13 days | pH 8.03 52.7 mS@18.5° C. | pH 8.05 49.7 mS@ 15.1° C. | pH 7.85 49.6 mS@ 22.0° C. | Clear |
| HIC B | 2 May 2006 | 15 May 2006 | 13 days | pH 8.06 0.699 mS@ 19.4° C. | pH 7.78 0.879 mS@ 16.7° C. | pH 7.81 0.842 mS@ 22.1° C. | Clear |
| Diafiltration buffer | 2 May 2006 | 15 May 2006 | 13 days | pH 8.05 0.668 mS@ 19.2° C. | pH 7.70 0.793 mS@ 18.2° C. | N/A | Clear |
| IEX A | 3 May 2006 | 15 May 2006 | 14 days | pH 8.00 1.585 mS@ 20.3° C. | pH 7.69 1.646 mS@ 18.2° C. | N/A | Clear |
| IEX B | 3 May 2006 | 15 May 2006 | 14 days | pH 8.00 34.6 mS@ 19.4° C. | pH 7.87 37.6 mS@ 18.8° C. | N/A | Clear |
| IEX Scrub | 3 May 2006 | 15 May 2006 | 14 days | pH 8.00 105.2 mS@ 19.0° C. | pH 7.95 122.9 mS @18.3° C. | N/A | Clear |
| Formulation | 3 May 2006 | 15 May 2006 | 14 days | pH 7.97 0.735 mS@ 18.5° C. | pH 7.89 0.987 mS @19.1° C. | NA | Clear |
| 3.0M AS Stock | 3 May 2006 | 15 May 2006 | 14 days | pH 7.95 251.0 mS 16.5° C. | pH 7.96 255 mS @19.9° C. | N/A | Clear |
| 3.0M AS Stock | 4 May 2006 | 15 May 2006 | 15 days | pH 8.00 224.0 mS@ 14.6° C. | pH 7.97 254 mS @20.4° C. | N/A | Clear |

Contaminant Identification by N-Terminal Sequencing

Three main impurities were detected for Process 3 by SDS-PAGE analysis. These appeared to be co eluted with the AUXI and AUXII collagenases and were only resolved by fractionation of the peaks eluted from the Q-Sepharose column. The contaminants were assigned by their apparent molecular mass on SDS-PAGE as 40 kDa, 55 kDa and 90 kDa contaminants. Fractions with elevated levels of a particular contaminant were submitted for N-terminal sequencing after excision of the band from SDS-PAGE.

Sequence analysis was successful for both the 55 kDa and 40 kDa contaminant isolated from the 20 L demonstration run. The N-terminus of the 55 kDa contaminant band associated with AUXI (Lanes 1-5; FIG. 89) was shown to match a intermediates and drug substance did not resolve the new contaminants as the assay development had originated around Process 2. In particular, the standard purity assay (RP-HPLC) could not be used to detect levels of the 40 kDa and 55 kDa contaminants.

Densitometry Analysis

20 L Demonstration Run

The 40 kDa, 55 kDa and 90 kDa contaminants associated with Process 3 were identified and resolved by SDS-PAGE. These contaminants were clearly detected in fractions eluted from the Q-Sepharose column and appeared to elute at the leading and trailing edges of the peak profile (see FIGS. 72-76). The decision for which fractions were included or excluded for further purification was based on experience of the relative intensity of staining for contaminants and product on Colloidal blue stained gels. In order to make this a less subjective estimation, densitometry was utilized to determine specific pooling criteria for fractions following the Q-Sepharose step. Densitometry was used in preference to the current QC assay for purity (RP-HPLC) since this assay could not resolve the new contaminants associated with Process 3.

Densitometry Data from Post Q Fractions from the 20 L Demonstration Run

The densitometry values from 2 separate analyses of the post-IEX fractions were averaged and are shown in table 48. Fractions 1-12 and the last 25% (tail) of peak 1 contain AUXII and the associated contaminating proteins of 40, 75 and 90 kDa. Fractions 13-27 and the last 25% (tail) of peak 2 contain AUXI and the associated contaminants of 55 and 90 kDa. The pools of the fractions selected, based on SDS-PAGE without densitometric analysis, are highlighted.

TABLE 48

| Fraction number | Relative percentage (%) of band intensity | | | |
|---|---|---|---|---|
| | AUXII | 40 | 75 | 90 |
| 1 | 55.9 | 44.1 | 0 | 0 |
| 2 | 57.8 | 42.2 | 0 | 0 |
| 3 | 68.0 | 32.0 | 0 | 0 |
| 4 | 83.2 | 16.8 | 0 | 0 |
| 5 | 93.3 | 6.7 | 0 | 0 |
| 6 | 98.3 | 1.7 | 0 | 0 |
| 7 | 100 | 0 | 0 | 0 |
| 8 | 100 | 0 | 0 | 0 |
| 9 | 100 | 0 | 0 | 0 |
| 10 | 98.1 | 0 | 0.7 | 1.2 |
| 11 | 94.2 | 0 | 1.9 | 3.9 |
| 12 | 94.3 | 0 | 2.2 | 3.5 |
| tail | 92.3 | 0 | 3.6 | 4.1 |
| | AUXI | 55 | 90 | |
| 13 | 80.4 | 12.4 | 7.2 | |
| 14 | 77.8 | 15.3 | 6.9 | |
| 15 | 75.7 | 19.1 | 5.2 | |
| 16 | 74.5 | 20.8 | 4.7 | |
| 17 | 77.9 | 17.5 | 4.6 | |
| 18 | 82.0 | 13.7 | 4.3 | |
| 19 | 87.8 | 9.7 | 2.5 | |
| 20 | 93.1 | 3.7 | 3.2 | |
| 21 | 94.1 | 3.0 | 2.9 | |
| 22 | 92.4 | 2.8 | 4.8 | |
| 23 | 94.7 | 0.9 | 4.4 | |
| 24 | 95.8 | 0.1 | 4.2 | |
| 25 | 93.6 | 0.1 | 6.2 | |
| 26 | 91.5 | 0.0 | 8.4 | |
| 27 | 90.0 | 0.1 | 9.8 | |
| tail | 88.6 | 0.5 | 10.8 | |

Densitometry Summary Documents from Post Q Fractions from the 200 L Demonstration Run Summary of Densitometry Analysis Post IEX fraction from the 200 L engineering run have been analysed multiple times to establish a pooling criteria that can be documented in the IEX BMR for the GMP campaign. This pooling criterion is based on the assumption that (i) the quality of material generated from the engineering run is appropriate for the GMP material and (ii) the approximation of the densitometry method is acceptable. If the aim is to generate material of higher quality in the GMP campaign, the specification for pooling criteria will need to be revised.

Specification for Pooling from the IEX

In total, the samples from the 200 L engineering run have been analyzed 6 times (2 operators and 3 repeats of each gel) and the average data presented in table 49. The fractions that were pooled for the engineering run are highlighted in red.

From this analysis, the following pooling criteria can be established:

(i) Any fraction of purity greater than or equal to 88.5% can be pooled (ii) Any fraction with a single impurity greater or equal to 10% cannot be pooled (iii) Fractions to be pooled must be from consecutive fractions.

(iv) The calculated theoretical purity of the pool should be:

Greater than or equal to 93% theoretical purity for AUXI

Greater than or equal to 96% theoretical purity for AUXII

This last point was based on the estimates from the 200 L engineering run in which the total protein in available fractions was estimated (although one limitation was that not all fractions were present for UV analysis for the AUXI). The data from this analysis is presented in table 50.

**NOTE: from these criteria, fraction 7 for AUXII peak would now be excluded.

Assay Variation

From the data of the post IEX fractions from the 200 L engineering run, the following level of accuracy has been estimated:

(i) for the product (AUXI and AUXII) the % CV had been calculated as 2.1% (AUXI) and 2.3% (AUXII). Therefore the purity specification of 88.6% for pooling could be in the range 86.3-90.9%.

(ii) for the impurities, the % CV is much greater and the range has been estimated as 18.5%-33.7% depending on the impurity. Consequently, the purity specification of excluding fractions with a single impurity of no greater than 10% could be for fractions with an actual impurity range of 6.63-13.37%. Therefore the value for the purity of the product (and not the impurities) is the most reliable value for pooling specification.

Estimated Purity of Final Material by Densitometry

Densitometry analysis of the final material (DS and intermediates) for the 200 L engineering run has also been determined by densitometry and is as follows:
 AUXI=96.0% (3.1% of 90 kDa contaminant)
 AUXII=98.7% (1.2% of 90 kDa contaminant)
 DS=97.6% (2.1% of 90 kDa contaminant)

(Note: This is the range determined for a single SDS-PAGE analysed 3 times by 3 different operators.)

Standardisation of the Method

Over the course of the repeat analysis, the densitometry method has been standardized to minimise error between operators and variation between gels and will be documented in an SOP. Most notably:
 (i) The standard loading of total protein in each lane of the gel will be 1 Hg.
 (ii) A maximum of 16 fractions will be selected for analysis from each of the product peaks (AUXI and AUXII). This will limit the number of gels for densitometry analysis to 4.

(iii) The 16 fractions selected will start at the last fraction to be collected for each peak and work forward consecutively. This is to ensure accuracy in the figure calculated for the average purity (since all fractions to be pooled are likely to be included).

TABLE 49

Average relative quantities of product and impurities in the post IEX fractions from the 200L Engineering run, as determined by densitometry analysis. The fractions pooled are highlighted in red.

| Fraction # | Quantity | Relative quantity (%) | | | | |
|---|---|---|---|---|---|---|
| AUXI (peak 2) | loaded (µg) | Product | 40 | 90 | 80 | 55 |
| 3 | 1 | 88.91 | 0 | 7.43 | 0 | 3.66 |
| 4 | 1 | 85.81 | 0 | 7.28 | 0 | 6.91 |
| 5 | 1 | 84.57 | 0 | 6.78 | 0 | 8.65 |
| 6 | 1 | 80.41 | 0 | 6.96 | 0 | 12.63 |
| 8 | 1 | 80.00 | 0 | 5.46 | 0 | 14.54 |
| 9 | 1 | 80.61 | 0 | 5.53 | 0 | 13.86 |
| 10 | 1 | 88.53 | 0 | 4.20 | 0 | 7.27 |
| 11 | 1 | 90.43 | 0 | 4.19 | 0 | 5.39 |
| 13 | 1 | 94.68 | 0 | 4.35 | 0 | 0.97 |
| 14 | 1 | 94.10 | 0 | 4.94 | 0 | 0.96 |
| 15 | 1 | 93.93 | 0 | 5.18 | 0 | 0.89 |
| 16 | 1 | 93.57 | 0 | 5.83 | 0 | 0.60 |
| 18 | 1 | 92.03 | 0 | 7.97 | 0 | 0 |
| 19 | 1 | 91.40 | 0 | 8.60 | 0 | 0 |
| 20 | 1 | 90.30 | 0 | 9.70 | 0 | 0 |
| 21 | 1 | 90.14 | 0 | 9.86 | 0 | 0 |

| | Quantity | Relative quantity (%) | | | | |
|---|---|---|---|---|---|---|
| AUXII (peak 1) | loaded (mg) | Product | 40 | 90 | 80 | 55 |
| 3 | 1 | 68.48 | 21.55 | 9.97 | 0 | 0 |
| 4 | 1 | 55.51 | 36.80 | 7.69 | 0 | 0 |
| 5 | 1 | 55.90 | 36.73 | 4.96 | 2.41 | 0 |
| 6 | 1 | 67.59 | 25.09 | 4.53 | 2.79 | 0 |
| 7 | 1 | 80.70 | 12.33 | 4.41 | 2.55 | 0 |
| 8 | 1 | 87.61 | 5.18 | 4.58 | 2.62 | 0 |
| 9 | 1 | 100 | 0 | 0 | 0 | 0 |
| 10 | 1 | 100 | 0 | 0 | 0 | 0 |
| 11 | 1 | 100 | 0 | 0 | 0 | 0 |
| 12 | 1 | 100 | 0 | 0 | 0 | 0 |
| 13 | 1 | 95.59 | 0 | 2.92 | 1.49 | 0 |
| 14 | 1 | 93.56 | 0 | 4.12 | 2.31 | 0 |
| 15 | 1 | 91.90 | 0 | 5.05 | 3.05 | 0 |
| 16 | 1 | 91.45 | 0 | 4.88 | 3.67 | 0 |
| 17 | 1 | 89.95 | 0 | 5.57 | 4.48 | 0 |
| 18 | 1 | 87.85 | 0 | 7.03 | 5.11 | 0 |

TABLE 50

Theoretical relative amounts of product and impurities in the post IEX pools from the 200L Engineering run, as determined by densitometry analysis. The fractions pooled are highlighted in red. The theoretical average product purity is calculated as 92.3% and 95.8% for the AUXI and AUXII intermediates respectively.

| | Total protein quantity (mg) | Product (AUXI) quantity (mg) | Quantity of all Impurities (mg) |
|---|---|---|---|
| AUXI | 954.09 | 844.67 | 109.42 |
| | 1290.61 | 1167.07 | 123.55 |
| | 1524.29 | 1443.16 | 81.13 |
| | 1507.35 | 1418.46 | 88.89 |
| | 1339.47 | 1258.18 | 81.29 |
| | 1256.06 | 1175.32 | 80.74 |
| | 1063.30 | 978.57 | 84.73 |
| | 972.75 | 889.05 | 83.70 |
| | 774.62 | 699.46 | 75.15 |
| | 588.06 | 530.06 | 58.00 |
| Total | 11270.60 | 10404.00 | 866.60 |
| % | | 92.31 | 7.69 |

| | Total protein quantity (mg) | Product (AUXII) quantity (mg) | Quantity of all Impurities (mg) |
|---|---|---|---|
| AUXII | 200.20 | 161.56 | 38.64 |
| | 323.14 | 283.11 | 40.02 |
| | 533.02 | 533.02 | 0.00 |
| | 882.09 | 882.09 | 0.00 |
| | 1226.58 | 1226.58 | 0.00 |
| | 1508.94 | 1508.94 | 0.00 |
| | 1206.73 | 1153.47 | 53.27 |
| | 943.48 | 882.75 | 60.73 |
| | 684.41 | 628.99 | 55.43 |
| | 537.35 | 491.40 | 45.95 |
| | 312.80 | 281.35 | 31.45 |
| | 348.53 | 306.19 | 42.34 |
| Total | 8707.28 | 8339.45 | 367.82 |
| % | | 95.78 | 4.22 |

GMP Pooling Criteria for Post Q-Sepharose Fractions

Detail to be Specified in the Ion Exchange BMR

A. The following pooling criteria is to be specified for fractions from both the AUXI and AUXII peaks which have been analysed by densitometry:

(i) A maximum of 16 fractions will be selected for analysis from each of the product peaks (AUXI and AUXII). This will limit the number of gels for densitometry analysis to 4.

(ii) Any fraction of purity greater than or equal to 90.00% (reported to 2 decimal places) can be pooled.

(iii) Any fraction with a single impurity greater than or equal to 9.00% (to 2 dp) cannot be pooled.

(iv) Fractions to be pooled must be from consecutive fractions.

B. The following pooling criteria is to be specified for fractions from the AUXII peak which have been analysed by SEC-HPLC:

(i) The maximum number of samples to be submitted for SEC-HPLC is 10 and must be from the last fraction collected for this peak and consecutive fractions forward.

(ii) Any fraction with greater than or equal to 2.00% (to 2 dp) aggregate cannot be pooled.

Details to be Recorded for Information Only

A. The estimated theoretical purity of the pool should be calculated for information only and is expected to be:

Greater than or equal to 93.00% theoretical purity for AUXI

Greater than or equal to 97.00% theoretical purity for AUXII

B. The minimum quantity of protein in each pool should be noted to establish if criteria for excluding fractions with less than 0.5 g could be used in the future.

C. Fractions for the AUXI peak will be submitted for RP-HPLC but will be analysed retrospectively and for information only. These data will NOT be considered as part of the pooling criteria.

Expected Impact on Pooling

The following has been calculated from the average data set presented in table 51 to reflect the effect on yield and fraction selection following the new pooling criteria:

TABLE 51

|  | AUXI | AUXII |
|---|---|---|
| Fractions pooled from the 200L engineering run | #10-21 | #7-18 |
| Total protein determined for the post IEX pools from the 200L engineering run | 13.18 g | 8.37 g |
| Fractions which would be pooled following GMP criteria | #11-21 | #9-16 |
| Estimated reduction in total protein due to fractions excluded by the GMP criteria | 0.95 g | 1.18 g |

TABLE 52

Average relative quantities of product and impurities in the post IEX fractions from the 200L Engineering run, as determined by densitometry analysis.

| Fraction # | Quantity | Relative quantity (%) | | | | |
|---|---|---|---|---|---|---|
| AUXI (peak 2) | loaded (µg) | Product | 40 | 90 | 80 | 55 |
| 3 | 1 | 88.91 | 0 | 7.43 | 0 | 3.66 |
| 4 | 1 | 85.81 | 0 | 7.28 | 0 | 6.91 |
| 5 | 1 | 84.57 | 0 | 6.78 | 0 | 8.65 |
| 6 | 1 | 80.41 | 0 | 6.96 | 0 | 12.63 |
| 8 | 1 | 80.00 | 0 | 5.46 | 0 | 14.54 |
| 9 | 1 | 80.61 | 0 | 5.53 | 0 | 13.86 |
| 10 | 1 | 88.53 | 0 | 4.20 | 0 | 7.27 |
| 11 | 1 | 90.43 | 0 | 4.19 | 0 | 5.39 |
| 13 | 1 | 94.68 | 0 | 4.35 | 0 | 0.97 |
| 14 | 1 | 94.10 | 0 | 4.94 | 0 | 0.96 |
| 15 | 1 | 93.93 | 0 | 5.18 | 0 | 0.89 |
| 16 | 1 | 93.57 | 0 | 5.83 | 0 | 0.60 |
| 18 | 1 | 92.03 | 0 | 7.97 | 0 | 0 |
| 19 | 1 | 91.40 | 0 | 8.60 | 0 | 0 |
| 20 | 1 | 90.30 | 0 | 9.70 | 0 | 0 |
| 21 | 1 | 90.14 | 0 | 9.86 | 0 | 0 |

|  | Quantity | Relative quantity (%) | | | | |
|---|---|---|---|---|---|---|
| AUXII (peak 1) | loaded (mg) | Product | 40 | 90 | 80 | 55 |
| 3 | 1 | 68.48 | 21.55 | 9.97 | 0 | 0 |
| 4 | 1 | 55.51 | 36.80 | 7.69 | 0 | 0 |
| 5 | 1 | 55.90 | 36.73 | 4.96 | 2.41 | 0 |
| 6 | 1 | 67.59 | 25.09 | 4.53 | 2.79 | 0 |
| 7 | 1 | 80.70 | 12.33 | 4.41 | 2.55 | 0 |
| 8 | 1 | 87.61 | 5.18 | 4.58 | 2.62 | 0 |
| 9 | 1 | 100 | 0 | 0 | 0 | 0 |
| 10 | 1 | 100 | 0 | 0 | 0 | 0 |
| 11 | 1 | 100 | 0 | 0 | 0 | 0 |
| 12 | 1 | 100 | 0 | 0 | 0 | 0 |
| 13 | 1 | 95.59 | 0 | 2.92 | 1.49 | 0 |
| 14 | 1 | 93.56 | 0 | 4.12 | 2.31 | 0 |
| 15 | 1 | 91.90 | 0 | 5.05 | 3.05 | 0 |
| 16 | 1 | 91.45 | 0 | 4.88 | 3.67 | 0 |
| 17 | 1 | 89.95 | 0 | 5.57 | 4.48 | 0 |
| 18 | 1 | 87.85 | 0 | 7.03 | 5.11 | 0 |

TABLE 53

Theoretical relative amounts of product and impurities in the post IEX pools from the 200L Engineering run, as determined by densitometry analysis. The fractions pooled are highlighted in red. The theoretical average product purity is calculated as 92.3% and 95.8% for the AUXI and AUXII intermediates respectively.

| AUXI | Total protein quantity (mg) | Product (AUXI) quantity (mg) | Quantity of all Impurities (mg) |
|---|---|---|---|
| #10 | 954.09 | 844.67 | 109.42 |
| #11 | 1290.61 | 1167.07 | 123.55 |
| #13 | 1524.29 | 1443.16 | 81.13 |
| #14 | 1507.35 | 1418.46 | 88.89 |
| #15 | 1339.47 | 1258.18 | 81.29 |
| #16 | 1256.06 | 1175.32 | 80.74 |
| #18 | 1063.30 | 978.57 | 84.73 |
| #19 | 972.75 | 889.05 | 83.70 |
| #20 | 774.62 | 699.46 | 75.15 |
| #21 | 588.06 | 530.06 | 58.00 |
| Total | 11270.60 | 10404.00 | 866.60 |
| % |  | 92.31 | 7.69 |

| AUXII | Total protein quantity (mg) | Product (AUXII) quantity (mg) | Quantity of all Impurities (mg) |
|---|---|---|---|
| #7 | 200.20 | 161.56 | 38.64 |
| #8 | 323.14 | 283.11 | 40.02 |
| #9 | 533.02 | 533.02 | 0.00 |
| #10 | 882.09 | 882.09 | 0.00 |
| #11 | 1226.58 | 1226.58 | 0.00 |
| #12 | 1508.94 | 1508.94 | 0.00 |
| #13 | 1206.73 | 1153.47 | 53.27 |
| #14 | 943.48 | 882.75 | 60.73 |
| #15 | 684.41 | 628.99 | 55.43 |
| #16 | 537.35 | 491.40 | 45.95 |
| #17 | 312.80 | 281.35 | 31.45 |
| #18 | 348.53 | 306.19 | 42.34 |
| Total | 8707.28 | 8339.45 | 367.82 |
| % |  | 95.78 | 4.22 |

A comparison of 2 data sets (i.e. the same in-process samples run on different gels by different operators) allowed the following retrospective pooling criteria to be noted for the average data set although one additional fraction (fraction 27 from AUXI) would be included from those actually pooled in the 20 L run:

AUXI

Pool all fractions with a purity of ≧87% but which do not have a single impurity of ≧10%.

AUXII

Pool all fractions with a purity of ≧94% but which do not have a single impurity of ≧4%.

QC data from the analysis of the final material from the 20 L demonstration run showed that the AUXII intermediate was 99.4% pure, the AUXI intermediate was 99.1% pure and the drug substance was 99.9% collagenase by RP-HPLC. Therefore, the criteria specified for the pooling process would be expected to result in material that passes the release specifications for the final material.

200 L Demonstration Run

The criteria established for the 20 L demonstration run previously mentioned was different to that implemented for the 200 L engineering run. In this case, pooling was specified for both the AUXI and AUXII products as fractions with a purity of ≧86.5% but which did not have a single impurity contaminant of ≧10%. AUXII samples with an impurity level ≧2% detected by SEC-HPLC for were also excluded. The resulting AUXI/AUXII intermediates and drug substance were also analyzed by densitometry, using a standardized method, and shown to have the following estimated purity based on analysis of a single gel 3 times (3 different operators): AUXI=96.0% (3.1% of 90 kDa contaminant); AUXII=98.7% (1.2% of 90 kDa contaminant); DS=97.6% (2.1% of 90 kDa contaminant).

In addition, the QC determined purity of the intermediates and drug substance was show to pass specification by the RP-HPLC assay (AUXI=98.2%; AUXII=98.1%; drug substance=99.4%). Consequently, the pooling criteria followed for the 200 L engineering run was successful in delivering product of suitable purity based on the current available analytical methods.

Materials and Methods

MUSTANG Q Chromatography (20 L Scale Run)

Equipment:

MUSTANG Q Chromatography Capsule, 60 mL (CL3MSTGQP1, Pall)

Conductivity and pH Meter 4330 (Jenway)

Chemicals:

Sodium chloride (USP grade, Merck)

Sodium hydroxide solution (volumetric 4M) (AnalaR, BDH)

Tris (hydroxymethyl) methylamine (USP grade, Merck)

Ammonium sulphate (Extra Pure, Merck)

Hyclone Water for Injection—Quality Water (WFI-QW)

A 60 mL bed volume MUSTANG Q chromatography capsule was sanitised with 1M NaOH at a flow rate of 30 mL/min for 30 minutes. The capsule was then preconditioned for the same time and flow-rate using 1M NaCl. The capsule was equilibrated with 2 L of MUSTANG Q Equilibration buffer (10 mM Tris, 1M ammonium sulphate, pH 8), at a flow rate of 60 mL/min. The outlet flow was checked to ensure the pH was ≦8. Supernatant (22 L) from 200 L fermentation PP3 (which had been 0.2 µm filtered) was loaded onto the capsule at a flow rate of 540 mL/min (approximately 40 min. duration). The maximum recommended operating flow rate for the capsule was 600 mL/min. The filtered material was stored in 2×10 L Stedim bags at 2-8° C. overnight.

Hydrophobic Interaction Chromatography (20 L scale run)

Equipment:

AKTA Pilot installed with Unicorn V 5.01 software (GE Healthcare)

Vantage S130 column (cross sectional area 125 cm2, Millipore)

Conductivity and pH Meter 4330 (Jenway)

Sartopore 2 0.8+0.45 µm filter capsule (Sartorius)

Medical Refrigeration Unit MP 150 (Electrolux)

Chemicals:

Phenyl Sepharose 6 FF low sub (GE Healthcare)

Sodium hydroxide solution (volumetric 4M) (AnalaR, BDH)

Sodium chloride (USP grade, Merck)

Tris(hydroxymethyl)methylamine (USP grade, Merck)

Ammonium sulphate (Extra Pure, Merck)

Leupeptin (MP Biomedicals, Inc)

Hyclone Water For Injection—Quality Water (WFI-QW)

HIC Column Packing 2400 mL of Phenyl Sepharose 6 FF Low Sub (Lot# 312089) slurry was settled for 3 hours and the ethanol removed and replaced with 1800 mL WFI. The media was reslurried (50%), settled and washed once with WFI and twice with 1800 mL 200 mM NaCl, with settling overnight between washes. The media was reslurried with 1800 mL 200 mM NaCl, poured into the column and allowed to settle for 1 h. The adaptor was brought down to ~1 cm above the resin bed (removing all air bubbles) and the media packed in 200 mM NaCl at a flow rate of 400 mL/min (192 cm/hr) for 10 mins. This packing flow rate was utilized as equivalent to the maximum operating flow rate for the K-prime system available in GMP. The adaptor was brought down to the top of the bed and the column packed at 192 cm/hr for 10 mins before screwing the adaptor into the top of the resin and packing at 192 cm/hr for a further 10 mins, during which no compression of the resin was observed. The pack test was carried out using the AKTA Pilot method: HIC 1500 mL Pack Test. For this, the column was equilibrated with 1 column volume (CV) of 200 mM NaCl in WFI and pack tested with 15 mL (1% CV) of 1M NaCl in WFI at a flow rate of 313 mL/min (150 cm/hr). The column was flushed with 2CV WFI and stored with 2CV 10 mM NaOH. The packed column had an asymmetry of 1.2, a plate count of 2659 plates/meter, a CV of 1525 mL and bed height of 12.2 cm.

Column Sanitisation and Equilibration

The Phenyl Sepharose 6 FF (low sub) column was sanitised with 0.5M NaOH for 60 minutes, washed with 2 column volumes (CV) WFI and equilibrated with 5CV 10 mM Tris, pH 8 (HIC Buffer B) followed by 5CV 10 mM Tris, 1.0M ammonium sulphate, pH 8 (HIC Buffer A).

Preparation of the HIC Load 13.48 kg (11.05 L) of 3.0M ammonium sulphate, 10 mM Tris, pH 8 was added to 22.1 kg fermentation filtrate after the MUSTANG Q filter treatment (section 3.1). The filtrate was mixed for 5 minutes before filtering through a 0.05 m$^2$ filter capsule (0.8+0.45 µm). The filtered material (denoted the HIC load material) was stored on ice (approximately 30 minutes duration) until use.

HIC Column Run

The HIC run was performed at a constant linear flow rate of 150 cm/hour using chilled buffers maintained at 2-8° C. 30 L feedstock (equivalent to 20 L post-MUSTANG Q filtrate) was loaded onto the 1525 mL Phenyl Sepharose 6 FF (low sub) column previously equilibrated with 2 CV 10 mM Tris, 1.0M ammonium sulphate, pH 8 (HIC Buffer A). Unbound material was washed off the column with 10 CV HIC Buffer A. The column was then washed with 5 CV 10 mM Tris, 0.3 M ammonium sulphate, pH 8 (HIC Buffer A2) and bound proteins eluted with 10 CV 10 mM Tris, pH 8 (HIC Buffer B). The first 0.67 CV (1 L) of the elution buffer was discarded and a post-HIC pool of 4CV was collected. Leupeptin was added (126.4 mL) to the post-HIC pool (6191.3 g) to a final concentration of 20004 from a stock solution of 10 mM leupeptin, 10 mM Tris, pH 8. The mixed solution (6.3 kg) was stored at 2-8° C. for 2 days before further processing by tangential flow filtration.

Tangential Flow Filtration step 1 (TFF1 20 L scale run)

Equipment:

ProFlux M12 TFF system (Millipore)

Conductivity and pH meter 4330 (Jenways)

Sartopore 2 0.8+0.45 µm filter capsule (Sartorius)

Pellicon 2 "Mini" Filter 0.1 m$^2$ 30 kDa MWCO PES membranes (Millipore)

Medical Refrigeration Unit MP 150 (Electrolux)

Materials/Chemicals.

Sodium hydroxide solution (volumetric 4M) (AnalaR, BDH)

Tris(hydroxymethyl)methylamine (USP grade, Merck)

Leupeptin (MP Biomedicals, Inc)

Hyclone Water For Injection Quality Water (WFI-QW)

System Step Up

The ProFlux M12 TFF system was set up according to the manufacturer's instructions with two Pellicon 2 "Mini" Filter 30 kDa MWCO PES membranes, sanitised with 0.5M NaOH for 60 minutes and stored in 0.1M NaOH until use. The system was drained and flushed with 14 L WFI and the normal water permeability (NWP) measured as 23 L/m2/hr/psi at 25° C. at a trans-membrane pressure (TMP) of 15 psig (inlet pressure of 20 psig and outlet pressure of 10 psig). The system was flushed with 0.5 L 10 mM Tris, pH 8 (diafiltration buffer) and equilibrated with 1 L of the same buffer for 10 minutes. The conductivity and pH of the permeate was determined and checked against that of the diafiltration buffer to ensure the membranes were equilibrated prior to use.

Concentration and Diafiltration

The concentration and diafiltration steps were performed with chilled diafiltration buffer (10 mM Tris, pH 8) containing 200 µM leupeptin. The TFF system was flushed with 1 L chilled buffer just before use. 2 L of the post-HIC material (6.3 L total volume) was pumped into the TFF system reservoir and recirculated for 10 minutes without back-pressure to condition the membrane. The level sensor on the reservoir was set to 1.2 L and the post-HIC material concentrated at a TMP of 15 psig (inlet pressure of 20 psig and outlet pressure of 10 psig) until all the material had entered the system. The permeate was collected and stored at 2-8° C. for analysis. The inlet tubing was connected to the diafiltration buffer and diafiltration of the material was performed at a TMP of 15 psig (inlet pressure of 20 psig and outlet pressure of 10 psig) for approximately 8.5 turnover volumes (TOV), maintaining the volume of material in the reservoir at 1.2 L. The conductivity and pH of the permeate was determined after 5, 7 and 8.5 TOV and checked against that of the diafiltration buffer. The retentate was drained from the system and stored at 2-8° C. 250 mL diafiltration buffer was pumped into the reservoir, recirculated around the system for 10 minutes without back-pressure to rinse the system, drained, the rinse repeated and both rinses were stored separately at 2-8° C. The protein concentration of the retentate and rinses were determined (by UV) and the first rinse (204.8 g weight) added to the retentate (1231.4 g weight). This post TFF1 material (1.4 kg) was then filtered through a Sartopore 2 0.8+0.45 µm filter capsule and stored at 2-8° C. overnight until further processing by Q Sepharose ion exchange chromatography.

Ion Exchange Chromatography (20 L Scale Run)

Equipment.

ÄKTA Pilot installed with Unicorn 5.01 software (GE Healthcare)

Conductivity and pH Meter 4330 (Jenway)

Vantage S90 Column (cross sectional area 62 cm2, Millipore)

Medical Refrigeration Unit MP150 (Electrolux)

Chemicals:

Sodium hydroxide solution (volumetric 4M) (AnalaR, BDH)

Sodium chloride (USP grade, Merck)

Tris(hydroxymethyl)methylamine (USP grade, Merck)

Calcium chloride 2-hydrate (USP grade, Merck)

Leupeptin (MP Biomedicals, Inc.)

Q Sepharose HP (GE Healthcare)

Hyclone Water For Injection—Quality Water (WFI-QW)

Column Packing and Preparation

A Vantage S90 column was packed using an AKTA Pilot chromatography system with Q Sepharose HP media in WFI to give a packed column with a 10 cm bed height, therefore a column volume (CV) of 620 mL. The packing was performed in accordance to the manufacturers instruction but with the pressure limit of the Vantage column imposed (0.3 MPa) which equated to a packing flow rate of 210 cm/hr and pressure limit of 0.28 MPa. After packing, the column was equilibrated with 2CV of 0.2M NaCl and pack tested with 1% CV (6.2 mL) 1M NaCl at a flow rate of 100 cm/hr (103 mL/min). The packed column had an asymmetry of 1.6 and a plate count of 12605 plates/meter, which was within specification for the media (asymmetry between 0.8 and 1.8, with a plate count >10,000). The column was stored in 10 mM NaOH until required.

Prior to use, the Q Sepharose column washed with 1.5 column volumes (CV) of WFI to remove the storage buffer, sanitised with 0.5M NaOH for 60 mins at 40 cm/hr before flushing again with 1.5CV WFI. The column was then charged and equilibrated in accordance with the manufacturers instructions with 2CV 10 mM Tris, 3 mM calcium chloride, pH 8 followed by 2CV 10 mM Tris, 3 mM $CaCl_2$, 360 mM NaCl, pH 8 and finally 5CV 10 mM Tris, 3 mM $CaCl_2$, pH 8.

Column Run

Immediately prior to the sample being loaded onto the column, the column was reequilibrated with chilled 10 mM Tris, 3 mM $CaCl_2$, 200 µM leupeptin pH 8 (IEX Buffer A). 1216 mL of chilled post TFF 1 material at a concentration of 2.55 mg/mL (determined by UV) was loaded onto the column at a flow rate of 100 cm/hr (103 mL/min). This equated to a column load of 5 mg total protein per mL of media. Following loading of the product, the column washed with 3 column volumes (CV) of IEX Buffer A and the protein eluted with 10 mM Tris, 3 mM $CaCl_2$, 360 mM NaCl, 200 µM leupeptin, pH 8 (IEX Buffer B) with a gradient of 0-40% elution buffer (A to B), over 20CV at a flow rate of 70.2 ml/min (68 cm/hr). Elution was monitored at 280 nm and 260 nm and 100 mL fractions collected across the two product peaks containing AUX II and AUX I. Fraction collection was started from the breakthrough of the peak and continued until 25% of the peak height on the trailing edge. A total of 12 fractions were collected across the AUX II peak and 15 fractions across the AUX I peak. The Q Sepharose HP chromatography was carried out at a standard laboratory temperature of 18-23° C., although the buffers used were pre-chilled. Fractions were stored at 2-8° C. until a result was obtained from the SDSPAGE analysis. Fractions 6 to 12 (peak 1) were pooled as AUX II collagenase with the volume determined as 683 g (after sampling) and the concentration by UV analysis measured as 1.17 mg/mL. Fractions 19 to 26 (peak 2) were pooled as AUX I collagenase with the volume determined as 796 g (after sampling) and the concentration by UV measured as 1.08 mg/mL.

Tangential Flow Filtration Step 2 (TFF2 20 L Scale Run)

Equipment:

ProFlux M12 TFF system (Millipore)

Conductivity and pH meter 4330 (Jenways)

Pellicon 2 "Mini" Filter 0.1 $m_2$ 30 kDa MWCO PES membrane (Millipore)

90 mm Filter Unit (1 L) 0.2 μm PES membrane (Nalgene)

Medical Refrigeration Unit MP 150 (Electrolux)

Materials/Chemicals:

Sodium hydroxide solution (volumetric 4M) (AnalaR, BDH)

Tris(hydroxymethyl)methylamine (USP grade, Merck)

Sucrose (BP grade, Merck)

Leupeptin (MP Biomedicals, Inc.)

Hyclone Water For Injection—Quality Water (WFI-QW)

Frensius Kabi Water For Injection (WFI)

System Set Up

The ProFlux M12 TFF system was set up according to the manufacturer's instructions with one Pellicon 2 "Mini" Filter 30 kDa MWCO PES membrane, sanitised with 0.5M NaOH for 60 minutes and stored in 0.1M NaOH until use. The system was drained and flushed with 14 L WFI and the normal water permeability (NWP) measured as 19.5 L/m$_2$/hr/psi for the membrane used for AUXI and as 14.5 L/m$_2$/hr/psi at 25° C. for the membrane used for AUXII at 25° C. and at a trans-membrane pressure (TMP) of 15 psig (inlet pressure of 20 psig and outlet pressure of 10 psig). The system was flushed with 0.5 L 10 mM Tris, 60 mM sucrose, pH8 (formulation buffer), and equilibrated with 1 L of the same buffer for 10 minutes. The conductivity and pH of the permeate was determined and checked against that of the formulation buffer.

Concentration and Formulation

The concentration and diafiltration steps were performed separately on each of the post IEX pools of AUXI and AUXII. All steps were performed using chilled formulation buffer (10 mM Tris, 60 mM sucrose, pH 8) maintained at 2-8° C. The TFF system was flushed with 1 L chilled buffer just before use. The post-IEX pool (683 g weight of AUXII and 796 g weight of AUXI) was pumped into the TFF system reservoir and recirculated at 10% pump speed for 10 minutes without backpressure to condition the membrane. The level sensor on the reservoir was set to approximately 400 mL and the AUXI or AUXII pool concentrated at a TMP of 15 psig (inlet pressure of 20 psig and outlet pressure of 10 psig) until the volume in the reservoir had been reduced to approximately 360-390 mL (this assumed a system hold up volume of 100 mL). The target volume reduction was based on achieving a theoretical concentration of 1.75 mg/mL for the product assuming no loss in protein during the concentration operation. The permeate was collected and stored at 2-8° C. for analysis. For the diafiltration operation the inlet tubing was connected to the formulation buffer and diafiltration performed at a TMP of 15 psig (inlet pressure of 20 psig and outlet pressure of 10 psig). Approximately 12 turnover volumes (TOV) were performed for AUXII and 8.5 TOV's for AUXI, maintaining the volume of material in the reservoir at ~400 mL. The conductivity and pH of the permeate was determined after 12 TOV for AUXII and after 6, 7, and 8.5 TOVs for AUXI and checked against that of the formulation buffer. The retentate was drained from the system and stored at 2-8° C. 250 mL formulation buffer was used to wash residual product from the membranes by re-circulated around the system for 10 minutes (without backpressure). After draining the rinse solution, a second wash was performed and both rinse 1 and rinse 2 were stored at 2-8° C. After UV protein content determination of the retentate and rinses, the first rinse was added to the retentate, mixed and a UV protein concentration of the mix determined. For AUXII, 122 g of the second rinse was also added to the retentate plus rinse 1 to give a theoretical AUXII concentration of 1.1 mg/mL. For AUXI, 94 g of the second rinse was added to the material to give a theoretical AUXI concentration of 1.1 mg/mL. Both the AUXI and AUXII material were filtered through a 1 L Nalgene 0.2 μm filter unit in a Class II hood and the post filtered protein concentration determined. The AUXI and AUXII intermediates were stored at 2-8° C.

Protein Concentration Determination

Absorbance

Equipment:

DU800 Spectrophotometer (Beckman)

In process samples were analysed by UV spectrophotometry by performing a UV scan of samples between 220 and 330 nm. The appropriate buffer was used as a blank and a scan of the buffer blank performed before scanning the samples. If necessary, samples were diluted with the same buffer to ensure the $A_{280}$<1.0 AU. Protein concentrations (mg/mL) were determined according to the Beer-Lambert law, c=A/b.ϵ, where A is the absorbance ($A_{280}$-$A_{330}$), b is the pathlength (1.0 cm) and ϵ is the extinction coefficient of the protein. Extinction coefficients of 1.48 mg-$_1$ cm-$_1$mL for AUXI, 1.576 mg-$_1$ cm-$_1$mL for AUXII and 1.428 mg-$_1$ cm-$_1$mL for an AUXI/AUXII mix were used.

Bradford Assay

Materials:

Lyophilised BSA (hydrated to 1.4 mg/mL)

Chemicals:

Protein Assay Dye Reagent Concentrate (500-0006, Bio-Rad)

A BSA standard curve was prepared by diluting the BSA with water, to known concentrations. The Bio-Rad protein assay dye reagent was prepared by diluting one part concentrate with four parts water. Test samples were prepared by diluting with water. 50 μL of test sample either neat or diluted was added to a cuvette and 2.5 mL diluted regent added. Samples were prepared in duplicate. The samples were incubated for 10 minutes before reading the OD. The standard curve of $OD_{595\ nm}$ vs. protein concentration was obtained by measuring the $OD_{595\ nm}$ of BSA solutions of known concentration. The test samples were then assayed and the protein concentration determined from the standard protein assay curve. Samples from the post MUSTANG Q step were always analysed without dilution in order to standardise the contribution from the pigment. In this case, 50 μL of the undiluted post MUSTANG Q material was utilised in the assay.

SDS-PAGE Analysis

Equipment:

Xcell SureLock Mini-Cell Electrophoresis System (Invitrogen)

Electrophoresis Power Supply EPS 601, (Amersham Pharmacia Biotech)

Rocky shaker platform, (Scientific Laboratory Supplies)

Chemicals:

SDS-PAGE Standards High Molecular Weight (161-0303, Bio Rad)

Mark12 Unstained Standard (LC5677, Invitrogen)

Novex 8% Tris-Glycine gels, 1.5 mm, 10 well (EC6018BOX, Invitrogen)

NuPAGE Novex 4-12% Bis-Tris gels, 1.0 mm, 12 well (NPO$_{322}$BOX, Invitrogen)

Novex Tris-Glycine SDS Running Buffer (10×) (LC2675, Invitrogen)

NuPAGE MES SDS Running Buffer (20×) (NP0002, Invitrogen)

Novex Tris-Glycine SDS Sample Buffer (2×) (LC2676, Invitrogen)

NuPAGE LDS Sample Buffer (4×) (NP0007, Invitrogen)

NuPAGE Sample Reducing Agent (10×) (NP0009, Invitrogen)

Colloidal Blue Staining kit (LC6025, Invitrogen)

Ethylenediaminetetra-acetic acid disodium salt AnalaR R (BDH)

Tris-Glycine Gels

Samples were prepared for reducing SDS-PAGE by adding 12 µl of sample to 20 µl sample Buffer (2×), 4 µl reducing agent (10×) and 41 l of 0.1M EDTA (to achieve final concentration of 10 mM). The high molecular weight (HMW) marker was prepared by adding 110 l of concentrated stock to 80 µl reducing agent (10×), 310 l WFI and 400p sample buffer (2×). The diluted HMW standard was then heated at 95oC for 5 minutes before aliquoting and storage at −20oC for use in subsequent gels. Samples (20 µl load volume) containing collagenases were run directly (i.e. with no prior heat treatment) on 8% Tris-Glycine gels using Tris-Glycine running buffer at 130 V for ~2 hours. After electrophoresis, the gels were stained with colloidal blue stain reagent as per the manufacturers instructions.

Bis-Tris Gels

Samples were prepared for reducing SDS-PAGE by adding 16.5 µl of sample to 7.5 µl sample buffer (4×), 3 µl reducing agent (10×) and 3 µl of 0.1M EDTA (to achieve final concentration of 10 mM). MARK 12 marker loaded neat (10 µl). Samples (15 µl load volume) containing collagenases were run directly (i.e. with no prior heat treatment) on 4-12% Bis-Tris gels using either MES running buffer at 200 V for ~40 mins. After electrophoresis, the gels were stained with either colloidal blue stain reagent as per the manufacturers instructions or silver stained using a standard procedure (GE Healthcare).

Densitometry Analysis of Post-IEX Fractions

Equipment:

Xcell SureLock Mini-Cell Electrophoresis System (Invitrogen)

Electrophoresis Power Supply EPS 601, (Amersham Pharmacia Biotech)

Rocky shaker platform, (Scientific Laboratory Supplies)

Flatbed scanner (Hewlett Packard)

Materials/Chemicals:

NuPAGE Novex 4-12% Bis-Tris gels, 1.0 mm, 12 well (NPO$_{322}$BOX, Invitrogen)

NuPAGE MES SDS Running Buffer (20×) (NP0002, Invitrogen)

NuPAGE LDS Sample Buffer (4×) (NP0007, Invitrogen)

NuPAGE Sample Reducing Agent (10×) (NP0009, Invitrogen)

Mark12 Unstained Standard (LC5677, Invitrogen)

Colloidal Blue Staining kit (LC6025, Invitrogen)

Ethylenediaminetetra-acetic acid disodium salt (EDTA) (AnalaR, BDH)

Purified water

Reducing SDS-PAGE

The post-IEX samples were run on 4-12% Bis-Tris gels using MES running buffer at 1 µg/lane loading. Samples were prepared by adding 20 L of diluted post-IEX material to 8 µL Sample Buffer (4×), 31 L Reducing Agent (10×) and 3.411 L of 0.1M EDTA. 15 µL of each sample was loaded into the well directly after mixing (i.e. with no heat treatment) and run at 200 V for 40 mins. After electrophoresis, the gels were stained with Colloidal Blue stain reagent according to the manufacturers instructions but with a fixed staining duration to reduce staining variation (10 minute fix, 5 hours stain, 15-20 hours destain with purified water).

Gel Scanning and Densitometry

Gels were placed between 2 sheets of acetate ensuring removal of all air bubbles, scanned on a flat-bed scanner at 600 dpi resolution and the image cropped, resized and colour corrected with HP Image zone software. The image was converted to an 8-bit greyscale TIFF image with Alpha EaseFC software and the protein bands were analysed using QuantityOne gel documentation software (BioRad). After background substitution, the intensity peak areas of selected bands were converted to relative percentage values of product (AUXI or AUXII) and impurity(s) in each lane.

Buffer Stability

Equipment:

Peristaltic Pump (Watson Marlow)

125 ml PETG biotainers (Cellon)

Watson Marlow Tubing for peristaltic pump

Conductivity and pH Meter 4330 (Jenway)

Sartopore 2 300 (0.45/0.2 µm) filter capsule (Sartorius)

Buffers for the 20 L demonstration run were filtered after preparation through a 0.45/0.2 µm filter capsule into 10 or 20 L Stedim bags for storage at 2-8° C. prior to use. When the majority of the buffer had been filtered, approximately 75 mls of the remaining buffer was collected into pre-labelled 125 ml PETG biotainers and stored at 2-8oC. The pH, conductivity, temperature and date of buffer preparation were recorded. On completion of the 20 L demonstration run, the buffer samples were retrieved from cold storage and retested for pH, conductivity, and appearance. The temperature of the buffer at the time of testing was also recorded.

Preparation of Samples for N-Terminal Sequencing Analysis

Equipment:

Electrophoresis Power Supply EPS 601, (Amersham Pharmacia Biotech)

Xcell SureLock Mini-Cell Electrophoresis System, (Invitrogen)

Rocky shaker platform, (Scientific Laboratory Supplies)

Chemicals:

Novex 8% Tris-Glycine Gel, 1.5 mm, 10 well, (Invitrogen)

High Molecular Weight Marker, (BioRad)

NuPAGE Sample Reducing Agent (10×), (Invitrogen)

Novex Tris-Glycine SDS Running Buffer (10×), (Invitrogen)

Novex Tris-Glycine SDS Sample Buffer (2×), (Invitrogen)

Colloidal Blue Staining Kit, (Invitrogen)

Ethylenediaminetetra-acetic acid disodium salt (EDTA) (AnalaR, BDH)

Methanol, AnalaR (BDH)

Acetic Acid, AnalaR (BDH)

Water for injection (WFI)

Purified Water

Samples for N-terminal sequencing were prepared and separated on 8% Tris-Glycine gels as outlined previously. Samples identified as enriched for the 40 kDa contaminant (fraction 2 from the post IEX AUXII peak, CTL2006#0610H) and 55 kDa contaminant (fraction 16 from the post IEX AUXI peak, CTL2006#0611H) were each loaded in 5 lanes of the gel to provide enough material for sequencing (FIG. 89). Post IEX fractions from a previous 20 L fermentation (20 L PP3), which were enriched for the 90 kDa contaminants associated with both AUXI (fraction B7 R2, CTL2006#0581P) and AUXII (fraction DI, CTL2006#0582P) were also loaded in multiple lanes (FIG. 90). After electrophoresis, the gels were stained with colloidal blue stain reagent according to the manufacturers instructions and the contaminant bands excised and submitted to Alta Bioscience (Birmingham University, UK) for N-terminal sequencing. The 90 kDa AUXI associated contaminant (CTL2006#0612H) from the 20 L demonstration run was also submitted for sequencing but no data was obtained.

Summary of the Manufacturing of Process 3

Fermentation

The Phytone fed-batch fermentation process (Process 2) for production of collagenase from Clostridium histolyticum had been shown to be highly variable due to batch-to-batch variability in the Phytone peptone. For this reason Proteose Peptone #3 (PP3) was evaluated in 5 L fermentations. The evaluation demonstrated that when one specific batch of PP3 was used at 50 g/L the fermentation process was robust and reproducible. However when other batches of PP3 were employed at 50 g/L large variations were seen in the growth profiles of the cultivations. The maximum biomass concentration the various batches of PP3 would support were assessed in a small scale evaluation. These batches were deemed "good" or "poor" based on their ability to support high or low biomass concentrations of C. histolyticum respectively. When two fermentations were carried out at 5 L scale with "poor" and "good" batches of PP3 at 100 g/L both demonstrated highly similar growth profiles and product yields. This experiment showed that increasing the concentration of PP3 to 100 g/L alleviated the problem associated to batch to batch variation in the peptone.

A scale up fermentation was carried out at 200 L. The fermentation used the optimized concentration of PP3 (100 g/L). The fermentation was successful and replicated both the growth profile and product yield/quality observed at 5 L scale. The harvest process (clarification by filtration) developed for Process 2 was evaluated during the 200 L scale up fermentation. The cell culture was successfully clarified using the existing process with no blockage of the filtration train.

The quantification of collagenase concentration in crude fermentation samples was improved using densitometry analysis of Coomassie stained Tris Glycine gels. A standard curve of mixed AUXI and AUXII was loaded with dilutions of fermentation samples. The relationship between collagenase concentration and densitometry peak area was shown to be linear within the range of the sample dilutions. The concentrations of collagenase in the samples were then extrapolated using their peak area and the standard curve. This method estimated the yield of collagenase to be 280-350 mg/L from the 100 g/L PP3 process at 5 and 200 L scale.

The optimised PP3 fermentation process generated a higher biomass concentration (OD600 7 units) and increased product yield (280-350 mg/L total collagenase, by quantitative densitometry) when compared to the Phytone fed-batch process. The fermentation filtrate contained significantly less clostripain than the Phytone process. The ratio of AUXI: AUXII was closer to 1 compared to that observed during evaluation of Process 2. In summary the PP3 process increased the product yield, purity (post-fermentation) and reproducibility of the fermentation.

Purification

Process 3 was developed in an accelerated time frame in order to improve the processes previously developed at Cobra (Process 2) and run at 20 L scale in GMP. Major improvements to the process were made in order to simplify the purification procedure, facilitate robustness as well as make the process more amenable to scale up to 200 L. These improvements were also considered key to assisting process validation.

Process 3 was performed using material from a 200 L fermentation of Clostridium histolyticum in which a full 20 L of fermentation was purified. Material was processed directly from the fermentation and no hold steps were implemented. Following filtration, product was passed through a MUSTANG Q filter since small-scale experiments demonstrated reduction of dsDNA (as detected by pico green analysis) using this procedure. Analysis of in-process samples from the 20 L demonstration run however, showed no reduction in dsDNA suggesting that the robustness and application of this step required further investigation. A comparison of the parameters used for the 20 L run-through and previous small-scale experiments demonstrated dsDNA removal when the capsule was oversized by a factor of 1000 (based on the DNA binding capabilities of 15-25 mg DNA/mL capsule described by the manufacturer). In comparison, the capsule used in the 20 L run-through was oversized by a factor of approximately 177-296. Material from the MUSTANG Q capsule was held overnight at 2-8° C. An off-line stability study on sample material taken at this stage in the process indicated that maintaining a low temperature was key to the product stability at this point in the process since samples incubated at RT and 37° C. were susceptible to degradation as indicated by SDS-PAGE analysis.

Product from the MUSTANG Q capsule was prepared for hydrophobic interaction chromatography (HIC) by the addition and mixing of an ammonium sulphate solution (3M) to achieve a final concentration of 1M. This provided conditions suitable for collagenase binding to Phenyl Sepharose FF (low sub) media. A proportion of protein contaminants and pigment were then eluted from the HIC column using a step elution of 0.3M ammonium sulphate followed by collagenase product elution with a solution containing no ammonium sulphate. Criteria for collection of the product peak were established as a fixed volume of 4 column volumes (although this was later extended to 5 column volumes for the 200 L scale demonstration run). Leupeptin was then added immediately following elution and the material held for a period of 2 days at 2-8° C.

The yield from this step was difficult to determine accurately due to the complex nature of the feedstock. The process step yield was estimated as (i) 38% based on Bradford assay of the load and UV of the eluted material or (ii) 47% based on collagenase content in the load estimated by densitometry and UV of the eluted material. Alternatively, 0.17 g of total protein was eluted from the HIC column for the equivalent of every 1 L of fermentation filtrate applied.

The post HIC pool was prepared for Q-Sepharose purification by concentration (5-fold) and buffer exchange using tangential flow filtration (TFF 1) using 2×0.1 m2 30 kDa membranes. No loss was detected over this step and the reported increase in protein recovered may reflect the inaccuracy of UV at this point in the process. Inaccuracy could be attributed to pigment contamination or the use of the extinction coefficient for collagenases, which will be less accurate for material earlier in the purification when a complex of proteins are likely to be present. The TFF step was completed by a product filtration step before holding the material at 2-8° C. over night.

As with Process 2, the Q-Sepharose column was a key purification step in Process 3 and resulted in the separation of the AUXI and AUXII collagenases. The contaminants associated with process 3, however, were different to those in process 2 and appeared to closely co-purify with the AUXI and AUXII products. It was possible however, to remove the contaminants from the products by fractionation of the product peaks since the contaminants appeared to elute at either the leading or tail edges of both peaks. The contaminants were denoted by their relative molecular mass on reducing SDS-PAGE. Those associated with the AUXII product (the first peak eluted from the Q-Sepharose column) were identified as (i) 40 kDa (associated with the leading edge of the peak) and (ii) 75 kDa and 90 kDa (associated with the trailing edge of the peak). N-terminal amino acid sequencing indicated that the 40 kDa was AUXII related since the sequence matched identity with a region of the Col H sequence. In comparison, no identity could be confirmed for the 90 kDa contaminant due to issues of low signal. Contaminants associated with AUXI product (the second peak eluted form the Q-Sepharose column) were (i) 55 kDa (associated with the leading edge of the peak) and (ii) 90 kDa (associated with the trailing edge of the peak). N-terminal sequencing showed both the 55 kDa and 90 kDa contaminants to be identified as AUXI-related where the 55 kDa contaminant showed sequence identity with a mid region in the Col G sequence and the 90 kDa showed identical N-terminal match to AUXI. Consequently, the major impurities identified at this stage in the process were all product related and either identified as internal cleavage products of AUXI (55 kDa) and AUXII (40 kDa) or a C-terminally cleaved product of AUXI (90 kDa).

Following the Q-Sepharose column, a key process step was in the decision as to which fractions should go forward for further purification. For the 20 L demonstration run this criteria was based on the relative staining intensities of contaminants to product when analysed by 4-12% SDS-PAGE and stained with Colloidal Blue stain. The decision was subjective and based on the collective experience of the process development group as well as requests from the client. In order to establish defined criteria that described the pooling procedure, densitometry was performed on SDSPAGE. From this, the pooling was described as including fractions that were ≧87% pure (with no single impurity ≧10%) for AUXI and ≧94% pure (with no single impurity ≧4%) for AUXII. This resulted in a step yield based on UV estimation of 27.7% and 25.8% for AUXI and AUXII respectively. Further refinement and standardization of the densitometry method was achieved from data acquired from the 200 L scale demonstration run which resulted in definition of modified criteria for the subsequent GMP run.

Fractions containing AUXI or AUXII product from the Q-Sepharose column were formulated separately by TFF (denoted TFF2) using 1×0.1 m2 30 kDa membrane for each collagenase. The formulation buffer of 10 mM Tris, 60 mM sucrose pH 8, had been established by KBI BioPharma Inc. Product was filtered following the TFF2 step and the overall step yields for TFF and filtration estimated as 97.5% for AUXI and 92.2% for AUXII. At this stage samples were referred to as intermediates and were retained at 2-8° C. for QC analysis and prior to mixing of the drug substance. A retrospective stability study indicated the intermediates were stable over a period of at least 5 days at 2-8° C. as determined by SDS-PAGE, UV, RP-HPLC and SEC-HPLC analysis. The only detected deterioration in intermediates was identified in the AUXII intermediate after a 12 day hold in which aggregate levels increased from 0 to 0.62%.

The AUXI and AUXII intermediates were mixed in equal ratio (as determined by UV) to generate the drug substance before performing a final product filtration. Only 400 mg of drug substance was prepared of which 200 mg was shipped to KBI BioPharma Inc. along with 25 mg of each intermediate. The overall process yield was estimated for the 20 L demonstration run in which all available material from the 20 L of fermentation feedstock had been processed and assuming all material had been mixed as drug substance. This gave a predicted yield of 1.6 g drug substance for the 20 L scale purification. This equated to a process recovery of 17.8% based on then assumption that the initial estimate of 9 g (using the Bradford assay) for the amount of total protein available to load onto the HIC column was accurate. Alternatively, if the total available protein was related to the collagenase content in the HIC load (as estimated by densitometry) the overall process yield was calculated as 22%.

In addition to the process run-through, some preliminary studies were preformed on sample and buffer retains taken from the process to assess stability. These data indicated that for the product, low temperature was a key factor in controlling degradation and samples taken early in the purification (prior to the Q-Sepharose column) were more susceptible to proteolysis. A product hold study showed however, that the combination of leupeptin and temperature control (2-8° C.) was successful in maintaining the product quality over the time courses anticipated for the GMP process.

Tables 54 and 55 detailed the analytical specifications AUX-I and AUX-II intermediates and also for Drug Substance for Process 3.

TABLE 54

Analytical Specifications for Process 3 AUX-I and AUX-II Intermediates

| | Specification | |
| --- | --- | --- |
| Test | AUX-I | AUX-II |
| Appearance | Clear colorless and free from particulate matter | Clear colorless and free from particulate matter |

TABLE 54-continued

Analytical Specifications for Process 3 AUX-I and AUX-II Intermediates

| Test | Specification AUX-I | AUX-II |
|---|---|---|
| *Endotoxin | ≦10 EU/mL | ≦10 EU/mL |
| Identity (and purity) by SDS-PAGE (Reduced conditions, Coomasie and silver stained) | Major band between 98-188 kDa, and no minor bands | Major band between 98-188 kDa, and no minor bands |
| *Total Protein by Absorbance Spectroscopy | 0.8-1.2 mg/mL | 0.8-1.2 mg/mL |
| SRC assay (AUX-I) | 12 000-21 000 fSRC units/mg | Not applicable |
| GPA assay (AUX-II) | Not applicable | 370 000-680 000 fGPA units/mg |
| Analysis of Proteins using the Agilent 1100 HPLC System (Aggregation by size exclusion chromatography) | ≧98% main peak | ≧98% main peak |
| *Analysis of Proteins using the Agilent 1100 HPLC System (Purity by reverse phase liquid chromatography) | ≧97% by area | ≧97% by area |
| Analysis of Proteins using the Agilent 1100 HPLC System (Residual gelatinase by anion exchange chromatography) | ≦1% by area | ≦1% by area |
| Analysis of Proteins using the Agilent 1100 HPLC System (Residual clostripain by reverse phase liquid chromatography) | ≦1% by area | ≦1% by area |
| Identity by Peptide Mapping | Conforms to reference | Conforms to reference |
| Bioburden | ≦100 CFU/mL | ≦100 CFU/mL |

*Tests required for provisional release of intermediates for further manufacturing

TABLE 55

Analytical Specifications for Process 3 Drug Substance

| Test | Specification AUX-I | AUX-II |
|---|---|---|
| Appearance | Clear colorless and essentially free from particulate matter | |
| Potentiometric Measure of pH of Solution | 7.5 to 8.5 | |
| Endotoxin | <10 EU/mL | |
| Identity (and purity) by SDS-PAGE (Reduced conditions, Coomasie and silver stained) | Major collagenase band between 98-188 kDa MW markers | Major collagenase band between 97-200 kDa; MW markers; major bands comparable to reference standard |
| *Total Protein by Absorbance Spectroscopy | 0.8-1.2 mg/mL | |
| *SRC assay (AUX-I) | 13 000-23 000 fSRC units/mg | NA |
| *GPA assay (AUX-II) | NA | 200 000-380 000 fGPA units/mg |
| Residual host cell protein | Comparable to reference standard; no individual impurity band exhibiting greater intensity than 1% BSA intensity marker | |
| Residual host cell DNA | ≦10 pg/dose | |
| Analysis of Proteins using the Agilent 1100 HPLC System (Aggregation by size exclusion chromatography) | ≧98% main peak; ≦2% aggregates by area | |
| *Analysis of Proteins using the Agilent 1100 HPLC System (Identity and purity by reverse phase liquid chromatography) | 2 major peaks (AUX I & AUX II), combined ≧97% by area; Retention times of AUX-I and AUX-II within 5% of reference | |

TABLE 55-continued

Analytical Specifications for Process 3 Drug Substance

| | Specification | |
|---|---|---|
| Test | AUX-I | AUX-II |
| Analysis of Proteins using the Agilent 1100 HPLC System (Residual clostripain by reverse phase liquid chromatography | | ≦1% by area |
| Analysis of Proteins using the Agilent 1100 HPLC System (Residual gelatinase by anion exchange chromatography) | | ≦1% by area |
| Residual leupeptin by reverse phase chromatography | | ≦1 ug/mg w/w |
| *Bioburden | | <1 cfu/mL |

*Tests required for provisional release of Drug Substance for further manufacturing.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A drug product consisting of isolated and purified collagenase I and collagenase II having the sequence of *Clostridium histolyticum* collagenase I and collagenase II, respectively, wherein the collagenase I and collagenase II have a mass ratio of about 1 to 1 and the drug product is at least 97% by area pure as determined by reverse phase high performance liquid chromatography.

2. The drug product of claim 1, wherein the drug product contains less than about 2% by area aggregated protein as determined by reverse phase high performance liquid chromatography.

3. The drug product of claim 1, wherein the drug product contains less than about 1% by area of clostripain as determined by reverse phase high performance liquid chromatography.

4. The drug product of claim 1, wherein the drug product contains less than about 1% by area of gelatinase as determined by anion exchange chromatography.

5. The drug product of claim 1, wherein the drug product contains less than about 1 ug/mg (w/w) of leupeptin.

6. The drug product of claim 1, wherein the drug product has a bioburden less than 1 cfu/ml, and wherein the drug product is sterile.

7. The drug product of claim 6, wherein the drug product contains less than 10 EU/ml of endotoxin.

8. The drug product of claim 6, wherein the drug product contains less than 5 EU/mg of endotoxin.

9. A drug product consisting of isolated and purified collagenase I and collagenase II having the sequence of *Clostridium histolyticum* collagenase I and collagenase II, respectively, wherein the collagenase I and collagenase II have a mass ratio of about 1 to 1 and the drug product is at least 97% by area pure as determined by reverse phase high performance liquid chromatography, wherein the preparation of the drug product comprises the steps of:
   a) fermenting *Clostridium histolyticum*;
   b) harvesting a crude fermentation comprising collagenase I and collagenase II;
   c) purifying collagenase I and collagenase II from the crude harvest via filtration and column chromatography comprising the steps of:
      i) filtering the crude harvest through an anion exchange filter;
      ii) adding ammonium sulphate;
      iii) subjecting the harvest through a HIC column;
      iv) adding leupeptin to the filtrate;
      v) removing the ammonium sulfate;
      vi) filtering the mixture of step (v); and
      vii) separating collagenase I and collagenase II using ion-exchange;
   d) combining the collagenase I and collagenase II purified from step (c) at a ratio of about 1 to 1.

10. The drug product of claim 9, wherein the drug product is at least 98% by area pure as determined by reverse phase high performance liquid chromatography.

11. The drug product of claim 9, wherein preparation of the drug product further comprises the step of conducting cell bank preparations in the presence of phytone peptone or vegetable peptone.

12. The drug product of claim 9, wherein the fermentation step comprises the steps of:
   a) inoculating the medium in a first stage with *Clostridium histolyticum* and agitating the mixture;
   b) incubating the mixture from step (a) to obtain an aliquot;
   c) inoculating the medium in a second stage with aliquots resulting from step (b) and agitating the mixture;
   d) incubating mixtures from step (c) to obtain an aliquot;
   e) inoculating the medium in a third stage with aliquots resulting from step (d) and agitating;
   f) incubating mixtures from step (e) to obtain an aliquot;
   g) inoculating the medium in a fourth stage with an aliquot resulting from step (f) and agitating; and
   h) incubating mixtures from step (g).

13. The drug product of claim 9, wherein the drug product is stored at a temperature of about −70° C.

14. A process for producing a drug product consisting of isolated and purified collagenase I and collagenase II having the sequence of *Clostridium histolyticum* collagenase I and collagenase II, respectively, wherein the collagenase I and collagenase II have a mass ratio of about 1 to 1 and the drug product is at least 97% by area pure as determined by reverse phase high performance liquid chromatography, comprising the steps of:
   a) fermenting *Clostridium histolyticum*;
   b) harvesting a crude fermentation comprising collagenase I and collagenase II;
   c) purifying collagenase I and collagenase II from the crude harvest via filtration and column chromatography comprising the steps of:
      i) filtering the crude harvest through an anion exchange filter;
      ii) adding ammonium sulphate;
      iii) subjecting the harvest through a HIC column;
      iv) adding leupeptin to the filtrate;
      v) removing the ammonium sulfate;
      vi) filtering the mixture of step (v); and
      vii) separating collagenase I and collagenase II using ion-exchange;
   d) combining the collagenase I and collagenase II purified from step (c) at a ratio of about 1 to 1.

15. The process of claim 14, wherein the drug product is at least 98% by area pure as determined by reverse phase high performance liquid chromatography.

16. The process of claim 14, further comprising the step of conducting cell bank preparations the presence of phytone peptone or vegetable peptone.

17. The process of claim 14, wherein the fermentation step comprises the steps of
   a) inoculating the medium in a first stage with *Clostridium histolyticum* and agitating the mixture;
   b) incubating the mixture from step (a) to obtain an aliquot;
   c) inoculating the medium in a second stage with aliquots resulting from step (b) and agitating the mixture;
   d) incubating mixtures from step (c) to obtain an aliquot;
   e) inoculating the medium in a third stage with aliquots resulting from step (d) and agitating;
   f) incubating mixtures from step (e) to obtain an aliquot;
   g) inoculating the medium in a fourth stage with an aliquot resulting from step (f) and agitating; and
   h) incubating mixtures from step (g).

18. The process of claim 14, wherein the drug product is stored at a temperature of about −70° C.

19. A pharmaceutical formulation comprising a pharmaceutically acceptable excipient and a drug product consisting of isolated and purified collagenase I and collagenase II having the sequence of *Clostridium histolyticum* collagenase I and collagenase II, respectively, wherein the collagenase I and collagenase II have a mass ratio of about 1 to 1 and the drug product is at least 97% by area pure as determined by reverse phase high performance liquid chromatography.

20. The pharmaceutical formulation of claim 19, wherein the drug product is a sterile lyophilized powder and is stored at a temperature of about 5° C.

21. The pharmaceutical formulation of claim 19, wherein the formulation is a lyophilized injectable composition formulated with Sucrose, Tris and with a pH level of about 8.0.

22. The pharmaceutical formulation of claim 21, wherein the formulation is a lyophilized injectable composition formulation comprising about 0.9 mg of the said drug product, about 18.5 mg of sucrose and about 1.1 mg of Tris, and wherein the targeting vial fill volume is about 0.9 mL.

23. The pharmaceutical formulation of claim 21, wherein the formulation is a lyophilized injectable composition formulation comprising about 0.58 mg of the said drug product, about 12.0 mg of sucrose and about 0.7 mg of Tris.

24. A pharmaceutical composition comprising a pharmaceutically acceptable excipient and a drug product consisting of isolated and purified collagenase I and collagenase II having the sequence of *Clostridium histolyticum* collagenase I and collagenase II, respectively, wherein the collagenase I and collagenase II have a mass ratio of about 1 to 1 and the drug product is at least 97% by area pure as determined by reverse phase high performance liquid chromatography, wherein the preparation of the drug product comprises the steps of:
   a) fermenting *Clostridium histolyticum*;
   b) harvesting a crude fermentation comprising collagenase I and collagenase II;
   c) purifying collagenase I and collagenase II from the crude harvest via filtration and column chromatography comprising the steps of:
      i) filtering the crude harvest through an anion exchange filter;
      ii) adding ammonium sulphate;
      iii) subjecting the harvest through a HIC column;
      iv) adding leupeptin to the filtrate;
      v) removing the ammonium sulfate;
      vi) filtering the mixture of step (v); and
      vii) separating collagenase I and collagenase II using ion-exchange;
   d) combining the collagenase I and collagenase II purified from step (c) at a ratio of about 1 to 1.

25. The pharmaceutical formulation of claim 24, wherein the drug product is a sterile lyophilized powder.

26. The pharmaceutical formulation of claim 25, wherein the formulation is a lyophilized injectable composition formulated with sucrose, Tris and with a pH level of about 8.0.

27. The pharmaceutical formulation of claim 26, wherein the formulation is a lyophilized injectable composition formulation comprising about 0.9 mg of the said drug product, about 18.5 mg of sucrose and about 1.1 mg of Tris, and wherein the targeting vial fill volume is about 0.9 mL.

28. The pharmaceutical formulation of claim 26, wherein the drug product is a lyophilized injectable composition formulation comprising about 0.58 mg of the said drug product, about 12.0 mg of sucrose and about 0.7 mg of Tris.

29. A drug product consisting of collagenase I and collagenase II, wherein the collagenase I and collagenase II are isolated and purified from *Clostridium histolyticum* and wherein the collagenase I and collagenase II have a mass ratio of about 1 to 1 and the drug product is at least 97% by area pure as determined by reverse phase high performance liquid chromatography.

* * * * *

UNITED STATES PATENT AND TRADEMARK OFFICE
CERTIFICATE OF CORRECTION

PATENT NO. : 7,811,560 B2
APPLICATION NO. : 11/699302
DATED : October 12, 2010
INVENTOR(S) : Gregory L. Sabatino et al.

Page 1 of 1

It is certified that error appears in the above-identified patent and that said Letters Patent is hereby corrected as shown below:

On the Title Page

Item (75):
"Inventors: Gregory L. Sabatino, Chester Springs,
PA (US); Benjamin J. Del Tito, Jr.,
Doylestown, PA (US); Phillip J. Bassett,
Newcastle-under-Lyme (GB); Hazel A.
Tharia, Nr Crewe (GB); Antony G.
Hitchcock, Crewe (GB)"

Should be replaced with:
--Inventors: Gregory L. Sabatino, Chester Springs,
PA (US); Benjamin J. Del Tito, Jr.,
Doylestown, PA (US); Phillip J. Bassett,
Newcastle-under-Lyme (GB); Hazel A.
Tharia, Nr Crewe (GB); Antony G.
Hitchcock, Crewe (GB), Thomas L.
Wegman, N. Merrick, NJ (US); Bo Yu,
Fresh Meadows, NY (US)--

Signed and Sealed this
First Day of September, 2020

Andrei Iancu
*Director of the United States Patent and Trademark Office*